(12) United States Patent
Nakamura et al.

(10) Patent No.: US 8,313,913 B2
(45) Date of Patent: Nov. 20, 2012

(54) METHOD OF ENHANCING OF BINDING ACTIVITY OF ANTIBODY COMPOSITION TO FCγ RECEPTOR IIIA

(75) Inventors: Kazuyasu Nakamura, Machida (JP); Kenya Shitara, Machida (JP)

(73) Assignee: Kyowa Hakko Kirin Co., Ltd, Tokyo (JP)

( * ) Notice: Subject to any disclaimer, the term of this patent is extended or adjusted under 35 U.S.C. 154(b) by 74 days.

(21) Appl. No.: 12/550,160

(22) Filed: Aug. 28, 2009

(65) Prior Publication Data

US 2010/0092997 A1 Apr. 15, 2010

Related U.S. Application Data

(62) Division of application No. 10/409,611, filed on Apr. 9, 2003, now abandoned.

(30) Foreign Application Priority Data

Apr. 9, 2002 (JP) ................. 2002-106950

(51) Int. Cl.
*G01N 31/00* (2006.01)
*C07K 16/00* (2006.01)
(52) U.S. Cl. ..................... 435/7.1; 530/387.1
(58) Field of Classification Search ........................ None
See application file for complete search history.

(56) References Cited

U.S. PATENT DOCUMENTS

| | | | |
|---|---|---|---|
| 6,602,684 | B1 | 8/2003 | Umana et al. |
| 6,946,292 | B2 | 9/2005 | Kanda et al. |
| 7,214,775 | B2 | 5/2007 | Hanai et al. |
| 2005/0272916 | A1 | 12/2005 | Hanai et al. |
| 2005/0276805 | A1 | 12/2005 | Hanai et al. |
| 2006/0024800 | A1 | 2/2006 | Hanai et al. |

FOREIGN PATENT DOCUMENTS

| | | |
|---|---|---|
| EP | 1176195 A1 | 1/2002 |
| EP | 1331266 A1 | 7/2003 |
| WO | 97/27303 A1 | 7/1997 |
| WO | 99/54342 A1 | 10/1999 |
| WO | 00/61739 A1 | 10/2000 |
| WO | 02/31140 A1 | 4/2002 |

OTHER PUBLICATIONS

Shusaku Yanagidani et al., "Purification and cDNA Cloning of GDP-L-Fuc: N-Acetyl-β-D-Glucosaminide: α1-6 Fucosyltransferase (α1-6 FucT) from Human Gastric Cancer MKN45 Cells", J. Biochem., 1997, 121:626-632.
Hisaki Hayashi et al., "Molecular Cloning of Mouse Alpha-1,6-Fucosyltransferase and Expression of Its mRNA in the Developing Cerebrum", DNA Sequence, 2000, 11(1-2): 91-96.
Ann Wright et al., "Effect of glycosylation on antibody function: implications for genetic engineering", Trends in Biotechnology, 1997, 15(1): 26-32.
Pablo Umana et al., "Engineered glycoforms of an antineuroblastoma IgG1 with optimized antibody-dependent cellular cytotoxic activity", Nature Biotechnology, 1999, 17: 176-180.
Yang Wang et al., "Purification and Characterization of a GDP-fucose: Polypeptide Fucosyltransferase from Chinese Hamster Ovary Cells", Journal of Biological Chemistry, 1998, 273(14): 8112-8118.
Jukka Finne et al., "Lectin-Resistant Variants and Revertants of Mouse Melanoma Cells: Differential Expression of a Fucosylated Cell-Surface Antigen and Altered Metastasizing Capacity", Int. J. Cancer, 1989, 43: 300-304.
Tachibana et al., "Glycosylation of Antibody in a Lectin-Resistant Human Hybridoma is Insensitive to Glucose", In Vitro Cellular and Developmental Biology, 1995, 31: 261-262.
Li Xing et al., "Adenovirus-mediated expression of antisense RNA transcripts complementary to pig α(1,3) galactosyltransferase mRNA inhibits expression of Gal α(1,3) Gal epitope", Acta Pharmacologica Sinica, 2000, 21(11): 1005-1010.
Florence Hallouin et al., "Increased Tumorigenicity of Rat Colon Carcinoma Cells After α1,2-fucosyltransferase FTA Anti-Sense cDNA Transfection", Int. J. Cancer, 1999, 80:606-611.
Eeva M. Valve et al., "Increased Expression of FGF-8 Isoforms and FGF Receptors in Human Premalignant Prostatic Intraepithelial Neoplasia Lesions and Prostate Cancer", Laboratory Investigation, 2001, 81(6): 815-826.
Johanna K. Ruohola et al., "Enhanced Invasion and Tumor Growth of Fibroblast Growth Factor 8b-overexpressing MCF-7 Human Breast Cancer Cells", Cancer Research, 2001, 61: 4229-4237.
Supplementary European Search Report issued Nov. 14, 2006 in EP 03723098.4.
Paul M. Sondel et al., "Combination Therapy with Interleukin-2 and Antitumor Monoclonal Antibodies", Cancer Journal from Scientific American, 1997, 3: S121-S127.
James Ripka et al., "Two Chinese Hamster Ovary Glycosylation Mutants Affected in the Conversion of GDP-Mannose to GDP-Fucose", Archives of Biochemistry and Biophysics, 1986, 249(2): 533-545.
Kenya Shitara et al., "A new vector for the high level expression of chimeric antibodies in myeloma cells", Journal of Immunological Methods, 1994, 167: 271-278.
Julian Davies, "Expression of GnTIII in a Recombinant Anti-CD20 CHO Production Cell Line: Expression of Antibodies with Altered Glycoforms Leads to an Increase in ADCC Through Higher Affinity for FcγRIII", Biotechnology and Bioengineering, 2001, 74(4): 288-294.

(Continued)

*Primary Examiner* — Robert M Kelly
(74) *Attorney, Agent, or Firm* — Sughrue Mion, PLLC

(57) ABSTRACT

A method for enhancing a binding activity of an antibody composition to Fcγ receptor IIIa, which comprises modifying a complex N-glycoside-linked sugar chain which is bound to the Fc region of an antibody molecule; a method for enhancing an antibody-dependent cell-mediated cytotoxic activity of an antibody composition; a process for producing an antibody composition having an enhanced binding activity to Fcγ receptor IIIa; a method for detecting the ratio of a sugar chain in which fucose is not bound to N-acetylglucosamine in the reducing end in the sugar chain among total complex N-glycoside-linked sugar chains bound to the Fc region in an antibody composition; an Fc fusion protein composition produced by using a cell resistant to a lectin which recognizes a sugar chain in which 1-position of fucose is bound to 6-position of N-acetylglucosamine in the reducing end through α-bond in a complex N-glycoside-linked sugar chain; and a process for producing the same.

1 Claim, 38 Drawing Sheets

OTHER PUBLICATIONS

John Hackett et al., "Recombinant Mouse-Human Chimeric Antibodies as Calibrators in Immunoassays That Measure Antibodies to *Toxoplasma gondii*", Journal of Clinical Microbiology, 1998, 36(5): 1277-1284.

Sayda M. Elbashir et al., "Duplexes of 21-nucleotide RNAs mediate RNA interference in cultured mammalian cells", Nature, 2001, 411: 494-498.

Robert L. Shields et al., "High Resolution Mapping of the Binding Site on Human IgG1 for FcγRI, FcγRII, FcγRIII, and FcRn and Design of IgG1 Variants with Improved Binding to the FcγR", Journal of Biological Chemistry, 2001, 276(9): 6591-6604.

Robert L. Shields et al., "Lack of Fucose on Human IgG1 N-Linked Oligosaccharide Improves Binding to Human FcγRIII and Antibody-dependent Cellular Toxicity", Journal of Biological Chemistry, 2002, 277(30): 26733-26740.

Toyohide Shinkawa et al., "The Absence of Fucose but Not the Presence of Galactose or Bisecting N-Acetylglucosamine of Human IgG1 Complex-type Oligosaccharides Shows the Critical Role of Enhancing Antibody-dependent Cellular Cytotoxicity", Journal of Biological Chemistry, 2003, 278(5): 3466-3473.

Erika Staudacher et al., "Fucose in N-glycans: from plant to man", Biochimica et Biophysica Acta, 1999, 1473: 216-236.

N. Schiavone et al., "Antisense Oligonucleotide Drug Design", Current Pharmaceutical Design, 2004, 10:769-784.

Lubert Stryer, Biochemistry, Third Edition, 1988, Freeman and Co., New York, NY, pp. 35-37.

DT Jones, "Critically assessing the state-of-the-art in protein structure prediction", Pharmacogenomics Journal, 2001, 1: 126-134.

Abul K. Abbas et al., Cellular and Molecular Immunology, Second Edition, 1994, W.B. Saunders Co., Philadelphia, PA, p. 219.

Chikara Ohyama et al., Molecular Cloning and Expression of GDP-D-mannose-4,6-dehydratase, a Key Enzyme for Fucose Metabolism Defective in Lec13 Cells, Journal of Biological Chemistry, 1998, 272(23): 14582-14587.

Alessandra Cambi et al., "How C-type lectins detect pathogens", Cellular Microbiology, 2005, 7(4): 481-488.

Lokesh Joshi et al., "Bioprospecting in plants for engineered proteins", Current Opinion in Plant Biology, 2005, 8: 223-226.

Shinkawa et al., Journal of Biological Chemistry, 2003, 278(5): 3466-3473.

Tobias Willer et al., "Targeted disruption of the Walker-Warburg syndrome gene *Pomt1* in mouse results in embryonic lethality", PNAS, 2004, 101(39): 14126-14131.

Joanna S. Kruszewska et al., "Dolichol phosphate mannose synthase from the filamentous fungus *Trichoderma reesei* belongs to the human and *Schizosaccharomyces pombe* class of the enzyme", Glycobiology, 2000, 10(10): 983-991.

- ANTI-GD3 CHIMERIC ANTIBODY (50%)
- ANTI-GD3 CHIMERIC ANTIBODY (45%)
- ANTI-GD3 CHIMERIC ANTIBODY (29%)
- ANTI-GD3 CHIMERIC ANTIBODY (24%)
- ANTI-GD3 CHIMERIC ANTIBODY (13%)
- ANTI-GD3 CHIMERIC ANTIBODY (7%)

FIG. 14
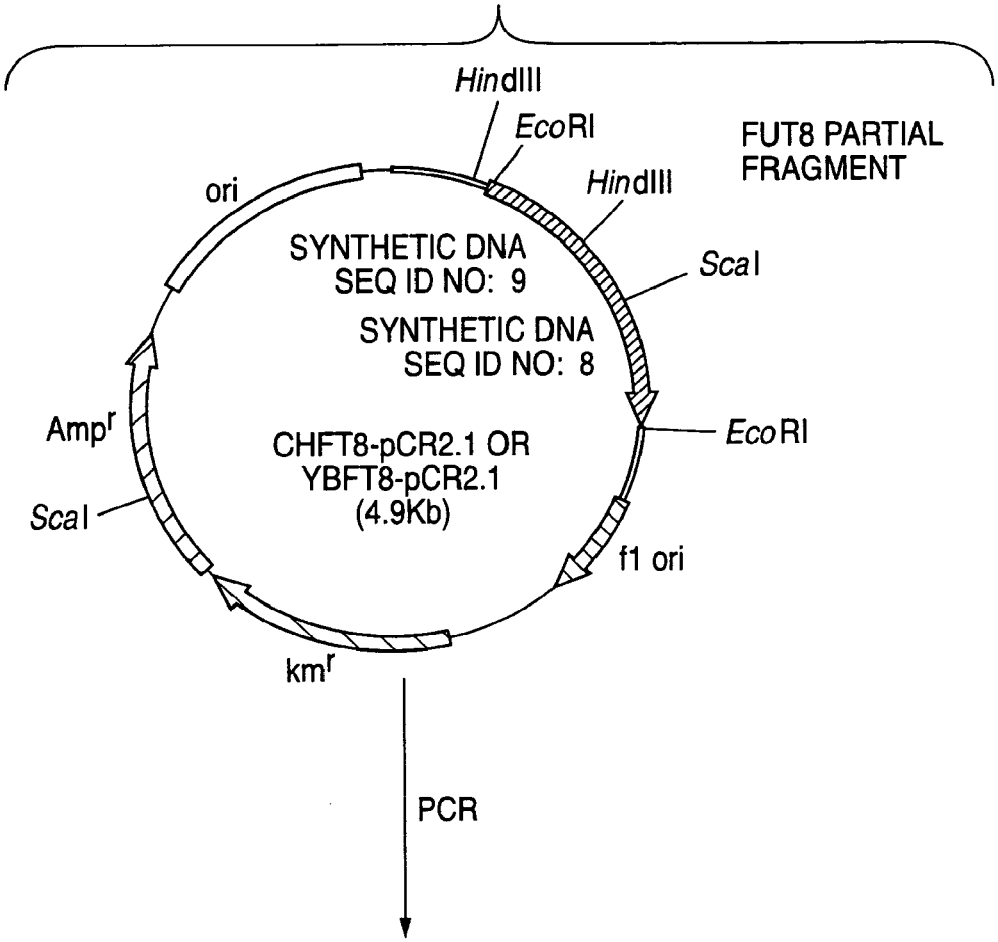
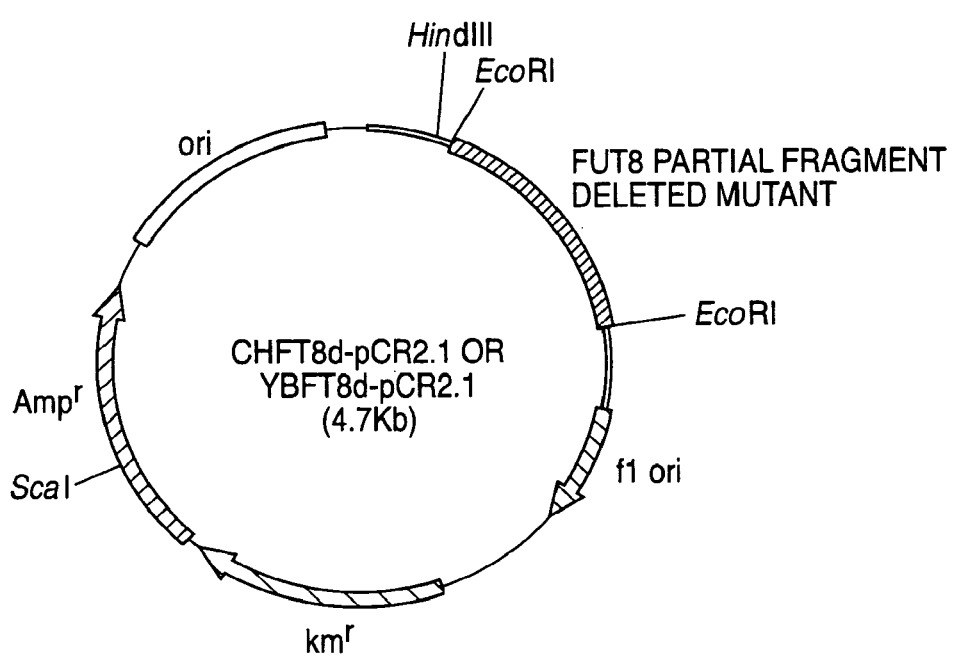

SEQUENCE LISTING

```
<160> NUMBER OF SEQ ID NOS: 100

<210> SEQ ID NO 1
<211> LENGTH: 2008
<212> TYPE: DNA
<213> ORGANISM: Cricetulus griseus

<400> SEQUENCE: 1
aacagaaact tattttcctg tgtggctaac tagaaccaga gtacaatgtt tccaattctt     60
tgagctccga gaagacagaa gggagttgaa actctgaaaa tgcgggcatg gactggttcc    120
tggcgttgga ttatgctcat tcttttgcc tgggggacct tattgtttta tataggtggt    180
catttggttc gagataatga ccaccctgac cattctagca gagaactctc caagattctt    240
gcaaagctgg agcgcttaaa acaacaaaat gaagacttga ggagaatggc tgagtctctc    300
cgaataccag aaggccctat tgatcagggg acagctacag gaagagtccg tgttttagaa    360
gaacagcttg ttaaggccaa agaacagatt gaaaattaca agaaacaagc taggaatgat    420
ctgggaaagg atcatgaaat cttaaggagg aggattgaaa atggagctaa agagctctgg    480 tttttctac aaagtgaatt gaagaaatta aagaaattag aaggaaacga actccaaaga    540
catgcagatg aaattctttt ggatttagga catcatgaaa ggtctatcat gacagatcta    600
tactacctca gtcaaacaga tggagcaggt gagtggcggg aaaaagaagc caaagatctg    660
acagagctgg tccagcggag aataacatat ctgcagaatc ccaaggactg cagcaaagcc    720
agaaagctgg tatgtaatat caacaaaggc tgtggctatg gatgtcaact ccatcatgtg    780
gtttactgct tcatgattgc ttatggcacc cagcgaacac tcatcttgga atctcagaat    840
tggcgctatg ctactggagg atgggagact gtgtttagac ctgtaagtga gacatgcaca    900
gacaggtctg gcctctccac tggacactgg tcaggtgaag tgaaggacaa aaatgttcaa    960
```

```
gtggtcgagc tccccattgt agacagcctc catcctcgtc ctccttactt acccttggct    1020
gtaccagaag accttgcaga tcgactcctg agagtccatg gtgatcctgc agtgtggtgg    1080
gtatcccagt ttgtcaaata cttgatccgt ccacaacctt ggctggaaag ggaaatagaa    1140
gaaaccacca agaagcttgg cttcaaacat ccagttattg gagtccatgt cagacgcact    1200
gacaaagtgg gaacagaagc agccttccat cccattgagg aatacatggt acacgttgaa    1260
gaacattttc agcttctcga acgcagaatg aaagtggata aaaaagagt gtatctggcc    1320 actgatgacc cttcttttgtt aaggaggca aagacaaagt actccaatta tgaatttatt    1380
agtgataact ctatttcttg gtcagctgga ctacacaacc gatacacaga aaattcactt    1440
cggggcgtga tcctggatat acactttctc tcccaggctg acttccttgt gtgtacttt    1500 tcatcccagg tctgtagggt tgcttatgaa atcatgcaaa cactgcatcc tgatgcctct    1560
gcaaacttcc attctttaga tgacatctac tattttggag ccaaaatgc ccacaaccag    1620 attgcagttt atcctcacca acctcgaact aaagaggaaa tccccatgga acctggagat    1680
atcattggtg tggctggaaa ccattggaat ggttactcta aggtgtcaa cagaaaacta    1740 ggaaaaacag gcctgtaccc ttcctacaaa gtccgagaga agatagaaac agtcaaatac    1800
cctacatatc ctgaagctga aaaatagaga tggagtgtaa gagattaaca acagaattta    1860
gttcagacca tctcagccaa gcagaagacc cagactaaca tatggttcat tgacagacat    1920
gctccgcacc aagagcaagt gggaaccctc agatgctgca ctggtggaac gcctctttgt    1980
gaagggctgc tgtgccctca gcccatg                                        2008

<210> SEQ ID NO 2
<211> LENGTH: 1728
<212> TYPE: DNA
<213> ORGANISM: Mus musculus

<400> SEQUENCE: 2
atgcgggcat ggactggttc ctggcgttgg attatgctca ttcttttttgc ctgggggacc      60 ttgttatttt atataggtgg tcatttggtt cgagataatg accaccctga tcactccagc     120
agagaactct ccaagattct tgcaaagctt gaacgcttaa acagcaaaaa tgaagacttg     180
aggcgaatgg ctgagtctct ccgaatacca gaaggcccca ttgaccaggg gacagctaca     240
ggaagagtcc gtgttttaga gaacagcttg gttaaggcca agaacagat tgaaaattac     300 aagaaacaag ctagaaatgg tctggggaag gatcatgaaa tcttaagaag gaggattgaa     360
aatggagcta aagagctctg gttttttttcta caaagcgaac tgaagaaatt aaagcattta    420
gaaggaaatg aactccaaag acatgcagat gaaattcttt tggattagg acaccatgaa     480 aggtctatca tgacagatct atactacctc agtcaaacag atggagcagg ggattggcgt     540
gaaaaagagg ccaaagatct gacagagctg gtccagcgga gaataacata tctccagaat     600
cctaaggact gcagcaaagc caggaagctg gtgtgtaaca tcaataaagg ctgtggctat     660
ggttgtcaac tccatcacgt ggtctactgt ttcatgattg cttatggcac ccagcgaaca     720
ctcatcttgg aatctcagaa ttggcgctat gctactggtg gatgggagac tgtgtttaga     780
cctgtaagtg agacatgtac agacagatct ggcctctcca ctggacactg gtcaggtgaa     840
gtaaatgaca aaaacattca agtggtcgag ctccccattg tagacagcct ccatcctcgg     900
cctccttact taccactggc tgttccagaa gaccttgcag accgactcct aagagtccat     960
ggtgaccctg cagtgtggtg ggtgtcccag tttgtcaaat acttgattcg tccacaacct    1020
tggctggaaa aggaaataga agaagccacc aagaagcttg gcttcaaaca tccagttatt    1080
```

```
ggagtccatg tcagacgcac agacaaagtg ggaacagaag cagccttcca ccccatcgag   1140
gagtacatgg tacacgttga agaacatttt cagcttctcg cacgcagaat gcaagtggat   1200
aaaaaaagag tatatctggc tactgatgat cctactttgt aaaggaggc aaagacaaag    1260 tactccaatt atgaatttat tagtgataac tctatttctt ggtcagctgg actacacaat   1320
cggtacacag aaaattcact tcggggtgtg atcctggata tacactttct ctcacaggct   1380
gactttctag tgtgtacttt ttcatcccag gtctgtcggg ttgcttatga aatcatgcaa   1440
accctgcatc ctgatgcctc tgcgaacttc cattctttgg atgacatcta ctattttgga   1500
ggccaaaatg cccacaatca gattgctgtt tatcctcaca aacctcgaac tgaagaggaa   1560
attccaatgg aacctggaga tatcattggt gtggctggaa accattggga tggttattct   1620
aaaggtatca acagaaaact tggaaaaaca ggcttatatc cctcctacaa agtccgagag   1680
aagatagaaa cagtcaagta tcccacatat cctgaagctg aaaaatag                1728
```

<210> SEQ ID NO 3
<211> LENGTH: 9196
<212> TYPE: DNA
<213> ORGANISM: Cricetulus griseus
<400> SEQUENCE: 3

```
tctagaccag ctggtctcg aactcacaga gaaccacctg cctctgccac ctgagtgctg    60
ggattaaagg tgtgcaccac caccgcccgg cgtaaaatca tattttgaa tattgtgata    120 atttacatta taattgtaag taaaaatttt cagcctattt tgttatacat ttttgcgtaa   180
attattcttt tttgaaagtt tgttgtcca taatagtcta gggaaacata agttataat    240 ttttgtctat gtatttgcat atatatctat ttaatctcct aatgtccagg aaataaatag   300
ggtatgtaat agcttcaaca tgtggtatga tagaatttt cagtgctata taagttgtta    360
cagcaaagtg ttattaattc atatgtccat atttcaattt tttatgaatt attaaattga   420
atccttaagc tgccagaact agaattttat tttaatcagg aagccccaaa tctgttcatt   480
ctttctatat atgtggaaag gtaggcctca ctaactgatt cttcacctgt tttagaacat   540
ggtccaagaa tggagttatg taaggggaat tacaagtgtg agaaaactcc tagaaaacaa   600
gatgagtctt gtgaccttag tttctttaaa aacacaaaat tcttggaatg tgttttcatg   660
ttcctcccag gtggatagga gtgagtttat ttcagattat ttattacaac tggctgttgt   720
tacttgtttc tatgtctta tagaaaaaca tattttttt gccacatgca gcttgtcctt     780
atgattttat acttgtgtga ctcttaactc tcagagtata aattgtctga tgctatgaat   840
aaagttggct attgtatgag acttcagccc acttcaatta ttggcttcat tctctcagat   900
cccaccacct ccagagtggt aaacaacttg aaccattaaa cagactttag tctttatttg   960
aatgatagat ggggatatca gatttatagg cacagggttt tgagaaaggg agaaggtaaa   1020
cagtagagtt taacaacaac aaaaagtata ctttgtaaac gtaaaactat ttattaaagt   1080
agtagacaag acattaaata ttccttggga ttagtgcttt ttgaatttg ctttcaaata    1140 atagtcagtg agtataccc tccccatcc tatatttag cagaaatcag aataaatggt     1200
gtttctggta cattcttttg tagagaattt attttctttg ggtttttgtg catttaaagt   1260 caataaaat taaggttcag taatagaaaa aaaactctga tttttggaat ccctttctt    1320 cagcttttct atttaatctc ttaatgataa tttaatttgt ggccatgtgg tcaaagtata   1380
tagccttgta tatgtaaatg ttttaaccaa cctgcctta cagtaactat ataatttat    1440 tctataatat atgactttc ttccatagct ttagagttgc ccagtcactt taagttacat   1500
```

```
tttcatatat gttctttgtg ggaggagata attttatttc taagagaatc ctaagcatac   1560
tgattgagaa atggcaaaca aaacacataa ttaaagctga taaagaacga acatttggag   1620
tttaaaatac atagccaccc taagggttta actgttgtta gccttctttt ggaattttta   1680
ttagttcata tagaaaaatg gattttatcg tgacatttcc atatatgtat ataatatatt   1740
tacatcatat ccacctgtaa ttattagtgt ttttaaatat atttgaaaaa ataatggtct   1800
ggtttgatcc atttgaacct tttgatgttt ggtgtggttg ccaattggtt gatggttatg   1860
ataacctttg cttctctaag gttcaagtca gtttgagaat atgtcctcta aaaatgacag   1920
gttgcaagtt aagtagtgag atgacagcga gatggagtga tgagaatttg tagaaatgaa   1980
ttcacttata ctgagaactt gttttgcttt tagataatga acatattagc ctgaagtaca   2040
tagccgaatt gattaattat tcaaagatat aatcttttaa tccctataaa agaggtatta   2100
cacaacaatt caagaaagat agaattagac ttccagtatt ggagtgaacc atttgttatc   2160
aggtagaacc ctaacgtgtg tggttgactt aaagtgttta cttttttacct gatactgggt   2220
agctaattgt ctttcagcct cctggccaaa gataccatga aagtcaactt acgttgtatt   2280
ctatatctca acaactcag ggtgtttctt actctttcca cagcatgtag agcccaggaa   2340
gcacaggaca agaaagctgc ctccttgtat caccaggaag atcttttgt aagagtcatc   2400
acagtatacc agagagacta attttgtctg aagcatcatg tgttgaaaca acagaaactt   2460
attttcctgt gtggctaact agaaccagag tacaatgttt ccaattcttt gagctccgag   2520
aagacagaag ggagttgaaa ctctgaaaat gcgggcatgg actggttcct ggcgttggat   2580
tatgctcatt cttttgcct gggggacctt attgtttat ataggtggtc atttggttcg   2640
agataatgac caccctgacc attctagcag agaactctcc aagattcttg caaagctgga   2700
gcgcttaaaa caacaaaatg aagacttgag gagaatggct gagtctctcc ggtaggtttg   2760
aaatactcaa ggatttgatg aaatactgtg cttgaccttt aggtatagg tctcagtctg   2820
ctgttgaaaa atataatttc tacaaaccgt ctttgtaaaa ttttaagtat tgtagcagac   2880
ttttaaaag tcagtgatac atctatatag tcaatatagg tttacatagt tgcaatctta   2940
ttttgcatat gaatcagtat atagaagcag tggcatttat atgcttatgt tgcatttaca   3000
attatgttta gacgaacaca aactttatgt gatttggatt agtgctcatt aaatttttt   3060
attctatgga ctacaacaga gacataaatt ttgaaaggct tagttactct taaattctta   3120
tgatgaaaag caaaaattca ttgttaaata aacagtgca tccggaatgt gggtaattat   3180
tgccatattt ctagtctact aaaaattgtg gcataactgt tcaaagtcat cagttgtttg   3240
gaaagccaaa gtctgattta aatggaaaac ataaacaatg atatctattt ctagataacct   3300
ttaacttgca gttactgagt ttacaagttg tctgacaact ttggattctc ttacttcata   3360
tctaagaatg atcatgtgta cagtgcttac tgtcacttta aaaactgca gggctagaca   3420
tgcagatatg aagactttga cattagatgt ggtaattggc actaccagca agtggtatta   3480
agatacagct gaatatatta cttttttgagg aacataattc atgaatggaa agtggagcat   3540
tagagaggat gccttctggc tctcccacac cactgtttgc atccattgca tttcacactg   3600
cttttagaac tcagatgttt catatggtat attgtgtaac tcaccatcag ttttatcttt   3660
aaatgtctat ggatgataat gttgtatgtt aacacttta caaaacaaa tgaagccata   3720
tcctcggtgt gagttgtgat ggtggtaatt gtcacaatag gattattcag caaggaacta   3780
agtcaggac aagaagtggg cgatactttg ttggattaaa tcatttact ggaagttcat   3840
cagggagggt tatgaaagtt gtggtctttg aactgaaatt atatgtgatt cattattctt   3900
```

```
gatttaggcc ttgctaatag taactatcat ttattgggaa tttgtcatat gtgccaattt    3960
gtcatgggcc agacagcgtg ttttactgaa tttctagata tctttatgag attctagtac    4020
tgttttcagc cattttacag atgaagaatc ttaaaaaatg ttaaataatt tagtttgccc    4080
aagattatac gttaacaaat ggtagaacct tctttgaatt ctggcagtat ggctacacag    4140
tccgaactct tatcttccta agctgaaaac agaaaaagca atgacccaga aaattttatt    4200
taaaagtctc aggagagact tcccatcctg agaagatctc ttttcccttt tataatttag    4260
gctcctgaat aatcactgaa ttttctccat gttccatcta tagtactgtt atttctgttt    4320 tcctttttc ttaccacaaa gtatcttgtt tttgctgtat gaaagaaaat gtgttattgt     4380
aatgtgaaat tctctgtccc tgcagggtcc cacatccgcc tcaatcccaa ataaacacac    4440
agaggctgta ttaattatga aactgttggt cagttggcta gggcttctta ttggctagct    4500
ctgtcttaat tattaaacca taactactat tgtaagtatt tccatgtggt cttatcttac    4560
caaggaaagg gtccagggac ctcttactcc tctggcgtgt tggcagtgaa gaggagagag    4620
cgatttccta tttgtctctg cttatttct gattctgctc agctatgtca cttcctgcct     4680
ggccaatcag ccaatcagtg ttttattcat tagccaataa agaaacatt tacacagaag     4740 gacttccccc atcatgttat ttgtatgagt tcttcagaaa atcatagtat cttttaatac    4800
taatttttat aaaaaattaa ttgtattgaa aattatgtgt atatgtgtct gtgtgtcgat    4860
ttgtgctcat aagtagcatg gagtgcagaa gagggaatca gatcttttt taagggacaa     4920 agagtttatt cagattacat tttaaggtga taatgtatga ttgcaaggtt atcaacatgg    4980
cagaaatgtg aagaagctgg tcacattaca tccagagtca agagtagaga gcaatgaatt    5040
gatgcatgca ttcctgtgct cagctcactt ttcctggagc tgagctgatt gtaagccatc    5100
tgatgtcttt gctgggaact aactcaaagg caagttcaaa acctgttctt aagtataagc    5160
catctctcca gtccctcata tggtctctta agacactttc tttatattct tgtacataga    5220
aattgaattc ctaacaactg cattcaaatt acaaaatagt ttttaaaagc tgatataata    5280
aatgtaaata caatctagaa cattttata aataagcata ttaactcagt aaaaataaat     5340
gcatggttat tttccttcat tagggaagta tgtctcccca ggctgttctc tagattctac    5400
tagtaatgct gtttgtacac catccacagg ggttttattt taaagctaag acatgaatga    5460
tggacatgct tgttagcatt tagacttttt tccttactat aattgagcta gtattttgt     5520 gctcagtttg atatctgtta attcagataa atgtaatagt aggtaatttc tttgtgataa    5580
aggcatataa attgaagttg gaaaacaaaa gcctgaaatg acagttttta agattcagaa    5640
caataatttt caaaagcagt tacccaactt tccaaataca atctgcagtt ttcttgatat    5700
gtgataaatt tagacaaaga aatagcacat tttaaaatag ctatttactc ttgatttttt    5760
tttcaaattt aggctagttc actagttgtg tgtaaggtta tggctgcaaa catctttgac    5820
tcttggttag ggaatccagg atgatttacg tgtttggcca aaatcttgtt ccattctggg    5880
tttcttctct atctaggtag ctagcacaag ttaaaggtgt ggtagtattg gaaggctctc    5940
aggtatatat ttctatattc tgtattttt tcctctgtca tatatttgct ttctgtttta    6000
ttgatttcta ctgttagttt gatacttact ttcttacact ttcttggga tttattttgc    6060 tgttctaaga tttcttagca agttcatatc actgatttta acagttgctt cttttgtaat    6120
atagactgaa tgcccttat ttgaaatgct tgggatcaga aactcagatt tgaacttttc     6180
ttttttaata tttccatcaa gtttaccagc tgaatgtcct gatccaagaa tatgaaatct    6240
gaaatgcttt gaaatctgaa acttttagag tgataaagct tccctttaaa ttaatttgtg    6300
```

```
ttctatattt tttgacaatg tcaacctttc attgttatcc aatgagtgaa catattttca   6360
atttttttgt ttgatctgtt atattttgat ctgaccatat ttataaaatt ttatttaatt   6420
tgaatgttgt gctgttactt atctttatta ttattttgc ttattttcta gccaaatgaa    6480
attatattct gtattatttt agtttgaatt ttactttgtg gcttagtaac tgccttttgt   6540
tggtgaatgc ttaagaaaaa cgtgtggtct actgatattg gttctaatct tatatagcat   6600
gttgtttgtt aggtagttga ttatgctggt cagattgtct tgagtttatg caaatgtaaa   6660
atatttagat gcttgttttg ttgtctaaga acaaagtatg cttgctgtct cctatcggtt   6720
ctggtttttc cattcatctc ttcaagctgt tttgtgtgtt gaatactaac tccgtactat   6780
cttgttttct gtgaattaac ccctttcaa aggtttcttt tcttttttttt tttaagggac    6840 aacaagttta ttcagattac attttaagct gataatgtat gattgcaagg ttatcaacat   6900
ggcagaaatg tgaagaagct aggcacatta catccacatg gagtcaagag cagagagcag   6960
tgaattaatg catgcattcc tgtggtcagc tcacttttcc tattcttaga tagtctagga   7020
tcataaacct ggggaatagt gctaccacaa tgggcatatc cacttacttc agttcatgca   7080
atcaaccaag gcacatccac aggaaaaact gatttagaca acctctcatt gagactcttc   7140
ccagatgatt agactgtgtc aagttgacaa ttaaaactat cacacctgaa gccatcacta   7200
gtaaatataa tgaaaatgtt gattatcacc ataattcatc tgtatccctt tgttattgta   7260
gattttgtga agttcctatt caagtccctg ttccttcctt aaaaacctgt tttttagtta   7320
aataggtttt ttagtgttcc tgtctgtaaa tactttttta aagttagata ttattttcaa   7380
gtatgttctc ccagtctttg gcttgtattt tcatcccttc aatacatata tttttgtaat   7440 ttatttttt tatttaaatt agaaacaaag ctgcttttac atgtcagtct cagttccctc     7500
tccctcccct cctcccctgc tccccaccta agccccaatt ccaactcctt tcttctcccc   7560
aggaagggtg aggccctcca tgggggaaat cttcaatgtc tgtcatatca tttggagcag   7620
ggcctagacc ctccccagtg tgtctaggct gagagagtat ccctctatgt ggagagggct   7680
cccaaagttc atttgtgtac taggggtaaa tactgatcca ctatcagtgg ccccatagat   7740
tgtccggacc tccaaactga cttcctcctt cagggagtct ggaacagttc tatgctggtt   7800
tcccagatat cagtctgggg tccatgagca accccttgtt caggtcagtt gtttctgtag   7860
gtttccccag cccggtcttg accccttgc tcatcacttc tccctctctg caactggatt     7920
ccagagttca gctcagtgtt tagctgtggg tgtctgcatc tgcttccatc agctactgga   7980
tgagggctct aggatggcat ataaggtagt catcagtctc attatcagag aagggctttt   8040
aaggtagcct cttgattatt gcttagattg ttagttgggg tcaaccttgt aggtctctgg   8100
acagtgacag aattctcttt aaacctataa tggctccctc tgtggtggta tcccttttct   8160
tgctctcatc cgttcctccc ctgactagat cttcctgctc cctcatgtcc tcctctcccc   8220
tccccttctc cccttctctt tcttctaact ccctctcccc tccacccacg atccccatta   8280
gcttatgaga tcttgtcctt attttagcaa aaccttttg gctataaaat taattaattt     8340
aatatgctta tatcaggttt attttggcta gtatttgtat gtgtttggtt agtgttttta   8400
accttaattg acatgtatcc ttatatttag acacagattt aaatatttga agttttttt     8460 tttttttttt ttaaagattt atttattttt tatgtcttct gcctgcatgc cagaagaggg   8520
caccagatct cattcaaggt ggttgtgagc caccatgtgg ttgctgggaa ttgaactcag   8580
gacctctgga agaacagtca gtgctcttaa ccgctgagcc atctctccag cccctgaagt   8640
gtttctttta aagaggatag cagtgcatca ttttcccctt tgaccaatga ctcctaccct   8700
```

```
actgaattgt tttagccatt tatatgtaat gctgttacca ggtttacatt ttcttttatc    8760
ttgctaaatt tcttccctgt ttgtctcatc tcttattttt gtctgttgga ttatataggc    8820 ttttatttt ctgtttttac agtaagttat atcaaattaa aattatttta tggaatgggt    8880
gtgttgacta catgtatgtc tgtgcaccat gtgctgacct ggtcttggcc agaagaaggt    8940
gtcatattct ctgaaactgg tattgtggat gttacgaact gccataggt gctaggaatc     9000 aaacccagc tcctctggaa aagcagccac tgctctgagc cactgagtcc tctcttcaag     9060
caggtgatgc caacttttaa tggttaccag tggataagag tgcttgtatc tctagcaccc    9120
atgaaaattt atgcattgct atatgggctt gtcacttcag cattgtgtga cagagacagg    9180
aggatcccaa gagctc                                                    9196

<210> SEQ ID NO 4
<211> LENGTH: 25
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 4
actcatcttg gaatctcaga attgg                                          25

<210> SEQ ID NO 5
<211> LENGTH: 24
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 5
cttgaccgtt tctatcttct ctcg                                           24

<210> SEQ ID NO 6
<211> LENGTH: 979
<212> TYPE: DNA
<213> ORGANISM: Cricetulus griseus

<400> SEQUENCE: 6
actcatcttg gaatctcaga attggcgcta tgctactgga ggatgggaga ctgtgtttag    60
acctgtaagt gagacatgca cagacaggtc tggcctctcc actggacact ggtcaggtga    120
agtgaaggac aaaaatgttc aagtggtcga gctccccatt gtagacagcc tccatcctcg    180
tcctccttac ttacccttgg ctgtaccaga agaccttgca gatcgactcc tgagagtcca    240
tggtgatcct gcagtgtggt gggtatccca gtttgtcaaa tacttgatcc gtccacaacc    300
ttggctggaa agggaaatag aagaaaccac caagaagctt ggcttcaaac atccagttat    360
tggagtccat gtcagacgca ctgacaaagt gggaacagaa gcagccttcc atcccattga    420
ggaatacatg gtacacgttg aagaacattt tcagcttctc gaacgcagaa tgaaagtgga    480 taaaaaaga gtgtatctgg ccactgatga cccttctttg ttaaaggagg caaagacaaa    540
gtactccaat tatgaattta ttagtgataa ctctatttct tggtcagctg gactacacaa    600
ccgatacaca gaaaattcac ttcggggcgt gatcctggat atacactttc tctcccaggc    660
tgacttcctt gtgtgtactt tttcatccca ggtctgtagg gttgcttatg aaatcatgca    720
aacactgcat cctgatgcct ctgcaaactt ccattcttta gatgacatct actatttggg    780
aggccaaaat gcccacaacc agattgcagt ttatcctcac caacctcgaa ctaaagagga    840
```

```
aatccccatg gaacctggag atatcattgg tgtggctgga aaccattgga atggttactc    900
taaaggtgtc aacagaaaac taggaaaaac aggcctgtac ccttcctaca aagtccgaga    960
gaagatagaa acggtcaag                                                 979
```

<210> SEQ ID NO 7
<211> LENGTH: 979
<212> TYPE: DNA
<213> ORGANISM: Rattus norvegicus

<400> SEQUENCE: 7

```
actcatcttg aatctcaga attggcgcta tgctactggt ggatgggaga ctgtgtttag     60
acctgtaagt gagacatgca cagacagatc tggcctctcc actggacact ggtcaggtga   120
agtgaatgac aaaaatattc aagtggtgga gctccccatt gtagacagcc ttcatcctcg   180
gcctccttac ttaccactgg ctgttccaga agaccttgca gatcgactcg taagagtcca   240
tggtgatcct gcagtgtggt gggtgtccca gttcgtcaaa tatttgattc gtccacaacc   300
ttggctagaa aaggaaatag aagaagccac caagaagctt ggcttcaaac atccagtcat   360
tggagtccat gtcagacgca cagacaaagt gggaacagag gcagccttcc atcccatcga   420
agagtacatg gtacatgttg aagaacattt tcagcttctc gcacgcagaa tgcaagtgga   480 taaaaaaga gtatatctgg ctaccgatga ccctgctttg ttaaaggagg caagacaaa    540 gtactccaat tatgaattta ttagtgataa ctctatttct tggtcagctg gactacacaa   600
tcggtacaca gaaaattcac ttcggggcgt gatcctggat atacactttc tctctcaggc   660
tgacttccta gtgtgtactt tttcatccca ggtctgtcgg gttgcttatg aaatcatgca   720
aaccctgcat cctgatgcct ctgcaaactt ccactcttta gatgacatct actattttgg   780
aggccaaaat gcccacaacc agattgccgt ttatcctcac aaacctcgaa ctgatgagga   840
aattccaatg gaacctggag atatcattgg tgtggctgga aaccattggg atggttattc   900
taaaggtgtc aacagaaaac ttggaaaaac aggcttatat ccctcctaca aagtccgaga   960
gaagatagaa acggtcaag                                                979
```

<210> SEQ ID NO 8
<211> LENGTH: 40
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 8

```
aagtataagc ttacatggat gacgatatcg ctgcgctcgt                           40
```

<210> SEQ ID NO 9
<211> LENGTH: 40
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 9

```
atttaactgc aggaagcatt tgcggtggac gatggagggg                           40
```

<210> SEQ ID NO 10
<211> LENGTH: 40
<212> TYPE: DNA
<213> ORGANISM: Artificial Sequence
<220> FEATURE:
<223> OTHER INFORMATION: Description of Artificial Sequence: Synthetic
DNA

<400> SEQUENCE: 10
atttaaggta ccgaagcatt tgcggtgcac gatggagggg                                40

<210> SEQ ID NO 11
<211> LENGTH: 23
<212> TYPE: DNA
<213> ORGANISM: Artificial Sequence
<220> FEATURE:
<223> OTHER INFORMATION: Description of Artificial Sequence: Synthetic
DNA

<400> SEQUENCE: 11
ctccaattat gaatttatta gtg                                                  23

<210> SEQ ID NO 12
<211> LENGTH: 25
<212> TYPE: DNA
<213> ORGANISM: Artificial Sequence
<220> FEATURE:
<223> OTHER INFORMATION: Description of Artificial Sequence: Synthetic
DNA

<400> SEQUENCE: 12
ggatgtttga agccaagctt cttgg                                                25

<210> SEQ ID NO 13
<211> LENGTH: 24
<212> TYPE: DNA
<213> ORGANISM: Artificial Sequence
<220> FEATURE:
<223> OTHER INFORMATION: Description of Artificial Sequence: Synthetic
DNA

<400> SEQUENCE: 13
gtccatggtg atcctgcagt gtgg                                                 24

<210> SEQ ID NO 14
<211> LENGTH: 23
<212> TYPE: DNA
<213> ORGANISM: Artificial Sequence
<220> FEATURE:
<223> OTHER INFORMATION: Description of Artificial Sequence: Synthetic
DNA

<400> SEQUENCE: 14
caccaatgat atctccaggt tcc                                                  23

<210> SEQ ID NO 15
<211> LENGTH: 24
<212> TYPE: DNA
<213> ORGANISM: Artificial Sequence
<220> FEATURE:
<223> OTHER INFORMATION: Description of Artificial Sequence: Synthetic
DNA

<400> SEQUENCE: 15
gatatcgctg cgctcgttgt cgac                                                 24

<210> SEQ ID NO 16
<211> LENGTH: 24
<212> TYPE: DNA
<213> ORGANISM: Artificial Sequence
<220> FEATURE:
<223> OTHER INFORMATION: Description of Artificial Sequence: Synthetic

DNA

<400> SEQUENCE: 16
caggaaggaa ggctggaaaa gagc                                          24

<210> SEQ ID NO 17
<211> LENGTH: 24
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 17
gatatcgctg cgctcgtcgt cgac                                          24

<210> SEQ ID NO 18
<211> LENGTH: 24
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 18
caggaaggaa ggctggaaga gagc                                          24

<210> SEQ ID NO 19
<211> LENGTH: 321
<212> TYPE: PRT
<213> ORGANISM: Cricetulus griseus

<400> SEQUENCE: 19

Met Gly Glu Pro Gln Gly Ser Arg Arg Ile Leu Val Thr Gly Gly Ser
 1               5                  10                  15

Gly Leu Val Gly Arg Ala Ile Gln Lys Val Val Ala Asp Gly Ala Gly
                20                  25                  30

Leu Pro Gly Glu Glu Trp Val Phe Val Ser Ser Lys Asp Ala Asp Leu
            35                  40                  45

Thr Asp Ala Ala Gln Thr Gln Ala Leu Phe Gln Lys Val Gln Pro Thr
        50                  55                  60

His Val Ile His Leu Ala Ala Met Val Gly Gly Leu Phe Arg Asn Ile
    65                  70                  75                  80

Lys Tyr Asn Leu Asp Phe Trp Arg Lys Asn Val His Ile Asn Asp Asn
                85                  90                  95

Val Leu His Ser Ala Phe Glu Val Gly Thr Arg Lys Val Val Ser Cys
               100                 105                 110

Leu Ser Thr Cys Ile Phe Pro Asp Lys Thr Thr Tyr Pro Ile Asp Glu
            115                 120                 125

Thr Met Ile His Asn Gly Pro Pro His Ser Ser Asn Phe Gly Tyr Ser
        130                 135                 140

Tyr Ala Lys Arg Met Ile Asp Val Gln Asn Arg Ala Tyr Phe Gln Gln
    145                 150                 155                 160

His Gly Cys Thr Phe Thr Ala Val Ile Pro Thr Asn Val Phe Gly Pro
                165                 170                 175

His Asp Asn Phe Asn Ile Glu Asp Gly His Val Leu Pro Gly Leu Ile
            180                 185                 190

His Lys Val His Leu Ala Lys Ser Asn Gly Ser Ala Leu Thr Val Trp
        195                 200                 205

Gly Thr Gly Lys Pro Arg Arg Gln Phe Ile Tyr Ser Leu Asp Leu Ala

```
                 210                 215                 220
Arg Leu Phe Ile Trp Val Leu Arg Glu Tyr Asn Glu Val Glu Pro Ile
225                 230                 235                 240

Ile Leu Ser Val Gly Glu Asp Glu Val Ser Ile Lys Glu Ala Ala
                245                 250                 255

Glu Ala Val Val Glu Ala Met Asp Phe Cys Gly Val Thr Phe Asp
                260                 265                 270

Ser Thr Lys Ser Asp Gly Gln Tyr Lys Lys Thr Ala Ser Asn Gly Lys
                275                 280                 285

Leu Arg Ala Tyr Leu Pro Asp Phe Arg Phe Thr Pro Phe Lys Gln Ala
                290                 295                 300

Val Lys Glu Thr Cys Ala Trp Phe Thr Asp Asn Tyr Glu Gln Ala Arg
305                 310                 315                 320

Lys

<210> SEQ ID NO 20
<211> LENGTH: 590
<212> TYPE: PRT
<213> ORGANISM: Cricetulus griseus

<400> SEQUENCE: 20

Met Ala Ser Leu Arg Glu Ala Ser Leu Arg Lys Leu Arg Arg Phe Ser
1               5                   10                  15

Glu Met Arg Gly Lys Pro Val Ala Thr Gly Lys Phe Trp Asp Val Val
                20                  25                  30

Val Ile Thr Ala Ala Asp Glu Lys Gln Glu Leu Ala Tyr Lys Gln Gln
                35                  40                  45

Leu Ser Glu Lys Leu Lys Arg Lys Glu Leu Pro Leu Gly Val Asn Tyr
            50                  55                  60

His Val Phe Thr Asp Pro Pro Gly Thr Lys Ile Gly Asn Gly Gly Ser
65                  70                  75                  80

Thr Leu Cys Ser Leu Gln Cys Leu Glu Ser Leu Tyr Gly Asp Lys Trp
                85                  90                  95

Asn Ser Phe Thr Val Leu Leu Ile His Ser Gly Gly Tyr Ser Gln Arg
                100                 105                 110

Leu Pro Asn Ala Ser Ala Leu Gly Lys Ile Phe Thr Ala Leu Pro Leu
            115                 120                 125

Gly Glu Pro Ile Tyr Gln Met Leu Asp Leu Lys Leu Ala Met Tyr Met
130                 135                 140

Asp Phe Pro Ser Arg Met Lys Pro Gly Val Leu Val Thr Cys Ala Asp
145                 150                 155                 160

Asp Ile Glu Leu Tyr Ser Ile Gly Asp Ser Glu Ser Ile Ala Phe Glu
                165                 170                 175

Gln Pro Gly Phe Thr Ala Leu Ala His Pro Ser Ser Leu Ala Val Gly
            180                 185                 190

Thr Thr His Gly Val Phe Val Leu Asp Ser Ala Gly Ser Leu Gln His
        195                 200                 205

Gly Asp Leu Glu Tyr Arg Gln Cys His Arg Phe Leu His Lys Pro Ser
    210                 215                 220

Ile Glu Asn Met His His Phe Asn Ala Val His Arg Leu Gly Ser Phe
225                 230                 235                 240

Gly Gln Gln Asp Leu Ser Gly Gly Asp Thr Thr Cys His Pro Leu His
                245                 250                 255

Ser Glu Tyr Val Tyr Thr Asp Ser Leu Phe Tyr Met Asp His Lys Ser
                260                 265                 270
```

```
Ala Lys Lys Leu Leu Asp Phe Tyr Glu Ser Val Gly Pro Leu Asn Cys
            275                 280                 285

Glu Ile Asp Ala Tyr Gly Asp Phe Leu Gln Ala Leu Gly Pro Gly Ala
            290                 295                 300

Thr Ala Glu Tyr Thr Lys Asn Thr Ser His Val Thr Lys Glu Glu Ser
305                 310                 315                 320

His Leu Leu Asp Met Arg Gln Lys Ile Phe His Leu Leu Lys Gly Thr
                325                 330                 335

Pro Leu Asn Val Val Val Leu Asn Asn Ser Arg Phe Tyr His Ile Gly
            340                 345                 350

Thr Thr Glu Glu Tyr Leu Leu His Phe Thr Ser Asn Gly Ser Leu Gln
            355                 360                 365

Ala Glu Leu Gly Leu Gln Ser Ile Ala Phe Ser Val Phe Pro Asn Val
            370                 375                 380

Pro Glu Asp Ser His Glu Lys Pro Cys Val Ile His Ser Ile Leu Asn
385                 390                 395                 400

Ser Gly Cys Cys Val Ala Pro Gly Ser Val Val Glu Tyr Ser Arg Leu
                405                 410                 415

Gly Pro Glu Val Ser Ile Ser Glu Asn Cys Ile Ile Ser Gly Ser Val
            420                 425                 430

Ile Glu Lys Ala Val Leu Pro Pro Cys Ser Phe Val Cys Ser Leu Ser
                435                 440                 445

Val Glu Ile Asn Gly His Leu Glu Tyr Ser Thr Met Val Phe Gly Met
            450                 455                 460

Glu Asp Asn Leu Lys Asn Ser Val Lys Thr Ile Ser Asp Ile Lys Met
465                 470                 475                 480

Leu Gln Phe Phe Gly Val Cys Phe Leu Thr Cys Leu Asp Ile Trp Asn
                485                 490                 495

Leu Lys Ala Met Glu Glu Leu Phe Ser Gly Ser Lys Thr Gln Leu Ser
                500                 505                 510

Leu Trp Thr Ala Arg Ile Phe Pro Val Cys Ser Ser Leu Ser Glu Ser
            515                 520                 525

Val Ala Ala Ser Leu Gly Met Leu Asn Ala Ile Arg Asn His Ser Pro
            530                 535                 540

Phe Ser Leu Ser Asn Phe Lys Leu Leu Ser Ile Gln Glu Met Leu Leu
545                 550                 555                 560

Cys Lys Asp Val Gly Asp Met Leu Ala Tyr Arg Glu Gln Leu Phe Leu
                565                 570                 575

Glu Ile Ser Ser Lys Arg Lys Gln Ser Asp Ser Glu Lys Ser
            580                 585                 590

<210> SEQ ID NO 21
<211> LENGTH: 25
<212> TYPE: PRT
<213> ORGANISM: Homo sapiens

<400> SEQUENCE: 21

Gln Val Thr Val Gln Ser Ser Pro Asn Phe Thr Gln His Val Arg Glu
 1               5                  10                  15

Gln Ser Leu Val Thr Asp Gln Leu Cys
                20                  25

<210> SEQ ID NO 22
<211> LENGTH: 32
<212> TYPE: DNA
<213> ORGANISM: Artificial Sequence
```

```
<220> FEATURE:
<223> OTHER INFORMATION: Description of Artificial Sequence: Synthetic
      DNA

<400> SEQUENCE: 22
taaatagaat tcggcatcat gtggcagctg ct                                       32

<210> SEQ ID NO 23
<211> LENGTH: 575
<212> TYPE: PRT
<213> ORGANISM: Cricetulus griseus

<400> SEQUENCE: 23
```

| | | | | | | | | | | | | | | |
|---|---|---|---|---|---|---|---|---|---|---|---|---|---|---|
| Met | Arg | Ala | Trp | Thr | Gly | Ser | Trp | Arg | Trp | Ile | Met | Leu | Ile | Leu | Phe |
| 1 | | | | 5 | | | | | 10 | | | | | 15 |

| Ala | Trp | Gly | Thr | Leu | Leu | Phe | Tyr | Ile | Gly | Gly | His | Leu | Val | Arg | Asp |
|---|---|---|---|---|---|---|---|---|---|---|---|---|---|---|---|
| | | | 20 | | | | | 25 | | | | | 30 | | |

| Asn | Asp | His | Pro | Asp | His | Ser | Ser | Arg | Glu | Leu | Ser | Lys | Ile | Leu | Ala |
|---|---|---|---|---|---|---|---|---|---|---|---|---|---|---|---|
| | | 35 | | | | | 40 | | | | | 45 | | | |

| Lys | Leu | Glu | Arg | Leu | Lys | Gln | Gln | Asn | Glu | Asp | Leu | Arg | Arg | Met | Ala |
|---|---|---|---|---|---|---|---|---|---|---|---|---|---|---|---|
| | 50 | | | | | 55 | | | | | 60 | | | | |

| Glu | Ser | Leu | Arg | Ile | Pro | Glu | Gly | Pro | Ile | Asp | Gln | Gly | Thr | Ala | Thr |
|---|---|---|---|---|---|---|---|---|---|---|---|---|---|---|---|
| 65 | | | | | 70 | | | | | 75 | | | | | 80 |

| Gly | Arg | Val | Arg | Val | Leu | Glu | Glu | Gln | Leu | Val | Lys | Ala | Lys | Glu | Gln |
|---|---|---|---|---|---|---|---|---|---|---|---|---|---|---|---|
| | | | | 85 | | | | | 90 | | | | | 95 | |

| Ile | Glu | Asn | Tyr | Lys | Lys | Gln | Ala | Arg | Asn | Asp | Leu | Gly | Lys | Asp | His |
|---|---|---|---|---|---|---|---|---|---|---|---|---|---|---|---|
| | | | 100 | | | | | 105 | | | | | 110 | | |

| Glu | Ile | Leu | Arg | Arg | Arg | Ile | Glu | Asn | Gly | Ala | Lys | Glu | Leu | Trp | Phe |
|---|---|---|---|---|---|---|---|---|---|---|---|---|---|---|---|
| | | 115 | | | | | 120 | | | | | 125 | | | |

| Phe | Leu | Gln | Ser | Glu | Leu | Lys | Lys | Leu | Lys | Leu | Glu | Gly | Asn | Glu | |
|---|---|---|---|---|---|---|---|---|---|---|---|---|---|---|---|
| | 130 | | | | | 135 | | | | | 140 | | | | |

| Leu | Gln | Arg | His | Ala | Asp | Glu | Ile | Leu | Leu | Asp | Leu | Gly | His | His | Glu |
|---|---|---|---|---|---|---|---|---|---|---|---|---|---|---|---|
| 145 | | | | | 150 | | | | | 155 | | | | | 160 |

| Arg | Ser | Ile | Met | Thr | Asp | Leu | Tyr | Tyr | Leu | Ser | Gln | Thr | Asp | Gly | Ala |
|---|---|---|---|---|---|---|---|---|---|---|---|---|---|---|---|
| | | | | 165 | | | | | 170 | | | | | 175 | |

| Gly | Glu | Trp | Arg | Glu | Lys | Glu | Ala | Lys | Asp | Leu | Thr | Glu | Leu | Val | Gln |
|---|---|---|---|---|---|---|---|---|---|---|---|---|---|---|---|
| | | | 180 | | | | | 185 | | | | | 190 | | |

| Arg | Arg | Ile | Thr | Tyr | Leu | Gln | Asn | Pro | Lys | Asp | Cys | Ser | Lys | Ala | Arg |
|---|---|---|---|---|---|---|---|---|---|---|---|---|---|---|---|
| | | 195 | | | | | 200 | | | | | 205 | | | |

| Lys | Leu | Val | Cys | Asn | Ile | Asn | Lys | Gly | Cys | Gly | Tyr | Gly | Cys | Gln | Leu |
|---|---|---|---|---|---|---|---|---|---|---|---|---|---|---|---|
| | 210 | | | | | 215 | | | | | 220 | | | | |

| His | His | Val | Val | Tyr | Cys | Phe | Met | Ile | Ala | Tyr | Gly | Thr | Gln | Arg | Thr |
|---|---|---|---|---|---|---|---|---|---|---|---|---|---|---|---|
| 225 | | | | | 230 | | | | | 235 | | | | | 240 |

| Leu | Ile | Leu | Glu | Ser | Gln | Asn | Trp | Arg | Tyr | Ala | Thr | Gly | Gly | Trp | Glu |
|---|---|---|---|---|---|---|---|---|---|---|---|---|---|---|---|
| | | | | 245 | | | | | 250 | | | | | 255 | |

| Thr | Val | Phe | Arg | Pro | Val | Ser | Glu | Thr | Cys | Thr | Asp | Arg | Ser | Gly | Leu |
|---|---|---|---|---|---|---|---|---|---|---|---|---|---|---|---|
| | | | 260 | | | | | 265 | | | | | 270 | | |

| Ser | Thr | Gly | His | Trp | Ser | Gly | Glu | Val | Lys | Asp | Lys | Asn | Val | Gln | Val |
|---|---|---|---|---|---|---|---|---|---|---|---|---|---|---|---|
| | | 275 | | | | | 280 | | | | | 285 | | | |

| Val | Glu | Leu | Pro | Ile | Val | Asp | Ser | Leu | His | Pro | Arg | Pro | Pro | Tyr | Leu |
|---|---|---|---|---|---|---|---|---|---|---|---|---|---|---|---|
| | 290 | | | | | 295 | | | | | 300 | | | | |

| Pro | Leu | Ala | Val | Pro | Glu | Asp | Leu | Ala | Asp | Arg | Leu | Leu | Arg | Val | His |
|---|---|---|---|---|---|---|---|---|---|---|---|---|---|---|---|
| 305 | | | | | 310 | | | | | 315 | | | | | 320 |

| Gly | Asp | Pro | Ala | Val | Trp | Trp | Val | Ser | Gln | Phe | Val | Lys | Tyr | Leu | Ile |
|---|---|---|---|---|---|---|---|---|---|---|---|---|---|---|---|
| | | | | 325 | | | | | 330 | | | | | 335 | |

| Arg | Pro | Gln | Pro | Trp | Leu | Glu | Arg | Glu | Ile | Glu | Glu | Thr | Thr | Lys | Lys |
|---|---|---|---|---|---|---|---|---|---|---|---|---|---|---|---|

```
                    340                 345                 350
Leu Gly Phe Lys His Pro Val Ile Gly Val His Val Arg Arg Thr Asp
            355                 360                 365
Lys Val Gly Thr Glu Ala Ala Phe His Pro Ile Glu Glu Tyr Met Val
        370                 375                 380
His Val Glu Glu His Phe Gln Leu Leu Glu Arg Arg Met Lys Val Asp
385                 390                 395                 400
Lys Lys Arg Val Tyr Leu Ala Thr Asp Asp Pro Ser Leu Leu Lys Glu
                405                 410                 415
Ala Lys Thr Lys Tyr Ser Asn Tyr Glu Phe Ile Ser Asp Asn Ser Ile
            420                 425                 430
Ser Trp Ser Ala Gly Leu His Asn Arg Tyr Thr Glu Asn Ser Leu Arg
        435                 440                 445
Gly Val Ile Leu Asp Ile His Phe Leu Ser Gln Ala Asp Phe Leu Val
    450                 455                 460
Cys Thr Phe Ser Ser Gln Val Cys Arg Val Ala Tyr Glu Ile Met Gln
465                 470                 475                 480
Thr Leu His Pro Asp Ala Ser Ala Asn Phe His Ser Leu Asp Asp Ile
                485                 490                 495
Tyr Tyr Phe Gly Gly Gln Asn Ala His Asn Gln Ile Ala Val Tyr Pro
            500                 505                 510
His Gln Pro Arg Thr Lys Glu Ile Pro Met Glu Pro Gly Asp Ile
        515                 520                 525
Ile Gly Val Ala Gly Asn His Trp Asn Gly Tyr Ser Lys Gly Val Asn
    530                 535                 540
Arg Lys Leu Gly Lys Thr Gly Leu Tyr Pro Ser Tyr Lys Val Arg Glu
545                 550                 555                 560
Lys Ile Glu Thr Val Lys Tyr Pro Thr Tyr Pro Glu Ala Glu Lys
                565                 570                 575

<210> SEQ ID NO 24
<211> LENGTH: 575
<212> TYPE: PRT
<213> ORGANISM: Mus musculus

<400> SEQUENCE: 24

Met Arg Ala Trp Thr Gly Ser Trp Arg Trp Ile Met Leu Ile Leu Phe
1               5                   10                  15
Ala Trp Gly Thr Leu Leu Phe Tyr Ile Gly Gly His Leu Val Arg Asp
            20                  25                  30
Asn Asp His Pro Asp His Ser Ser Arg Glu Leu Ser Lys Ile Leu Ala
        35                  40                  45
Lys Leu Glu Arg Leu Lys Gln Gln Asn Glu Asp Leu Arg Arg Met Ala
    50                  55                  60
Glu Ser Leu Arg Ile Pro Glu Gly Pro Ile Asp Gln Gly Thr Ala Thr
65                  70                  75                  80
Gly Arg Val Arg Val Leu Glu Glu Gln Leu Val Lys Ala Lys Glu Gln
                85                  90                  95
Ile Glu Asn Tyr Lys Lys Gln Ala Arg Asn Gly Leu Gly Lys Asp His
            100                 105                 110
Glu Ile Leu Arg Arg Ile Glu Asn Gly Ala Lys Glu Leu Trp Phe
        115                 120                 125
Phe Leu Gln Ser Glu Leu Lys Lys Leu Lys His Leu Glu Gly Asn Glu
    130                 135                 140
Leu Gln Arg His Ala Asp Glu Ile Leu Leu Asp Leu Gly His His Glu
```

```
                145                 150                 155                 160
            Arg Ser Ile Met Thr Asp Leu Tyr Tyr Leu Ser Gln Thr Asp Gly Ala
                            165                 170                 175

Gly Asp Trp Arg Glu Lys Glu Ala Lys Asp Leu Thr Glu Leu Val Gln
                            180                 185                 190

Arg Arg Ile Thr Tyr Leu Gln Asn Pro Lys Asp Cys Ser Lys Ala Arg
                            195                 200                 205

Lys Leu Val Cys Asn Ile Asn Lys Gly Cys Gly Tyr Gly Cys Gln Leu
                210                 215                 220

His His Val Val Tyr Cys Phe Met Ile Ala Tyr Gly Thr Gln Arg Thr
            225                 230                 235                 240

Leu Ile Leu Glu Ser Gln Asn Trp Arg Tyr Ala Thr Gly Gly Trp Glu
                            245                 250                 255

Thr Val Phe Arg Pro Val Ser Glu Thr Cys Thr Asp Arg Ser Gly Leu
                            260                 265                 270

Ser Thr Gly His Trp Ser Gly Glu Val Asn Asp Lys Asn Ile Gln Val
                            275                 280                 285

Val Glu Leu Pro Ile Val Asp Ser Leu His Pro Arg Pro Tyr Leu
                290                 295                 300

Pro Leu Ala Val Pro Glu Asp Leu Ala Asp Arg Leu Leu Arg Val His
            305                 310                 315                 320

Gly Asp Pro Ala Val Trp Trp Val Ser Gln Phe Val Lys Tyr Leu Ile
                            325                 330                 335

Arg Pro Gln Pro Trp Leu Glu Lys Glu Ile Glu Glu Ala Thr Lys Lys
                            340                 345                 350

Leu Gly Phe Lys His Pro Val Ile Gly Val His Val Arg Arg Thr Asp
                            355                 360                 365

Lys Val Gly Thr Glu Ala Ala Phe His Pro Ile Glu Glu Tyr Met Val
                370                 375                 380

His Val Glu Glu His Phe Gln Leu Leu Ala Arg Arg Met Gln Val Asp
            385                 390                 395                 400

Lys Lys Arg Val Tyr Leu Ala Thr Asp Asp Pro Thr Leu Leu Lys Glu
                            405                 410                 415

Ala Lys Thr Lys Tyr Ser Asn Tyr Glu Phe Ile Ser Asp Asn Ser Ile
                            420                 425                 430

Ser Trp Ser Ala Gly Leu His Asn Arg Tyr Thr Glu Asn Ser Leu Arg
                            435                 440                 445

Gly Val Ile Leu Asp Ile His Phe Leu Ser Gln Ala Asp Phe Leu Val
                450                 455                 460

Cys Thr Phe Ser Ser Gln Val Cys Arg Val Ala Tyr Glu Ile Met Gln
            465                 470                 475                 480

Thr Leu His Pro Asp Ala Ser Ala Asn Phe His Ser Leu Asp Asp Ile
                            485                 490                 495

Tyr Tyr Phe Gly Gly Gln Asn Ala His Asn Gln Ile Ala Val Tyr Pro
                            500                 505                 510

His Lys Pro Arg Thr Glu Glu Ile Pro Met Glu Pro Gly Asp Ile
                            515                 520                 525

Ile Gly Val Ala Gly Asn His Trp Asp Gly Tyr Ser Lys Gly Ile Asn
                530                 535                 540

Arg Lys Leu Gly Lys Thr Gly Leu Tyr Pro Ser Tyr Lys Val Arg Glu
            545                 550                 555                 560

Lys Ile Glu Thr Val Lys Tyr Pro Thr Tyr Pro Glu Ala Glu Lys
                            565                 570                 575
```

<210> SEQ ID NO 25
<211> LENGTH: 18
<212> TYPE: PRT
<213> ORGANISM: Homo sapiens

<400> SEQUENCE: 25

Asp Glu Ser Ile Tyr Ser Asn Tyr Tyr Leu Tyr Glu Ser Ile Pro Lys
 1               5                  10                  15

Pro Cys

<210> SEQ ID NO 26
<211> LENGTH: 34
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 26
aataaaggat cctggggtca tttgtcttga gggt                                34

<210> SEQ ID NO 27
<211> LENGTH: 788
<212> TYPE: DNA
<213> ORGANISM: Homo sapiens

<400> SEQUENCE: 27

```
gaa ttc ggc atc atg tgg cag ctg ctc ctc cca act gct ctg cta ctt      48
            Met Trp Gln Leu Leu Leu Pro Thr Ala Leu Leu Leu
             1               5                  10 cta gtt tca gct ggc atg cgg act gaa gat ctc cca aag gct gtg gtg      96
Leu Val Ser Ala Gly Met Arg Thr Glu Asp Leu Pro Lys Ala Val Val
         15                  20                  25 ttc ctg gag cct caa tgg tac agg gtg ctc gag aag gac agt gtg act     144
Phe Leu Glu Pro Gln Trp Tyr Arg Val Leu Glu Lys Asp Ser Val Thr
     30                  35                  40 ctg aag tgc cag gga gcc tac tcc cct gag gac aat tcc aca cag tgg     192
Leu Lys Cys Gln Gly Ala Tyr Ser Pro Glu Asp Asn Ser Thr Gln Trp
 45                  50                  55                  60 ttt cac aat gag agc ctc atc tca agc cag gcc tcg agc tac ttc att     240
Phe His Asn Glu Ser Leu Ile Ser Ser Gln Ala Ser Ser Tyr Phe Ile
                 65                  70                  75 gac gct gcc aca gtc gac gac agt gga gag tac agg tgc cag aca aac     288
Asp Ala Ala Thr Val Asp Asp Ser Gly Glu Tyr Arg Cys Gln Thr Asn
             80                  85                  90 ctc tcc acc ctc agt gac ccg gtg cag cta gaa gtc cat atc ggc tgg     336
Leu Ser Thr Leu Ser Asp Pro Val Gln Leu Glu Val His Ile Gly Trp
         95                  100                 105 ctg ttg ctc cag gcc cct cgg tgg gtg ttc aag gag gaa gac cct att     384
Leu Leu Leu Gln Ala Pro Arg Trp Val Phe Lys Glu Glu Asp Pro Ile
     110                 115                 120 cac ctg agg tgt cac agc tgg aag aac act gct ctg cat aag gtc aca     432
His Leu Arg Cys His Ser Trp Lys Asn Thr Ala Leu His Lys Val Thr
125                 130                 135                 140 tat tta cag aat ggc aaa ggc agg aag tat ttt cat cat aat tct gac     480
Tyr Leu Gln Asn Gly Lys Gly Arg Lys Tyr Phe His His Asn Ser Asp
                145                 150                 155 ttc tac att cca aaa gcc aca ctc aaa gac agc ggc tcc tac ttc tgc     528
Phe Tyr Ile Pro Lys Ala Thr Leu Lys Asp Ser Gly Ser Tyr Phe Cys
            160                 165                 170 agg ggg ctt ttt ggg agt aaa aat gtg tct tca gag act gtg aac atc     576
Arg Gly Leu Phe Gly Ser Lys Asn Val Ser Ser Glu Thr Val Asn Ile
```

```
                175                 180                 185
acc atc act caa ggt ttg gca gtg tca acc atc tca tca ttc ttt cca      624
Thr Ile Thr Gln Gly Leu Ala Val Ser Thr Ile Ser Ser Phe Phe Pro
    190                 195                 200 cct ggg tac caa gtc tct ttc tgc ttg gtg atg gta ctc ctt ttt gca      672
Pro Gly Tyr Gln Val Ser Phe Cys Leu Val Met Val Leu Leu Phe Ala
205                 210                 215                 220 gtg gac aca gga cta tat ttc tct gtg aag aca aac att cga agc tca      720
Val Asp Thr Gly Leu Tyr Phe Ser Val Lys Thr Asn Ile Arg Ser Ser
                    225                 230                 235 aca aga gac tgg aag gac cat aaa ttt aaa tgg aga aag gac cct caa      768
Thr Arg Asp Trp Lys Asp His Lys Phe Lys Trp Arg Lys Asp Pro Gln
            240                 245                 250 gac aaa tga ccc cag gat cc       788
Asp Lys

<210> SEQ ID NO 28
<211> LENGTH: 254
<212> TYPE: PRT
<213> ORGANISM: Homo sapiens

<400> SEQUENCE: 28

Met Trp Gln Leu Leu Leu Pro Thr Ala Leu Leu Leu Leu Val Ser Ala
1               5                   10                  15

Gly Met Arg Thr Glu Asp Leu Pro Lys Ala Val Val Phe Leu Glu Pro
            20                  25                  30

Gln Trp Tyr Arg Val Leu Glu Lys Asp Ser Val Thr Leu Lys Cys Gln
        35                  40                  45

Gly Ala Tyr Ser Pro Glu Asp Asn Ser Thr Gln Trp Phe His Asn Glu
    50                  55                  60

Ser Leu Ile Ser Ser Gln Ala Ser Ser Tyr Phe Ile Asp Ala Ala Thr
65                  70                  75                  80

Val Asp Asp Ser Gly Glu Tyr Arg Cys Gln Thr Asn Leu Ser Thr Leu
                85                  90                  95

Ser Asp Pro Val Gln Leu Glu Val His Ile Gly Trp Leu Leu Leu Gln
            100                 105                 110

Ala Pro Arg Trp Val Phe Lys Glu Glu Asp Pro Ile His Leu Arg Cys
        115                 120                 125

His Ser Trp Lys Asn Thr Ala Leu His Lys Val Thr Tyr Leu Gln Asn
    130                 135                 140

Gly Lys Gly Arg Lys Tyr Phe His His Asn Ser Asp Phe Tyr Ile Pro
145                 150                 155                 160

Lys Ala Thr Leu Lys Asp Ser Gly Ser Tyr Phe Cys Arg Gly Leu Phe
                165                 170                 175

Gly Ser Lys Asn Val Ser Ser Glu Thr Val Asn Ile Thr Ile Thr Gln
            180                 185                 190

Gly Leu Ala Val Ser Thr Ile Ser Ser Phe Phe Pro Pro Gly Tyr Gln
        195                 200                 205

Val Ser Phe Cys Leu Val Met Val Leu Leu Phe Ala Val Asp Thr Gly
    210                 215                 220

Leu Tyr Phe Ser Val Lys Thr Asn Ile Arg Ser Ser Thr Arg Asp Trp
225                 230                 235                 240

Lys Asp His Lys Phe Lys Trp Arg Lys Asp Pro Gln Asp Lys
                245                 250

<210> SEQ ID NO 29
<211> LENGTH: 51
```

<212> TYPE: DNA
<213> ORGANISM: Artificial Sequence
<220> FEATURE:
<223> OTHER INFORMATION: Description of Artificial Sequence: Synthetic DNA

<400> SEQUENCE: 29

```
tgttggatcc tgtcaatgat gatgatgatg atgaccttga gtgatggtga t         51
```

<210> SEQ ID NO 30
<211> LENGTH: 620
<212> TYPE: DNA
<213> ORGANISM: Homo sapiens

<400> SEQUENCE: 30

```
gaa ttc ggc atc atg tgg cag ctg ctc ctc cca act gct ctg cta ctt        48
                Met Trp Gln Leu Leu Leu Pro Thr Ala Leu Leu Leu
                 1               5                  10 cta gtt tca gct ggc atg cgg act gaa gat ctc cca aag gct gtg gtg        96
Leu Val Ser Ala Gly Met Arg Thr Glu Asp Leu Pro Lys Ala Val Val
         15                  20                  25 ttc ctg gag cct caa tgg tac agg gtg ctc gag aag gac agt gtg act       144
Phe Leu Glu Pro Gln Trp Tyr Arg Val Leu Glu Lys Asp Ser Val Thr
 30                  35                  40 ctg aag tgc cag gga gcc tac tcc cct gag gac aat tcc aca cag tgg       192
Leu Lys Cys Gln Gly Ala Tyr Ser Pro Glu Asp Asn Ser Thr Gln Trp
 45                  50                  55                  60 ttt cac aat gag agc ctc atc tca agc cag gcc tcg agc tac ttc att       240
Phe His Asn Glu Ser Leu Ile Ser Ser Gln Ala Ser Ser Tyr Phe Ile
                 65                  70                  75 gac gct gcc aca gtc gac gac agt gga gag tac agg tgc cag aca aac       288
Asp Ala Ala Thr Val Asp Asp Ser Gly Glu Tyr Arg Cys Gln Thr Asn
             80                  85                  90 ctc tcc acc ctc agt gac ccg gtg cag cta gaa gtc cat atc ggc tgg       336
Leu Ser Thr Leu Ser Asp Pro Val Gln Leu Glu Val His Ile Gly Trp
         95                 100                 105 ctg ttg ctc cag gcc cct cgg tgg gtg ttc aag gag gaa gac cct att       384
Leu Leu Leu Gln Ala Pro Arg Trp Val Phe Lys Glu Glu Asp Pro Ile
110                 115                 120 cac ctg agg tgt cac agc tgg aag aac act gct ctg cat aag gtc aca       432
His Leu Arg Cys His Ser Trp Lys Asn Thr Ala Leu His Lys Val Thr
125                 130                 135                 140 tat tta cag aat ggc aaa ggc agg aag tat ttt cat cat aat tct gac       480
Tyr Leu Gln Asn Gly Lys Gly Arg Lys Tyr Phe His His Asn Ser Asp
                145                 150                 155 ttc tac att cca aaa gcc aca ctc aaa gac agc ggc tcc tac ttc tgc       528
Phe Tyr Ile Pro Lys Ala Thr Leu Lys Asp Ser Gly Ser Tyr Phe Cys
            160                 165                 170 agg ggg ctt ttt ggg agt aaa aat gtg tct tca gag act gtg aac atc       576
Arg Gly Leu Phe Gly Ser Lys Asn Val Ser Ser Glu Thr Val Asn Ile
        175                 180                 185 acc atc act caa ggt cat cat cat cat cat cat tga cag gat cc           620
Thr Ile Thr Gln Gly His His His His His His
    190                 195
```

<210> SEQ ID NO 31
<211> LENGTH: 199
<212> TYPE: PRT
<213> ORGANISM: Homo sapiens

<400> SEQUENCE: 31

```
Met Trp Gln Leu Leu Leu Pro Thr Ala Leu Leu Leu Leu Val Ser Ala
 1               5                  10                  15
```

Gly Met Arg Thr Glu Asp Leu Pro Lys Ala Val Val Phe Leu Glu Pro
            20                  25                  30

Gln Trp Tyr Arg Val Leu Glu Lys Asp Ser Val Thr Leu Lys Cys Gln
        35                  40                  45

Gly Ala Tyr Ser Pro Glu Asp Asn Ser Thr Gln Trp Phe His Asn Glu
    50                  55                  60

Ser Leu Ile Ser Ser Gln Ala Ser Ser Tyr Phe Ile Asp Ala Ala Thr
65                  70                  75                  80

Val Asp Asp Ser Gly Glu Tyr Arg Cys Gln Thr Asn Leu Ser Thr Leu
                85                  90                  95

Ser Asp Pro Val Gln Leu Glu Val His Ile Gly Trp Leu Leu Leu Gln
            100                 105                 110

Ala Pro Arg Trp Val Phe Lys Glu Glu Asp Pro Ile His Leu Arg Cys
        115                 120                 125

His Ser Trp Lys Asn Thr Ala Leu His Lys Val Thr Tyr Leu Gln Asn
    130                 135                 140

Gly Lys Gly Arg Lys Tyr Phe His His Asn Ser Asp Phe Tyr Ile Pro
145                 150                 155                 160

Lys Ala Thr Leu Lys Asp Ser Gly Ser Tyr Phe Cys Arg Gly Leu Phe
                165                 170                 175

Gly Ser Lys Asn Val Ser Ser Glu Thr Val Asn Ile Thr Ile Thr Gln
            180                 185                 190

Gly His His His His His His
        195

<210> SEQ ID NO 32
<211> LENGTH: 24
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 32
aggaaggtgg cgctcatcac gggc                                          24

<210> SEQ ID NO 33
<211> LENGTH: 26
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 33
taaggccaca agtcttaatt gcatcc                                        26

<210> SEQ ID NO 34
<211> LENGTH: 27
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 34 cagggggtgtt cccttgagga ggtggaa                                      27

<210> SEQ ID NO 35
<211> LENGTH: 23
<212> TYPE: DNA

```
<213> ORGANISM: Artificial Sequence
<220> FEATURE:
<223> OTHER INFORMATION: Description of Artificial Sequence: Synthetic
      DNA

<400> SEQUENCE: 35
cccctcacgc atgaagcctg gag                                           23

<210> SEQ ID NO 36
<211> LENGTH: 28
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 36
ggcaggagac caccttgcga gtgcccac                                      28

<210> SEQ ID NO 37
<211> LENGTH: 28
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 37
ggcgctggct tacccggaga ggaatggg                                      28

<210> SEQ ID NO 38
<211> LENGTH: 28
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 38
aaaaggcctc agttagtgaa ctgtatgg                                      28

<210> SEQ ID NO 39
<211> LENGTH: 29
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 39
cgcggatcct caagcgttgg ggttggtcc                                     29

<210> SEQ ID NO 40
<211> LENGTH: 45
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 40
cccaagcttg ccaccatggc tcacgctccc gctagctgcc cgagc                   45

<210> SEQ ID NO 41
<211> LENGTH: 31
<212> TYPE: DNA
<213> ORGANISM: Artificial Sequence
<220> FEATURE:
```

<223> OTHER INFORMATION: Description of Artificial Sequence: Synthetic
      DNA

<400> SEQUENCE: 41
ccggaattct gccaagtatg agccatcctg g                                        31

<210> SEQ ID NO 42
<211> LENGTH: 17
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 42
gccatccaga aggtggt                                                        17

<210> SEQ ID NO 43
<211> LENGTH: 17
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 43
gtcttgtcag ggaagat                                                        17

<210> SEQ ID NO 44
<211> LENGTH: 28
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 44
ggcaggagac caccttgcga gtgcccac                                            28

<210> SEQ ID NO 45
<211> LENGTH: 28
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 45
gggtgggctg taccttctgg aacagggc                                            28

<210> SEQ ID NO 46
<211> LENGTH: 28
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 46
ggcgctggct tacccggaga ggaatggg                                            28

<210> SEQ ID NO 47
<211> LENGTH: 30
<212> TYPE: DNA
<213> ORGANISM: Artificial Sequence
<220> FEATURE:
<223> OTHER INFORMATION: Description of Artificial Sequence: Synthetic
      DNA

```
<400> SEQUENCE: 47
ggaatgggtg tttgtctcct ccaaagatgc                                           30

<210> SEQ ID NO 48
<211> LENGTH: 1316
<212> TYPE: DNA
<213> ORGANISM: Cricetulus griseus

<400> SEQUENCE: 48
gccccgcccc ctccacctgg accgagagta gctggagaat tgtgcaccgg aagtagctct          60
tggactggtg gaaccctgcg caggtgcagc aacaatgggt gagccccagg gatccaggag         120
gatcctagtg acaggggggct ctggactggt gggcagagct atccagaagg tggtcgdaga        180
tggcgctggc ttacccggag aggaatgggt gtttgtctcc tccaaagatg cagatctgac         240
ggatgcagca caaacccaag ccctgttcca gaaggtacag cccacccatg tcatccatct         300
tgctgcaatg gtaggaggcc ttttccggaa tatcaaatac aacttggatt ctggaggaa          360 gaatgtgcac atcaatgaca acgtcctgca ctcagctttc gaggtgggca ctcgcaaggt         420
ggtctcctgc ctgtccacct gtatcttccc tgacaagacc acctatccta ttgatgaaac         480
aatgatccac aatggtccac cccacagcag caattttggg tactcgtatg ccaagaggat         540
gattgacgtg cagaacaggg cctacttcca gcagcatggc tgcaccttca ctgctgtcat         600
ccctaccaat gtctttggac ctcatgacaa cttcaacatt gaagatggcc atgtgctgcc         660
tggcctcatc cataaggtgc atctggccaa gagtaatggt tcagccttga ctgtttgggg         720
tacagggaaa ccacggaggc agttcatcta ctcactggac ctagcccggc tcttcatctg        780
ggtcctgcgg gagtacaatg aagttgagcc catcatcctc tcagtgggcg aggaagatga         840
agtctccatt aaggaggcag ctgaggctgt agtggaggcc atggacttct gtggggaagt         900
cacttttgat tcaacaaagt cagatgggca gtataagaag acagccagca atggcaagct         960
tcgggcctac ttgcctgatt ccgtttcac acccttcaag caggctgtga aggagacctg       1020
tgcctggttc accgacaact atgagcaggc ccggaagtga agcatgggac aagcgggtgc      1080
tcagctggca atgcccagtc agtaggctgc agtctcatca tttgcttgtc aagaactgag      1140
gacagtatcc agcaacctga ccacatgct ggtctctctg ccagggggct tcatgcagcc      1200
atccagtagg gcccatgttt gtccatcctc ggggggaaggc cagaccaaca ccttgtttgt    1260
ctgcttctgc cccaacctca gtgcatccat gctggtcctg ctgtcccttg tctaga        1316

<210> SEQ ID NO 49
<211> LENGTH: 23
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 49
gatcctgctg ggaccaaaat tgg                                                  23

<210> SEQ ID NO 50
<211> LENGTH: 22
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 50
```

```
cttaacatcc caagggatgc tg                                          22

<210> SEQ ID NO 51
<211> LENGTH: 1965
<212> TYPE: DNA
<213> ORGANISM: Cricetulus griseus

<400> SEQUENCE: 51 acgggggct cccggaagcg gggaccatgg cgtctctgcg cgaagcgagc ctgcggaagc     60
tgcggcgctt ttccgagatg agaggcaaac ctgtggcaac tgggaaattc tgggatgtag   120
ttgtaataac agcagctgac gaaaagcagg agcttgctta caagcaacag ttgtcggaga   180
agctgaagag aaaggaattg ccccttggag ttaactacca tgttttcact gatcctcctg   240
gaaccaaaat tggaaatgga ggatcaacac tttgttctct tcagtgcctg gaaagcctct   300
atggagacaa gtggaattcc ttcacagtcc tgttaattca ctctggtggc tacagtcaac   360
gacttcccaa tgcaagcgct ttaggaaaaa tcttcacggc tttaccactt ggtgagccca   420
tttatcagat gttggactta aaactagcca tgtacatgga tttcccctca cgcatgaagc   480
ctggagtttt ggtcacctgt gcagatgata ttgaactata cagcattggg gactctgagt   540
ccattgcatt tgagcagcct ggctttactg ccctagccca tccatctagt ctggctgtag   600
gcaccacaca tggagtattt gtattggact ctgccggttc tttgcaacat ggtgacctag   660
agtacaggca atgccaccgt ttcctccata agcccagcat tgaaaacatg caccacttta   720
atgccgtgca tagactagga agctttggtc aacaggactt gagtgggggt gacaccacct   780
gtcatccatt gcactctgag tatgtctaca cagatagcct atttttacatg gatcataaat   840
cagccaaaaa gctacttgat ttctatgaaa gtgtaggccc actgaactgt gaaatagatg   900
cctatggtga ctttctgcag gcactgggac ctggagcaac tgcagagtac accaagaaca   960
cctcacacgt cactaaagag gaatcacact tgttggacat gaggcagaaa atattccacc  1020
tcctcaaggg aacacccctg aatgttgttg tccttaataa ctccaggttt tatcacattg  1080
gaacaacgga ggagtatctg ctacatttca cttccaatgg ttcgttacag gcagagctgg  1140
gcttgcaatc catagctttc agtgtctttc caaatgtgcc tgaagactcc catgagaaac  1200
cctgtgtcat tcacagcatc ctgaattcag gatgctgtgt ggcccctggc tcagtggtag  1260
aatattccag attaggacct gaggtgtcca tctcggaaaa ctgcattatc agcggttctg  1320
tcatagaaaa agctgttctg ccccccatgtt cttcgtgtg ctctttaagt gtggagataa  1380
atggacactt agaatattca actatggtgt ttggcatgga agacaacttg aagaacagtg  1440
ttaaaaccat atcagatata aagatgcttc agttctttgg agtctgtttc ctgacttgtt  1500
tagatatttg gaaccttaaa gctatggaag aactattttc aggaagtaag acgcagctga  1560
gcctgtggac tgctcgaatt ttccctgtct gttcttctct gagtgagtcg gttgcagcat  1620
cccttgggat gttaaatgcc attcgaaacc attcgccatt cagcctgagc aacttcaagc  1680
tgctgtccat ccaggaaatg cttctctgca agatgtagg agacatgctt gcttacaggg  1740
agcaactctt tctagaaatc agttcaaaga gaaaacagtc tgattcggag aaatcttaaa  1800
tacaatggat tttgcctgga aacaggattg caaatgcagg catattctat agatctctgg  1860
gttcttcttt ctttctcccc tctctccttt cctttccctt tgatgtaatg acaaaggtaa  1920
aaatggccac ttctgatgga aaaaaaaaaa aaaaaaaaa aaaaa                    1965

<210> SEQ ID NO 52
<211> LENGTH: 27
```

```
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 52
caggggtgtt cccttgagga ggtggaa                                              27

<210> SEQ ID NO 53
<211> LENGTH: 27
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 53
cactgagcca ggggccacac agcatcc                                              27

<210> SEQ ID NO 54
<211> LENGTH: 23
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 54 ccccteacgc atgaagcctg gag                                                  23

<210> SEQ ID NO 55
<211> LENGTH: 27
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 55
tgccaccgtt tcctccataa gcccagc                                              27

<210> SEQ ID NO 56
<211> LENGTH: 28
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 56
atggctcaag ctcccgctaa gtgcccga                                             28

<210> SEQ ID NO 57
<211> LENGTH: 27
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 57
tcaagcgttt gggttggtcc tcatgag                                              27

<210> SEQ ID NO 58
<211> LENGTH: 25
<212> TYPE: DNA
<213> ORGANISM: Artificial Sequence
```

```
<220> FEATURE:
<223> OTHER INFORMATION: Description of Artificial Sequence: Synthetic
      DNA

<400> SEQUENCE: 58
tccggggatg gcgagatggg caagc                                          25

<210> SEQ ID NO 59
<211> LENGTH: 24
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 59
cttgacatgg ctctgggctc caag                                           24

<210> SEQ ID NO 60
<211> LENGTH: 25
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 60
ccacttcagt cggtcggtag tattt                                          25

<210> SEQ ID NO 61
<211> LENGTH: 24
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 61
cgctcacccg cctgaggcga catg                                           24

<210> SEQ ID NO 62
<211> LENGTH: 32
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 62
ggcaggtgct gtcggtgagg tcaccatagt gc                                  32

<210> SEQ ID NO 63
<211> LENGTH: 24
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 63
ggggccatgc caaggactat gtcg                                           24

<210> SEQ ID NO 64
<211> LENGTH: 25
<212> TYPE: DNA
<213> ORGANISM: Artificial Sequence
<220> FEATURE:
<223> OTHER INFORMATION: Description of Artificial Sequence: Synthetic
```

-continued

DNA

<400> SEQUENCE: 64
atgtggctga tgttacaaaa tgatg                                      25

<210> SEQ ID NO 65
<211> LENGTH: 1504
<212> TYPE: DNA
<213> ORGANISM: Cricetulus griseus

<400> SEQUENCE: 65

| | | | | | | | | | | | | | | | | |
|---|---|---|---|---|---|---|---|---|---|---|---|---|---|---|---|---|
| atg | gct | cac | gct | ccc | gct | agc | tgc | ccg | agc | tcc | agg | aac | tct | ggg | gac | 48 |
| Met | Ala | His | Ala | Pro | Ala | Ser | Cys | Pro | Ser | Ser | Arg | Asn | Ser | Gly | Asp | |
| 1 | | | | 5 | | | | | 10 | | | | | 15 | | |
| ggc | gat | aag | ggc | aag | ccc | agg | aag | gtg | gcg | ctc | atc | acg | ggc | atc | acc | 96 |
| Gly | Asp | Lys | Gly | Lys | Pro | Arg | Lys | Val | Ala | Leu | Ile | Thr | Gly | Ile | Thr | |
| | | | 20 | | | | | 25 | | | | | 30 | | | |
| ggc | cag | gat | ggc | tca | tac | ttg | gca | gaa | ttc | ctg | ctg | gag | aaa | gga | tac | 144 |
| Gly | Gln | Asp | Gly | Ser | Tyr | Leu | Ala | Glu | Phe | Leu | Leu | Glu | Lys | Gly | Tyr | |
| | | 35 | | | | | 40 | | | | | 45 | | | | |
| gag | gtt | cat | gga | att | gta | cgg | cga | tcc | agt | tca | ttt | aat | aca | ggt | cga | 192 |
| Glu | Val | His | Gly | Ile | Val | Arg | Arg | Ser | Ser | Ser | Phe | Asn | Thr | Gly | Arg | |
| | 50 | | | | | 55 | | | | | 60 | | | | | |
| att | gaa | cat | tta | tat | aag | aat | cca | cag | gct | cat | att | gaa | gga | aac | atg | 240 |
| Ile | Glu | His | Leu | Tyr | Lys | Asn | Pro | Gln | Ala | His | Ile | Glu | Gly | Asn | Met | |
| 65 | | | | | 70 | | | | | 75 | | | | | 80 | |
| aag | ttg | cac | tat | ggt | gac | ctc | acc | gac | agc | acc | tgc | cta | gta | aaa | atc | 288 |
| Lys | Leu | His | Tyr | Gly | Asp | Leu | Thr | Asp | Ser | Thr | Cys | Leu | Val | Lys | Ile | |
| | | | | 85 | | | | | 90 | | | | | 95 | | |
| atc | aat | gaa | gtc | aaa | cct | aca | gag | atc | tac | aat | ctt | ggt | gcc | cag | agc | 336 |
| Ile | Asn | Glu | Val | Lys | Pro | Thr | Glu | Ile | Tyr | Asn | Leu | Gly | Ala | Gln | Ser | |
| | | | 100 | | | | | 105 | | | | | 110 | | | |
| cat | gtc | aag | att | tcc | ttt | gac | tta | gca | gag | tac | act | gca | gat | gtt | gat | 384 |
| His | Val | Lys | Ile | Ser | Phe | Asp | Leu | Ala | Glu | Tyr | Thr | Ala | Asp | Val | Asp | |
| | | 115 | | | | | 120 | | | | | 125 | | | | |
| gga | gtt | ggc | acc | ttg | cgg | ctt | ctg | gat | gca | att | aag | act | tgt | ggc | ctt | 432 |
| Gly | Val | Gly | Thr | Leu | Arg | Leu | Leu | Asp | Ala | Ile | Lys | Thr | Cys | Gly | Leu | |
| | 130 | | | | | 135 | | | | | 140 | | | | | |
| ata | aat | tct | gtg | aag | ttc | tac | cag | gcc | tca | act | agt | gaa | ctg | tat | gga | 480 |
| Ile | Asn | Ser | Val | Lys | Phe | Tyr | Gln | Ala | Ser | Thr | Ser | Glu | Leu | Tyr | Gly | |
| 145 | | | | | 150 | | | | | 155 | | | | | 160 | |
| aaa | gtg | caa | gaa | ata | ccc | cag | aaa | gag | acc | acc | cct | ttc | tat | cca | agg | 528 |
| Lys | Val | Gln | Glu | Ile | Pro | Gln | Lys | Glu | Thr | Thr | Pro | Phe | Tyr | Pro | Arg | |
| | | | | 165 | | | | | 170 | | | | | 175 | | |
| tcg | ccc | tat | gga | gca | gcc | aaa | ctt | tat | gcc | tat | tgg | att | gta | gtg | aac | 576 |
| Ser | Pro | Tyr | Gly | Ala | Ala | Lys | Leu | Tyr | Ala | Tyr | Trp | Ile | Val | Val | Asn | |
| | | | 180 | | | | | 185 | | | | | 190 | | | |
| ttt | cga | gag | gct | tat | aat | ctc | ttt | gcg | gtg | aac | ggc | att | ctc | ttc | aat | 624 |
| Phe | Arg | Glu | Ala | Tyr | Asn | Leu | Phe | Ala | Val | Asn | Gly | Ile | Leu | Phe | Asn | |
| | | 195 | | | | | 200 | | | | | 205 | | | | |
| cat | gag | agt | cct | aga | aga | gga | gct | aat | ttt | gtt | act | cga | aaa | att | agc | 672 |
| His | Glu | Ser | Pro | Arg | Arg | Gly | Ala | Asn | Phe | Val | Thr | Arg | Lys | Ile | Ser | |
| | 210 | | | | | 215 | | | | | 220 | | | | | |
| cgg | tca | gta | gct | aag | att | tac | ctt | gga | caa | ctg | gaa | tgt | ttc | agt | ttg | 720 |
| Arg | Ser | Val | Ala | Lys | Ile | Tyr | Leu | Gly | Gln | Leu | Glu | Cys | Phe | Ser | Leu | |
| 225 | | | | | 230 | | | | | 235 | | | | | 240 | |
| gga | aat | ctg | gac | gcc | aaa | cga | gac | tgg | ggc | cat | gcc | aag | gac | tat | gtc | 768 |
| Gly | Asn | Leu | Asp | Ala | Lys | Arg | Asp | Trp | Gly | His | Ala | Lys | Asp | Tyr | Val | |
| | | | | 245 | | | | | 250 | | | | | 255 | | |
| gag | gct | atg | tgg | ctg | atg | tta | caa | aat | gat | gaa | cca | gag | gac | ttt | gtc | 816 |
| Glu | Ala | Met | Trp | Leu | Met | Leu | Gln | Asn | Asp | Glu | Pro | Glu | Asp | Phe | Val | |

```
                260             265             270
ata gct act ggg gaa gtt cat agt gtc cgt gaa ttt gtt gag aaa tca      864
Ile Ala Thr Gly Glu Val His Ser Val Arg Glu Phe Val Glu Lys Ser
        275                 280                 285 ttc atg cac att gga aag acc att gtg tgg gaa gga aag aat gaa aat      912
Phe Met His Ile Gly Lys Thr Ile Val Trp Glu Gly Lys Asn Glu Asn
    290                 295                 300 gaa gtg ggc aga tgt aaa gag acc ggc aaa att cat gtg act gtg gat      960
Glu Val Gly Arg Cys Lys Glu Thr Gly Lys Ile His Val Thr Val Asp
305                 310                 315                 320 ctg aaa tac tac cga cca act gaa gtg gac ttc ctg cag gga gac tgc     1008
Leu Lys Tyr Tyr Arg Pro Thr Glu Val Asp Phe Leu Gln Gly Asp Cys
                325                 330                 335 tcc aag gcg cag cag aaa ctg aac tgg aag ccc cgc gtt gcc ttt gac     1056
Ser Lys Ala Gln Gln Lys Leu Asn Trp Lys Pro Arg Val Ala Phe Asp
            340                 345                 350 gag ctg gtg agg gag atg gtg caa gcc gat gtg gag ctc atg aga acc     1104
Glu Leu Val Arg Glu Met Val Gln Ala Asp Val Glu Leu Met Arg Thr
        355                 360                 365 aac ccc aac gcc tga gcacctctac aaaaaaattc gcgagacatg gactatggtg     1159
Asn Pro Asn Ala
    370 cagagccagc caaccagagt ccagccactc ctgagaccat cgaccataaa ccctcgactg     1219 cctgtgtcgt ccccacagct aagagctggg ccacaggttt gtgggcacca ggacggggac     1279 actccagagc taaggccact tcgcttttgt caaaggctcc tctcaatgat tttgggaaat     1339 caagaagttt aaaatcacat actcatttta cttgaaatta tgtcactaga caacttaaat     1399 ttttgagtct tgagattgtt tttctctttt cttattaaat gatctttcta tgacccagca     1459 aaaaaaaaaa aaaaaggga tataaaaaaa aaaaaaaaaa aaaaa                      1504

<210> SEQ ID NO 66
<211> LENGTH: 25
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 66
atgaagttgc actatggtga cctca                                           25

<210> SEQ ID NO 67
<211> LENGTH: 59
<212> TYPE: DNA
<213> ORGANISM: Cricetulus griseus

<400> SEQUENCE: 67
ccgacagcac ctgcctagta aaatcatca atgaagtcaa acctacagag atctacaat       59

<210> SEQ ID NO 68
<211> LENGTH: 25
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 68
gacttagcag agtacactgc agatg                                           25

<210> SEQ ID NO 69
```

```
<211> LENGTH: 25
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 69
accttggata gaaagggtg gtctc                                            25

<210> SEQ ID NO 70
<211> LENGTH: 125
<212> TYPE: DNA
<213> ORGANISM: Cricetulus griseus

<400> SEQUENCE: 70
ttgatggagt tggcaccttg cggcttctgg atgcaattaa gacttgtggc cttataaatt     60
ctgtgaagtt ctaccaggcc tcaactagtg aactgtatgg aaaagtgcaa gaataccccc   120
agaaa                                                                125

<210> SEQ ID NO 71
<211> LENGTH: 372
<212> TYPE: PRT
<213> ORGANISM: Cricetulus griseus

<400> SEQUENCE: 71
```

| | | | | | | | | | | | | | | | |
|---|---|---|---|---|---|---|---|---|---|---|---|---|---|---|---|
| Met | Ala | His | Ala | Pro | Ala | Ser | Cys | Pro | Ser | Ser | Arg | Asn | Ser | Gly | Asp |
| 1 | | | | 5 | | | | | 10 | | | | | 15 | |
| Gly | Asp | Lys | Gly | Lys | Pro | Arg | Lys | Val | Ala | Leu | Ile | Thr | Gly | Ile | Thr |
| | | | 20 | | | | | 25 | | | | | 30 | | |
| Gly | Gln | Asp | Gly | Ser | Tyr | Leu | Ala | Glu | Phe | Leu | Leu | Glu | Lys | Gly | Tyr |
| | | 35 | | | | | 40 | | | | | 45 | | | |
| Glu | Val | His | Gly | Ile | Val | Arg | Arg | Ser | Ser | Ser | Phe | Asn | Thr | Gly | Arg |
| | 50 | | | | | 55 | | | | | 60 | | | | |
| Ile | Glu | His | Leu | Tyr | Lys | Asn | Pro | Gln | Ala | His | Ile | Glu | Gly | Asn | Met |
| 65 | | | | | 70 | | | | | 75 | | | | | 80 |
| Lys | Leu | His | Tyr | Gly | Asp | Leu | Thr | Asp | Ser | Thr | Cys | Leu | Val | Lys | Ile |
| | | | | 85 | | | | | 90 | | | | | 95 | |
| Ile | Asn | Glu | Val | Lys | Pro | Thr | Glu | Ile | Tyr | Asn | Leu | Gly | Ala | Gln | Ser |
| | | | 100 | | | | | 105 | | | | | 110 | | |
| His | Val | Lys | Ile | Ser | Phe | Asp | Leu | Ala | Glu | Tyr | Thr | Ala | Asp | Val | Asp |
| | | 115 | | | | | 120 | | | | | 125 | | | |
| Gly | Val | Gly | Thr | Leu | Arg | Leu | Leu | Asp | Ala | Ile | Lys | Thr | Cys | Gly | Leu |
| | 130 | | | | | 135 | | | | | 140 | | | | |
| Ile | Asn | Ser | Val | Lys | Phe | Tyr | Gln | Ala | Ser | Thr | Ser | Glu | Leu | Tyr | Gly |
| 145 | | | | | 150 | | | | | 155 | | | | | 160 |
| Lys | Val | Gln | Glu | Ile | Pro | Gln | Lys | Glu | Thr | Thr | Pro | Phe | Tyr | Pro | Arg |
| | | | | 165 | | | | | 170 | | | | | 175 | |
| Ser | Pro | Tyr | Gly | Ala | Ala | Lys | Leu | Tyr | Ala | Tyr | Trp | Ile | Val | Val | Asn |
| | | | 180 | | | | | 185 | | | | | 190 | | |
| Phe | Arg | Glu | Ala | Tyr | Asn | Leu | Phe | Ala | Val | Asn | Gly | Ile | Leu | Phe | Asn |
| | | 195 | | | | | 200 | | | | | 205 | | | |
| His | Glu | Ser | Pro | Arg | Arg | Gly | Ala | Asn | Phe | Val | Thr | Arg | Lys | Ile | Ser |
| | 210 | | | | | 215 | | | | | 220 | | | | |
| Arg | Ser | Val | Ala | Lys | Ile | Tyr | Leu | Gly | Gln | Leu | Glu | Cys | Phe | Ser | Leu |
| 225 | | | | | 230 | | | | | 235 | | | | | 240 |
| Gly | Asn | Leu | Asp | Ala | Lys | Arg | Asp | Trp | Gly | His | Ala | Lys | Asp | Tyr | Val |
| | | | | 245 | | | | | 250 | | | | | 255 | |

```
Glu Ala Met Trp Leu Met Leu Gln Asn Asp Glu Pro Glu Asp Phe Val
            260                 265                 270

Ile Ala Thr Gly Glu Val His Ser Val Arg Glu Phe Val Glu Lys Ser
        275                 280                 285

Phe Met His Ile Gly Lys Thr Ile Val Trp Glu Gly Lys Asn Glu Asn
    290                 295                 300

Glu Val Gly Arg Cys Lys Glu Thr Gly Lys Ile His Val Thr Val Asp
305                 310                 315                 320

Leu Lys Tyr Tyr Arg Pro Thr Glu Val Asp Phe Leu Gln Gly Asp Cys
                325                 330                 335

Ser Lys Ala Gln Gln Lys Leu Asn Trp Lys Pro Arg Val Ala Phe Asp
            340                 345                 350

Glu Leu Val Arg Glu Met Val Gln Ala Asp Val Glu Leu Met Arg Thr
        355                 360                 365

Asn Pro Asn Ala
    370

<210> SEQ ID NO 72
<211> LENGTH: 420
<212> TYPE: DNA
<213> ORGANISM: Mus musculus

<400> SEQUENCE: 72 atg gaa tgg atc tgg atc ttt ctc ttc ttc ctc tca gga act aca ggt     48
Met Glu Trp Ile Trp Ile Phe Leu Phe Phe Leu Ser Gly Thr Thr Gly
 1               5                  10                  15 gtc tac tcc cag gtt cag ctg cag cag tct gga gct gag gtg gcg agg     96
Val Tyr Ser Gln Val Gln Leu Gln Gln Ser Gly Ala Glu Val Ala Arg
             20                  25                  30 ccc ggg gct tca gtg aaa ctg tcc tgc aag gct tct ggc tac acc ttc    144
Pro Gly Ala Ser Val Lys Leu Ser Cys Lys Ala Ser Gly Tyr Thr Phe
         35                  40                  45 act gac tac tat cta aac tgg gtg aag cag agg tct gga cag ggc ctt    192
Thr Asp Tyr Tyr Leu Asn Trp Val Lys Gln Arg Ser Gly Gln Gly Leu
     50                  55                  60 gag tgg att gga gag att gat cct gga agt gat agt ata tat tat aat    240
Glu Trp Ile Gly Glu Ile Asp Pro Gly Ser Asp Ser Ile Tyr Tyr Asn
 65                  70                  75                  80 gaa aac ttg gag ggc agg gcc aca ctg act gca gac aaa tcc tcc agc    288
Glu Asn Leu Glu Gly Arg Ala Thr Leu Thr Ala Asp Lys Ser Ser Ser
                 85                  90                  95 aca gcc tac atg cag ctc aac agc ctg aca tct gag gac tct gca gtc    336
Thr Ala Tyr Met Gln Leu Asn Ser Leu Thr Ser Glu Asp Ser Ala Val
            100                 105                 110 tat ttc tgt gca aga tat ggg tat tct aga tac gac gta agg ttt gtc    384
Tyr Phe Cys Ala Arg Tyr Gly Tyr Ser Arg Tyr Asp Val Arg Phe Val
        115                 120                 125 tac tgg ggc caa ggg act ctg gtc act gtc tct aca                    420
Tyr Trp Gly Gln Gly Thr Leu Val Thr Val Ser Thr
    130                 135                 140

<210> SEQ ID NO 73
<211> LENGTH: 140
<212> TYPE: PRT
<213> ORGANISM: Mus musculus

<400> SEQUENCE: 73

Met Glu Trp Ile Trp Ile Phe Leu Phe Phe Leu Ser Gly Thr Thr Gly
 1               5                  10                  15
```

```
Val Tyr Ser Gln Val Gln Leu Gln Gln Ser Gly Ala Glu Val Ala Arg
            20                  25                  30

Pro Gly Ala Ser Val Lys Leu Ser Cys Lys Ala Ser Gly Tyr Thr Phe
        35                  40                  45

Thr Asp Tyr Tyr Leu Asn Trp Val Lys Gln Arg Ser Gly Gln Gly Leu
    50                  55                  60

Glu Trp Ile Gly Glu Ile Asp Pro Gly Ser Asp Ser Ile Tyr Tyr Asn
65                  70                  75                  80

Glu Asn Leu Glu Gly Arg Ala Thr Leu Thr Ala Asp Lys Ser Ser Ser
                85                  90                  95

Thr Ala Tyr Met Gln Leu Asn Ser Leu Thr Ser Glu Asp Ser Ala Val
            100                 105                 110

Tyr Phe Cys Ala Arg Tyr Gly Tyr Ser Arg Tyr Asp Val Arg Phe Val
        115                 120                 125

Tyr Trp Gly Gln Gly Thr Leu Val Thr Val Ser Thr
    130                 135                 140

<210> SEQ ID NO 74
<211> LENGTH: 393
<212> TYPE: DNA
<213> ORGANISM: Mus musculus

<400> SEQUENCE: 74 atg aag ttg cct gtt agg ctg ttg gtg ctg atg ttc tgg att cct gct      48
Met Lys Leu Pro Val Arg Leu Leu Val Leu Met Phe Trp Ile Pro Ala
1               5                   10                  15 tcc agg agt gat gtt ttg atg acc caa act cca ctc tcc ctg cct gtc      96
Ser Arg Ser Asp Val Leu Met Thr Gln Thr Pro Leu Ser Leu Pro Val
            20                  25                  30 agt ctt gga gat caa gcc tcc atc tct tgc aga tct agt cag agt ctt     144
Ser Leu Gly Asp Gln Ala Ser Ile Ser Cys Arg Ser Ser Gln Ser Leu
        35                  40                  45 gta cat agt aat gga aga acc tat tta gaa tgg tac ctg cag aaa cct     192
Val His Ser Asn Gly Arg Thr Tyr Leu Glu Trp Tyr Leu Gln Lys Pro
    50                  55                  60 ggc cag tca cca aag gtc ctg atc tac aaa gtt tcc aac cga att tct     240
Gly Gln Ser Pro Lys Val Leu Ile Tyr Lys Val Ser Asn Arg Ile Ser
65                  70                  75                  80 ggg gtc cca gac agg ttc agt ggc agt gga tca ggg aca gat ttc aca     288
Gly Val Pro Asp Arg Phe Ser Gly Ser Gly Ser Gly Thr Asp Phe Thr
                85                  90                  95 ctc aaa atc agc aga gtg gag gct gag gat ctg gga gtt tat ttc tgc     336
Leu Lys Ile Ser Arg Val Glu Ala Glu Asp Leu Gly Val Tyr Phe Cys
            100                 105                 110 ttt cag ggt tca cat gtt ccg tac acg ttc gga ggg ggg acc aag ctg     384
Phe Gln Gly Ser His Val Pro Tyr Thr Phe Gly Gly Gly Thr Lys Leu
        115                 120                 125 gaa ata aaa                                                          393
Glu Ile Lys
    130

<210> SEQ ID NO 75
<211> LENGTH: 131
<212> TYPE: PRT
<213> ORGANISM: Mus musculus

<400> SEQUENCE: 75

Met Lys Leu Pro Val Arg Leu Leu Val Leu Met Phe Trp Ile Pro Ala
1               5                   10                  15

Ser Arg Ser Asp Val Leu Met Thr Gln Thr Pro Leu Ser Leu Pro Val
```

```
                    20                  25                  30
Ser Leu Gly Asp Gln Ala Ser Ile Ser Cys Arg Ser Gln Ser Leu
            35                  40                  45

Val His Ser Asn Gly Arg Thr Tyr Leu Glu Trp Tyr Leu Gln Lys Pro
        50                  55                  60

Gly Gln Ser Pro Lys Val Leu Ile Tyr Lys Val Ser Asn Arg Ile Ser
65                  70                  75                  80

Gly Val Pro Asp Arg Phe Ser Gly Ser Gly Ser Gly Thr Asp Phe Thr
                85                  90                  95

Leu Lys Ile Ser Arg Val Glu Ala Glu Asp Leu Gly Val Tyr Phe Cys
            100                 105                 110

Phe Gln Gly Ser His Val Pro Tyr Thr Phe Gly Gly Gly Thr Lys Leu
        115                 120                 125

Glu Ile Lys
    130

<210> SEQ ID NO 76
<211> LENGTH: 5
<212> TYPE: PRT
<213> ORGANISM: Mus musculus

<400> SEQUENCE: 76

Asp Tyr Tyr Leu Asn
1               5

<210> SEQ ID NO 77
<211> LENGTH: 17
<212> TYPE: PRT
<213> ORGANISM: Mus musculus

<400> SEQUENCE: 77

Glu Ile Asp Pro Gly Ser Asp Ser Ile Tyr Tyr Asn Glu Asn Leu Glu
1               5                   10                  15

Gly

<210> SEQ ID NO 78
<211> LENGTH: 12
<212> TYPE: PRT
<213> ORGANISM: Mus musculus

<400> SEQUENCE: 78

Tyr Gly Tyr Ser Arg Tyr Asp Val Arg Phe Val Tyr
1               5                   10

<210> SEQ ID NO 79
<211> LENGTH: 16
<212> TYPE: PRT
<213> ORGANISM: Mus musculus

<400> SEQUENCE: 79

Arg Ser Ser Gln Ser Leu Val His Ser Asn Gly Arg Thr Tyr Leu Glu
1               5                   10                  15

<210> SEQ ID NO 80
<211> LENGTH: 7
<212> TYPE: PRT
<213> ORGANISM: Mus musculus

<400> SEQUENCE: 80

Lys Val Ser Asn Arg Ile Ser
1               5
```

```
<210> SEQ ID NO 81
<211> LENGTH: 9
<212> TYPE: PRT
<213> ORGANISM: Mus musculus

<400> SEQUENCE: 81

Phe Gln Gly Ser His Val Pro Tyr Thr
 1               5

<210> SEQ ID NO 82
<211> LENGTH: 22
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 82
ctgaattcgc ggccgctagt cc                                              22

<210> SEQ ID NO 83
<211> LENGTH: 39
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 83
atgggccctt ggtggaggct gtagagacag tgaccagag                            39

<210> SEQ ID NO 84
<211> LENGTH: 22
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 84
ctgaattcgc ggccgctgct gt                                              22

<210> SEQ ID NO 85
<211> LENGTH: 28
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 85
atcgtacgtt ttatttccag cttggtcc                                        28

<210> SEQ ID NO 86
<211> LENGTH: 57
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 86
ttgttggtac cgaattcttt cagggccccg gagccccgag agcccaaatc ttgtgac        57

<210> SEQ ID NO 87
<211> LENGTH: 31
<212> TYPE: DNA
```

```
<213> ORGANISM: Artificial Sequence
<220> FEATURE:
<223> OTHER INFORMATION: Description of Artificial Sequence: synthetic
      DNA

<400> SEQUENCE: 87
gcgaattcca ccatgggcag cccccgctcc g                                    31

<210> SEQ ID NO 88
<211> LENGTH: 32
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 88
cgggatcccT atcggggctc cggggcccaa gt                                   32

<210> SEQ ID NO 89
<211> LENGTH: 1341
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 89
```

| | | | | | | | | | | | | | | | | |
|---|---|---|---|---|---|---|---|---|---|---|---|---|---|---|---|---|
| atg | ggc | agc | ccc | cgc | tcc | gcg | ctg | agc | tgc | ctg | ctg | ttg | cac | ttg | ctg | 48 |
| Met | Gly | Ser | Pro | Arg | Ser | Ala | Leu | Ser | Cys | Leu | Leu | Leu | His | Leu | Leu | |
| 1 | | | | 5 | | | | | 10 | | | | | 15 | | |
| gtt | ctc | tgc | ctc | caa | gcc | cag | gta | act | gtt | cag | tcc | tca | cct | aat | ttt | 96 |
| Val | Leu | Cys | Leu | Gln | Ala | Gln | Val | Thr | Val | Gln | Ser | Ser | Pro | Asn | Phe | |
| | | | | 20 | | | | | 25 | | | | | 30 | | |
| aca | cag | cat | gtg | agg | gag | cag | agc | ctg | gtg | acg | gat | cag | ctc | agc | cgc | 144 |
| Thr | Gln | His | Val | Arg | Glu | Gln | Ser | Leu | Val | Thr | Asp | Gln | Leu | Ser | Arg | |
| | | 35 | | | | | 40 | | | | | 45 | | | | |
| cgc | ctc | atc | cgg | acc | tac | cag | ctc | tac | agc | cgc | acc | agc | ggg | aag | cac | 192 |
| Arg | Leu | Ile | Arg | Thr | Tyr | Gln | Leu | Tyr | Ser | Arg | Thr | Ser | Gly | Lys | His | |
| | 50 | | | | | 55 | | | | | 60 | | | | | |
| gtg | cag | gtc | ctg | gcc | aac | aag | cgc | atc | aac | gcc | atg | gca | gaa | gac | gga | 240 |
| Val | Gln | Val | Leu | Ala | Asn | Lys | Arg | Ile | Asn | Ala | Met | Ala | Glu | Asp | Gly | |
| 65 | | | | | 70 | | | | | 75 | | | | | 80 | |
| gac | ccc | ttc | gcg | aag | ctc | att | gtg | gag | acc | gat | act | ttt | gga | agc | aga | 288 |
| Asp | Pro | Phe | Ala | Lys | Leu | Ile | Val | Glu | Thr | Asp | Thr | Phe | Gly | Ser | Arg | |
| | | | | 85 | | | | | 90 | | | | | 95 | | |
| gtc | cga | gtt | cgc | ggc | gca | gag | aca | ggt | ctc | tac | atc | tgc | atg | aac | aag | 336 |
| Val | Arg | Val | Arg | Gly | Ala | Glu | Thr | Gly | Leu | Tyr | Ile | Cys | Met | Asn | Lys | |
| | | | | 100 | | | | | 105 | | | | | 110 | | |
| aag | ggg | aag | cta | att | gcc | aag | agc | aac | ggc | aaa | ggc | aag | gac | tgc | gta | 384 |
| Lys | Gly | Lys | Leu | Ile | Ala | Lys | Ser | Asn | Gly | Lys | Gly | Lys | Asp | Cys | Val | |
| | | 115 | | | | | 120 | | | | | 125 | | | | |
| ttc | aca | gag | atc | gtg | ctg | gag | aac | aac | tac | acg | gcg | ctg | cag | aac | gcc | 432 |
| Phe | Thr | Glu | Ile | Val | Leu | Glu | Asn | Asn | Tyr | Thr | Ala | Leu | Gln | Asn | Ala | |
| | 130 | | | | | 135 | | | | | 140 | | | | | |
| aag | tac | gag | ggc | tgg | tac | atg | gcc | ttt | acc | cgc | aag | ggc | cgg | ccc | cgc | 480 |
| Lys | Tyr | Glu | Gly | Trp | Tyr | Met | Ala | Phe | Thr | Arg | Lys | Gly | Arg | Pro | Arg | |
| 145 | | | | | 150 | | | | | 155 | | | | | 160 | |
| aag | ggc | tcc | aag | acg | cgc | cag | cat | cag | cgc | gag | gtg | cac | ttc | atg | aag | 528 |
| Lys | Gly | Ser | Lys | Thr | Arg | Gln | His | Gln | Arg | Glu | Val | His | Phe | Met | Lys | |
| | | | | 165 | | | | | 170 | | | | | 175 | | |
| cgc | ctg | ccg | cgg | ggc | cac | cac | acc | acc | gag | cag | agc | ctg | cgc | ttc | gag | 576 |
| Arg | Leu | Pro | Arg | Gly | His | His | Thr | Thr | Glu | Gln | Ser | Leu | Arg | Phe | Glu | |
| | | | | 180 | | | | | 185 | | | | | 190 | | |

```
ttc ctc aac tac ccg ccc ttc acg cgc agc ctg cgc ggc agc cag agg      624
Phe Leu Asn Tyr Pro Pro Phe Thr Arg Ser Leu Arg Gly Ser Gln Arg
            195                 200                 205 act tgg gcc ccg gag ccc cga gag ccc aaa tct tgt gac aaa act cac      672
Thr Trp Ala Pro Glu Pro Arg Glu Pro Lys Ser Cys Asp Lys Thr His
210                 215                 220 aca tgc cca ccg tgc cca gca cct gaa ctc ctg ggg gga ccg tca gtc      720
Thr Cys Pro Pro Cys Pro Ala Pro Glu Leu Leu Gly Gly Pro Ser Val
225                 230                 235                 240 ttc ctc ttc ccc cca aaa ccc aag gac acc ctc atg atc tcc cgg acc      768
Phe Leu Phe Pro Pro Lys Pro Lys Asp Thr Leu Met Ile Ser Arg Thr
            245                 250                 255 cct gag gtc aca tgc gtg gtg gtg gac gtg agc cac gaa gac cct gag      816
Pro Glu Val Thr Cys Val Val Val Asp Val Ser His Glu Asp Pro Glu
        260                 265                 270 gtc aag ttc aac tgg tac gtg gac ggc gtg gag gtg cat aat gcc aag      864
Val Lys Phe Asn Trp Tyr Val Asp Gly Val Glu Val His Asn Ala Lys
    275                 280                 285 aca aag ccg cgg gag gag cag tac aac agc acg tac cgt gtg gtc agc      912
Thr Lys Pro Arg Glu Glu Gln Tyr Asn Ser Thr Tyr Arg Val Val Ser
290                 295                 300 gtc ctc acc gtc ctg cac cag gac tgg ctg aat ggc aag gag tac aag      960
Val Leu Thr Val Leu His Gln Asp Trp Leu Asn Gly Lys Glu Tyr Lys
305                 310                 315                 320 tgc aag gtc tcc aac aaa gcc ctc cca gcc ccc atc gag aaa acc atc     1008
Cys Lys Val Ser Asn Lys Ala Leu Pro Ala Pro Ile Glu Lys Thr Ile
            325                 330                 335 tcc aaa gcc aaa ggg cag ccc cga gaa cca cag gtg tac acc ctg ccc     1056
Ser Lys Ala Lys Gly Gln Pro Arg Glu Pro Gln Val Tyr Thr Leu Pro
        340                 345                 350 cca tcc cgg gat gag ctg acc aag aac cag gtc agc ctg acc tgc ctg     1104
Pro Ser Arg Asp Glu Leu Thr Lys Asn Gln Val Ser Leu Thr Cys Leu
    355                 360                 365 gtc aaa ggc ttc tat ccc agc gac atc gcc gtg gag tgg gag agc aat     1152
Val Lys Gly Phe Tyr Pro Ser Asp Ile Ala Val Glu Trp Glu Ser Asn
370                 375                 380 ggg cag ccg gag aac aac tac aag acc acg cct ccc gtg ctg gac tcc     1200
Gly Gln Pro Glu Asn Asn Tyr Lys Thr Thr Pro Pro Val Leu Asp Ser
385                 390                 395                 400 gac ggc tcc ttc ttc ctc tac agc aag ctc acc gtg gac aag agc agg     1248
Asp Gly Ser Phe Phe Leu Tyr Ser Lys Leu Thr Val Asp Lys Ser Arg
            405                 410                 415 tgg cag cag ggg aac gtc ttc tca tgc tcc gtg atg cat gag gct ctg     1296
Trp Gln Gln Gly Asn Val Phe Ser Cys Ser Val Met His Glu Ala Leu
        420                 425                 430 cac aac cac tac acg cag aag agc ctc tcc ctg tct ccg ggt aaa         1341
His Asn His Tyr Thr Gln Lys Ser Leu Ser Leu Ser Pro Gly Lys
    435                 440                 445

<210> SEQ ID NO 90
<211> LENGTH: 447
<212> TYPE: PRT
<213> ORGANISM: homo sapiens

<400> SEQUENCE: 90

Met Gly Ser Pro Arg Ser Ala Leu Ser Cys Leu Leu Leu His Leu Leu
 1               5                  10                  15

Val Leu Cys Leu Gln Ala Gln Val Thr Val Gln Ser Ser Pro Asn Phe
            20                  25                  30

Thr Gln His Val Arg Glu Gln Ser Leu Val Thr Asp Gln Leu Ser Arg
```

```
                35                  40                  45
Arg Leu Ile Arg Thr Tyr Gln Leu Tyr Ser Arg Thr Ser Gly Lys His
 50                  55                  60

Val Gln Val Leu Ala Asn Lys Arg Ile Asn Ala Met Ala Glu Asp Gly
 65                  70                  75                  80

Asp Pro Phe Ala Lys Leu Ile Val Glu Thr Asp Thr Phe Gly Ser Arg
                 85                  90                  95

Val Arg Val Arg Gly Ala Glu Thr Gly Leu Tyr Ile Cys Met Asn Lys
                100                 105                 110

Lys Gly Lys Leu Ile Ala Lys Ser Asn Gly Lys Gly Lys Asp Cys Val
                115                 120                 125

Phe Thr Glu Ile Val Leu Glu Asn Asn Tyr Thr Ala Leu Gln Asn Ala
130                 135                 140

Lys Tyr Glu Gly Trp Tyr Met Ala Phe Thr Arg Lys Gly Arg Pro Arg
145                 150                 155                 160

Lys Gly Ser Lys Thr Arg Gln His Gln Arg Glu Val His Phe Met Lys
                165                 170                 175

Arg Leu Pro Arg Gly His His Thr Thr Glu Gln Ser Leu Arg Phe Glu
                180                 185                 190

Phe Leu Asn Tyr Pro Pro Phe Thr Arg Ser Leu Arg Gly Ser Gln Arg
                195                 200                 205

Thr Trp Ala Pro Glu Pro Arg Glu Pro Lys Ser Cys Asp Lys Thr His
210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
                260                 265                 270

Val Lys Phe Asn Trp Tyr Val Asp Gly Val Gln Val His Asn Ala Lys
                275                 280                 285

Thr Lys Pro Arg Glu Glu Gln Tyr Asn Ser Thr Tyr Arg Val Val Ser
290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
                340                 345                 350

Pro Ser Arg Asp Glu Leu Thr Lys Asn Gln Val Ser Leu Thr Cys Leu
                355                 360                 365

Val Lys Gly Phe Tyr Pro Ser Asp Ile Ala Val Glu Trp Glu Ser Asn
                370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
                420                 425                 430

His Asn His Tyr Thr Gln Lys Ser Leu Ser Leu Ser Pro Gly Lys
                435                 440                 445

<210> SEQ ID NO 91
<211> LENGTH: 1245
```

```
<212> TYPE: DNA
<213> ORGANISM: Cricetulus griseus

<400> SEQUENCE: 91
gaacttcacc caagccatgt gacaattgaa ggctgtaccc ccagaccct a acatcttgga    60
gccctgtaga ccagggagtg cttctggccg tggggtgacc tagctcttct accaccatga   120
acagggcccc tctgaagcgg tccaggatcc tgcgcatggc gctgactgga ggctccactg   180
cctctgagga ggcagatgaa gacagcagga acaagccgtt tctgctgcgg gcgctgcaga   240
tcgcgctggt cgtctctctc tactgggtca cctccatctc catggtattc ctcaacaagt   300
acctgctgga cagcccctcc ctgcagctgg atacccctat cttcgtcact ttctaccaat   360
gcctggtgac ctctctgctg tgcaagggcc tcagcactct ggccacctgc tgccctggca   420
ccgttgactt ccccacccctg aacctggacc ttaaggtggc ccgcagcgtg ctgccactgt   480
cggtagtctt cattggcatg ataagtttca ataacctctg cctcaagtac gtaggggtgg   540
ccttctacaa cgtggggcgc tcgctcacca ccgtgttcaa tgtgcttctg tcctacctgc   600
tgctcaaaca gaccacttcc ttctatgccc tgctcacatg tggcatcatc attggtggtt   660
tctggctggg tatagaccaa gagggagctg agggcaccct gtccctcata ggcaccatct   720
tcggggtgct ggccagcctc tgcgtctccc tcaatgccat ctataccaag aaggtgctcc   780
cagcagtgga caacagcatc tggcgcctaa ccttctataa caatgtcaat gcctgtgtgc   840
tcttcttgcc cctgatggtt ctgctgggtg agctccgtgc cctccttgac tttgctcatc   900
tgtacagtgc ccacttctgg ctcatgatga cgctgggtgg cctcttcggc tttgccattg   960
gctatgtgac aggactgcag atcaaattca ccagtcccct gacccacaat gtatcaggca  1020
cagccaaggc ctgtgcgcag acagtgctgg ccgtgctcta ctatgaagag actaagagct  1080
tcctgtggtg gacaagcaac ctgatggtgc tgggtggctc ctcagcctat acctgggtca  1140
ggggctggga gatgcagaag acccaagagg accccagctc caagagggt gagaagagtg  1200
ctattggggt gtgagcttct tcagggacct gggactgaac ccaag               1245

<210> SEQ ID NO 92
<211> LENGTH: 365
<212> TYPE: PRT
<213> ORGANISM: Cricetulus griseus

<400> SEQUENCE: 92

Met Asn Arg Ala Pro Leu Lys Arg Ser Arg Ile Leu Arg Met Ala Leu
  1               5                  10                  15

Thr Gly Gly Ser Thr Ala Ser Glu Glu Ala Asp Glu Asp Ser Arg Asn
                 20                  25                  30

Lys Pro Phe Leu Leu Arg Ala Leu Gln Ile Ala Leu Val Val Ser Leu
             35                  40                  45

Tyr Trp Val Thr Ser Ile Ser Met Val Phe Leu Asn Lys Tyr Leu Leu
         50                  55                  60

Asp Ser Pro Ser Leu Gln Leu Asp Thr Pro Ile Phe Val Thr Phe Tyr
 65                  70                  75                  80

Gln Cys Leu Val Thr Ser Leu Leu Cys Lys Gly Leu Ser Thr Leu Ala
                 85                  90                  95

Thr Cys Cys Pro Gly Thr Val Asp Phe Pro Thr Leu Asn Leu Asp Leu
                100                 105                 110

Lys Val Ala Arg Ser Val Leu Pro Leu Ser Val Val Phe Ile Gly Met
            115                 120                 125

Ile Ser Phe Asn Asn Leu Cys Leu Lys Tyr Val Gly Val Ala Phe Tyr
```

```
                130               135              140
Asn Val Gly Arg Ser Leu Thr Thr Val Phe Asn Val Leu Leu Ser Tyr
145                 150                 155                 160

Leu Leu Leu Lys Gln Thr Thr Ser Phe Tyr Ala Leu Leu Thr Cys Gly
                165                 170                 175

Ile Ile Ile Gly Gly Phe Trp Leu Gly Ile Asp Gln Glu Gly Ala Glu
                180                 185                 190

Gly Thr Leu Ser Leu Ile Gly Thr Ile Phe Gly Val Leu Ala Ser Leu
                195                 200                 205

Cys Val Ser Leu Asn Ala Ile Tyr Thr Lys Lys Val Leu Pro Ala Val
        210                 215                 220

Asp Asn Ser Ile Trp Arg Leu Thr Phe Tyr Asn Asn Val Asn Ala Cys
225                 230                 235                 240

Val Leu Phe Leu Pro Leu Met Val Leu Leu Gly Glu Leu Arg Ala Leu
                245                 250                 255

Leu Asp Phe Ala His Leu Tyr Ser Ala His Phe Trp Leu Met Met Thr
                260                 265                 270

Leu Gly Gly Leu Phe Gly Phe Ala Ile Gly Tyr Val Thr Gly Leu Gln
                275                 280                 285

Ile Lys Phe Thr Ser Pro Leu Thr His Asn Val Ser Gly Thr Ala Lys
                290                 295                 300

Ala Cys Ala Gln Thr Val Leu Ala Val Leu Tyr Tyr Glu Glu Thr Lys
305                 310                 315                 320

Ser Phe Leu Trp Trp Thr Ser Asn Leu Met Val Leu Gly Gly Ser Ser
                325                 330                 335

Ala Tyr Thr Trp Val Arg Gly Trp Glu Met Gln Lys Thr Gln Glu Asp
                340                 345                 350

Pro Ser Ser Lys Glu Gly Glu Lys Ser Ala Ile Gly Val
                355                 360                 365

<210> SEQ ID NO 93
<211> LENGTH: 1095
<212> TYPE: DNA
<213> ORGANISM: Homo sapiens

<400> SEQUENCE: 93
atgaataggg cccctctgaa gcggtccagg atcctgcaca tggcgctgac cggggcctca    60
gacccctctg cagaggcaga ggccaacggg gagaagccct ttctgctgcg ggcattgcag   120
atcgcgctgg tggtctccct ctactgggtc acctccatct ccatggtgtt ccttaataag   180
tacctgctgg acagcccctc cctgcggctg acaccccca tcttcgtcac cttctaccag   240
tgcctggtga ccacgctgct gtgcaaaggc ctcagcgctc tggccgcctg ctgccctggt   300
gccgtggact cccccagctt gcgcctggac ctcagggtgg cccgcagcgt cctgcccctg   360
tcggtggtct tcatcggcat gatcaccttc aataacctct gcctcaagta cgtcggtgtg   420
gccttctaca atgtgggccg ctcactcacc accgtcttca acgtgctgct ctcctacctg   480
ctgctcaagc agaccaccct cttctatgcc ctgctcacct gcggtatcat catcggggc    540 ttctggcttg gtgtggacca ggaggggca gaaggcaccc tgtcgtggct gggcaccgtc   600
ttcggcgtgc tggctagcct ctgtgtctcg ctcaacgcca tctacaccac gaaggtgctc   660
ccggcggtgg acggcagcat ctggcgcctg actttctaca caacgtcaa cgcctgcatc   720 ctcttcctgc ccctgctcct gctgctcggg gagcttcagg ccctgcgtga ctttgcccag   780
ctgggcagtg cccacttctg ggggatgatg acgctgggcg gcctgtttgg ctttgccatc   840
```

```
ggctacgtga caggactgca gatcaagttc accagtccgc tgacccacaa tgtgtcgggc    900
acggccaagg cctgtgccca gacagtgctg gccgtgctct actacgagga gaccaagagc    960
ttcctctggt ggacgagcaa catgatggtg ctgggcggct cctccgccta cacctgggtc   1020
aggggctggg agatgaagaa gactccggag gagcccagcc ccaaagacag cgagaagagc   1080
gccatggggg tgtga                                                    1095
```

<210> SEQ ID NO 94
<211> LENGTH: 364
<212> TYPE: PRT
<213> ORGANISM: Homo sapiens

<400> SEQUENCE: 94

```
Met Asn Arg Ala Pro Leu Lys Arg Ser Arg Ile Leu His Met Ala Leu
  1               5                  10                  15

Thr Gly Ala Ser Asp Pro Ser Ala Glu Ala Glu Ala Asn Gly Glu Lys
             20                  25                  30

Pro Phe Leu Arg Ala Leu Gln Ile Ala Leu Val Val Ser Leu Tyr
         35                  40                  45

Trp Val Thr Ser Ile Ser Met Val Phe Leu Asn Lys Tyr Leu Leu Asp
 50                  55                  60

Ser Pro Ser Leu Arg Leu Asp Thr Pro Ile Phe Val Thr Phe Tyr Gln
 65                  70                  75                  80

Cys Leu Val Thr Thr Leu Leu Cys Lys Gly Leu Ser Ala Leu Ala Ala
                 85                  90                  95

Cys Cys Pro Gly Ala Val Asp Phe Pro Ser Leu Arg Leu Asp Leu Arg
            100                 105                 110

Val Ala Arg Ser Val Leu Pro Leu Ser Val Val Phe Ile Gly Met Ile
        115                 120                 125

Thr Phe Asn Asn Leu Cys Leu Lys Tyr Val Gly Val Ala Phe Tyr Asn
    130                 135                 140

Val Gly Arg Ser Leu Thr Thr Val Phe Asn Val Leu Leu Ser Tyr Leu
145                 150                 155                 160

Leu Leu Lys Gln Thr Thr Ser Phe Tyr Ala Leu Leu Thr Cys Gly Ile
                165                 170                 175

Ile Ile Gly Gly Phe Trp Leu Gly Val Asp Gln Glu Gly Ala Glu Gly
            180                 185                 190

Thr Leu Ser Trp Leu Gly Thr Val Phe Gly Val Leu Ala Ser Leu Cys
        195                 200                 205

Val Ser Leu Asn Ala Ile Tyr Thr Thr Lys Val Leu Pro Ala Val Asp
    210                 215                 220

Gly Ser Ile Trp Arg Leu Thr Phe Tyr Asn Asn Val Asn Ala Cys Ile
225                 230                 235                 240

Leu Phe Leu Pro Leu Leu Leu Leu Gly Glu Leu Gln Ala Leu Arg
                245                 250                 255

Asp Phe Ala Gln Leu Gly Ser Ala His Phe Trp Gly Met Met Thr Leu
            260                 265                 270

Gly Gly Leu Phe Gly Phe Ala Ile Gly Tyr Val Thr Gly Leu Gln Ile
        275                 280                 285

Lys Phe Thr Ser Pro Leu Thr His Asn Val Ser Gly Thr Ala Lys Ala
    290                 295                 300

Cys Ala Gln Thr Val Leu Ala Val Leu Tyr Tyr Glu Glu Thr Lys Ser
305                 310                 315                 320

Phe Leu Trp Trp Thr Ser Asn Met Met Val Leu Gly Gly Ser Ser Ala
                325                 330                 335
```

Tyr Thr Trp Val Arg Gly Trp Glu Met Lys Lys Thr Pro Glu Glu Pro
                340                 345                 350

Ser Pro Lys Asp Ser Glu Lys Ser Ala Met Gly Val
                355                 360

<210> SEQ ID NO 95
<211> LENGTH: 2609
<212> TYPE: DNA
<213> ORGANISM: Mus musculus

<400> SEQUENCE: 95

| | | | | | |
|---|---|---|---|---|---|
| gagccgaggg | tggtgctgca | ggtgcacccg | agggcaccgc | cgagggtgag | caccaggtcc | 60 |
| ctgcatcagc | caggacacca | gagcccagtc | gggtggacgg | acgggcgcct | ctgaagcggt | 120 |
| ccaggatcct | gcgcatggcg | ctgactggag | tctctgctgt | ctccgaggag | tcagagagcg | 180 |
| ggaacaagcc | atttctgctc | cgggctctgc | agatcgcgct | ggtggtctct | ctctactggg | 240 |
| tcacctccat | ttccatggta | ttcctcaaca | agtacctgct | ggacagcccc | tccctgcagc | 300 |
| tggataccc | cattttttgtc | accttctacc | aatgcctggt | gacctcactg | ctgtgcaagg | 360 |
| gcctcagcac | tctggccacc | tgctgccccg | gcatggtaga | cttccccacc | ctaaacctgg | 420 |
| acctcaaggt | ggcccgaagt | gtgctgccgc | tgtcagtggt | ctttatcggc | atgataacct | 480 |
| tcaataacct | ctgcctcaag | tacgtagggg | tgcccttcta | caacgtggga | cgctcgctca | 540 |
| ccaccgtgtt | caacgttctt | ctctcctacc | tgctgctcaa | acagaccact | tccttctatg | 600 |
| ccctgctcac | ctgcggcgtc | atcattggtg | gtttctggct | gggtatagac | caagaaggag | 660 |
| ctgagggaac | cttgtccctg | acgggcacca | tcttcggggt | gctggccagc | ctctgcgtct | 720 |
| ccctcaatgc | catctatacc | aagaaggtgc | tccctgcagt | agaccacagt | atctggcgcc | 780 |
| taaccttcta | taacaatgtc | aatgcctgcg | tgctcttctt | gccccctgatg | atagtgctgg | 840 |
| gcgagctccg | tgccctcctg | gccttcactc | atctgagcag | tgcccacttc | tggctcatga | 900 |
| tgacgctggg | tggcctgttt | ggctttgcca | tcggctatgt | gacaggactg | cagatcaaat | 960 |
| tcaccagtcc | cctgacccat | aacgtgtcag | gcacggccaa | ggcctgtgca | cagacagtgc | 1020 |
| tggccgtgct | ctactacgaa | gagattaaga | gcttcctgtg | gtggacaagc | aacctgatgg | 1080 |
| tgctgggtgg | ctcctccgcc | tacacctggg | tcaggggctg | ggagatgcag | aagacccagg | 1140 |
| aggaccccag | ctccaaagat | ggtgagaaga | gtgctatcag | ggtgtgagct | ccttcaggga | 1200 |
| gccagggctg | agctcgggtg | gggcctgccc | agcacggaag | gcttcccata | gagcctactg | 1260 |
| ggtatggccc | tgagcaataa | tgtttacatc | cttctcagaa | gaccatctaa | gaagagccag | 1320 |
| gttctttcct | gataatgtca | gaaagctgcc | aaatctcctg | cctgccccat | cttctagtct | 1380 |
| tgggaaagcc | ctaccaggag | tggcaccctt | cctgcctcct | cctggggcct | gtctacctcc | 1440 |
| atatggtctc | tggggttggg | gccagctgca | ctctttgggc | actggactga | tgaagtgatg | 1500 |
| tcttactttc | tacacaaggg | agatgggttg | tgacccatcc | atagctagtt | gaagggagct | 1560 |
| gtgtaaccc | acatctctgg | ggccctgggc | aggtagcata | atagctaggt | gctattaaca | 1620 |
| tcaataacac | ttcagactac | ctttggaggc | agttgggagc | tgagccgaga | gagagagatg | 1680 |
| gccattctgc | cctcttctgt | gtggatgggt | atgacagacc | aactgtccat | ggggtgactg | 1740 |
| acacctccac | acttcatatt | tcaacttta | gaaaggggg | agccacacgt | tttacagatt | 1800 |
| aagtggagtg | atgaatgcct | ctacagcccc | taaccccact | ttccctgcct | ggcttctctt | 1860 |
| ggcccagaag | ggccaccatc | ctgttctcca | acacctgacc | cagctatctg | gctatactct | 1920 |
| ctttctgtac | tcccttcccc | ttcccccccc | cattagcctc | ctccccaaca | cctccatctt | 1980 |

-continued

```
caggcaggaa gtggggtcca ctcagcctct gttcccatct gcttggaccc ctgagcctct   2040
catgaaggta ggcttatgtt ctctgaggct ggggccggag gagcgcactg attctcggag   2100
ttatcccatc aggctcctgt cacaaaatag cctaggccgt gtgtctaaga acagtggagg   2160
ttggcttata actgttctgg gggcagcgaa gcccacatca aggtactcat agacccagta   2220
tttctgagga aaccctgtc cacatcctca cttggtaaag gcacagataa tctccctcag    2280
gcctcttgta taggagcact agccctggga gggctccgcc ccatgacctg atcaccccaa   2340
agccttcaac agaaggattc caacatgaat ttggggacag aagcactcag accacgatgc   2400
ccagcaccac accctcctat cctcagggta gctgtcactg tcctagtccc ttctgtttgg   2460
ccttttgtac cctcatttcc ttggcgtcat gtttgatgtc tttgtctctt tcgtgagaag   2520
atggggaaac catgtcagcc tctgcttccg acttcccatg ggttctaatg aagttggtgg   2580
ggcctgatgc cctgagttgt atgtgattt                                     2609
```

<210> SEQ ID NO 96
<211> LENGTH: 350
<212> TYPE: PRT
<213> ORGANISM: Mus musculus

<400> SEQUENCE: 96

```
Met Ala Leu Thr Gly Val Ser Ala Val Ser Glu Glu Ser Glu Ser Gly
  1               5                  10                  15

Asn Lys Pro Phe Leu Arg Ala Leu Gln Ile Ala Leu Val Val Ser
             20                  25                  30

Leu Tyr Trp Val Thr Ser Ile Ser Met Val Phe Leu Asn Lys Tyr Leu
         35                  40                  45

Leu Asp Ser Pro Ser Leu Gln Leu Asp Thr Pro Ile Phe Val Thr Phe
     50                  55                  60

Tyr Gln Cys Leu Val Thr Ser Leu Leu Cys Lys Gly Leu Ser Thr Leu
 65                  70                  75                  80

Ala Thr Cys Cys Pro Gly Met Val Asp Phe Pro Thr Leu Asn Leu Asp
                 85                  90                  95

Leu Lys Val Ala Arg Ser Val Leu Pro Leu Ser Val Val Phe Ile Gly
            100                 105                 110

Met Ile Thr Phe Asn Asn Leu Cys Leu Lys Tyr Val Gly Val Pro Phe
        115                 120                 125

Tyr Asn Val Gly Arg Ser Leu Thr Thr Val Phe Asn Val Leu Leu Ser
    130                 135                 140

Tyr Leu Leu Leu Lys Gln Thr Thr Ser Phe Tyr Ala Leu Leu Thr Cys
145                 150                 155                 160

Gly Val Ile Ile Gly Gly Phe Trp Leu Gly Ile Asp Gln Glu Gly Ala
                165                 170                 175

Glu Gly Thr Leu Ser Leu Thr Gly Thr Ile Phe Gly Val Leu Ala Ser
            180                 185                 190

Leu Cys Val Ser Leu Asn Ala Ile Tyr Thr Lys Lys Val Leu Pro Ala
        195                 200                 205

Val Asp His Ser Ile Trp Arg Leu Thr Phe Tyr Asn Asn Val Asn Ala
    210                 215                 220

Cys Val Leu Phe Leu Pro Leu Met Ile Val Leu Gly Glu Leu Arg Ala
225                 230                 235                 240

Leu Leu Ala Phe Thr His Leu Ser Ser Ala His Phe Trp Leu Met Met
                245                 250                 255

Thr Leu Gly Gly Leu Phe Gly Phe Ala Ile Gly Tyr Val Thr Gly Leu
```

```
                  260                   265                   270
Gln Ile Lys Phe Thr Ser Pro Leu Thr His Asn Val Ser Gly Thr Ala
            275                 280                 285

Lys Ala Cys Ala Gln Thr Val Leu Ala Val Leu Tyr Tyr Glu Glu Ile
            290                 295                 300

Lys Ser Phe Leu Trp Trp Thr Ser Asn Leu Met Val Leu Gly Gly Ser
305                 310                 315                 320

Ser Ala Tyr Thr Trp Val Arg Gly Trp Glu Met Gln Lys Thr Gln Glu
                325                 330                 335

Asp Pro Ser Ser Lys Asp Gly Glu Lys Ser Ala Ile Arg Val
            340                 345                 350

<210> SEQ ID NO 97
<211> LENGTH: 1053
<212> TYPE: DNA
<213> ORGANISM: Rattus norvegiucus

<400> SEQUENCE: 97
```

| | | | | | |
|---|---|---|---|---|---|
| atggcgctga | ctggagcctc | tgctgtctct | gaggaggcag | acagcgagaa | caagccattt | 60 |
| ctgctacggg | ctctgcagat | cgcgctggtg | gtttctctct | actgggtcac | ctccatctcc | 120 |
| atggtattcc | tcaacaagta | cctgctggac | agccctccc | tgcagctgga | taccccatc | 180 |
| ttcgtcacct | tctaccaatg | cctggtgacc | tcactgctgt | gcaagggcct | cagcactctg | 240 |
| gccacctgct | gccctggcat | ggtagacttc | cccaccctaa | acctggacct | caaggtggcc | 300 |
| cgaagtgtgc | tgccgctgtc | cgtggtcttt | atcggcatga | taaccttcaa | taacctctgc | 360 |
| ctcaagtacg | tgggggtggc | cttctacaac | gtgggacgct | cgctcactac | cgtgttcaat | 420 |
| gtgcttctct | cctacctgct | gcttaaacag | accacttcct | tttatgccct | gctcacctgt | 480 |
| gccatcatca | ttggtggttt | ctggctggga | atagatcaag | agggagctga | gggcaccctg | 540 |
| tccctgacgg | gcaccatctt | cggggtgctg | gccagcctct | gtgtctcact | caatgccatc | 600 |
| tacaccaaga | aggtgctccc | tgccgtagac | cacagtatct | ggcgcctaac | cttctataac | 660 |
| aacgtcaacg | cctgtgtgct | cttcttgccc | ctgatggtag | tgctgggcga | gctccatgct | 720 |
| ctcctggcct | tcgctcatct | gaacagcgcc | cacttctggg | tcatgatgac | gctgggtgga | 780 |
| ctcttcggct | tgccattggg | ctatgtgaca | ggactgcaga | tcaaattcac | cagtcccctg | 840 |
| acccataatg | tgtcgggcac | agccaaggcc | tgtgcacaga | cagtgctggc | tgtgctctac | 900 |
| tatgaagaga | ttaagagctt | cctgtggtgg | acaagcaact | tgatggtgct | gggtggctcc | 960 |
| tctgcctaca | cctgggtcag | gggctggag | atgcagaaga | cccaggagga | ccccagctcc | 1020 |
| aaagagggtg | agaagagtgc | tatcggggtg | tga | | | 1053 |

```
<210> SEQ ID NO 98
<211> LENGTH: 350
<212> TYPE: PRT
<213> ORGANISM: Rattus norvegiucus

<400> SEQUENCE: 98

Met Ala Leu Thr Gly Ala Ser Ala Val Ser Glu Glu Ala Asp Ser Glu
1               5                   10                  15

Asn Lys Pro Phe Leu Leu Arg Ala Leu Gln Ile Ala Leu Val Val Ser
            20                  25                  30

Leu Tyr Trp Val Thr Ser Ile Ser Met Val Phe Leu Asn Lys Tyr Leu
        35                  40                  45

Leu Asp Ser Pro Ser Leu Gln Leu Asp Thr Pro Ile Phe Val Thr Phe
    50                  55                  60
```

Tyr Gln Cys Leu Val Thr Ser Leu Leu Cys Lys Gly Leu Ser Thr Leu
65                  70                  75                  80

Ala Thr Cys Cys Pro Gly Met Val Asp Phe Pro Thr Leu Asn Leu Asp
                85                  90                  95

Leu Lys Val Ala Arg Ser Val Leu Pro Leu Ser Val Val Phe Ile Gly
            100                 105                 110

Met Ile Thr Phe Asn Asn Leu Cys Leu Lys Tyr Val Gly Val Ala Phe
        115                 120                 125

Tyr Asn Val Gly Arg Ser Leu Thr Thr Val Phe Asn Val Leu Leu Ser
130                 135                 140

Tyr Leu Leu Leu Lys Gln Thr Thr Ser Phe Tyr Ala Leu Leu Thr Cys
145                 150                 155                 160

Ala Ile Ile Ile Gly Gly Phe Trp Leu Gly Ile Asp Gln Glu Gly Ala
                165                 170                 175

Glu Gly Thr Leu Ser Leu Thr Gly Thr Ile Phe Gly Val Leu Ala Ser
            180                 185                 190

Leu Cys Val Ser Leu Asn Ala Ile Tyr Thr Lys Lys Val Leu Pro Ala
        195                 200                 205

Val Asp His Ser Ile Trp Arg Leu Thr Phe Tyr Asn Asn Val Asn Ala
210                 215                 220

Cys Val Leu Phe Leu Pro Leu Met Val Val Leu Gly Glu Leu His Ala
225                 230                 235                 240

Leu Leu Ala Phe Ala His Leu Asn Ser Ala His Phe Trp Val Met Met
                245                 250                 255

Thr Leu Gly Gly Leu Phe Gly Phe Ala Ile Gly Tyr Val Thr Gly Leu
            260                 265                 270

Gln Ile Lys Phe Thr Ser Pro Leu Thr His Asn Val Ser Gly Thr Ala
        275                 280                 285

Lys Ala Cys Ala Gln Thr Val Leu Ala Val Leu Tyr Tyr Glu Glu Ile
290                 295                 300

Lys Ser Phe Leu Trp Trp Thr Ser Asn Leu Met Val Leu Gly Gly Ser
305                 310                 315                 320

Ser Ala Tyr Thr Trp Val Arg Gly Trp Glu Met Gln Lys Thr Gln Glu
                325                 330                 335

Asp Pro Ser Ser Lys Glu Gly Glu Lys Ser Ala Ile Gly Val
            340                 345                 350

<210> SEQ ID NO 99
<211> LENGTH: 7752
<212> TYPE: DNA
<213> ORGANISM: Mus musculus

<400> SEQUENCE: 99
agcgttgcaa gttcagccga gggtggtgct gcaggtgcac ccgagggcac cgccgagggt      60
gagcaccagg tccctgcatc agccaggaca ccagagccca gtcgggtgga cggacggtac     120
gttctggaag ggaaagggcc ccgggaaggg gatacagcat tgagaagctc agaggctttg     180
gtctgggcat ccagaatgga ctttatctgg aggaggtgac atggcttctc gcctctggaa     240
gtgctgcttg gatctccggg acttcatgtc ctgactaggt ctggaagcgg tgaaaatagg     300
ggtaggaaaa aaggagagga ctgcaacaag gtcttcccga gtggcctgag ctcgagggac     360
gagggaggtg caacggtggg gagccgggcg caagggctgg gcggagggag ggggggggtc     420
tccctaagca gaaaggtggt attccatttt ctgggtagat ggtgaagatg cacctgaccg     480
agtctggtcg atctgaagat atcaggggaa aagatagtgc gggtggaggg gagaatgaca     540

```
gaaccttcca gaaaatggga gaggctatag cacttgcaaa cccttccctg atctccgggg    600
actcccggaa gaagagggca ggtctgtggg cataggtgca gacttgccgg ggagctcttg    660
acggccgcgg gaagtggcaa cggcctgcga gctggccctt taaggcggct cgtaggcgtg    720
tcaggaaatg cgcgcagggc ccgccctgct cggtaagtgg cccgggaccc gcgtcgctga    780
gccggaactt gaattcggct cgtggcaacc gcagggcctt gctccggtca ggcccctgtc    840
cgtgtccctc gagacgcctt cctgagcctc ggtgatctcc ctgcagcacg ccctcctttc    900
ggctctgcgg gtgcttccgg gggttcccgc agcccatgct tcccacgcgg tccgcgtcca    960
gttatttcct cctccgctcc gtccttcctt cgctctctcg cttcctttct ccctgcgact   1020
cacgtgtccc ctgtcctcaa actggccatg gctgtcaaag cccacatcct tagttaggcc   1080
ccttctccct tccctgggtc ttgtttcgtg acaccacctc cctccccgc cccgggagcg    1140 agcaagatga ggagcggtgc acctcggcaa atccggaagc agaacttcat ccaagaagga   1200
ggggaccgat aggtcatccc atgtgacagt tgaaggctgc agccacagac cctagctgct   1260
tgaagccctg tagtccaggg actgcttctg gccgtaaggt gacccagctc ttctgccacc   1320
atgaacaggg cgcctctgaa gcggtccagg atcctgcgca tggcgctgac tggagtctct   1380
gctgtctccg aggagtcaga gagcgggaac aagccatttc tgctccgggc tctgcagatc   1440
gcgctggtgg tctctctcta ctgggtcacc tccatttcca tggtattcct caacaagtac   1500
ctgctggaca gcccctccct gcagctggat acccccattt ttgtcacctt ctaccaatgc   1560
ctggtgacct cactgctgtg caagggcctc agcactctgg ccacctgctg ccccggcatg   1620
gtagacttcc ccaccctaaa cctggacctc aaggtggccc gaagtgtgct gccgctgtca   1680 gtggtctttta tcggcatgat aaccttcaat aacctctgcc tcaagtacgt agggggtgccc  1740 ttctacaacg tgggacgctc gctcaccacc gtgttcaacg ttcttctctc ctacctgctg   1800
ctcaaacaga ccacttcctt ctatgccctg ctcacctgcg gcgtcatcat tggtgagtgg   1860 gactggggc gtggggagca ggaatcgtaa agatcaatac cacattactc attatctgtc    1920
ccaggtcttt tgcaccacca gtcataggga gagacctgta gagaacaaat aacttcctta   1980
ctgtgactca gtaagttagg gatccagcca aggtgaacat aataatgtta ggcagacact   2040
acagcaaagc cagccagaca ctcagatcta gctaagcatt tgagccatgt taatgtaacg   2100
gatccccatt acaaggtata atatagctgc gtttatgga gagaaaccca aggcacagag    2160
aagctaagta gctgggatca cacaggtaat cactgacgta gcagaaattt gcacataagc   2220
agttacctcc ataggttaca ctcttgacca acacaccact gttctcaaga ggtcaagggt   2280
gaactcaggt catcacaatt ggcacaagta cctctaccca ctgagccatt tcagtggtcc   2340
agtcaatatg tgtgtgcttt aagaggcttt aactaccttc tcagatgtga ccataagtaa   2400
ttaattaccg ataggagcgt tgtgctgatc attacacttg tagcatcctc tttattgtac   2460
ccataagctc tctgagtggc ggcatctctg tgaaactgca gctcggagag gctgcgctcc   2520
ttgccacagc cccacaacta agaagcagat agtctgggac gcagtcccca gttggtcata   2580
ctccctggcc tgtgtttcaa gccagtctgc tttgctcctg acccttggga gttagcgcaa   2640
tgaaaaccaa cactatcact acagtctaaa tgtgctttta aatgaaagcc caggaacttt   2700
gaagcatccg gcccttaac ggcagccact atgtcctgat tccgcaaca tcttttcagt    2760 gcccggcagt cacatggagc aagggcctct tggcttggac agcatgtgtt agggaacatg   2820
tttgccactt tgaatgaatt tagtggctgc tgggttacag agaccagggc atctttcccc   2880
tcagagtcct gaatgaacga aaagcaacct tcatttgtac ctgctctgga ttttagttcg   2940
```

```
tcttgtttgg cctatttaga tgtccctggt gtctctgagg cccaggctgg gtgctctaga   3000
tgtagggacc aggccaacct gtactgtctt ccctagaaac attgccctgg ttgggcagct   3060
cctggatcca gggttaaggg gtctgggcgg agagaggtca gatagtggca ggatgcctcc   3120
cactgccccc acatacatac cctaagagat ctggtactcc tccttccagc ctacaagcta   3180
ccgtggggtc ccacttcagt ccaccagccc tgccaacgtt agaggggatg ggcctcctag   3240
taggagaact tacatgcagg aaggtacagt ctctggagaa cctgagcccg ggtccccaaa   3300
gggacaagta gctgatagtg aggcagctga gccccatggc ggcctgccca gtggcacgg    3360 gaaagtggag ctctctgctg cccccactac tggccccatc tcttggctct ccctcccctt   3420
cctcctgtgg agaaggccca tctctggaaa ggcctcctag acatgcggca ctttgcaaag   3480
cctgtcgggc tcacagcccc tctagggtct aggaccttga gaatgaagaa tggagtcact   3540
tctagactct agtggtaacc accaggaggt acagggtgct ctgactgtgc agggaaaccc   3600
accgtgggct ctgctgagcc aagtgcctgt gaggctggag agtctggtgc ccttgttctg   3660
agatagcatc ttgctatgtt gccctcaagt cccaggcaac tggggctgca ggagcaccac   3720
cttgcctctc tccagcttct tgaagacttg taccttctc ctagcagtct ctatctgctc    3780
tcactccatc cattgagcag ctattagctt gtggccaagt attttccagg ccctgtactg   3840
agttttaggg tacaagtttg agaaaggaag ggtgggtcc ttgctcctgg tccgtgaatg    3900
atgttgatgg cagaaacgat agttacacta gatgctaagg gctgtgggta tctagaggga   3960
gcagggagca tgtgggataa cctgagcagg cctagctgaa aagtcattgc tggcatgaga   4020
ctgctccagt agtacaggct gggaacacac atttgaatgt ttcctgaaga cagttgggag   4080
ccacaggaaa tatccactgt agaaagatta tttagttgta agacagagta gtagattggt   4140
taacatagta gcaaaaacgt ggcccagtt tttacagatg aagggaattg gaactcagag    4200
aggttaagta acttctccca agcagctcag ctacaaaaat cacagaacag gcaggggcct   4260
gatggctctg atgcctgtgc tggtcccact attccatgtt gctaattcct gcagcagcag   4320
taaacctctg ccttgtggaa atgaggagtc taaataaaga gaccatagca ttgccacaag   4380
caggtttcta ccaactgggg gtggcaagga atgctgtgtt agcagcagga agctgggaag   4440
aggctgagta ctgggggat gaggaaggga tccccaggag aggctgactt tggccttgaa    4500
gaatggtgga gtccctggaa agatgcagat acacagagct ctgtggatat acagagaagt   4560
ggggagctaa gtaggtggct tggggccatc atgtgacaga ggaagtcggg ctagatgcag   4620
gaagcccggt gctgtggcct agggagccat gtaggttctt tgagcagggg gcggggggg    4680 gggggggtga cccaggagtg actgtaaaca acatcaggcc atgagcagct ctgacctaat   4740
gttctcacca agggagccag aaccaaggct tagagccctg tccctttta gtgtccaagg    4800 tcactttact ggccctcttc ctttacagct gttggccccc acaggccatc aggcacctat   4860
gctattttat tttatagcct tcattacaat gactacaatt gtaattagag agttgacagg   4920
gtcacatctg tccttatata ttcccctct gctaagttct gcctgggaga atgtggaggg    4980
tattggtgaa atttggggaa gttataaccc cccaccccct gccccaccc cctgctttgc    5040 tccctttatc tgcagggcat ttctgtgccc actttagccc atatagctcc caaataaatg   5100
acacagaaac ctggtatttt cattaacaaa ctgctggcac tctgctgggc aggttctgag   5160
ctgttctaac cctctaagct gctaatgccc agatagatgc cccaatgctt gccatccgag   5220
tctttctctg gcttgctctg ctccatgtgt gacctcatgg tgaatcctcc tgatttcccc   5280
acatggcctc tccacacttt tccttctccc ctctctctac cagggaccct ctcactggga   5340
```

```
cccgatgtcc catctgtact gtcctctccc acccagtcat aggctgattg agtctttatt    5400
aaccaatcag agatgatgga aaaacagttt ttacatagca ctgaggatgg agatgcttga    5460
cccttgagat gcttgcccgt aacctgtact gtatccagat gtctgggccc ccaaatcagc    5520
aggtgaatac acagtacaca ggactgaccc ccaacagagg gggaacacag gttctcactc    5580
tgggctccac gccctcggcc ctttcttagt gcaggggtta gactttgtat gtgttgatga    5640
tgaggtaagg gccatggaac agtcagaacg gtggtgtcag aatcctgtcc ctctccctcc    5700
tgtcctcatc cctccttacc gtgtcactct tctgtctgtt gcaggtggtt tctggctggg    5760
tatagaccaa gaaggagctg agggaacctt gtccctgacg ggcaccatct tcgggtgct    5820 ggccagcctc tgcgtctccc tcaatgccat ctataccaag aaggtgctcc ctgcagtaga    5880
ccacagtatc tggcgcctaa ccttctataa caatgtcaat gcctgcgtgc tcttcttgcc    5940
cctgatgata gtgctgggcg agctccgtgc cctcctggcc ttcactcatc tgagcagtgc    6000
ccacttctgg ctcatgatga cgctgggtgg cctgtttggc tttgccatcg gctatgtgac    6060
aggactgcag atcaaattca ccagtcccct gacccataac gtgtcaggca cggccaaggc    6120
ctgtgcacag acagtgctgg ccgtgctcta ctacgaagag attaagagct tcctgtggtg    6180
gacaagcaac ctgatggtgc tgggtggctc ctccgcctac acctgggtca ggggctggga    6240
gatgcagaag acccaggagg accccagctc caaagatggt gagaagagtg ctatcagggt    6300
gtgagctcct tcaggagcc agggctgagc tcgggtgggg cctgcccagc acggaaggct    6360
tcccatagag cctactgggt atggccctga gcaataatgt ttacatcctt ctcagaagac    6420
catctaagaa gagccaggtt cttttcctgat aatgtcagaa agctgccaaa tctcctgcct    6480
gccccatctt ctagtcttgg gaaagcccta ccaggagtgg cacccttcct gcctcctcct    6540
ggggcctgtc tacctccata tggtctctgg ggttggggcc agctgcactc tttgggcact    6600
ggactgatga agtgatgtct tactttctac acaagggaga tgggttgtga ccctactata    6660
gctagttgaa gggagctgtg taaccccaca tctctggggc cctgggcagg tagcataata    6720
gctaggtgct attaacatca ataacacttc agactaccctt tggaggcagt tgggagctga    6780
gccgagagag agagatggcc attctgccct ctttgtgtg gatgggtatg acagaccaac    6840
tgtccatggg gtgactgaca cctccacact tcatattttc aactttagaa aaggggagc    6900 cacacgtttt acagattaag tggagtgatg aatgcctcta cagcccctaa ccccactttc    6960
cctgcctggc ttctcttggc ccagaagggc caccatcctg ttctccaaca cctgacccag    7020
ctatctggct atactctctt tctgtactcc cttcccctt ccccccccat tagcctcctc    7080
cccaacacct ccatcttcag gcaggaagtg gggtccactc agcctctgtt cccatctgct    7140
tggacccctg agcctctcat gaaggtaggc ttatgttctc tgaggctggg gccggaggag    7200
cgcactgatt ctcggagtta tcccatcagg ctcctgtcac aaaatagcct aggccgtgtg    7260
tctaagaaca gtggaggttg gcttataact gttctggggg cagcgaagcc cacatcaagg    7320
tactcataga cccagtattt ctgaggaaac ccctgtccac atcctcactt ggtaaaggca    7380
cagataatct ccctcaggcc tcttgtatag gagcactagc cctgggaggg ctccgcccca    7440
tgacctgatc accccaaagc cttcaacaga aggattccaa catgaatttg gggacagaag    7500
cactcagacc acgatgccca gcaccacacc ctcctatcct cagggtagct gtcactgtcc    7560
tagtcccttc tgtttggcct tttgtaccct catttccttg gcgtcatgtt tgatgtcttt    7620
gtctctttcg tgagaagatg gggaaaccat gtcagcctct gcttccgact tcccatgggt    7680
tctaatgaag ttggtggggc ctgatgccct gagttgtatg tgatttaata aaaaaaaaat    7740
```

```
tttttttaaaa ac                                                 7752

<210> SEQ ID NO 100
<211> LENGTH: 4039
<212> TYPE: DNA
<213> ORGANISM: Cricetulus griseus

<400> SEQUENCE: 100
gaacttcacc caagccatgt gacaattgaa ggctgtaccc ccagacccta acatcttgga    60
gccctgtaga ccagggagtg cttctggccg tggggtgacc tagctcttct accaccatga   120
acagggcccc tctgaagcgg tccaggatcc tgcgcatggc gctgactgga ggctccactg   180
cctctgagga ggcagatgaa gacagcagga acaagccgtt tctgctgcgg gcgctgcaga   240
tcgcgctggt cgtctctctc tactgggtca cctccatctc catggtattc ctcaacaagt   300
acctgctgga cagcccctcc ctgcagctgg ataccccctat cttcgtcact ttctaccaat   360
gcctggtgac ctctctgctg tgcaagggcc tcagcactct ggccacctgc tgccctggca   420
ccgttgactt ccccacccctg aacctggacc ttaaggtggc ccgcagcgtg ctgccactgt   480
cggtagtctt cattggcatg ataagtttca ataacctctg cctcaagtac gtaggggtgg   540
ccttctacaa cgtggggcgc tcgctcacca ccgtgttcaa tgtgcttctg tcctacctgc   600
tgctcaaaca gaccacttcc ttctatgccc tgctcacatg tggcatcatc attggtgagt   660
ggggcccggg ggctgtggga gcaggatggg catcgaactg aagccctaaa ggtcaacact   720
gtaggtacct ttacttactg tcccaggtcc cttgcatcag cagttacagg aagagccctg   780
tagaaaacaa ataacttcct tatggtcatt caacaagtta gggacccagc cagggtgaaa   840
ataatgttag cagcaactac agcaaagatg gctctcgcca cttgcatgat taaaatgtgc   900
caggtactca gatcyaagca ttggatccac attaactcaa ctaatcccta ttacaaggta   960
aaatatatcc gaatttttaca gagggaaaac caaggcacag agaggctaag tagcttgacc  1020
aggatcacac agctaataat cactgacata gctgggattt aaacataagc agttacctcc  1080
atagatcaca ctatgaccac catgccactg ttccttctca agagttccag gatcctgtct  1140
gtccagttct ctttaaagag gacaaacact ctgacattgc tacctgagg taacatttga  1200 aatagtgggt agacatatgt tttaagtttt attcttrctt tttatgygtg tgtgtttggg  1260
gggccaccac agtgtatggg tggagataag gggacaactt aagaattggt cctttctccc  1320
accacatggg tgctgaggtc tgaactcagg tcatcaggat tggcacaaat ccctttaccc  1380
actgagccat ttcactggtc caatatatgt gtgcttttaa gaggctttaa ctattttccc  1440
agatgtgaat gtcctgctga tcattatccc cttttacccg gaagccctct gggaggtgcc  1500
atccctgtgg tcgtctgcat acaaatgggg aaactgcaac tcagagaaac aaggctactt  1560
gccagggccc cacaagtaag ataggctggg atgccatccc agactggcca cactccctgg  1620
cctgtgcttc aagccagttt actttgttcc tgcccattgg aagttagcat gttgcagtca  1680
aacacaataa ctacaggcca aaagtgcttt taaattaaag tcagatgaac ttttaaacat  1740
ccagagctcc tcaactgcag gagttacaac ctgattctgc aaccatcttt gcagtgcccg  1800
gtagtcatat gtagctagag gctcttggct aggacagcat gtgttaggaa acatctggcc  1860
```

-continued

```
ctgagatcat tgaattgagt gactgctggg tgacaaagac caaggcatcc gttccctgag      1920
agtcctgggc aagcagcaat gtgaccttca tttgtaccta ctcaggttct ttatctgtcc      1980
tgtttgacct acttagtctc ctctggtgtc tcagaggccc aggctgggta ctctggatgt      2040
caggatcagg ccaatgcgca catctgccct agaaatgtcc ccctggttga gcagctcctg      2100
aatccatcgg taaagggtct ggaccaggga ggagtcagat aaaaagctga cagcactggg      2160
ggactccatg gggaactccc acctgccccc acacatccat cctaagagaa ctggtattcc      2220
ttgtttcctc tttgtcctac aaggcaccct gggatcccac ttcagtctcc cagccttgcc      2280
agggttagag ggcatgagcc tccttgtggg gaatttagat gcaagaaggt acagtcacta      2340
gagaacctga gctcagatcc ccaaagtaac cagtacctga tagtgaggca gctgagaacc      2400
gcagcagcct gcctgagtgg ctgaactctg cggcctccgg aactggcccc aactgttggg      2460
tctcctcttc cttcctcctg tgagggaggg cccatctctg ataagtgctg tggggactct      2520
agagtaggga ggaggaggag caatctaagc aggccttact gagaagtcct tgctggcatg      2580
tggctgcctg aggagtacag actgggaaca cccatttgaa tgagtaaggt ttttcctgaa      2640
ggccatgggg agccacggag gaaaatcatt ttagttacaa gacaaagagt agattggtta      2700
acatgggagc arggacatgg ccccaatttt cattgatgaa ggaaattgga actcrgagag      2760
gttaagtaac ttctcccaaa tagctcagct tcataatcac agaacagtca gagtctagat      2820
ctctctgatg cctgtgatgg tcctgccatt ccatgttgct gatccctgtg gcatcagtaa      2880
gcctctacct tgtgggaatg caggatctaa atgaagagag raagtgctgg ccccatgctg      2940
tggtctggaa agctatgcag gctctttgag cagagagtga cccacaagtg aatagagtcc      3000
tatgagactc aaagcaacat ccaccottaa gcagctctaa ccaaatgctc acactgaggg      3060
agccaaagcc aagttagagt cctgtgcttg cccaaggtca ctttgcctgg ccctcctcct      3120
atagcacccg tgttatctta tagccctcat tacagtgatt acaattataa ttagagaggt      3180
aacagggcca cactgtcctt acacattccc ctgctagatt gtagctggga gaggggagga      3240
tgtaggtggc tgggggagtg ggagggaaga tgcagatttt cattctgggc tctactccct      3300
cagccatttt ttggtgtggg agttagactt tggatatgtt gatgatgagg taagggccac      3360
agaacagtct gaactgtggt atcagaatcc tgtccctctc cctctctcct catccctctt      3420
caccttgtca ctcctctgtc tgctacaggt ggtttctggc tgggtataga ccaagaggga      3480
gctgagggca ccctgtccct cataggcacc atcttcgggg tgctggccag cctctgcgtc      3540
tccctcaatg ccatctatac caagaaggtg ctcccagcag tggacaacag catctggcgc      3600
ctaaccttct ataacaatgt caatgcctgt gtgctcttct tgcccctgat ggttctgctg      3660
ggtgagctcc gtgccctcct tgactttgct catctgtaca gtgcccactt ctggctcatg      3720
atgacgctgg gtgcctcttc ggctttgcc attggctatg tgacaggact gcagatcaaa      3780
ttcaccagtc ccctgaccca caatgtatca ggcacagcca aggcctgtgc gcagacagtg      3840
ctggccgtgc tctactatga agagactaag agcttcctgt ggtggacaag caacctgatg      3900
gtgctgggtg gctcctcagc ctatacctgg gtcaggggct gggagatgca gaagacccaa      3960
gaggaccccg gctccaaaga gggtgagaag agtgctattg gggtgtgagc ttcttcaggg      4020
acctgggact gaacccaag                                                   4039
```

METHOD OF ENHANCING OF BINDING ACTIVITY OF ANTIBODY COMPOSITION TO FCγ RECEPTOR IIIA

CROSS-REFERENCE TO RELATED APPLICATIONS

This is a divisional of application Ser. No. 10/409,611 filed Apr. 9, 2003 (now abandoned). The entire disclosure of the prior application, application Ser. No. 10/409,611 is considered part of the disclosure and is hereby incorporated by reference.

BACKGROUND OF THE INVENTION

1. Field of the Invention

The present invention relates to a method for enhancing a binding activity of an antibody composition to Fcγ receptor IIIa, which comprises modifying a complex N-glycoside-linked sugar chain which is bound to the Fc region of an antibody molecule; a method for enhancing an antibody-dependent cell-mediated cytotoxic activity of an antibody composition; a process for producing an antibody composition having an enhanced binding activity to Fcγ receptor IIIa; a method for detecting the ratio of a sugar chain in which fucose is not bound to N-acetylglucosamine in the reducing end in the sugar chain among total complex N-glycoside-linked sugar chains bound to the Fc region in an antibody composition; an Fc fusion protein composition produced by using a cell resistant to a lectin which recognizes a sugar chain in which 1-position of fucose is bound to 6-position of N-acetylglucosamine in the reducing end through α-bond in a complex N-glycoside-linked sugar chain; and a process for producing the same.

2. Brief Description of the Background Art

Since antibodies have high binding activity, binding specificity and high stability in blood, their applications to diagnosis, prevention and treatment of various human diseases have been attempted [*Monoclonal Antibodies: Principles and Applications*, Wiley-Liss, Inc., Chapter 2.1 (1995)]. Also, production of a humanized antibody such as a human chimeric antibody or a human complementarity determining region (hereinafter referred to as "CDR")-grafted antibody from a non-human animal antibody have been attempted by using genetic recombination techniques. The human chimeric antibody is an antibody in which its antibody variable region (hereinafter referred to as "V region") is derived from a non-human animal antibody and its constant region (hereinafter referred to as "C region") is derived from a human antibody. The human CDR-grafted antibody is an antibody in which the CDR of a human antibody is replaced by CDR derived from a non-human animal antibody.

It has been revealed that five classes, namely IgM, IgD, IgG, IgA and IgE, are present in mammal antibodies. Antibodies of human IgG class are mainly used for the diagnosis, prevention and treatment of various human diseases because they have functional characteristics such as long half-life in blood and various effector functions [*Monoclonal Antibodies: Principles and Applications*, Wiley-Liss, Inc., Chapter 1 (1995)]. The human IgG class antibody is further classified into the following 4 subclasses: IgG1, IgG2, IgG3 and IgG4. A large number of studies have so far been conducted for antibody-dependent cell-mediated cytotoxic activity (hereinafter referred to as "ADCC activity") and complement-dependent cytotoxic activity (hereinafter referred to as "CDC activity") as effector functions of the IgG class antibody, and it has been reported that among antibodies of the human IgG class, the IgG1 subclass has the highest ADCC activity and CDC activity [*Chemical Immunology*, 65, 88 (1997)]. In view of the above, most of the anti-tumor humanized antibodies, including commercially available Rituxan and Herceptin, which require high effector functions for the expression of their effects, are antibodies of the human IgG1 subclass.

Expression of ADCC activity and CDC activity of the human IgG1 subclass antibodies requires binding of the Fc region of the antibody to a receptor for an antibody (hereinafter referred to as "FcγR") existing on the surface of effector cells such as killer cells, natural killer cells or activated macrophages and various complement components are bound. Regarding the binding, it has been suggested that several amino acid residues in the hinge region and the second domain of C region (hereinafter referred to as "Cγ2 domain") of the antibody are important [*Eur. J. Immunol.*, 23, 1098 (1993), *Immunology*, 86, 319 (1995), *Chemical Immunology*, 65, 88 (1997)] and that a sugar chain in the Cγ2 domain [*Chemical Immunology*, 65, 88 (1997)] is also important.

Regarding the sugar chain, Boyd et al. have examined effects of a sugar chain on the ADCC activity and CDC activity by treating a human CDR-grafted antibody CAMPATH-1H (human IgG1 subclass) produced by a Chinese hamster ovary cell (hereinafter referred to as "CHO cell") or a mouse myeloma NS0 cell (hereinafter referred to as "NS0 cell") with various glycosidases, and reported that elimination of sialic acid in the non-reducing end did not have influence upon both activities, but the CDC activity alone was affected by further removal of galactose residue and about 50% of the activity was decreased, and that complete removal of the sugar chain caused disappearance of both activities [*Molecular Immunol.*, 32, 1311 (1995)]. Also, Lifely et al. have analyzed the sugar chain bound to a human CDR-grafted antibody CAMPATH-1H (human IgG1 subclass) which was produced by CHO cell, NS0 cell or rat myeloma Y0 cell (hereinafter referred to as "Y0 cell"), measured its ADCC activity, and reported that the CAMPATH-1H derived from Y0 cell showed the highest ADCC activity, suggesting that N-acetylglucosamine (hereinafter sometimes referred to as "GlcNAc") at the bisecting position is important for the activity [*Glycobiology*, 5, 813 (1995); WO99/54342]. These reports indicate that the structure of the sugar chain plays an important role in the effector functions of human antibodies of IgG1 subclass and that it is possible to prepare an antibody having much higher effector function by modifying the structure of the sugar chain. However, structures of sugar chains are various and complex actually, and it cannot be said that an important structure for the effector function was completely identified.

Thus, the sugar chain bound to the CH2 domain of an IgG class antibody has great influence on the induction of effector functions of an antibody. As described above, some of effector functions of an antibody are exerted via interaction with FcγR present on the effector cell surface [*Annu. Rev. Immunol.*, 18, 709 (2000), *Annu. Rev. Immunol.*, 19, 275 (2001)].

It has been found that 3 different types are present in FcγR, and they are respectively called FcγRI (CD64), FcγRII (CD32) and FcγRIII (CD16). In human, FcγRII and FcγRIII are further classified into FcγRIIa and FcγRIIb, and FcγRIIIa and FcγRIIIb, respectively. FcγR is a membrane protein belonging to the immunoglobulin super family, FcγRII and FcγRIII have an α chain having an extracellular region containing two immunoglobulin-like domains, FcγRI has an α chain having an extracellular region containing three immunoglobulin-like domains, as a constituting component, and the α chain is involved in the IgG binding activity. In addition, FcγRI and FcγRIII have a γ chain or ζ chain as a constituting component which has a signal transduction function in association with the α chain [*Annu. Rev. Immunol.*, 18, 709 (2000), *Annu. Rev. Immunol.*, 19, 275 (2001)].

FcγRI is a high affinity receptor having a binding constant (hereinafter referred to as "$K_A$") value of $10^8$ to $10^9$ $M^{-1}$ and also has high binding activity for monomeric IgG [*Ann. Hematol.*, 76, 231 (1998)]. On the other hand, FcγRII and FcγRIII are low affinity receptors which have a low $K_A$ value of $10^5$ to $10^7$ $M^{-1}$ for monomeric IgG and efficiently bind to an IgG immune complex polymerized by binding to an antigen or the like [*Ann. Hematol.*, 76, 231 (1998)]. Based on its functions, FcγR is classified into an activating receptor and an inhibitory receptor [*Annu. Rev. Immunol.*, 19, 275 (2001)].

In the activating receptor, there is a sequence consisting of 19 amino acid residues, called immunoreceptor tyrosine-based activation motif (hereinafter referred to as "ITAM") in the intracellular region of the α chain or the associating γ chain or ζ chain. According to the binding of an IgG immune complex, a tyrosine kinase such as Src or Syk which interacts with ITAM is activated to induce various activation reactions.

In the inhibitory receptor, there is a sequence consisting of 13 amino acid residues, called immunoreceptor tyrosine-based inhibitory motif (hereinafter referred to as "ITIM") in the intracellular region of the α chain. When ITIM is phosphorylated via its association with the activating receptor, various reactions including activation of a phosphatase called SHIP are induced to suppress activation signal from the activation receptor.

In human, the high affinity FcγRI and the low affinity FcγRIIa and FcγRIIIa function as activating receptors. In FcγRI, an ITAM sequence is present in the intracellular region of the associated γ chain. FcγRI is expressed on macrophages, monocytes, dendritic cells, neutrophils, eosinophils and the like. FcγRIIa comprises a single α chain, and an ITAM-like sequence is present in the intracellular region. FcγRIIa is expressed on macrophages, mast cells, monocytes, dendritic cells, Langerhans cells, neutrophils, eosinophils, platelets and a part of B cells. FcγRIIIa has an ITAM sequence present in the intracellular region of the associated γ chain or ζ chain and is expressed on NK cells, macrophages, monocytes, mast cells, dendritic cells, Langerhans cells, eosinophils and the like, but is not expressed on neutrophils, B cells and T cells.

On the other hand, the low affinity receptor FcγRIIb comprises a single a chain, and the amino acid sequence in the extracellular region has homology of about 90% with FcγRIIa. However, since an ITMI sequence is present in the intracellular region, it functions as a suppressing receptor. FcγRIIb is expressed on B cells, macrophages, mast cells, monocytes, dendritic cells, Langerhans cells, basophils, neutrophils and eosinophils, but is not expressed on NK cells and T cells. FcγRIIIb comprises a single a chain, and the amino acid sequence in the extracellular region has a homology of about 95% with FcγRIIIa. However, it is specifically expressed on neutrophils as a glycosylphosphatidylinositol (hereinafter referred to as "GPI")—anchored membrane protein. FcγRIIIb binds to an IgG immune complex but cannot activate cells by itself, and it is considered to function via its association with a receptor having an ITAM sequence such as FcγRIIa. Thus, in vivo effector functions of IgG class antibodies are obtained as the result of complex interaction with activating and suppressing FcγRs expressed on various effector cells.

It is considered that ADCC activity as one of the effector functions of IgG class antibodies is generated as a result of activation of effector cells such as NK cells, neutrophils, monocytes and macrophages, and among these, NK cells play an important role [*Blood*, 76, 2421 (1990), *Trends in Immunol.*, 22, 633 (2001), *Int. Rev. Immunol.*, 20, 503 (2001)].

FcγR expressed on NK cells is FcγRIIIa. Accordingly, it is considered that the ADCC activity can be enhanced by enhancing the activation signal from FcγRIIIa expressed on the NK cells.

As Fc fusion protein, Etanercept (trade name: Enbrel, manufactured by Immunex) (U.S. Pat. No. 5,605,690) and Alefacept (trade name: Amevive, manufactured by Biogen) (U.S. Pat. No. 5,914,111) and the like are known. Also, it is known that it has no ADCC activity when CH2 domain of an antibody is absent.

SUMMARY OF THE INVENTION

The present invention relates to the following (1) to (48).
(1) A method for enhancing a binding activity of an antibody composition to Fcγ receptor IIIa, which comprises modifying a complex N-glycoside-linked sugar chain which is bound to the Fc region of an antibody molecule.
(2) The method according to (1), wherein the modification of a complex N-glycoside-linked sugar chain which is bound to the Fc region of an antibody molecule is to bind a sugar chain in which 1-position of fucose is not bound to 6-position of N-acetylglucosamine in the reducing end through α-bond in the complex N-glycoside-linked sugar chain to the Fc region in the antibody molecule.
(3) The method according to (1) or (2), wherein the sugar chain is synthesized by a cell in which the activity of a protein relating to modification of a sugar chain in which fucose is bound to N-acetylglucosamine in the reducing end in the complex N-glycoside-linked sugar chain is decreased or deleted.
(4) The method according to (3), wherein the protein relating to modification of a sugar chain in which fucose is bound to N-acetylglucosamine in the reducing end in the complex N-glycoside-linked sugar chain is selected from the group consisting of the following (a), (b) and (c):
   (a) a protein relating to synthesis of an intracellular sugar nucleotide, GDP-fucose;
   (b) a protein relating to modification of a sugar chain in which 1-position of fucose is bound to 6-position of N-acetylglucosamine in the reducing end through α-bond in a complex N-glycoside-linked sugar chain;
   (c) a protein relating to transport of an intracellular sugar nucleotide, GDP-fucose to the Golgi body.
(5) The method according to (3) or (4), wherein the cell is resistant to a lectin which recognizes a sugar chain structure in which 1-position of fucose is bound to 6-position of N-acetylglucosamine in the reducing end through α-bond in a complex N-glycoside-linked sugar chain.
(6) The method according to any one of (3) to (5), wherein the cell is resistant to at least one lectin selected from the group consisting of the following (a) to (d):
   (a) a *Lens culinaris* lectin;
   (b) a *Pisum sativum* lectin;
   (c) a *Vicia faba* lectin;
   (d) an *Aleuria aurantia* lectin.
(7) The method according to any one of (3) to (6), wherein the cell is selected from the group consisting of a yeast, an animal cell, an insect cell and a plant cell.
(8) The method according to any one of (3) to (7), wherein the cell is selected from the group consisting of the following (a) to (i):
   (a) a CHO cell derived from a Chinese hamster ovary tissue;

(b) a rat myeloma cell line YB2/3HL.P2.G11.16Ag.20 cell;
(c) a BHK cell derived from a Syrian hamster kidney tissue;
(d) a mouse myeloma cell line NS0 cell;
(e) a mouse myeloma cell line SP2/0-Ag14 cell;
(f) a hybridoma cell;
(g) a human leukemic cell line Namalwa cell;
(h) an embryonic stem cell;
(i) a fertilized egg cell.
(9) The method according to any one of (1) to (8), wherein the antibody molecule is selected from the group consisting of the following (a) to (d):
(a) a human antibody;
(b) a humanized antibody;
(c) an antibody fragment comprising the Fc region of (a) or (b);
(d) a fusion protein comprising the Fc region of (a) or (b).
(10) The method according to any one of (1) to (9), wherein the antibody molecule belongs to an IgG class.
(11) The method according to any one of (1) to (10), wherein, in the complex N-glycoside-linked sugar chain which is bound to the Fc region of an antibody molecule, the ratio of a sugar chain in which 1-position of fucose is not bound to 6-position of N-acetylglucosamine in the reducing end through α-bond is 20% or more of total complex N-glycoside-linked sugar chains.
(12) A method for enhancing an antibody-dependent cell-mediated cytotoxic activity of an antibody composition, which comprises using the method according to any one of (1) to (11).
(13) A process for producing an antibody composition having an enhanced binding activity to Fcγ receptor IIIa, which comprises modifying a complex N-glycoside-linked sugar chain which is bound to the Fc region of an antibody molecule.
(14) The process according to (13), wherein the modification of a complex N-glycoside-linked sugar chain which is bound to the Fc region of an antibody molecule is to bin a sugar chain in which 1-position of fucose is not bound to 6-position of N-acetylglucosamine in the reducing end through α-bond in the complex N-glycoside-linked sugar chain to the Fc region in the antibody molecule.
(15) The process according to (13) or (14), wherein the sugar chain is synthesized by a cell in which the activity of a protein relating to modification of a sugar chain in which fucose is bound to N-acetylglucosamine in the reducing end in the complex N-glycoside-linked sugar chain is decreased or deleted.
(16) The process according to (15), wherein the protein relating to modification of a sugar chain in which fucose is bound to N-acetylglucosamine in the reducing end in the complex N-glycoside-linked sugar chain is selected from the group consisting of the following (a), (b) and (c):
(a) a protein relating to synthesis of an intracellular sugar nucleotide, GDP-fucose;
(b) a protein relating to modification of a sugar chain in which 1-position of fucose is bound to 6-position of N-acetylglucosamine in the reducing end through α-bond in a complex N-glycoside-linked sugar chain;
(c) a protein relating to transport of an intracellular sugar nucleotide, GDP-fucose to the Golgi body.
(17) The process according to (15) or (16), wherein the cell is resistant to a lectin which recognizes a sugar chain structure in which 1-position of fucose is bound to 6-position of N-acetylglucosamine in the reducing end through α-bond in a complex N-glycoside-linked sugar chain.
(18) The process according to any one of (15) to (17), wherein the cell is resistant to at least one lectin selected from the group consisting of the following (a) to (d):
(a) a *Lens culinaris* lectin;
(b) a *Pisum sativum* lectin;
(c) a *Vicia faba* lectin;
(d) an *Aleuria aurantia* lectin.
(19) The process according to any one of (15) to (18), wherein the cell is selected from the group consisting of a yeast, an animal cell, an insect cell and a plant cell.
(20) The process according to any one of (15) to (19), wherein the cell is selected from the group consisting of the following (a) to (i):
(a) a CHO cell derived from a Chinese hamster ovary tissue;
(b) a rat myeloma cell line YB2/3HL.P2.G11.16Ag.20 cell;
(c) a BHK cell derived from a Syrian hamster kidney tissue;
(d) a mouse myeloma cell line NS0 cell;
(e) a mouse myeloma cell line SP2/0-Ag14 cell;
(f) a hybridoma cell;
(g) a human leukemic cell line Namalwa cell;
(h) an embryonic stem cell;
(i) a fertilized egg cell.
(21) The process according to any one of (13) to (20), wherein the antibody molecule is selected from the group consisting of the following (a) to (d):
(a) a human antibody;
(b) a humanized antibody;
(c) an antibody fragment comprising the Fc region of (a) or (b);
(d) a fusion protein comprising the Fc region of (a) or (b).
(22) The process according to any one of (13) to (21), wherein the antibody molecule belongs to an IgG class.
(23) The method according to any one of (13) to (22), wherein, in the complex N-glycoside-linked sugar chain which is bound to the Fc region of an antibody molecule, the ratio of a sugar chain in which 1-position of fucose is not bound to 6-position of N-acetylglucosamine in the reducing end through α-bond is 20% or more of total complex N-glycoside-linked sugar chains.
(24) A process for producing an antibody composition having an increased antibody-dependent cell-mediated cytotoxic activity, which comprises using the process according to (12).
(25) An antibody composition produced by the process according to any one of (13) to (24).
(26) A method for detecting the ratio of a sugar chain in which fucose is not bound to N-acetylglucosamine in the reducing end in the sugar chain among total complex N-glycoside-linked sugar chains bound to the Fc region in an antibody composition, which comprises: reacting an antigen with a tested antibody composition to form a complex of the antigen and the antibody composition; contacting the complex with an Fcγ receptor IIIa to measure the binding activity to the Fcγ receptor IIIa; and detecting the ratio of a sugar chain in a standard antibody composition with a standard curve showing the binding activity to the Fcγ receptor IIIa.
(27) A method for detecting the antibody-dependent cell-mediated cytotoxic activity in an antibody composition, which comprises: reacting an antigen with a tested antibody composition to form a complex of the antigen and the antibody composition; contacting the complex with an Fcγ receptor IIIa to measure the binding activity to the Fcγ receptor IIIa; and detecting the ratio of a sugar chain in a standard antibody composition with a standard curve showing the binding activity to the Fcγ receptor IIIa.

(28) A method for detecting the ratio of a sugar chain in which fucose is not bound to N-acetylglucosamine in the reducing end in the sugar chain among total complex N-glycoside-linked sugar chains bound to the Fc region in an antibody composition, which comprises: contacting a tested antibody composition with a Fcγ receptor IIIa to measure the binding activity of the antibody composition to the Fcγ receptor IIIa; and detecting the ratio of a sugar chain in a standard antibody composition with a standard curve showing the binding activity to the Fcγ receptor IIIa.

(29) A method for detecting the antibody-dependent cell-mediated cytotoxic activity in an antibody composition, which comprises: contacting a tested antibody composition with a Fcγ receptor IIIa to measure the binding activity of the antibody composition to the Fcγ receptor IIIa; and detecting the ratio of a sugar chain in a standard antibody composition with a standard curve showing the binding activity to the Fcγ receptor IIIa.

(30) An Fc fusion protein composition produced by using a cell resistant to a lectin which recognizes a sugar chain structure in which 1-position of fucose is bound to 6-position of N-acetylglucosamine in the reducing end through α-bond in a complex N-glycoside-linked sugar chain.

(31) The Fc fusion protein composition according to (30), wherein the cell is selected from the group consisting of the following (a), (b) and (c):

(a) an enzyme protein relating to synthesis of an intracellular sugar nucleotide, GDP-fucose;

(b) an enzyme protein relating to modification of a sugar chain in which 1-position of fucose is bound to 6-position of N-acetylglucosamine in the reducing end through α-bond in a complex N-glycoside-linked sugar chain;

(c) a protein relating to transport of an intracellular sugar nucleotide, GDP-fucose to the Golgi body, wherein the activity of the protein is decreased or deleted.

(32) The Fc fusion protein composition according to (30) or (31), wherein the cell is resistant to at least one lectin selected from the group consisting of the following (a) to (d):

(a) a *Lens culinaris* lectin;
(b) a *Pisum sativum* lectin;
(c) a *Vicia faba* lectin;
(d) an *Aleuria aurantia* lectin.

(33) The Fc fusion protein composition according to any one of (30) to (32), wherein the cell is a cell into which a gene encoding an Fc fusion protein is introduced.

(34) The Fc fusion protein composition according to (33), wherein the Fc is derived from an IgG class of an antibody molecule.

(35) The Fc fusion protein composition according to any one of (30) to (34), wherein the cell is selected from the group consisting of a yeast, an animal cell, an insect cell and a plant cell.

(36) The Fc fusion protein composition according to any one of (30) to (35), wherein the cell is a mouse myeloma cell.

(37) The Fc fusion protein composition according to (36), wherein the mouse myeloma cell is NS0 cell or SP2/0-Ag14 cell.

(38) The Fc fusion protein composition according to any one of (30) to (37), wherein the cell is selected from the group consisting of the following (a) to (g):

(a) a CHO cell derived from a Chinese hamster ovary tissue;

(b) a rat myeloma cell line YB2/3HL.P2.G11.16Ag.20 line;

(c) a BHK cell derived from a Syrian hamster kidney tissue;
(d) an antibody-producing hybridoma cell;
(e) a human leukemic cell line Namalwa cell;
(f) an embryonic stem cell;
(g) a fertilized egg cell.

(39) An Fc fusion protein composition comprising an Fc fusion protein having an complex N-glycoside-linked sugar chain at the Fc region of an antibody molecule, wherein the ratio of a sugar chain in which fucose is not bound to N-acetylglucosamine in the reducing end in the sugar chain is 20% or more of total complex N-glycoside-linked sugar chains which are bound to the Fc region in the composition.

(40) The Fc fusion protein composition according to (39), wherein the sugar chain in which fucose is not bound is a sugar chain in which 1-position of fucose is not bound to 6-position of N-acetylglucosamine in the reducing end in the complex N-glycoside-linked sugar chain through α-bond.

(41) The Fc fusion protein composition according to (39) or (40), wherein the antibody molecule belongs to an IgG class.

(42) The Fc fusion protein composition according to any one of (30) to (41), wherein the Fc fusion protein composition is Fc-fused fibroblast growth factor-8.

(43) A cell which produces the Fc fusion protein composition according to any one of (30) to (42).

(44) The cell according to (43), which is selected from the group consisting of a yeast, an animal cell, an insect cell and a plant cell.

(45) The cell according to (43) or (44), which is a mouse myeloma cell.

(46) The cell according to (45), wherein the mouse myeloma cell is NS0 cell or SP2/0-Ag14 cell.

(47) The cell according to any one of (43) to (46), which is selected from the group consisting of the following (a) to (g):

(a) a CHO cell derived from a Chinese hamster ovary tissue;

(b) a rat myeloma cell line YB2/3HL.P2.G11.16Ag.20 line;

(c) a BHK cell derived from a Syrian hamster kidney tissue;
(d) an antibody-producing hybridoma cell;
(e) a human leukemic cell line Namalwa cell;
(f) an embryonic stem cell;
(g) a fertilized egg cell.

(48) A process for producing an Fc fusion protein composition, which comprises culturing the cell according to any one of (43) to (47) in a medium to form and accumulate an Fc fusion protein composition in the culture, and recovering the Fc fusion protein composition from the culture.

BRIEF DESCRIPTION OF THE DRAWINGS

FIG. 1 shows photographs of electrophoresis patterns of SDS-PAGE of five kinds of purified anti-GD3 chimeric antibodies (using gradient gel from 4 to 15%).

FIG. 6 shows results of ADCC activities using an effector cell of each donor.

FIG. 14 shows construction of plasmids CHFT8d-pCR2.1 and YBFT8d-pCR2.1.

CCR4-LCA, the clone CHO/CCR4-AAL and the clone CHO/CCR4-PHA, respectively.

Figure 20:
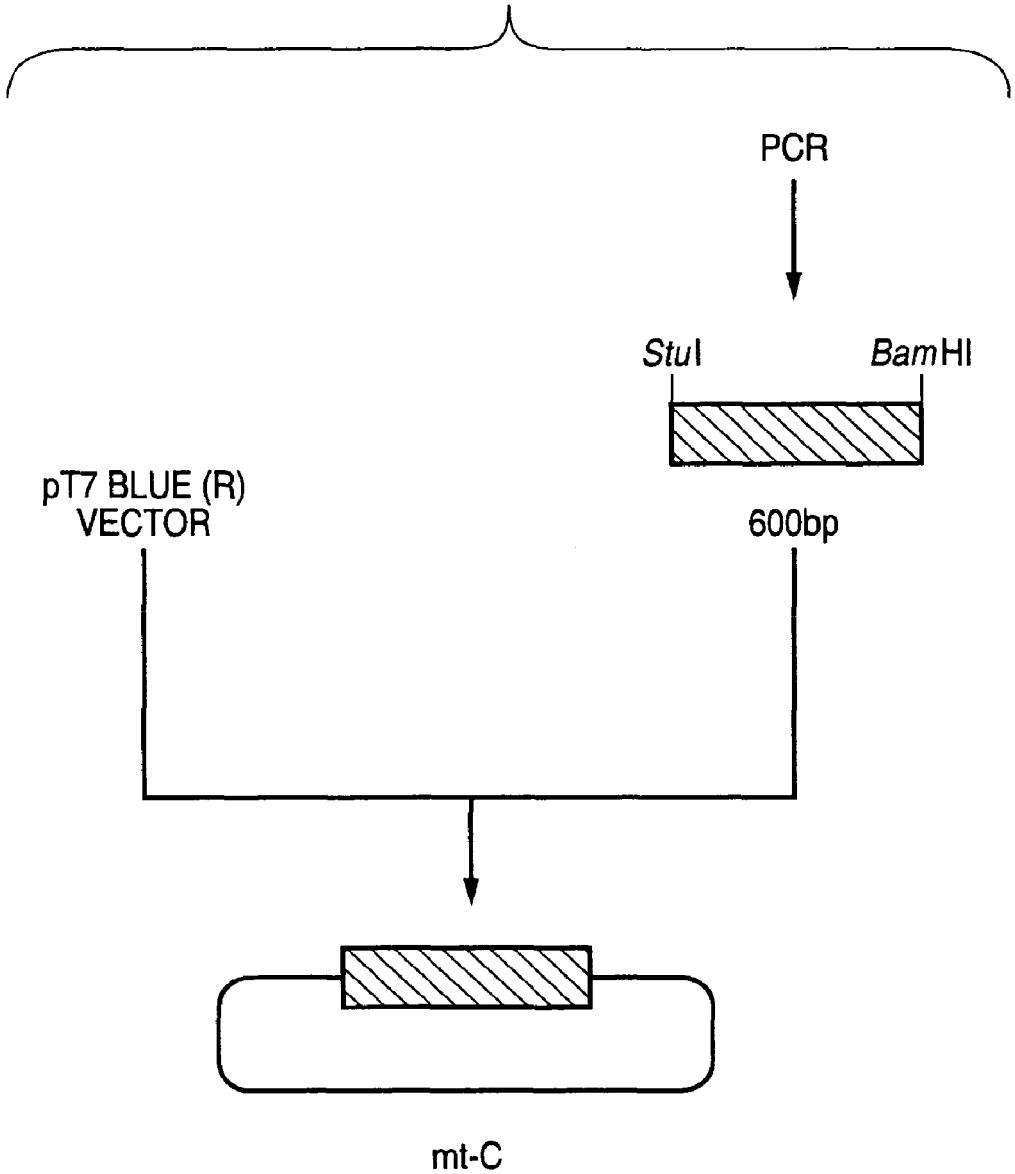

FIG. 20 shows the 1st step of construction of an expression vector of CHO cell-derived GMD (6 steps in total).

Figure 21:
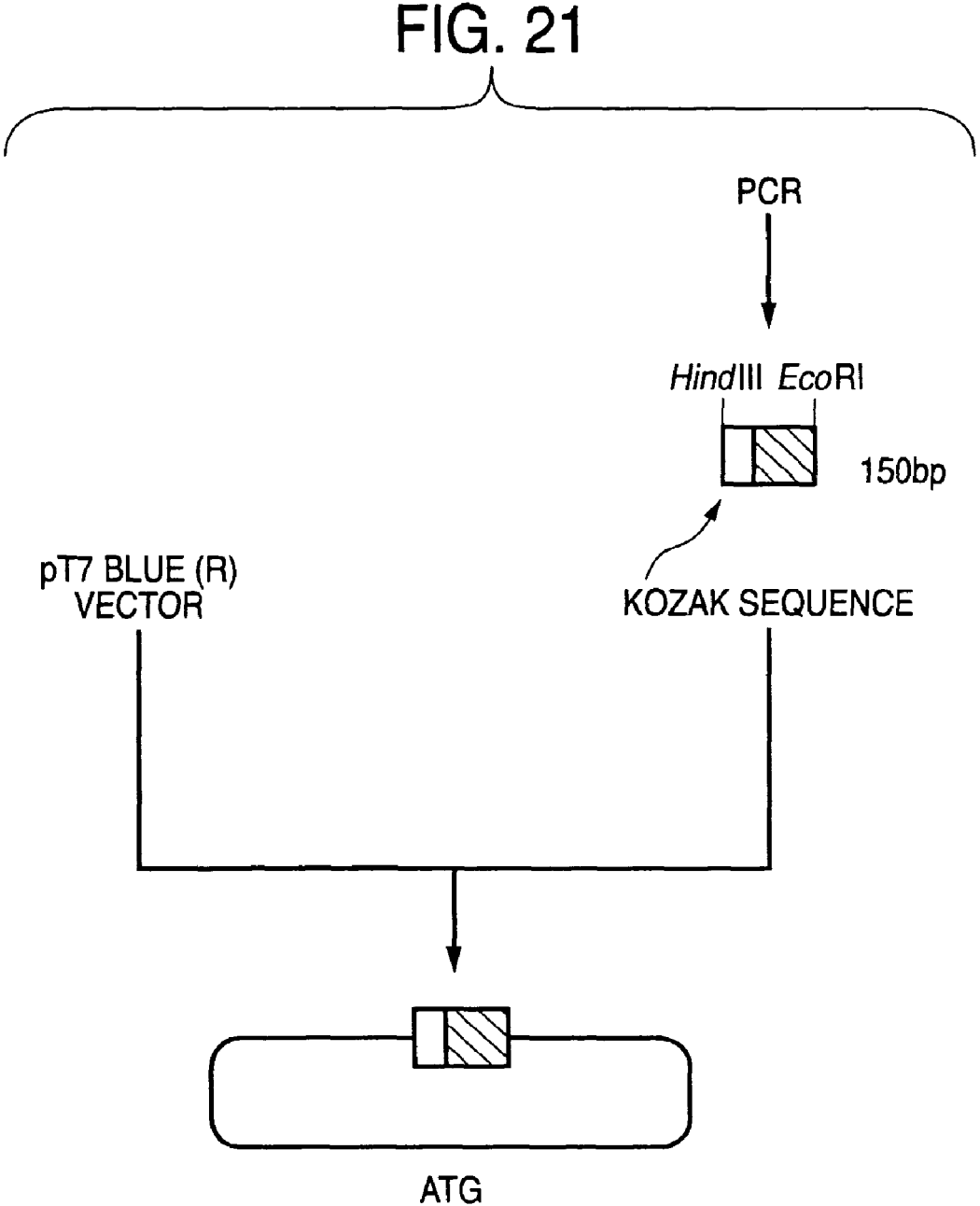

FIG. 21 shows the 2nd step of construction of the expression vector of CHO cell-derived GMD (6 steps in total).

Figure 22:
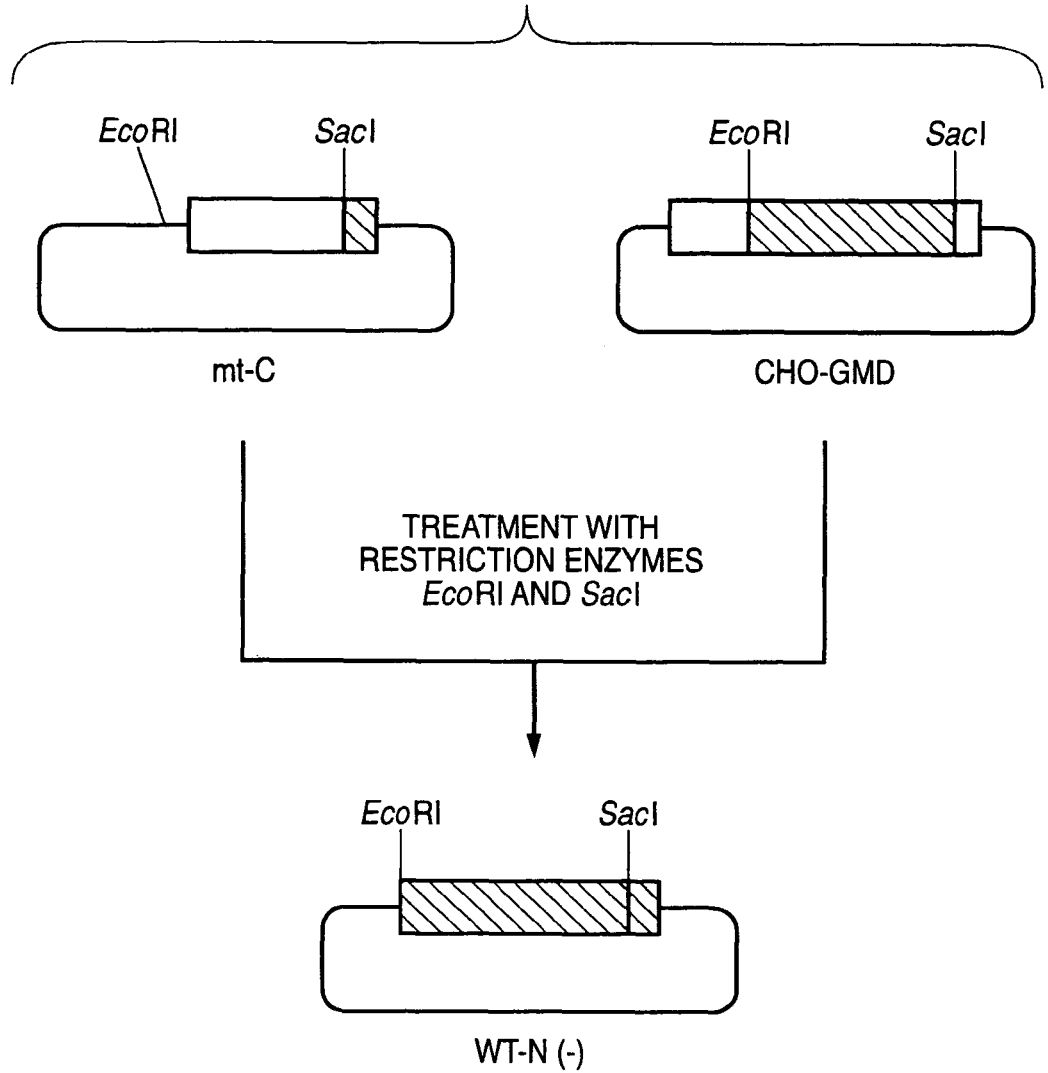

FIG. 22 shows the 3rd step of construction of the expression vector of CHO cell-derived GMD (6 steps in total).

Figure 23:
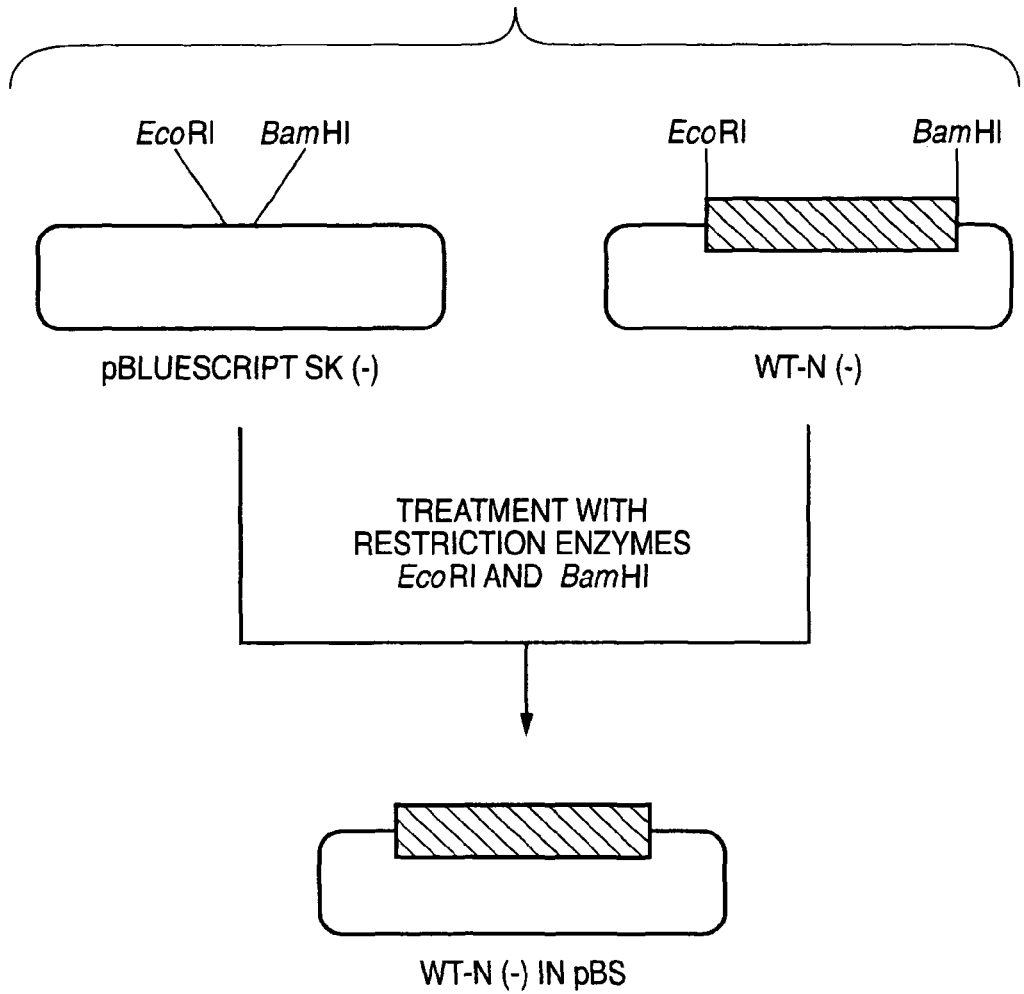

FIG. 23 shows the 4th step of construction of the expression vector of CHO cell-derived GMD (6 steps in total).

Figure 24:
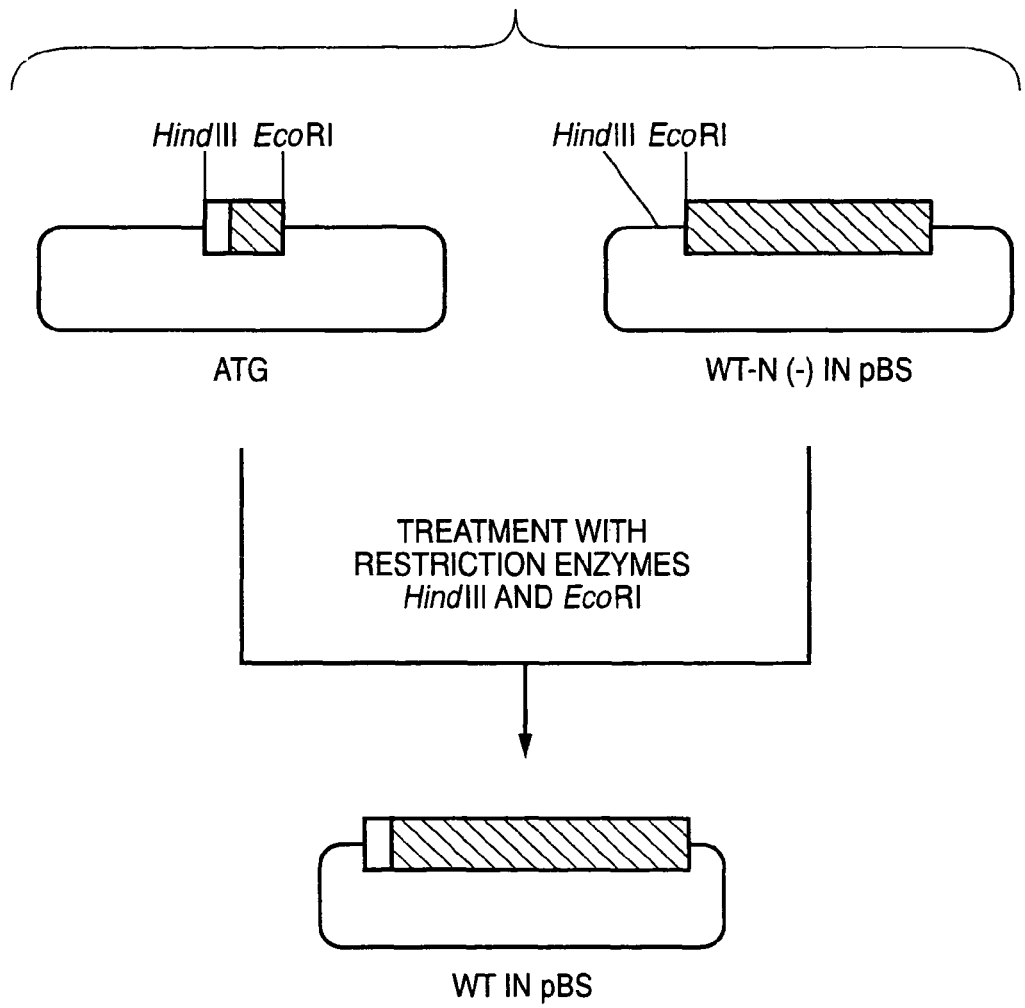

FIG. 24 shows the 5th step of construction of the expression vector of CHO cell-derived GMD (6 steps in total).

Figure 25:
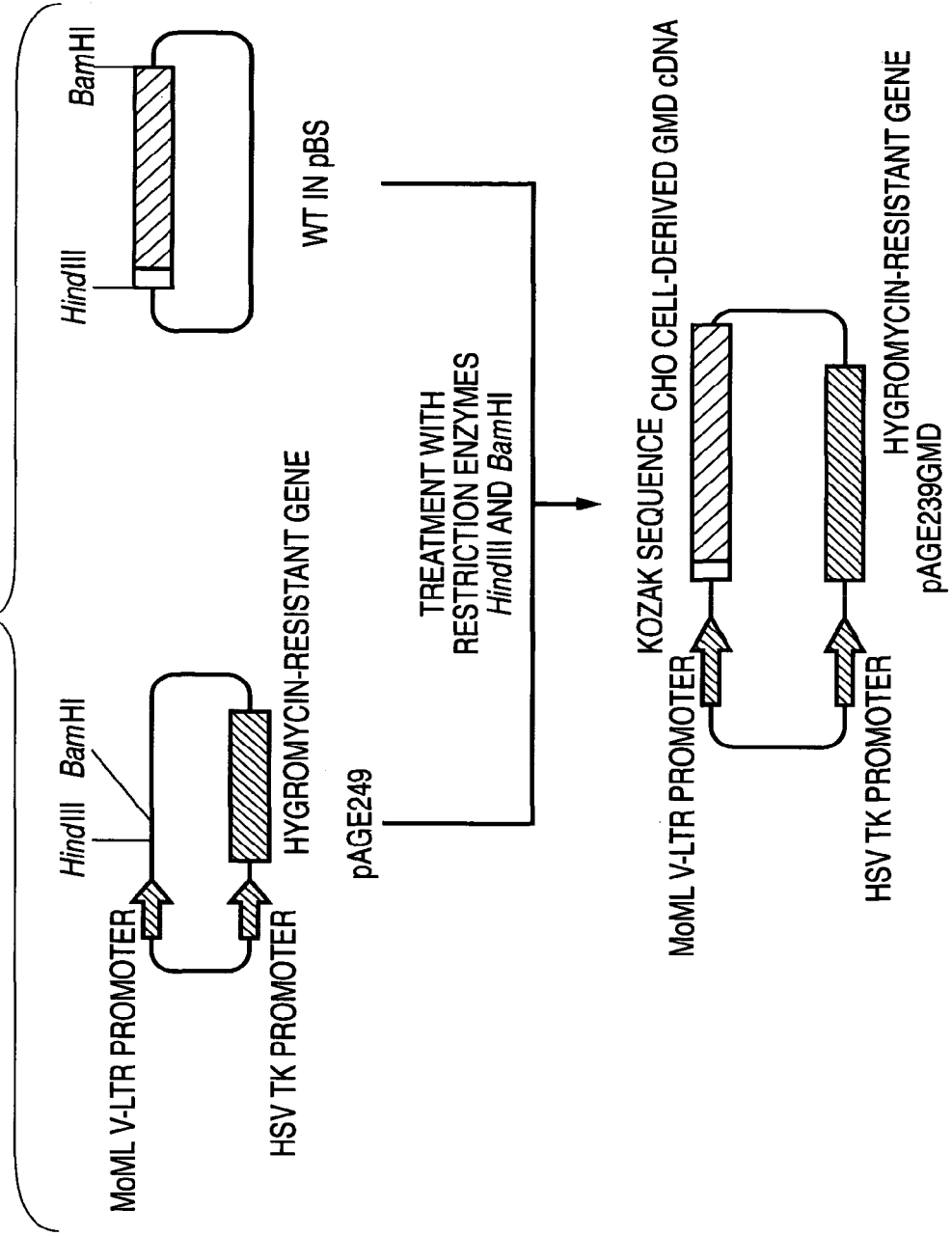

FIG. 25 shows the 6th step of construction of the expression vector of CHO cell-derived GMD (6 steps in total).

Figure 26:
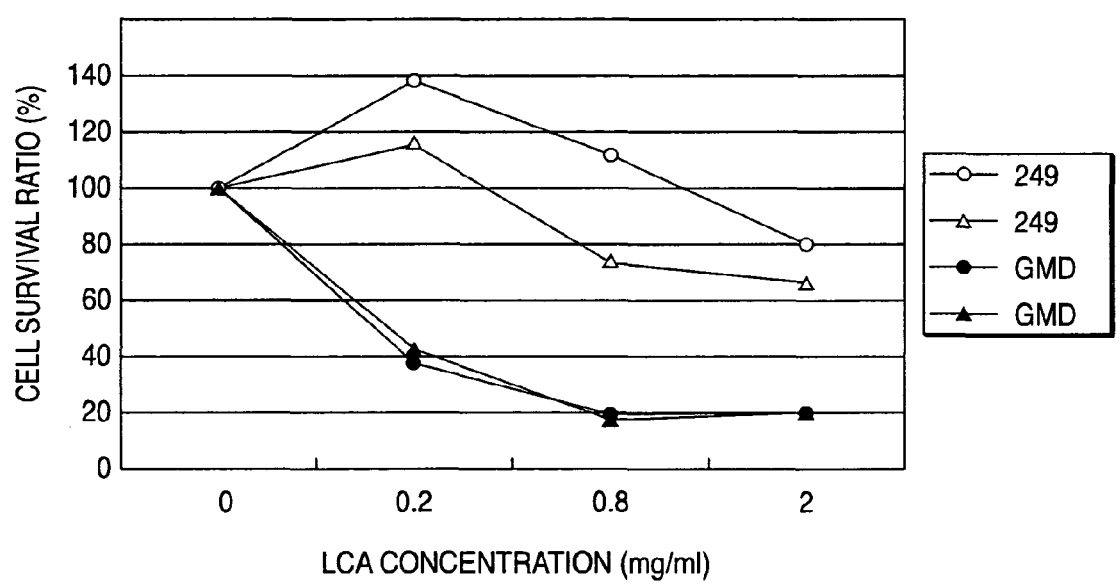

FIG. 26 shows resistance of GMD-expressed clone CHO/CCR4-LCA for LCA lectin. The measurement was carried out twice by defining the survival rate of a group of cells cultured without adding LCA lectin as 100%. In the drawing, "249" shows the survival rate of the clone CHO/CCR4-LCA introduced with an expression vector to LCA lectin. GMD shows resistance of the clone CHO/CCR4-LCA introduced with a GMD expression vector pAGE249GMD to LCA lectin.

Figure 27:
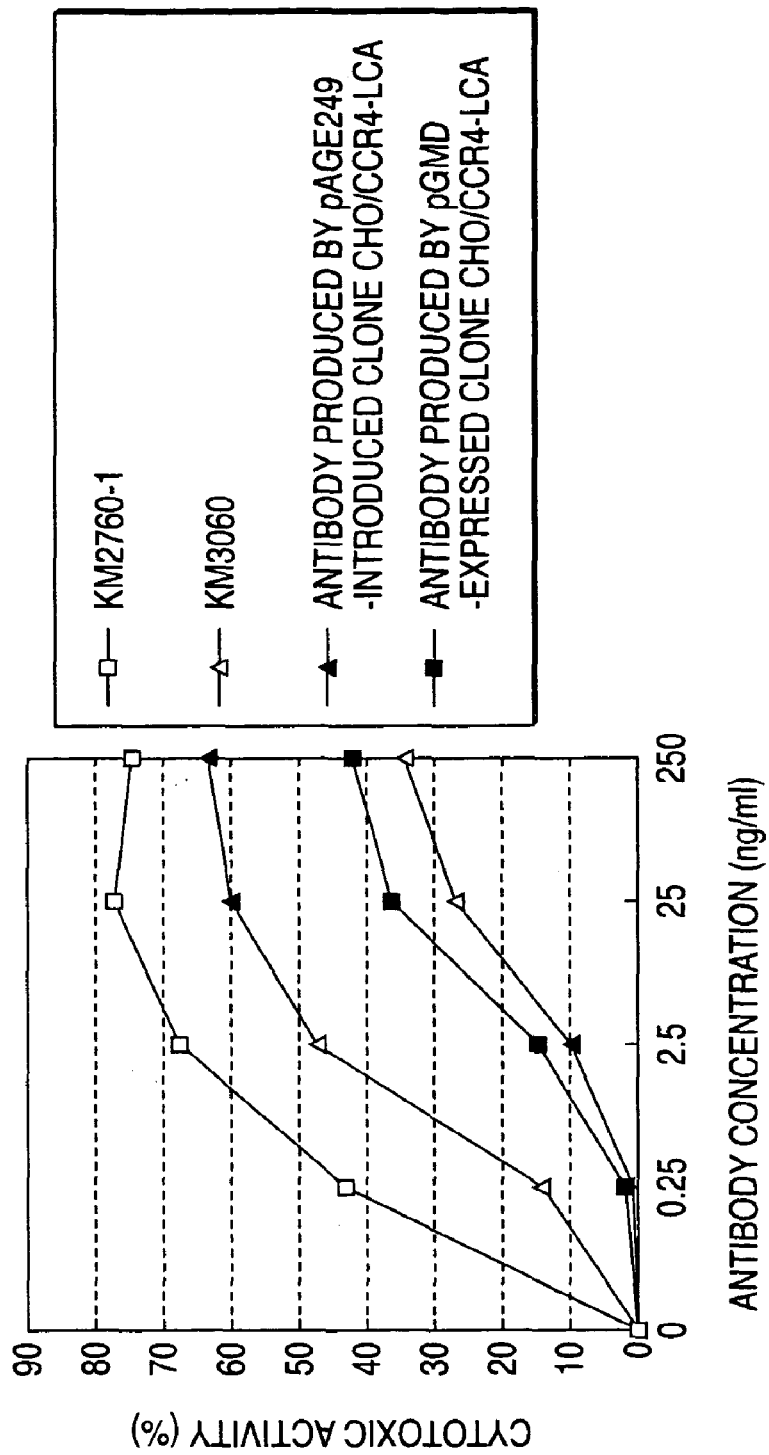
FIG. 27A, FIG. 27B, FIG. 27C and FIG. 27D show results of analyses of antibodies produced by the clone 5-03, the clone CHO/

FIG. 27 shows ADCC activities of an anti-CCR4 chimeric antibody produced by cells of GMD-expressed clone CHO/CCR4-LCA. The ordinate and the abscissa show the cytotoxic activity and the antibody concentration, respectively.

Figure 28:
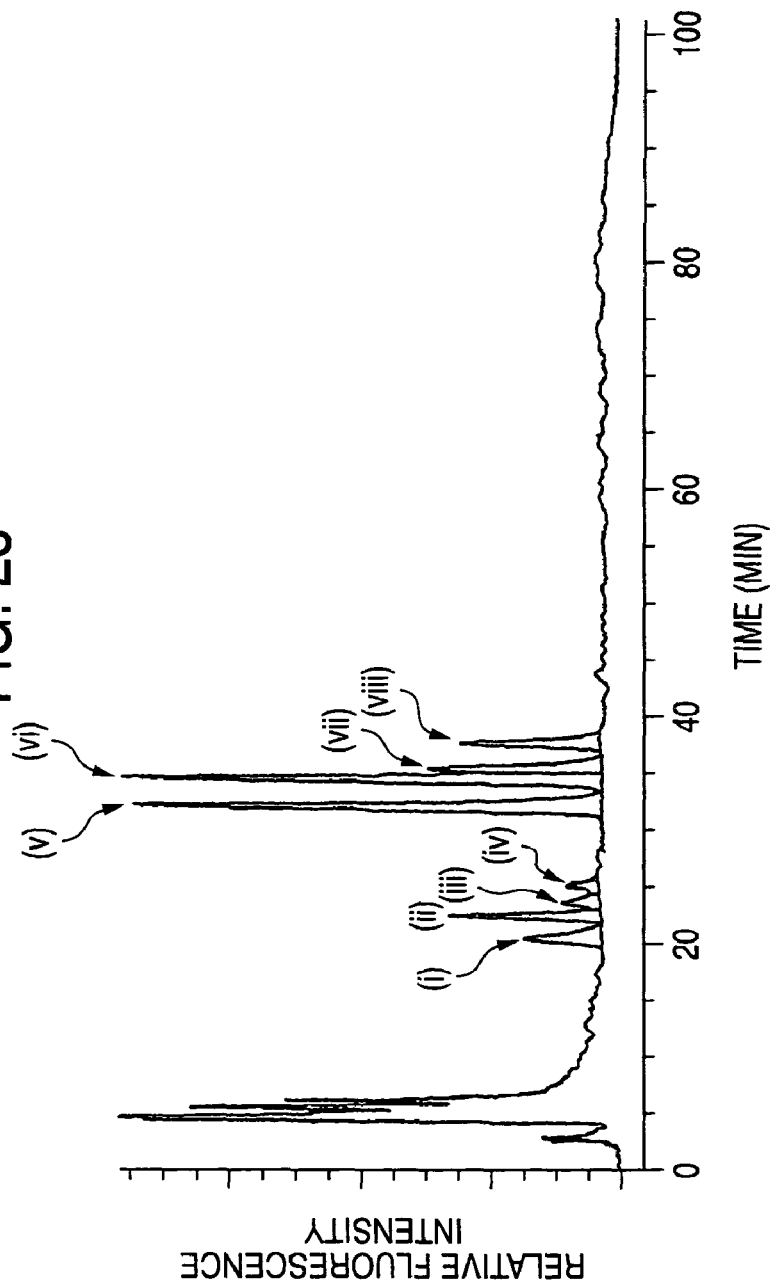

FIG. 28 shows elution patterns of PA-treated sugar chains prepared from an anti-CCR4 human chimeric antibody purified from GMD gene-expressed clone CHO/CCR4-LCA, obtained by analyzing them with reverse phase HPLC. The ordinate and the abscissa show the relative fluorescence intensity and the elution time, respectively.

Figure 29:
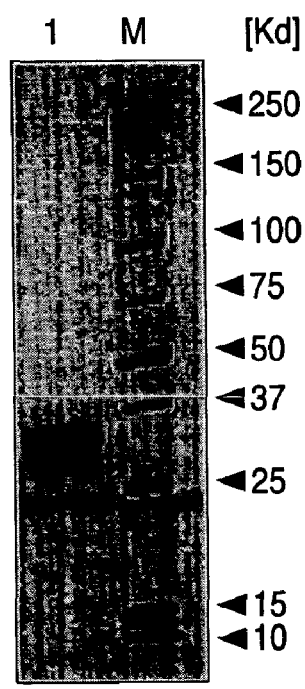

FIG. 29 shows a photograph of SDS-PAGE (using 4 to 15% gradient gel) electrophoresis pattern of purified shFcγRIIIa under reduced conditions. Lane 1 and lane M show electrophoresis patterns of shFcγRIIIa and molecular weight markers, respectively.

Figure 30:
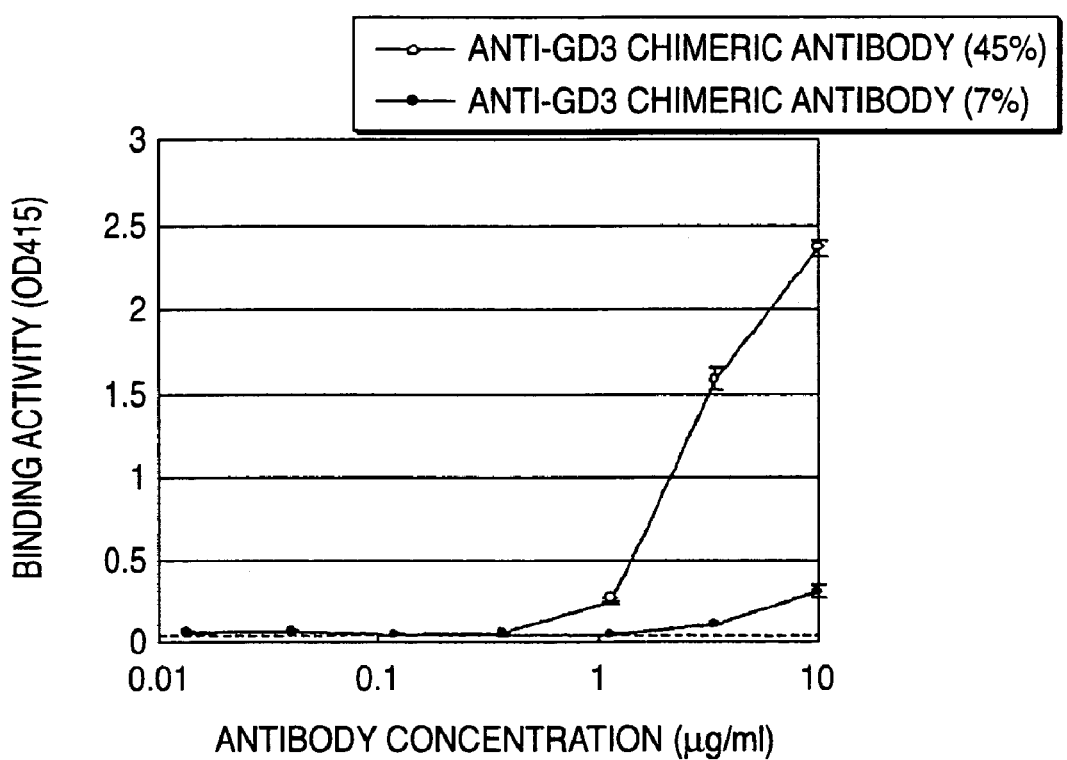

FIG. 30 shows binding activities of various anti-GD3 chimeric antibodies to shFcγRIIIa. The ordinate and abscissa show the cytotoxic activity and the antibody concentration, respectively. "○" and "●" show the activities of anti-GD3 chimeric antibody (45%) and anti-GD3 chimeric antibody (7%), respectively.

Figure 31:
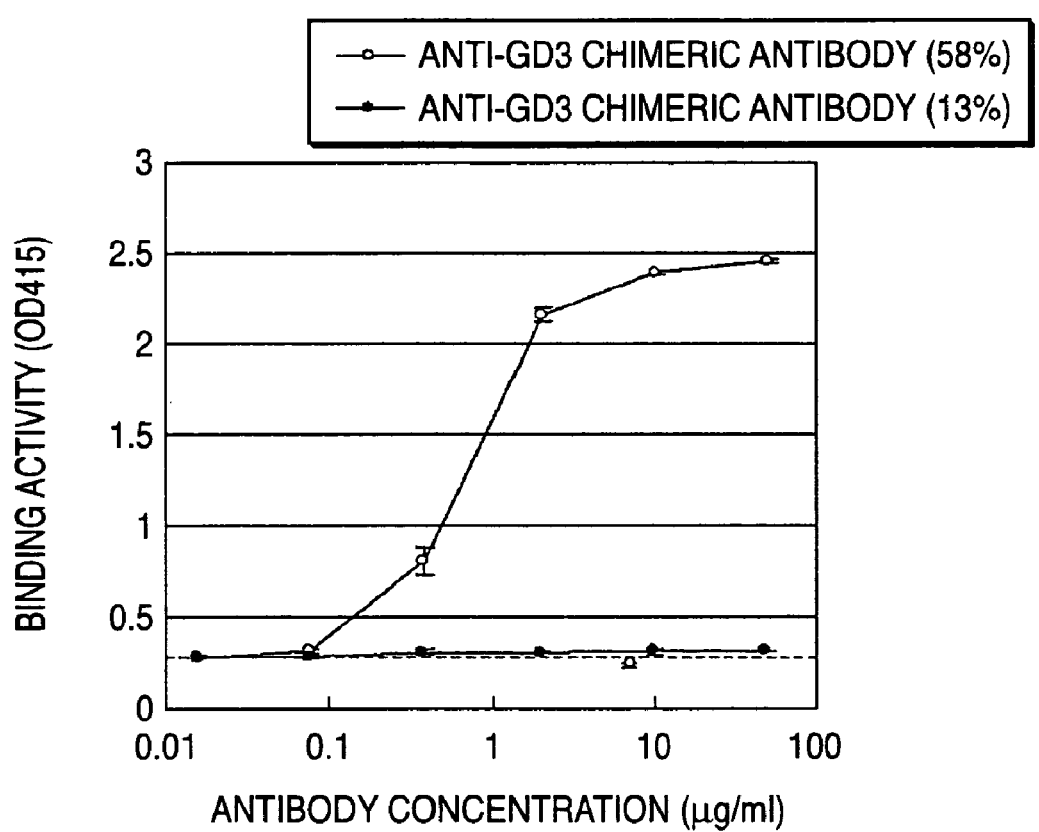

FIG. 31 shows binding activities of various anti-fibroblast growth factor-8 (FGF-8) chimeric antibodies to shFcγRIIIa. The ordinate and abscissa show the cytotoxic activity and the antibody concentration, respectively. "○" and "●" show the activities of anti-FGF-8 chimeric antibody (58%) and anti-FGF-8 chimeric antibody (13%), respectively.

Figure 32A:
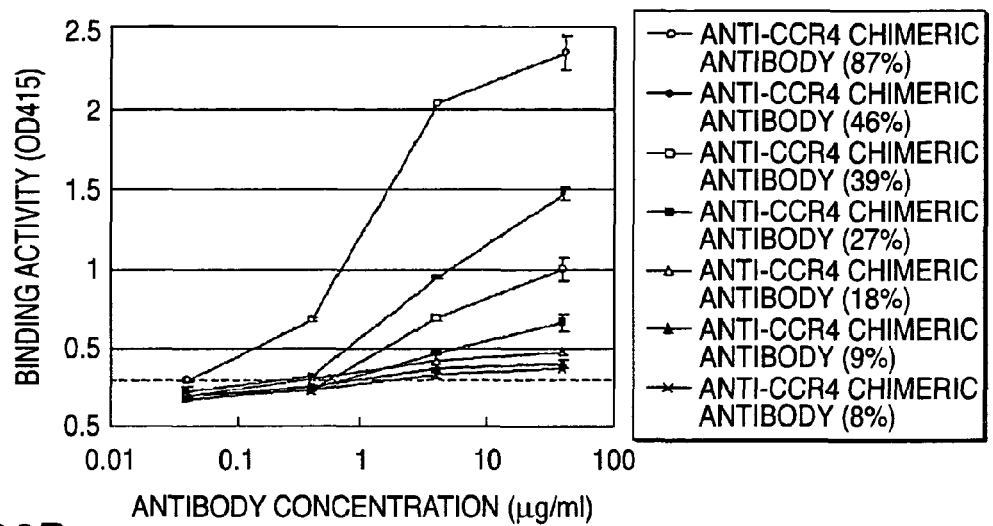
Figure 32B:
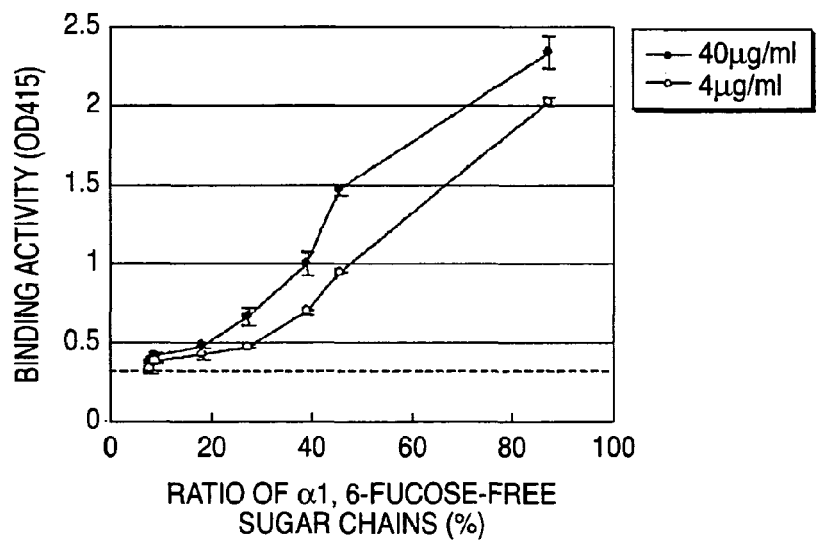

FIG. 32 shows binding activities of various anti-CCR4 chimeric antibodies to shFcγRIIIa. In FIG. 32A, the ordinate and abscissa show the cytotoxic activity and the antibody concentration, respectively. "○", "●", "□", "■", "Δ", "▲" and "x" show the activities of anti-CCR4 chimeric antibody (87%), anti-CCR4 chimeric antibody (46%), anti-CCR4 chimeric antibody (39%), anti-CCR4 chimeric antibody (27%), anti-CCR4 chimeric antibody (18%), anti-CCR4 chimeric antibody (9%) and anti-CCR4 chimeric antibody (8%), respectively. In FIG. 32B, the ordinate and abscissa show the cytotoxic activity and the ratio of a sugar chain in which 1-position of fucose is not bound to 6-position of N-acetylglucosamine in the reducing end through α-bond, respectively. "●" and "○" show the activities at 40 μg/mL and 4 μg/mL, respectively.

Figure 33:
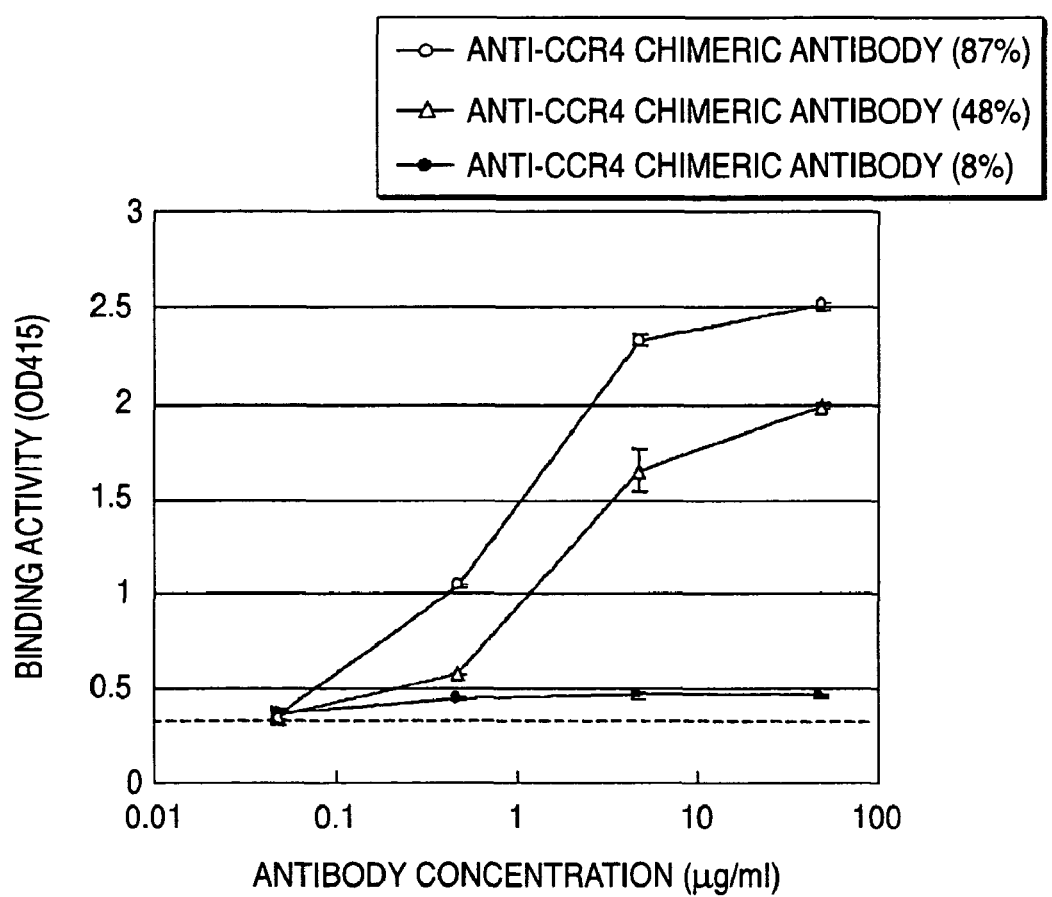

FIG. 33 shows binding activities of various anti-CCR4 chimeric antibodies to shFcγRIIIa. The ordinate and abscissa show the cytotoxic activity and the antibody concentration, respectively. "○", "Δ" and "●" show the activities of anti-CCR4 chimeric antibody (87%), anti-CCR4 chimeric antibody (48%) and anti-CCR4 chimeric antibody (8%), respectively.

Figure 34:
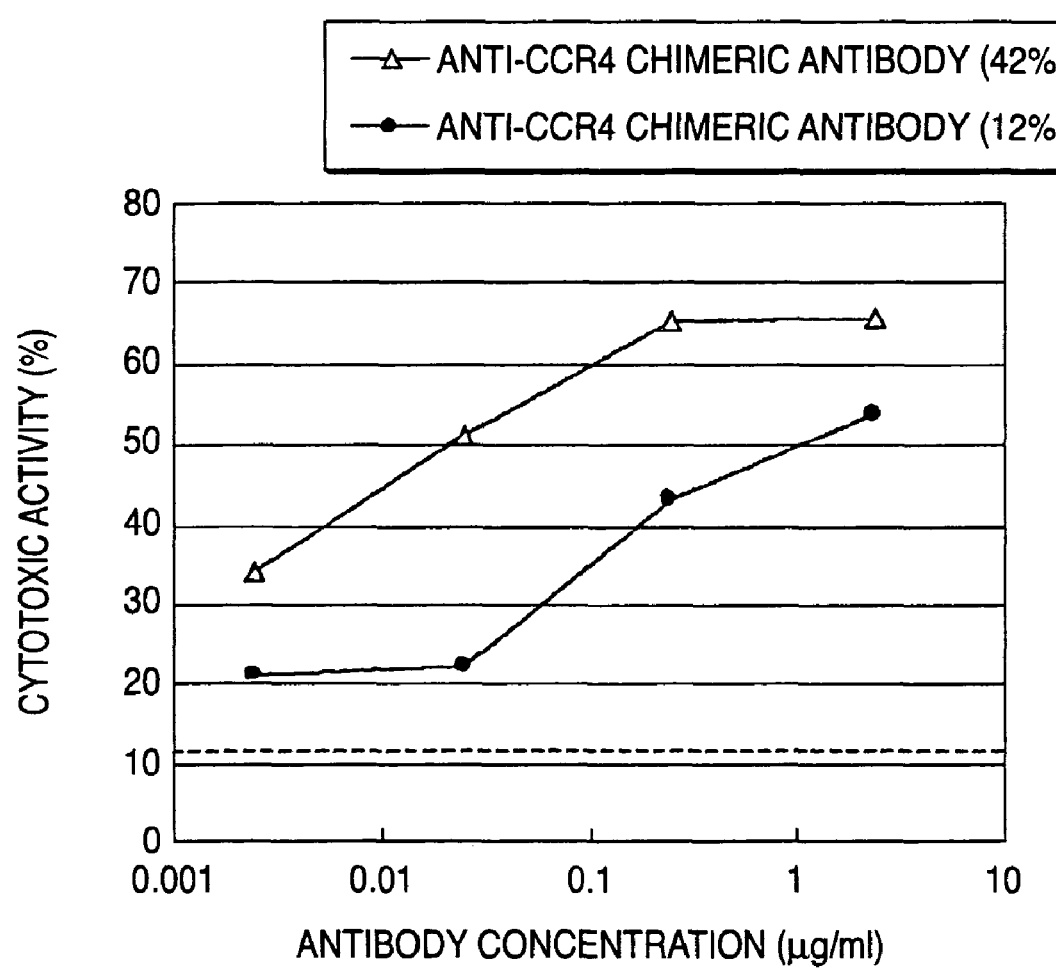

FIG. 34 shows ADCC activities of various anti-GD3 chimeric antibodies to human myeloma cell line G-361. The ordinate and abscissa show the cytotoxic activity and the antibody concentration, respectively. "▲" and "●" show the activities of anti-GD3 chimeric antibody (42%) and anti-GD3 chimeric antibody (7%), respectively.

Figure 35:
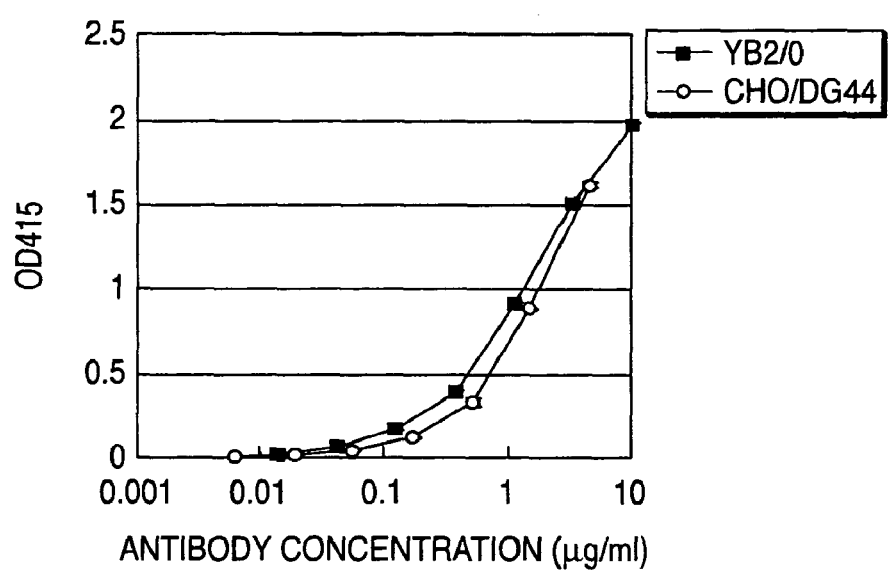

FIG. 35 shows results of measurement of binding activities of FGF-8/Fc fusion proteins to KM1334. The ordinate and abscissa show the binding activity and the antibody concentration, respectively. "■" and "○" show the activities of FGF-8/Fc fusion proteins produced by the cell line YB2/0 and the cell line CHO/DG44, respectively, as the host cell.

Figure 36:
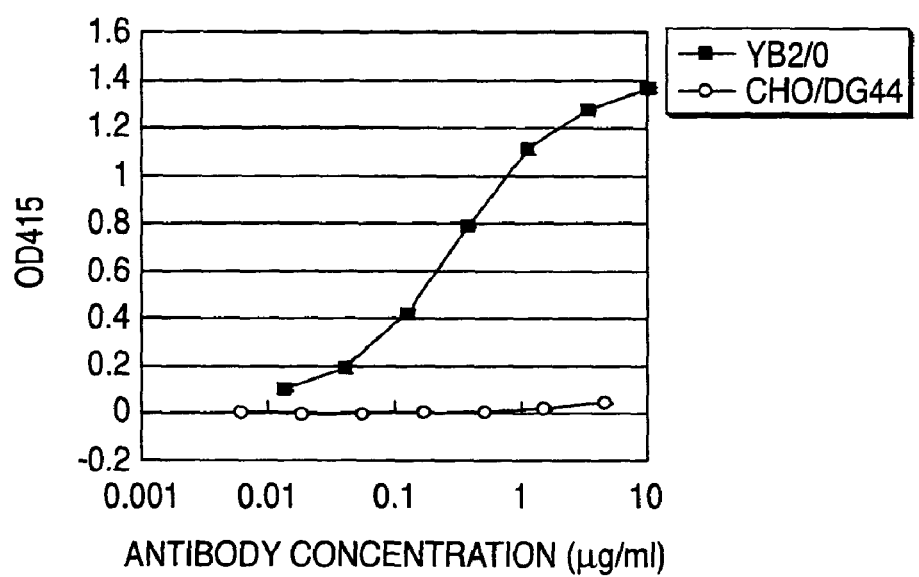

FIG. 36 shows results of measurement of binding activities of various FGF-8/Fc fusion proteins to shFcγRIIIa (V). The ordinate and abscissa show the binding activity and the antibody concentration, respectively. "■" and "○" show the activities of FGF8/Fc fusion proteins produced by the cell line YB2/0 and the cell line CHO/DG44, respectively, as the host cell.

Figure 37:
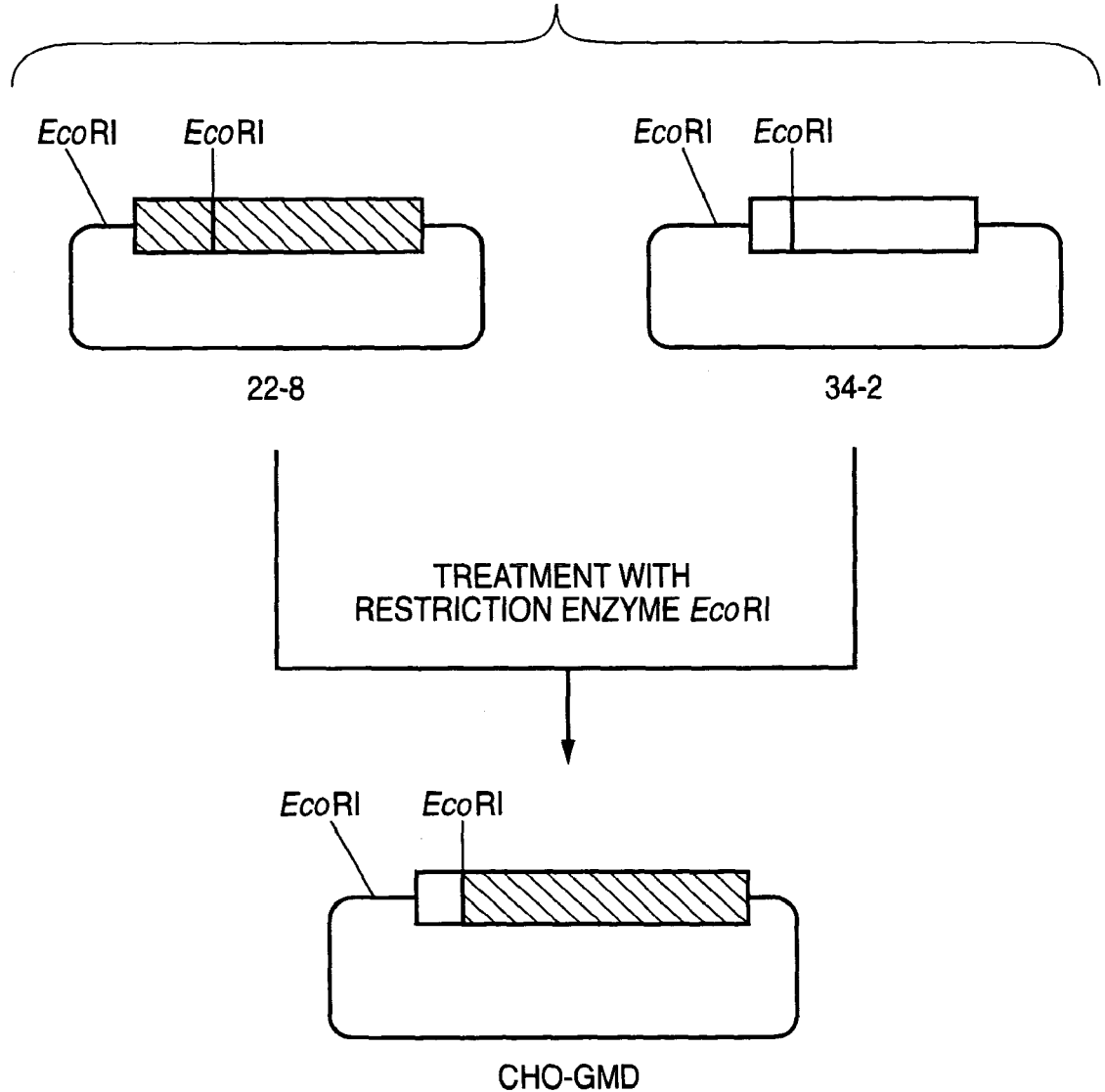

FIG. 37 show a construction step of a plasmid CHO-GMD in which the 5'-terminal of a clone 34-2 is introduced into the 5'-terminal of a CHO cell-derived GMD cDNA clone 22-8.

Figure 38:
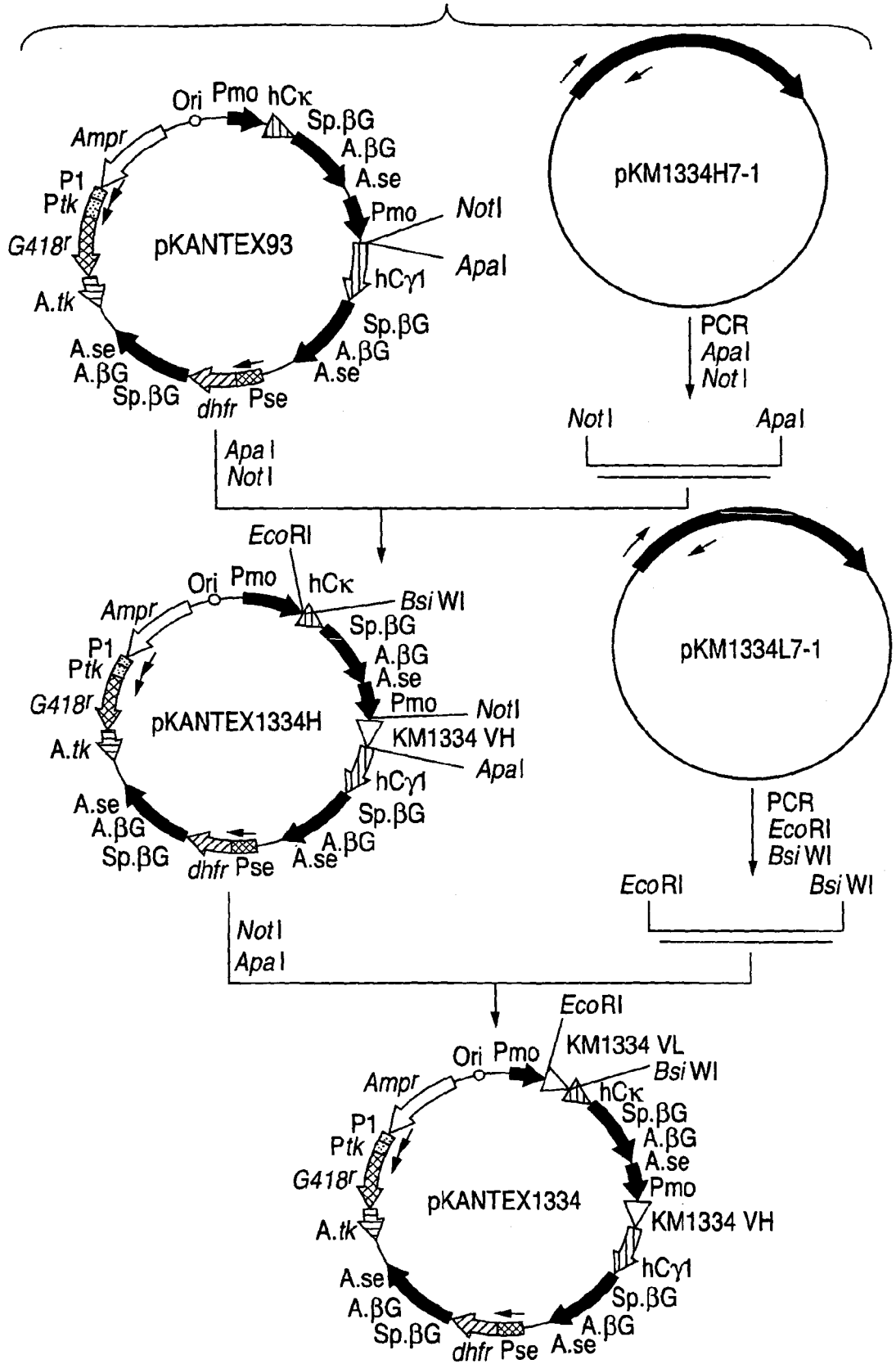

FIG. 38 shows construction steps of plasmid pKANTEX1334H and pKANTEX 1334.

DETAILED DESCRIPTION OF THE INVENTION

The present invention relates to a method for enhancing a binding activity of an antibody composition to Fcγ receptor IIIa, which comprises modifying a complex N-glycoside-linked sugar chain which is bound to the Fc region of an antibody molecule.

In the present invention, the antibody molecule may be any antibody molecule, so long as it is a molecule comprising the Fc region of an antibody. Examples include an antibody, an antibody fragment, a fusion protein comprising an Fc region, and the like.

An antibody is a protein, which is produced in vivo by immunization as the result of extra-antigen stimulation. The antibody has a specific binding activity to an antigen. The antibody includes an antibody secreted by a hybridoma cell prepared from a spleen cell of an animal immunized with an antigen; an antibody prepared by genetic engineering technique, i.e., an antibody obtained by introducing an antibody gene-inserted antibody expression vector into a host cell; and the like. Examples include an antibody produced by a hybridoma, a humanized antibody, a human antibody and the like.

A hybridoma is a cell which is obtained by cell fusion between a B cell obtained by immunizing a non-human mammal with an antigen and a myeloma cell derived from mouse or the like and can produce a monoclonal antibody having the desired antigen specificity.

The humanized antibody includes a human chimeric antibody, a human CDR-grafted antibody and the like.

A human chimeric antibody is an antibody which comprises an antibody heavy chain V region (hereinafter referred to heavy chain as "H chain", and referred to as "HV" or "VH") and an antibody light chain V region (hereinafter referred to light chain as "L chain", and referred to as "LV" or "VL"), both of a non-human animal, a human antibody H chain C region (hereinafter also referred to as "CH") and a human antibody L chain C region (hereinafter also referred to as "CL"). The non-human animal may be any animal such as mouse, rat, hamster or rabbit, so long as a hybridoma can be prepared therefrom.

The human chimeric antibody can be produced by obtaining cDNAs encoding VH and VL from a monoclonal antibody-producing hybridoma, inserting them into an expression vector for host cell having genes encoding human antibody CH and human antibody CL to thereby construct a vector for expression of human chimeric antibody, and then introducing the vector into a host cell to express the antibody.

The CH of human chimeric antibody may be any CH, so long as it belongs to human immunoglobulin (hereinafter referred to as "hIg") can be used. Those belonging to the hIgG class are preferred and any one of the subclasses belonging to the hIgG class such as hIgG1, hIgG2, hIgG3 and hIgG4 can be used. Also, as the CL of human chimeric antibody, any CL can be used, so long as it belongs to the hIg class, and those belonging to the κ class or λ class can also be used.

A human CDR-grafted antibody is an antibody in which amino acid sequences of CDRs of VH and VL of a non-human animal antibody are grafted into appropriate positions of VH and VL of a human antibody.

The human CDR-grafted antibody can be produced by constructing cDNAs encoding V regions in which CDR sequences of VH and VL of a non-human animal antibody are grafted into CDR sequences of VH and VL of a desired human antibody, inserting them into an expression vector for host cell having genes encoding human antibody CH and human antibody CL to thereby construct a vector for expression of human CDR-grafted antibody, and then introducing the expression vector into a host cell to express the human CDR-grafted antibody.

The CH of human CDR-grafted antibody may be any CH, so long as it belongs to the hIg. Those of the hIgG class are preferred and any one of the subclasses belonging to the hIgG class, such as hIgG1, hIgG2, hIgG3 and hIgG4, can be used. Also, as the CL of human CDR-grafted antibody, any CL can be used, so long as it belongs to the hIg class, and those belonging to the κ class or λ class can also be used.

A human antibody is originally an antibody naturally existing in the human body, but it also includes antibodies obtained from a human antibody phage library, a human antibody-producing transgenic non-human animal and a human antibody-producing transgenic plant, which are prepared based on the recent advance in genetic engineering, cell engineering and developmental engineering techniques.

Regarding the antibody existing in the human body, a lymphocyte capable of producing the antibody can be cultured by isolating a human peripheral blood lymphocyte, immortalizing it by its infection with EB virus or the like and then cloning it, and the antibody can be purified from the culture.

The human antibody phage library is a library in which antibody fragments such as Fab and single chain antibody are expressed on the phage surface by inserting a gene encoding an antibody prepared from a human B cell into a phage gene. A phage expressing an antibody fragment having the desired antigen binding activity can be recovered from the library based on the activity to bind to an antigen-immobilized substrate. The antibody fragment can be converted further into a human antibody molecule comprising two full H chains and two full L chains by genetic engineering techniques.

A human antibody-producing transgenic non-human animal is an animal in which a human antibody gene is introduced into cells. Specifically, a human antibody-producing transgenic mouse can be prepared by introducing a human antibody gene into ES cell of a mouse, transplanting the ES cell into an early stage embryo of other mouse and then developing it. By introducing a human antibody-gene into a fertilized egg of an animal and developing it, the transgenic non-human animal can be also prepared. Regarding the preparation method of a human antibody from the human antibody-producing transgenic non-human animal, the human antibody can be produced and accumulated in a culture by obtaining a human antibody-producing hybridoma by a hybridoma preparation method usually carried out in non-human mammals and then culturing it.

The transgenic non-human animal includes cattle, sheep, goat, pig, horse, mouse, rat, fowl, monkey, rabbit and the like.

Moreover, in the present invention, the antibody is preferably an antibody which recognizes a tumor-related antigen, an antibody which recognizes an allergy- or inflammation-related antigen, an antibody which recognizes cardiovascular disease-related antigen, an antibody which recognizes autoimmune disease-related antigen or an antibody which recognizes a viral or bacterial infection-related antigen. Also, the class of the antibody is preferably IgG.

An antibody fragment is a fragment which comprises at least part of the Fc region of the above antibody. The Fc region is a region at the C-terminal side of H chain of an antibody, such as CH2 region and CH3 region, and includes a natural type and a mutant type. The at least part of the Fc region is preferably a fragment comprising CH2 region, and more preferably a region comprising aspartic acid at position 1 existing in CH2 region. The Fc region of the IgG class is from Cys at position 226 to the C-terminal or from Pro at position 230 to the C-terminal according to the numbering of EU Index of Kabat et al. [*Sequences of Proteins of Immunological Interest*, 5$^{th}$ Ed., Public Health Service, National Institutes of Health, Bethesda, Md. (1991)]. The antibody fragment includes an H chain monomer, an H chain dimer and the like.

A fusion protein comprising a part of Fc region is a substance in which an antibody comprising the part of Fc region of an antibody or the antibody fragment is fused with a protein such as an enzyme or a cytokine (hereinafter referred to as "Fc fusion protein").

In the present invention, N-glycoside-linked sugar chain bound to the Fc region of the antibody molecule includes a complex type in which the non-reducing end side of the core structure has one or more parallel branches of galactose-N-acetylglucosamine (hereinafter referred to as "Gal-GlcNAc") and further the non-reducing end side of Gal-GlcNAc has a structure of sialic acid, bisecting N-acetylglucosamine or the like.

Since the Fc region in the antibody molecule has positions to which N-glycoside-linked sugar chains are separately bound, two sugar chains are bound per one antibody molecule. Since many sugar chains having different structures are present for the two N-glycoside-linked sugar chains bound to the antibody, homology of antibody molecules can be judged in view of the sugar chain structure bound to the Fc region.

The antibody composition is a composition which comprises an antibody molecule having complex N-glycoside-linked sugar chains in the Fc region, and may comprise an antibody molecule having the same sugar chain structure or an antibody molecule having different sugar chain structures.

Modification of the N-glycoside-linked sugar chain bound to the Fc region of an antibody molecule is preferably carried out by binding a sugar chain in which fucose is not bound to N-acetylglucosamine in the reducing end in the complex N-glycoside-linked sugar chain to the Fc region of an antibody molecule.

In the present invention, the sugar chain in which fucose is not bound to N-acetylglucosamine in the reducing end in the complex N-glycoside-linked sugar chain is a complex N-glycoside-linked sugar chain in which 1-position of fucose is not bound to 6-position of N-acetylglucosamine in the reducing end through α-bond in the complex N-glycoside-linked sugar chain.

The sugar chain can be synthesized by a cell in which the activity of an enzyme protein relating to the modification of a sugar chain in which fucose is not bound to N-acetylglucosamine in the reducing end in the complex N-glycoside-linked sugar chain is decreased or deleted.

In the present invention, the enzyme protein relating to the modification of a sugar chain in which 1-position of fucose is not bound to 6-position of N-acetylglucosamine in the reducing end in the complex N-glycoside-linked sugar chain includes:

(a) an enzyme protein relating to synthesis of an intracellular sugar nucleotide, GDP-fucose (hereinafter referred to as "GDP-fucose synthase");

(b) an enzyme protein relating to modification of a sugar chain in which 1-position of fucose is bound to 6-position of N-acetylglucosamine in the reducing end through α-bond in a complex N-glycoside-linked sugar chain (hereinafter referred to as "α-1,6-fucose modifying enzyme"); and (c) a protein relating to transport of an intracellular sugar nucleotide, GDP-fucose, to the Golgi body (hereinafter referred to as "GDP-fucose transport protein").

In the present invention, the GDP-fucose synthase may be any enzyme, so long as it is an enzyme relating to the synthesis of the intracellular sugar nucleotide, GDP-fucose, as a supply source of fucose to a sugar chain, and includes an enzyme which has influence on the synthesis of the intracellular sugar nucleotide, GDP-fucose.

The intracellular sugar nucleotide, GDP-fucose, is supplied by a de novo synthesis pathway or a salvage synthesis pathway. Thus, all enzymes relating to the synthesis pathways are included in the GDP-fucose synthase.

The GDP-fucose synthase relating to the de novo synthesis pathway includes GDP-mannose 4-dehydratase (hereinafter referred to as "GMD"), GDP-keto-6-deoxymannose 3,5-epimerase, 4-reductase (hereinafter referred to as "Fx") and the like.

The GDP-fucose synthase relating to the salvage synthesis pathway includes GDP-beta-L-fucose pyrophosphorylase (hereinafter referred to as "GFPP"), fucokinase and the like.

As the enzyme which has influence on the synthesis of an intracellular sugar nucleotide, GDP-fucose, an enzyme which has influence on the activity of the enzyme relating to the synthesis pathway of the intracellular sugar nucleotide, GDP-fucose, and an enzyme which has influence on the structure of substances as the substrate of the enzyme are also included.

In the present invention, the GMD includes a protein encoded by a DNA selected from the group consisting of (a) and (b), a protein selected from the group consisting of (c), (d) and (e), and the like:

(a) a DNA comprising the nucleotide sequence represented by SEQ ID NO:65;

(b) a DNA which hybridizes with the DNA comprising the nucleotide sequence represented by SEQ ID NO:65 under stringent conditions and encodes a protein having GMD activity, (c) a protein comprising the amino acid sequence represented by SEQ ID NO:71, (d) a protein which comprises an amino acid sequence in which at least one amino acid is deleted, substituted, inserted and/or added in the amino acid sequence represented by SEQ ID NO:71 and has GMD activity, and (e) a protein which comprises an amino acid sequence having a homology of 80% or more with the amino acid sequence represented by SEQ ID NO:71 and has GMD activity.

Fx includes a protein encoded by a DNA selected from the group consisting of (a) and (b), a protein selected from the group consisting of (c), (d) and (e), and the like:

(a) a DNA comprising the nucleotide sequence represented by SEQ ID NO:48;

(b) a DNA which hybridizes with the DNA comprising the nucleotide sequence represented by SEQ ID NO:48 under stringent conditions and encodes a protein having Fx activity, (c) a protein comprising the amino acid sequence represented by SEQ ID NO:19, (d) a protein which comprises an amino acid sequence in which at least one amino acid is deleted, substituted, inserted and/or added in the amino acid sequence represented by SEQ ID NO:19 and has Fx activity, and (e) a protein which comprises an amino acid sequence having a homology of 80% or more with the amino acid sequence represented by SEQ ID NO:19 and has Fx activity.

GFPP includes a protein encoded by a DNA selected from the group consisting of (a) and (b), a protein selected from the group consisting of (c), (d) and (e), and the like:

(a) a DNA comprising the nucleotide sequence represented by SEQ ID NO:51;

(b) a DNA which hybridizes with the DNA comprising the nucleotide sequence represented by SEQ ID NO:51 under stringent conditions and encodes a protein having GFPP activity, (c) a protein comprising the amino acid sequence represented by SEQ ID NO:20, (d) a protein which comprises an amino acid sequence in which at least one amino acid is deleted, substituted, inserted and/or added in the amino acid sequence represented by SEQ ID NO:20 and has GFPP activity, and (e) a protein which comprises an amino acid sequence having a homology of 80% or more with the amino acid sequence represented by SEQ ID NO:20 and has GFPP activity.

In the present invention, the α-1,6-fucose modifying enzyme includes any enzyme, so long as it is an enzyme relating to the reaction of binding of 1-position of fucose to 6-position of N-acetylglucosamine in the reducing end through α-bond in the complex N-glycoside-linked sugar chain. The enzyme relating to the reaction of binding of 1-position of fucose to 6-position of N-acetylglucosamine in the reducing end through α-bond in the complex N-glycoside-linked sugar chain includes an enzyme which has influence on the reaction of binding of 1-position of fucose to 6-position of N-acetylglucosamine in the reducing end through α-bond in the complex N-glycoside-linked sugar chain.

The α1,6-fucose modifying enzyme includes α1,6-fucosyltransferase, α-L-fucosidase and the like.

Also, an enzyme which has influence on the activity of the above enzyme relating to the reaction of binding of 1-position of fucose to 6-position of N-acetylglucosamine in the reducing end through α-bond in the complex N-glycoside-linked sugar chain and an enzyme which has influence on the structure of substances as the substrate of the enzyme are included.

The α1,6-fucosyltransferase includes a protein encoded by a DNA selected from the group consisting of the following (a), (b), (c) and (d), a protein selected from the group consisting of the following (e), (f), (g), (h), (i) and (j), and the like:

(a) a DNA comprising the nucleotide sequence represented by SEQ ID NO:1;

(b) a DNA comprising the nucleotide sequence represented by SEQ ID NO:2;

(c) a DNA which hybridizes with the DNA comprising the nucleotide sequence represented by SEQ ID NO:1 under stringent conditions and encodes a protein having α1,6-fucosyltransferase activity;

(d) a DNA which hybridizes with the DNA comprising the nucleotide sequence represented by SEQ ID NO:2 under stringent conditions and encodes a protein having α1,6-fucosyltransferase activity;

(e) a protein comprising the amino acid sequence represented by SEQ ID NO:23, (f) a protein comprising the amino acid sequence represented by SEQ ID NO:24, (g) a protein which comprises an amino acid sequence in which at least one amino acid is deleted, substituted, inserted and/or added in the amino acid sequence represented by SEQ ID NO:23 and has α1,6-fucosyltransferase activity, (h) a protein which comprises an amino acid sequence in which at least one amino acid is deleted, substituted, inserted and/or added in the amino acid sequence represented by SEQ ID NO:24 and has α1,6-fucosyltransferase activity, (i) a protein which comprises an amino acid sequence having a homology of 80% or more with the amino acid sequence represented by SEQ ID NO:23 and has α1,6-fucosyltransferase activity, and (j) a protein which comprises an amino acid sequence having a homology of 80% or more with the amino acid sequence represented by SEQ ID NO:24 and has α1,6-fucosyltransferase activity.

The GDP-fucose transport protein may be any protein, so long as it is a protein relating to the transportation of the intracellular sugar nucleotide, GDP-fucose to the Golgi body or a protein which has an influence on the reaction to transport the intracellular sugar nucleotide, GDP-fucose to the Golgi body.

The GDP-fucose transport protein includes a GDP-fucose transporter and the like.

Furthermore, the protein which has an influence on the reaction to transport the intracellular sugar nucleotide, GDP-fucose to the Golgi body includes a protein which has an influence on the above GDP-fucose transport protein or has an influence on the expression thereof.

In the present invention, the GDP-fucose transporter includes a protein encoded by a DNA selected from the group consisting of the following (a) to (h), and the like:

(a) a DNA comprising the nucleotide sequence represented by SEQ ID NO:91;

(b) a DNA comprising the nucleotide sequence represented by SEQ ID NO:93;

(c) a DNA comprising the nucleotide sequence represented by SEQ ID NO:95;

(d) a DNA comprising the nucleotide sequence represented by SEQ ID NO:97;

(e) a DNA which hybridizes with the DNA comprising the nucleotide sequence represented by SEQ ID NO:91 under stringent conditions and encodes a protein having GDP-fucose transporter activity;

(f) a DNA which hybridizes with the DNA comprising the nucleotide sequence represented by SEQ ID NO:93 under stringent conditions and encodes a protein having GDP-fucose transporter activity;

(g) a DNA which hybridizes with the DNA comprising the nucleotide sequence represented by SEQ ID NO:95 under stringent conditions and encodes a protein having GDP-fucose transporter activity; and (h) a DNA which hybridizes with the DNA comprising the nucleotide sequence represented by SEQ ID NO:97 under stringent conditions and encodes a protein having GDP-fucose transporter activity.

Furthermore, the GDP-fucose transporter of the present invention includes a protein selected from the group consisting of the following (i) to (t), and the like:

(i) a protein comprising the amino acid sequence represented by SEQ ID NO:92, (j) a protein comprising the amino acid sequence represented by SEQ ID NO:94, (k) a protein comprising the amino acid sequence represented by SEQ ID NO:96, (l) a protein comprising the amino acid sequence represented by SEQ ID NO:98, (m) a protein which comprises an amino acid sequence in which at least one amino acid is deleted, substituted, inserted and/or added in the amino acid sequence represented by SEQ ID NO:92 and has GDP-fucose transporter activity, (n) a protein which comprises an amino acid sequence in which at least one amino acid is deleted, substituted, inserted and/or added in the amino acid sequence represented by SEQ ID NO:94 and has GDP-fucose transporter activity, (o) a protein which comprises an amino acid sequence in which at least one amino acid is deleted, substituted, inserted and/or added in the amino acid sequence represented by SEQ ID NO:96 and has GDP-fucose transporter activity, (p) a protein which comprises an amino acid sequence in which at least one amino acid is deleted, substituted, inserted and/or added in the amino acid sequence represented by SEQ ID NO:98 and has GDP-fucose transporter activity, (q) a protein which comprises an amino acid sequence having a homology of 80% or more with the amino acid sequence represented by SEQ ID NO:92 and has GDP-fucose transporter activity, (r) a protein which comprises an amino acid sequence having a homology of 80% or more with the amino acid sequence represented by SEQ ID NO:94 and has GDP-fucose transporter activity, (s) a protein which comprises an amino acid sequence having a homology of 80% or more with the amino acid sequence represented by SEQ ID NO:96 and has GDP-fucose transporter activity, and (t) a protein which comprises an amino acid sequence having a homology of 80% or more with the amino acid sequence represented by SEQ ID NO:98 and has GDP-fucose transporter activity.

A DNA which hybridizes under stringent conditions is a DNA obtained, e.g., by a method such as colony hybridization, plaque hybridization or Southern blot hybridization using a DNA such as the DNA having the nucleotide sequence represented by SEQ ID NO:1, 2, 48, 51, 65, 91, 93, 95 or 97 or a partial fragment thereof as the probe, and specifically includes a DNA which can be identified by carrying out hybridization at 65° C. in the presence of 0.7 to 1.0 mol/l sodium chloride using a filter to which colony- or plaque-derived DNAs are immobilized, and then washing the filter at 65° C. using 0.1 to 2×SSC solution (composition of the 1×SSC solution comprising 150 mmol/l sodium chloride and 15 mmol/l sodium citrate). The hybridization can be carried out in accordance with the methods described, e.g., in *Molecular Cloning, A Laboratory Manual*, 2nd Ed., Cold Spring Harbor Laboratory Press (1989) (hereinafter referred to as "*Molecular Cloning*, Second Edition"), *Current Protocols in Molecular Biology*, John Wiley & Sons, 1987-1997 (hereinafter referred to as "*Current Protocols in Molecular Biology*"); *DNA Cloning 1: Core Techniques, A Practical*

Approach, Second Edition, Oxford University (1995); and the like. The hybridizable DNA includes a DNA having at least 60% or more, preferably 70% or more, more preferably 80% or more, still more preferably 90% or more, far more preferably 95% or more, and most preferably 98% or more, of homology with the nucleotide sequence represented by SEQ ID NO:1, 2, 48, 51, 65, 91, 93, 95 or 97.

The protein which comprises an amino acid sequence in which at least one amino acid is deleted, substituted, inserted and/or added in the amino acid sequence represented by SEQ ID NO:19, 20, 23, 24, 71, 92, 94, 96 or 98 and has α1,6-fucosyltransferase activity, GMD activity, Fx activity, GFPP activity or GFP-fucose transporter activity can be obtained, e.g., by introducing a site-directed mutation into a DNA encoding a protein having the amino acid sequence represented by SEQ ID NO:1, 2, 48, 51 or 65, respectively, using the site-directed mutagenesis described, e.g., in *Molecular Cloning*, Second Edition; *Current Protocols in Molecular Biology; Nucleic Acids Research*, 10, 6487 (1982); *Proc. Natl. Acad. Sci. USA*, 79, 6409 (1982); *Gene*, 34, 315 (1985); *Nucleic Acids Research*, 13, 4431 (1985); *Proc. Natl. Acad. Sci. USA*, 82, 488 (1985); and the like. The number of amino acids to be deleted, substituted, inserted and/or added is one or more, and the number is not particularly limited, but is a number which can be deleted, substituted or added by a known technique such as the site-directed mutagenesis, e.g., it is 1 to several tens, preferably 1 to 20, more preferably 1 to 10, and most preferably 1 to 5.

Also, in order to maintain the α1,6-fucosyltransferase activity, GMD activity, Fx activity, GFPP activity or GDP-fucose transporter activity of the protein to be used in the present invention, it has at least 80% or more, preferably 85% or more, more preferably 90% or more, still more preferably 95% or more, far more preferably 97% or more, and most preferably 99% or more, of homology with the amino acid sequence represented by SEQ ID NO:19, 20, 23, 24, 71, 92, 94, 96 or 98, when calculated using an analyzing soft such as BLAST [*J. Mol. Biol.*, 215, 403 (1990)] or FASTA [*Methods in Enzymology*, 183, 63 (1990)].

As the method for obtaining the above cells, any technique can be used, so long as it can decrease or delete the enzyme activity of interest. The technique for decreasing or deleting the enzyme activity includes:

(a) a gene disruption technique which comprises targeting a gene encoding the enzyme, (b) a technique for introducing a dominant negative mutant of a gene encoding the enzyme, (c) a technique for introducing mutation into the enzyme, and (d) a technique for surprising transcription and/or translation of a gene encoding the enzyme, and the like.

Also, the method includes a method for selecting a cell having resistance to lectin which recognizes the structure of a sugar chain in which 1-position of fucose is bound to 6-position of N-acetylglucosamine in the reducing end through α-bond in a complex N-glycoside-linked sugar chain.

The growth of lectin-resistant cell is not inhibited in the presence of a lectin at an effective concentration during cell culturing.

In the present invention, the effective concentration of a lectin which does not inhibit the growth can be decided depending on the cell line, and is generally 10 μg/ml to 10.0 mg/ml, preferably 0.5 to 2.0 mg/ml. The effective concentration of lectin in the case where mutation is introduced into a parent cell is a concentration in which the parent cell cannot normally grow or higher than the concentration, and is a concentration which is preferably similar to, more preferably 2 to 5 times, still more preferably 10 times, and most preferably 20 times or more, higher than the concentration in which the parent cell cannot normally grow.

The lectin which recognizes a sugar chain structure in which 1-position of fucose is bound to 6-position of N-acetylglucosamine through α-bond includes any lectin, so long as it is a lectin which is capable of recognizing the sugar chain structure. Examples include lentil agglutinin derived from *Lens culinaris* (*Lens culinaris* lectin LCA), pea lectin derived from *Pisum sativum* a (pea lectin PSA), (agglutinin derived from *Vicia faba* (broad bean lectin VFA), lectin derived from *Aleuria aurantia* (*Aleuria aurantia* lectin AAL) and the like.

The parent cell is a cell before a certain treatment is applied, namely a cell before the step for selecting the lectin-resistant cell used in the present invention is carried out or a cell before genetic engineering techniques for decreasing or deleting the above enzyme activity is carried out.

Although the parent cell is not particularly limited, the following cells are exemplified.

The parent cell of NS0 cell includes NS0 cells described in literatures such as *BIO/TECHNOLOGY*, 10, 169 (1992) and *Biotechnol. Bioeng.*, 73, 261 (2001). Furthermore, it includes NS0 cell line (RCB 0213) registered at RIKEN Cell Bank, The Institute of Physical and Chemical Research, sub-cell lines obtained by acclimating these cell lines to media in which they can grow, and the like.

The parent cell of SP2/0-Ag14 cell includes SP2/0-Ag14 cells described in literatures such as *J. Immunol.*, 126, 317 (1981), *Nature*, 276, 269 (1978) and *Human Antibodies and Hybridomas*, 3, 129 (1992). Furthermore, it includes SP2/0-Ag14 cell (ATCC CRL-1581) registered at ATCC, sub-cell lines obtained by naturalizing these cell lines to media in which they can grow (ATCC CRL-1581.1), and the like.

The parent cell of CHO cell derived from Chinese hamster ovary tissue includes CHO cells described in literatures such as *Journal of Experimental Medicine*, 108, 945 (1958), *Proc. Natl. Acad. Sci. USA*, 60, 1275 (1968), *Genetics*, 55, 513 (1968), *Chromosoma*, 41, 129 (1973), *Methods in Cell Science*, 18, 115 (1996), *Radiation Research*, 148, 260 (1997), *Proc. Natl. Acad. Sci. USA*, 77, 4216 (1980), *Proc. Natl. Acad. Sci. USA*, 60, 1275 (1968), *Cell*, 6, 121 (1975) and *Molecular Cell Genetics*, Appendix I, II (p. 883-900). Furthermore, it includes cell line CHO-K1 (ATCC CCL-61), cell line DUXB11 (ATCC CRL-9060) and cell line Pro-5 (ATCC CRL-1781) registered at ATCC, commercially available cell line CHO-S (Cat # 11619 of Life Technologies), sub-cell lines obtained by acclimating these cell lines to media in which they can grow, and the like.

The parent cell of a rat myeloma cell line YB2/3HL.P2.G11.16Ag.20 cell includes cell lines established from Y3/Ag1.2.3 cell (ATCC CRL-1631) such as YB2/3HL.P2.G11.16Ag.20 cell described in literatures such as *J. Cell. Biol.*, 93, 576 (1982) and *Methods Enzymol.*, 73B, 1 (1981). Furthermore, it include YB2/3HL.P2.G11.16Ag.20 cell (ATCC CRL-1662) registered at ATCC, sub-lines obtained by acclimating these cell lines to media in which they can grow, and the like.

In the present invention, FcγR means an Fc receptor (hereinafter also referred to as "FcR") against an IgG class antibody. FcR means a receptor which binds to the Fc region of an antibody [*Annu. Rev. Immunol.*, 9, 457 (1991)]. Furthermore, FcγR includes FcγRI, FcγRII and FcγRIII subclasses and their allele mutants and isoforms formed by alternative splicing. In addition, FcγRII includes FcγRIIa and FcγRIIb, and FcγRIII includes FcγRIIIa and FcγRIIIb [*Annu. Rev. Immunol.*, 9, 457 (1991)].

The binding activity to FcγRIIIa can be increased by binding sugar chains to the Fc region of an antibody molecule so as to adjust the ratio of a sugar chain in which fucose is not bound to N-acetylglucosamine in the reducing end in the sugar chain among the total complex N-glycoside-linked sugar chains bound to the Fc region to preferably 20% or more, more preferably 30% or more, still more preferably 40% or more, particularly preferably 50% or more, and most preferably 100%.

The ratio of a sugar chain in which fucose is not bound to N-acetylglucosamine in the reducing end in the sugar chain among the total complex N-glycoside-linked sugar chains bound to the Fc region contained in the antibody composition is a ratio of the number of a sugar chain in which fucose is not bound to N-acetylglucosamine in the reducing end in the sugar chain to the total number of the complex N-glycoside-linked sugar chains bound to the Fc region contained in the composition. Also, the ratio of a sugar chain is preferably a ratio of a sugar chain in which 1-position of fucose is not bound to 6-position of N-acetylglucosamine in the reducing end through α-bond in the sugar chain.

The sugar chain in which fucose is not bound to N-acetylglucosamine in the reducing end in the complex N-glycoside-linked sugar chain is a sugar chain in which fucose is not bound to N-acetylglucosamine in the reducing end through α-bond in the complex N-glycoside-linked sugar chain. Preferably, it is a sugar chain in which 1-position of fucose is not bound to 6-position of N-acetylglucosamine in the complex N-glycoside-linked sugar chain through α-bond.

The ratio of a sugar chain in which fucose is not bound to N-acetylglucosamine in the reducing end in the sugar chain contained in the composition which comprises an antibody molecule having complex N-glycoside-linked sugar chains in the Fc region can be determined by releasing the sugar chain from the antibody molecule using a known method such as hydrazinolysis, enzyme digestion or the like [*Biochemical Experimentation Methods* 23-*Method for Studying Glycoprotein Sugar Chain* (Japan Scientific Societies Press), edited by Reiko Takahashi (1989)], carrying out fluorescence labeling or radioisotope labeling of the released sugar chain, and then separating the labeled sugar chain by chromatography. Also, the released sugar chain can be determined by analyzing it with the HPAED-PAD method [*J. Liq. Chromatogr.*, 6, 1577 (1983)]. The antibody composition in which binding activity to FcγRIIIa has been enhanced by the method of the present invention has high ADCC activity.

In the present invention, the ADCC activity is a cytotoxic activity in which an antibody bound to a cell surface antigen on a cell such as a tumor cell in the living body activates an effector cell mediated the antibody Fc region and an Fc receptor existing on effector cell surface and thereby injures the tumor cell and the like [*Monoclonal Antibodies: Principles and Applications*, Wiley-Liss, Inc., Chapter 2.1 (1995)]. The effector cell includes killer cells, natural killer cells, monocytes, macrophages, and the like.

A process for producing a host cell in which the activity of a protein relating to modification of a sugar chain in which fucose is bound to N-acetylglucosamine in the reducing end in the complex N-glycoside-linked sugar chain is decreased or deleted used in the method of the present invention is explained below in detail.

1. Preparation of Host Cell Used in the Method of the Invention

The host cell used in the method of the present invention can be prepared by the following techniques.

(1) Gene Disruption Technique which Comprises Targeting a Gene Encoding an Enzyme The host cell used in the method of the present invention can be prepared by targeting a gene encoding a GDP-fucose synthase, α1,6-fucose modifying enzyme or a GDP-fucose transport protein by using a gene disruption technique. The GDP-fucose synthase includes GMD, Fx, GFPP, fucokinase and the like. The α1,6-fucose modifying enzyme includes α1,6-fucosyltransferase, α-L-fucosidase and the like. The GDP-fucose transport protein includes GDP-fucose transporter.

The gene as used herein includes DNA and RNA.

The gene disruption method may be any method, so long as it can disrupt the gene encoding the target enzyme. Examples include an antisense method, a ribozyme method, a homologous recombination method, an RNA-DNA oligonucleotide (RDO) method, an RNA interference (RNAi) method, a method using retrovirus, a method using transposon and the like. The methods are specifically described below.

(a) Preparation of Host Cell Used in the Present Invention by the Antisense Method or the Ribozyme Method The host cell used in the method of the present invention can be prepared by targeting the GDP-fucose synthase, α1,6-fucose modifying enzyme or the GDP-fucose transport protein according to the antisense or ribozyme method described in *Cell Technology*, 12, 239 (1993); *BIO/TECHNOLOGY*, 17, 1097 (1999); *Hum. Mol. Genet.*, 5, 1083 (1995); *Cell Technology*, 13, 255 (1994); *Proc. Natl. Acad. Sci. USA*, 96, 1886 (1999); or the like, e.g., in the following manner.

A cDNA or a genomic DNA encoding GDP-fucose synthase, α1,6-fucose modifying enzyme or the GDP-fucose transport protein is prepared.

The nucleotide sequence of the prepared cDNA or genomic DNA is determined.

Based on the determined DNA sequence, an antisense gene or ribozyme construct of an appropriate length comprising a DNA moiety which encodes the GDP-fucose synthase, α1,6-fucose modifying enzyme or the GDP-fucose transport protein, a part of its untranslated region or an intron is designed.

In order to express the antisense gene or ribozyme in a cell, a recombinant vector is prepared by inserting a fragment or total length of the prepared DNA into downstream of the promoter of an appropriate expression vector.

A transformant is obtained by introducing the recombinant vector into a host cell suitable for the expression vector.

The host cell used in the method of the present invention can be obtained by selecting a transformant based on the activity of the GDP-fucose synthase, the α1,6-fucose modifying enzyme or the GDP-fucose transport protein. The host cell of the present invention can also be obtained by selecting a transformant based on the sugar chain structure of a glycoprotein on the cell membrane or the sugar chain structure of the produced antibody molecule.

As the host cell used for preparing the host cell used in the method of the present invention, any cell such as yeast, an animal cell, an insect cell or a plant cell can be used, so long as it has a gene encoding the target GDP-fucose synthase, α1,6-fucose modifying enzyme or GDP-fucose transport protein. Examples include host cells described in the following item 3.

As the expression vector, a vector which is autonomously replicable in the host cell or can be integrated into the chromosome and comprises a promoter at such a position that the designed antisense gene or ribozyme can be transferred is used. Examples include expression vectors described in the following item 3.

As the method for introducing a gene into various host cells, the methods for introducing recombinant vectors suitable for various host cells described in the following item 3, can be used.

The method for selecting a transformant based on the activity of the GDP-fucose synthase, the α1,6-fucose modifying enzyme or the GDP-fucose transport protein includes biochemical methods or genetic engineering techniques described in *New Biochemical Experimental Series (Shin-Jikken Kagaku Koza)* 3-*Saccharides (Toshitsu) I*, Glycoprotein (Totanpakushitu) (Tokyo Kagaku Dojin), edited by Japanese Biochemical Society (1988); *Cell Engineering (Saibo Kogaku)*, Supplement, Experimental Protocol Series, Glycobiology Experimental Protocol, Glycoprotein, Glycolipid and Proteoglycan (Shujun-sha), edited by Naoyuki Taniguchi, Akemi Suzuki, Kiyoshi Furukawa and Kazuyuki Sugawara (1996); *Molecular Cloning*, Second Edition; *Current Protocols in Molecular Biology*; and the like. The biochemical method includes a method in which the enzyme activity is evaluated using an enzyme-specific substrate and the like. The genetic engineering technique include the Northern analysis, RT-PCR and the like which measures the amount of mRNA of a gene encoding the enzyme.

The method for selecting a transformant based on the sugar chain structure of a glycoprotein on the cell membrane includes the methods described in the following item 1(5). The method for selecting a transformant based on the sugar chain structure of a produced antibody molecule includes the methods described in the following items 6 and 7.

As the method for preparing cDNA encoding the GDP-fucose synthase, α1,6-fucose modifying enzyme or the GDP-fucose transport protein, the following method is exemplified.
Preparation of DNA:

A total RNA or mRNA is prepared from a human or non-human animal tissue or cell.

The mRNA of a human or non-human tissue or cell may be a commercially available product (e.g., manufactured by Clontech) or may be prepared from a human or non-human animal tissue or cell as follows. The method for preparing a total RNA from a human or non-human animal tissue or cell includes the guanidine thiocyanate-cesium trifluoroacetate method [*Methods in Enzymology*, 154, 3 (1987)], the acidic guanidine thiocyanate phenol chloroform (AGPC) method [*Analytical Biochemistry*, 162, 156 (1987); *Experimental Medicine*, 9, 1937 (1991)] and the like.

Also, the mRNA can be prepared as poly(A)$^+$ RNA from a total RNA by the oligo(dT)-immobilized cellulose column method (*Molecular Cloning*, Second Edition) and the like.

In addition, mRNA can be prepared using a kit such as Fast Track mRNA Isolation Kit (manufactured by Invitrogen) or Quick Prep mRNA Purification Kit (manufactured by Pharmacia).

A cDNA library is prepared from the prepared mRNA of a human or non-human animal tissue or cell. The method for preparing cDNA library includes the methods described in *Molecular Cloning*, Second Edition; *Current Protocols in Molecular Biology*; and the like, or methods using a commercially available kit such as SuperScript Plasmid System for cDNA Synthesis and Plasmid Cloning (manufactured by Life Technologies) or ZAP-cDNA Synthesis Kit (manufactured by STRATAGENE).

As the cloning vector for the preparation of the cDNA library, any vector such as a phage vector or a plasmid vector can be used, so long as it is autonomously replicable in *Escherichia coli* K12. Examples include ZAP Express [manufactured by STRATAGENE, *Strategies*, 5, 58 (1992)], pBluescript II SK(+) [*Nucleic Acids Research*, 17, 9494 (1989)], Lambda ZAP II (manufactured by STRATAGENE), λgt10 and λgt11 [*DNA Cloning, A Practical Approach*, 1, 49 (1985)], λTriplEx (manufactured by Clontech), λExCell (manufactured by Pharmacia), pT7T318U (manufactured by Pharmacia), pcD2 [*Mol. Cell. Biol.*, 3, 280 (1983)], pUC18 [*Gene*, 33, 103 (1985)] and the like.

Any microorganism can be used as the host microorganism for the preparation of the cDNA library, and *Escherichia coli* is preferably used. Examples include *Escherichia coli* XL1-Blue MRF' [manufactured by STRATAGENE, *Strategies*, 5, 81 (1992)], *Escherichia coli* C600 [*Genetics*, 39, 440 (1954)], *Escherichia coli* Y1088 [*Science*, 222, 778 (1983)], *Escherichia coli* Y1090 [*Science*, 222, 778 (1983)], *Escherichia coli* NM522 [*J. Mol. Biol.*, 166, 1 (1983)], *Escherichia coli* K802 [*J. Mol. Biol.*, 16, 118 (1966)], *Escherichia coli* JM105 [*Gene*, 38, 275 (1985)] and the like.

The cDNA library can be used as such in the following analysis, and in order to obtain a full length cDNA as efficient as possible by decreasing the ratio of an infull length cDNA, a cDNA library prepared by using the oligo cap method developed by Sugano et al. [*Gene*, 138, 171 (1994); *Gene*, 200, 149 (1997); *Protein, Nucleic Acid and Protein*, 41, 603 (1996); *Experimental Medicine*, 11, 2491 (1993); cDNA Cloning (Yodo-sha) (1996); *Methods for Preparing Gene Libraries* (Yodo-sha) (1994)] can be used in the following analysis.

Based on the amino acid sequence of the GDP-fucose synthase, the α1,6-fucose modifying enzyme or the GDP-fucose transport protein, degenerative primers specific for the 5'-terminal and 3'-terminal nucleotide sequences of a nucleotide sequence presumed to encode the amino acid sequence are prepared, and DNA is amplified by PCR [*PCR Protocols*, Academic Press (1990)] using the prepared cDNA library as the template to obtain a gene fragment encoding the GDP-fucose synthase, the α1,6-fucose modifying enzyme or the GDP-fucose transport protein.

It can be confirmed that the obtained gene fragment is a DNA encoding the GDP-fucose synthase, the α1,6-fucose modifying enzyme or the GDP-fucose transport protein by a method generally used for analyzing a nucleotide such as the dideoxy method of Sanger et al. [*Proc. Natl. Acad. Sci. USA*, 74, 5463 (1977)] or by using a nucleotide sequence analyzer such as ABIPRISM 377 DNA Sequencer (manufactured by PE Biosystems).

A DNA encoding the GDP-fucose synthase, the α1,6-fucose modifying enzyme or the GDP-fucose transport protein can be obtained by carrying out colony hybridization or plaque hybridization (*Molecular Cloning*, Second Edition) for the cDNA or cDNA library synthesized from the mRNA contained in the human or non-human animal tissue or cell, using the gene fragment as a DNA probe.

Also, using the primers used for obtaining the gene fragment encoding the GDP-fucose synthase, the α1,6-fucose modifying enzyme or the GDP-fucose transport protein, a DNA encoding the GDP-fucose synthase, the α1,6-fucose modifying enzyme or the GDP-fucose transport protein can also be obtained by carrying out screening by PCR using the cDNA or cDNA library synthesized from the mRNA contained in a human or non-human animal tissue or cell as the template.

The nucleotide sequence of the obtained DNA encoding the GDP-fucose synthase, the α1,6-fucose modifying enzyme or the GDP-fucose transport protein is analyzed from its terminus and determined by a method generally used for analyzing a nucleotide such as the dideoxy method of Sanger et al. [*Proc. Natl. Acad. Sci. USA*, 74, 5463 (1977)] or by using a nucleotide sequence analyzer such as ABIPRISM 377 DNA Sequencer (manufactured by PE Biosystems).

A gene encoding the GDP-fucose synthase, the α1,6-fucose modifying enzyme or the GDP-fucose transport protein can also be determined from genes in data bases by searching nucleotide sequence data bases such as GenBank, EMBL and DDBJ using a homology retrieving program such as BLAST based on the determined cDNA nucleotide sequence.

The nucleotide sequence of the gene encoding the GDP-fucose synthase obtained by the above method includes the nucleotide sequence represented by SEQ ID NO:48, 51 or 65. The nucleotide sequence of the gene encoding the α1,6-fucose modifying enzyme includes the nucleotide sequence represented by SEQ ID NO:1 or 2. The nucleotide sequence of the gene encoding the GDP-fucose transport protein includes the nucleotide sequence represented by SEQ ID NO:91, 93, 95 or 97.

The cDNA encoding the GDP-fucose synthase, the α1,6-fucose modifying enzyme or the GDP-fucose transport protein can also be obtained by chemically synthesizing it with a DNA synthesizer such as DNA Synthesizer model 392 manufactured by Perkin Elmer using the phosphoamidite method, based on the determined DNA nucleotide sequence.

The method for preparing a genomic DNA encoding the GDP-fucose synthase, the α1,6-fucose modifying enzyme or the GDP-fucose transport protein includes known methods described in *Molecular Cloning*, Second Edition; *Current Protocols in Molecular Biology*; and the like. Furthermore, the genomic DNA can be prepared by using a kit such as Genome DNA Library Screening System (manufactured by Genome Systems) or Universal GenomeWalker™ Kits (manufactured by CLONTECH).

The nucleotide sequence of the genomic DNA encoding the GDP-fucose synthase obtained by the method includes the nucleotide sequence represented by SEQ ID NO:67 or 70. The nucleotide sequence of the genomic DNA encoding the α1,6-fucose modifying enzyme includes the nucleotide sequence represented by SEQ ID NO:3. The nucleotide sequence of the genomic DNA encoding the GDP-fucose transport protein includes the nucleotide sequence represented by SEQ ID NO:99 or 100.

In addition, the host cell can also be obtained without using an expression vector, by directly introducing an antisense oligonucleotide or ribozyme into a host cell, which is designed based on the nucleotide sequence encoding the GDP-fucose synthase, the α1,6-fucose modifying enzyme or the GDP-fucose transport protein.

The antisense oligonucleotide or ribozyme can be prepared in the usual method or by using a DNA synthesizer. Specifically, it can be prepared based on the sequence information of an oligonucleotide having a corresponding sequence of continued 5 to 150 bases, preferably 5 to 60 bases, and more preferably 5 to 40 bases, among nucleotide sequences of a cDNA and a genomic DNA encoding the GDP-fucose synthase, the α1,6-fucose modifying enzyme or the GDP-fucose transport protein by synthesizing an oligonucleotide which corresponds to a sequence complementary to the oligonucleotide (antisense oligonucleotide) or a ribozyme comprising the oligonucleotide sequence.

The oligonucleotide includes oligo RNA and derivatives of the oligonucleotide (hereinafter referred to as "oligonucleotide derivatives").

The oligonucleotide derivatives includes oligonucleotide derivatives in which a phosphodiester bond in the oligonucleotide is converted into a phosphorothioate bond, an oligonucleotide derivative in which a phosphodiester bond in the oligonucleotide is converted into an N3'-P5' phosphoamidate bond, an oligonucleotide derivative in which ribose and a phosphodiester bond in the oligonucleotide are converted into a peptide-nucleic acid bond, an oligonucleotide derivative in which uracil in the oligonucleotide is substituted with C-5 propynyluracil, an oligonucleotide derivative in which uracil in the oligonucleotide is substituted with C-5 thiazoleuracil, an oligonucleotide derivative in which cytosine in the oligonucleotide is substituted with C-5 propynylcytosine, an oligonucleotide derivative in which cytosine in the oligonucleotide is substituted with phenoxazine-modified cytosine, an oligonucleotide derivative in which ribose in the oligonucleotide is substituted with 2'-O-propylribose and an oligonucleotide derivative in which ribose in the oligonucleotide is substituted with 2'-methoxyethoxyribose [*Cell Technology* (*Saibo Kogaku*), 16, 1463 (1997)].

(b) Preparation of Host Cell Used in the Method of the Present Invention by Homologous Recombination The host cell used in the method of the present invention can be prepared by targeting a gene encoding the GDP-fucose synthase, the α1,6-fucose modifying enzyme or the GDP-fucose transport protein and modifying the target gene on chromosome through a homologous recombination technique.

The target gene on the chromosome can be modified by using a method described in *Manipulating the Mouse Embryo, A Laboratory Manual*, Second Edition, Cold Spring Harbor Laboratory Press (1994) (hereinafter referred to as "*Manipulating the Mouse Embryo, A Laboratory Manual*"); *Gene Targeting, A Practical Approach*, IRL Press at Oxford University Press (1993); *Biomanual Series* 8, *Gene Targeting, Preparation of Mutant Mice using ES*, Yodo-sha (1995) (hereinafter referred to as "*Preparation of Mutant Mice using ES Cells*"); or the like, for example, as follows.

A genomic DNA encoding the GDP-fucose synthase, the α1,6-fucose modifying enzyme or the GDP-fucose transport protein is prepared.

Based on the nucleotide sequence of the genomic DNA, a target vector is prepared for homologous recombination of a target gene to be modified (e.g., structural gene encoding the GDP-fucose synthase, the α1,6-fucose modifying enzyme or the GDP-fucose transport protein or a promoter gene).

The host cell used in the method of the present invention can be produced by introducing the prepared target vector into a host cell and selecting a cell in which homologous recombination occurred between the target gene and target vector.

As the host cell, any cell such as yeast, an animal cell, an insect cell or a plant cell can be used, so long as it has a gene encoding the GDP-fucose synthase, the α1,6-fucose modifying enzyme or the GDP-fucose transport protein. Examples include the host cells described in the following item 3.

The method for preparing a genomic DNA encoding the GDP-fucose synthase, the α1,6-fucose modifying enzyme or the GDP-fucose transport protein includes the methods described in "Preparation method of genomic DNA" in the item 1(1)(a) and the like.

The nucleotide sequence of the genomic DNA encoding the GDP-fucose synthase obtained by the above method includes the nucleotide sequence represented by SEQ ID NO:67 or 70. The nucleotide sequence of the genomic DNA of the α1,6-fucose modifying enzyme includes the nucleotide sequence represented by SEQ ID NO:3. The nucleotide sequence of the genomic DNA of the GDP-fucose transport protein includes the nucleotide sequence represented by SEQ ID NO:99 or 100.

The target vector for the homologous recombination of the target gene can be prepared in accordance with a method described in *Gene Targeting, A Practical Approach*, IRL Press at Oxford University Press (1993); *Preparation of Mutant Mice using ES Cells*; or the like. The target vector can be used as either a replacement type or an insertion type.

For introducing the target vector into various host cells, the methods for introducing recombinant vectors suitable for various host cells described in the following item 3 can be used.

The method for efficiently selecting a homologous recombinant includes a method such as the positive selection, promoter selection, negative selection or polyA selection described in *Gene Targeting, A Practical Approach*, IRL Press at Oxford University Press (1993); *Preparation of Mutant Mice using ES Cells*; or the like. The method for selecting the homologous recombinant of interest from the selected cell lines includes the Southern hybridization method for genomic DNA (*Molecular Cloning*, Second Edition), PCR [*PCR Protocols*, Academic Press (1990)], and the like.

(c) Preparation of Cell of the Present Invention by RDO Method

The host cell used in the method of the present invention can be prepared by targeting a gene encoding the GDP-fucose synthase, the α1,6-fucose modifying enzyme or the GDP-fucose transport protein according to an RDO method, for example, as follows.

A cDNA or a genomic DNA encoding the GDP-fucose synthase, the α1,6-fucose modifying enzyme or the GDP-fucose transport protein is prepared.

The nucleotide sequence of the prepared cDNA or genomic DNA is determined.

Based on the determined DNA sequence, an RDO construct of an appropriate length comprising a DNA encoding the GDP-fucose synthase, the α1,6-fucose modifying enzyme or the GDP-fucose transport protein, a DNA encoding a untranslated region or a DNA encoding an intron, is designed and synthesized.

The host cell used in the method of the present invention can be obtained by introducing the synthesized RDO into a host cell and then selecting a transformant in which a mutation occurred in the target enzyme, i.e., the GDP-fucose synthase, the α1,6-fucose modifying enzyme or the GDP-fucose transport protein.

As the host cell, any cell such as yeast, an animal cell, an insect cell or a plant cell can be used, so long as it has a gene encoding the target GDP-fucose synthase, α1,6-fucose modifying enzyme or GDP-fucose transport protein. Examples include the host cells described in the following item 3.

The method for introducing RDO into various host cells includes the methods for introducing recombinant vectors suitable for various host cells described in the following item 3.

The method for preparing cDNA encoding the GDP-fucose synthase, the α1,6-fucose modifying enzyme or the GDP-fucose transport protein includes the methods described in "Preparation of DNA" in the item 1(1)(a) and the like.

The method for preparing a genomic DNA encoding the GDP-fucose synthase, α1,6-fucose modifying enzyme or the GDP-fucose transport protein includes the methods described in "Preparation method of genomic DNA" in the item 1(1)(a) and the like.

The nucleotide sequence of the DNA can be determined by digesting it with appropriate restriction enzymes, cloning the fragments into a plasmid such as pBluescript SK(−) (manufactured by Stratagene), subjecting the clones to the reaction generally used as a method for analyzing a nucleotide sequence such as the dideoxy method of Sanger et al. [*Proc. Natl. Acad. Sci. USA*, 74, 5463 (1977)] or the like, and then analyzing the clones using an automatic nucleotide sequence analyzer such as ABI PSISM 377DNA Sequencer (manufactured by PE Biosystems) or the like.

The RDO can be prepared in the usual method or by using a DNA synthesizer.

The method for selecting a cell in which a mutation occurred, by introducing the RDO into the host cell, in the gene encoding the targeting enzyme, the GDP-fucose synthase, the α1,6-fucose modifying enzyme or the GDP-fucose transport protein includes the methods for directly detecting mutations in chromosomal genes described in *Molecular Cloning*, Second Edition, *Current Protocols in Molecular Biology* and the like.

Furthermore, the method described in the item 1(1)(a) for selecting a transformant based on the activity of the introduced GDP-fucose synthase, α1,6-fucose modifying enzyme or GDP-fucose transport protein and the method for selecting a transformant based on the sugar chain structure of a glycoprotein on the cell membrane described later in the item 1(5), and the method for selecting a transformant based on the sugar structure of a produced antibody molecule described later in the item 6 or 7 can also be used.

The construct of the RDO can be designed in accordance with the methods described in *Science*, 273, 1386 (1996); *Nature Medicine*, 4, 285 (1998); *Hepatology*, 25, 1462 (1997); *Gene Therapy*, 5, 1960 (1999); *J. Mol. Med.*, 75, 829 (1997); *Proc. Natl. Acad. Sci. USA*, 96, 8774 (1999); *Proc. Natl. Acad. Sci. USA*, 96, 8768 (1999); *Nuc. Acids. Res.*, 27, 1323 (1999); *Invest. Dematol.*, 111, 1172 (1998); *Nature Biotech.*, 16, 1343 (1998); *Nature Biotech.*, 18, 43 (2000); *Nature Biotech.*, 18, 555 (2000); and the like.

(d) Preparation of Host Cell Used in the Method of the Present Invention by RNAi Method The host cell used in the method of the present invention can be prepared by targeting a gene encoding the GDP-fucose synthase, the α1,6-fucose modifying enzyme or the GDP-fucose transport protein according to the RNAi method, for example, as follows.

A cDNA encoding the GDP-fucose synthase, the α1,6-fucose modifying enzyme or the GDP-fucose transport protein is prepared.

The nucleotide sequence of the prepared cDNA is determined.

Based on the determined DNA sequence, an RNAi gene construct of an appropriate length comprising a DNA encoding the GDP-fucose synthase, the α1,6-fucose modifying enzyme or the GDP-fucose transport protein or a DNA encoding a untranslated region, is designed.

In order to express the RNAi gene in a cell, a recombinant vector is prepared by inserting a fragment or full length of the prepared DNA into downstream of the promoter of an appropriate expression vector.

A transformant is obtained by introducing the recombinant vector into a host cell suitable for the expression vector.

The host cell used in the method of the present invention can be obtained by selecting a transformant based on the activity of the introduced GDP-fucose synthase, α1,6-fucose modifying enzyme or GDP-fucose transport protein, or the sugar chain structure of the produced antibody molecule or of a glycoprotein on the cell membrane.

As the host cell, any cell such as yeast, an animal cell, an insect cell or a plant cell can be used, so long as it has a gene encoding the target GDP-fucose synthase, α1,6-fucose modifying enzyme or GDP-fucose transport protein. Examples include the host cells described in the following item 3.

As the expression vector, a vector which is autonomously replicable in the above host cell or can be integrated into the chromosome and comprises a promoter at such a position that the designed RNAi gene can be transferred is used. Examples include the expression vectors described in the following item 3.

As the method for introducing a gene into various host cells, the methods for introducing recombinant vectors suitable for various host cells described in the following item 3 can be used.

The method for selecting a transformant based on the activity of the GDP-fucose synthase, the α1,6-fucose modifying enzyme or the GDP-fucose transport protein includes the methods described in the item 1(1)(a).

The method for selecting a transformant based on the sugar chain structure of a glycoprotein on the cell membrane includes the methods described in the following item 1(5). The method for selecting a transformant based on the sugar chain structure of a produced antibody molecule includes the methods described in the following item 6 or 7.

The method for preparing cDNA of the GDP-fucose synthase, the α1,6-fucose modifying enzyme or the GDP-fucose transport protein includes the methods described in "Preparation of DNA" in the item 1(1)(a) and the like.

In addition, the host cell used in the method of the present invention can also be obtained without using an expression vector, by directly introducing an RNAi gene designed based on the nucleotide sequence of the GDP-fucose synthase, the α1,6-fucose modifying enzyme or the GDP-fucose transport protein.

The RNAi gene can be prepared in the usual method or by using a DNA synthesizer.

The RNAi gene construct can be designed in accordance with the methods described in *Nature*, 391, 806 (1998); *Proc. Natl. Acad. Sci. USA*, 95, 15502 (1998); *Nature*, 395, 854 (1998); *Proc. Natl. Acad. Sci. USA*, 96, 5049 (1999); *Cell*, 95, 1017 (1998); *Proc. Natl. Acad. Sci. USA*, 96, 1451 (1999); *Proc. Natl. Acad. Sci. USA*, 95, 13959 (1998); *Nature Cell Biol.*, 2, 70 (2000); and the like.

(e) Preparation of Host Cell Used in the Method of the Present Invention by Method Using Transposon The host cell used in the method of the present invention can be prepared by selecting a mutant based on the activity of the GDP-fucose synthase, the α1,6-fucose modifying enzyme or the GDP-fucose transport protein or the sugar chain structure of a produced antibody molecule or of a glycoprotein on the cell membrane by using a transposon system described in *Nature Genet.*, 25, 35 (2000) or the like.

The transposon system is a system in which a mutation is induced by randomly inserting an exogenous gene into chromosome, wherein an exogenous gene interposed between transposons is generally used as a vector for inducing a mutation, and a transposase expression vector for randomly inserting the gene into chromosome is introduced into the cell at the same time.

Any transposase can be used, so long as it is suitable for the sequence of the transposon to be used.

As the exogenous gene, any gene can be used, so long as it can induce a mutation in the DNA of a host cell.

As the host cell, any cell such as yeast, an animal cell, an insect cell or a plant cell can be used, so long as it has a gene encoding the targeting GDP-fucose synthase, α1,6-fucose modifying enzyme or GDP-fucose transport protein. Examples include the host cells described in the following item 3. For introducing the gene into various host cells, the method for introducing recombinant vectors suitable for various host cells described in the following item 3, can be used.

The method for selecting a mutant based on the activity of the GDP-fucose synthase, the α1,6-fucose modifying enzyme or the GDP-fucose transport protein includes the methods which will be described above in the item 1(1)(a).

The method for selecting a mutant based on the sugar chain structure of a glycoprotein on the cell membrane includes the methods described in the following item 1(5). The method for selecting a transformant based on the sugar chain structure of a produced antibody molecule includes the methods described in the following item 6 or 7.

(2) Method for Introducing Dominant Negative Mutant of Enzyme

The host cell used in the method of the present invention can be prepared by targeting a gene encoding the GDP-fucose synthase, the α1,6-fucose modifying enzyme or the GDP-fucose transport protein according to a technique for introducing a dominant negative mutant of the enzyme. The GDP-fucose synthase includes GMD, Fx, GFPP, fucokinase and the like. The α1,6-fucose modifying enzyme includes α1,6-fucosyltransferase, α-L-focosidase and the like. The GDP-fucose transport protein includes GDP-fucose transporter and the like.

The enzymes catalyze specific reactions having substrate specificity, and dominant negative mutants of the enzymes can be prepared by disrupting the active center of the enzymes which have the catalytic activity having substrate specificity. The method for preparing a dominant negative mutant is specifically described as follows with reference to GMD among the target enzymes.

As a result of the analysis of the three-dimensional structure of *E. coli*-derived GMD, it has been found that 4 amino acids (threonine at position 133, glutamic acid at position 135, tyrosine at position 157 and lysine at position 161) have an important function on the enzyme activity [*Structure*, 8, 2 (2000)]. That is, when mutants were prepared by substituting the 4 amino acids with other different amino acids based on the three-dimensional structure information, the enzyme activity of all of the mutants was significantly decreased. On the other hand, changes in the ability of GMD to bind to GMD coenzyme NADP and its substrate GDP-mannose were hardly observed in the mutants. Accordingly, a dominant negative mutant can be prepared by substituting the 4 amino acids which control the enzyme activity of GMD. A dominant negative mutant can be prepared by comparing the homology and predicting the three-dimensional structure using the amino acid sequence information based on the results of the *E. coli*-derived GMD. For example, in GMD (SEQ ID NO:65) derived from CHO cell, a dominant negative mutant can be prepared by substituting threonine at position 155, glutamic acid at position 157, tyrosine at position 179 and lysine at position 183. Such a gene into which amino acid substitution is introduced can be prepared by the site-directed mutagenesis described in *Molecular Cloning*, Second Edition, *Current Protocols in Molecular Biology* or the like.

The host cell can be prepared by using the above prepared dominant negative mutant gene of the target enzyme according to the method described in *Molecular Cloning*, Second Edition, *Current Protocols in Molecular Biology, Manipulating the Mouse Embryo*, Second Edition or the like, for example, as follows.

A gene encoding the dominant negative mutant of the GDP-fucose synthase, the α1,6-fucose modifying enzyme or the GDP-fucose transport protein (hereinafter referred to as "dominant negative mutant gene") is prepared.

Based on the full length DNA of the prepared dominant negative mutant gene, a DNA fragment of an appropriate length containing a DNA encoding the antibody molecule is prepared, if necessary.

A recombinant vector is prepared by inserting the DNA fragment or full length DNA into downstream of the promoter of an appropriate expression vector.

A transformant is obtained by introducing the recombinant vector into a host cell suitable for the expression vector.

The host cell used in the method of the present invention can be prepared by selecting a transformant based on the activity of the GDP-fucose synthase, the α1,6-fucose modifying enzyme or the GDP-fucose transport protein, or the sugar chain structure of a produced antibody molecule or of a glycoprotein on the cell membrane.

As the host cell, any cell such as yeast, an animal cell, an insect cell or a plant cell can be used, so long as it has a gene encoding the GDP-fucose synthase, the α1,6-fucose modifying enzyme or the GDP-fucose transport protein. Examples include the host cells described in the following item 3.

As the expression vector, a vector which is autonomously replicable in the host cell or can be integrated into the chromosome and comprises a promoter at a position where transcription of the DNA encoding the dominant negative mutant of interest can be effected is used. Examples include the expression vectors described in the following item 3.

For introducing the gene into various host cells, the method for introducing recombinant vectors suitable for various host cells described in the following item 3, can be used.

The method for selecting a mutant based on the activity of the GDP-fucose synthase, the α1,6-fucose modifying enzyme or the GDP-fucose transport protein includes the methods which will be described in the above item 1(1)(a).

The method for selecting a mutant based on the sugar chain structure of a glycoprotein on the cell membrane includes the methods described in the following item 1(5). The method for selecting a transformant based on the sugar chain structure of a produced antibody molecule includes the methods described in the following item 6 or 7.

(3) Method for Introducing Mutation into Enzyme

The host cell used in the method of the present invention can be prepared by introducing a mutation into a gene encoding the GDP-fucose synthase, the α1,6-fucose modifying enzyme or the GDP-fucose transport protein, and then selecting a cell line of interest in which the mutation occurred in the enzyme.

The GDP-fucose synthase includes GMD, Fx, GFPP, fucokinase and the like. The α1,6-fucose modifying enzyme includes α1,6-fucosyltransferase, α-L-focosidase and the like. The GDP-fucose transport protein includes GDP-fucose transporter and the like.

The method for introducing mutation into an enzyme includes 1) a method in which a desired clone is selected from mutants obtained by a mutation-inducing treatment of a parent cell line with a mutagen or spontaneously generated mutants, based on the activity of the GDP-fucose synthase, the α1,6-fucose modifying enzyme or the GDP-fucose transport protein, 2) a method in which a desired clone is selected from mutants obtained by a mutation-inducing treatment of a parent cell line with a mutagen or spontaneously generated mutants, based on the sugar chain structure of a produced antibody molecule, 3) a method in which a desired clone is selected from mutants obtained by a mutation-inducing treatment of a parent cell line with a mutagen or spontaneously generated mutants, based on the sugar chain structure of a glycoprotein on the cell membrane, and the like.

As the mutation-inducing treatment, any treatment can be used, so long as it can induce a point mutation or a deletion or frame shift mutation in the DNA of cells of the parent cell line.

Examples include treatment with ethyl nitrosourea, nitrosoguanidine, benzopyrene or an acridine pigment and treatment with radiation. Also, various alkylating agents and carcinogens can be used as mutagens. The method for allowing a mutagen to act upon cells includes the methods described in *Tissue Culture Techniques,* 3rd edition (Asakura Shoten), edited by Japanese Tissue Culture Association (1996), *Nature Genet.,* 24, 314 (2000) and the like.

The spontaneously generated mutant includes mutants which are spontaneously formed by continuing subculture under general cell culture conditions without applying special mutation-inducing treatment.

The method for measuring the activity of the GDP-fucose synthase, the α1,6-fucose modifying enzyme or the GDP-fucose transport protein includes the methods described above in the item 1(1)(a). The method for distinguishing the sugar chain structure of a produced antibody molecule includes the methods described in the following item 6 or 7. The method for distinguishing the sugar chain structure of a glycoprotein on the cell membrane includes the methods described in the following item 1(5).

(4) Method for Suppressing Transcription and/or Translation of Enzyme

The host cell used in the method of the present invention can be prepared by targeting a gene encoding the GDP-fucose synthase or the α1,6-fucose modifying enzyme or the GDP-fucose transport protein and suppressing transcription and/or translation of the target gene according to the antisense RNA/DNA technique [*Bioscience and Industry,* 50, 322 (1992); *Chemistry,* 46, 681 (1991); *Biotechnology,* 9, 358 (1992); *Trends in Biotechnology,* 10, 87 (1992); *Trends in Biotechnology,* 10, 152 (1992); *Cell Engineering,* 16, 1463 (1997)], the triple helix technique [*Trends in Biotechnology,* 10, 132 (1992)] or the like.

The GDP-fucose synthase includes GMD, Fx, GFPP, fucokinase and the like. The α1,6-fucose modifying enzyme includes α1,6-fucosyltransferase, α-L-focosidase and the like. The GDP-fucose transport protein includes GDP-fucose transporter and the like.

(5) Method for Selecting Clone Resistant to Lectin which Recognizes Sugar Chain Structure in which 1-Position of Fucose is Bound to 6-Position of N-acetylglucosamine in the Reducing End Through α-Bond in the N-glycoside-Linked Sugar Chain The host cell used in the method of the present invention can be prepared by using a method for selecting a clone resistant to a lectin which recognizes a sugar chain structure in which 1-position of fucose is bound to 6-position of N-acetylglucosamine in the reducing end through α-bond in the N-glycoside-linked sugar chain.

The method for selecting a clone resistant to a lectin which recognizes a sugar chain structure in which 1-position of fucose is bound to 6-position of N-acetylglucosamine in the reducing end through α-bond in the N-glycoside-linked sugar chain includes the methods using lectin described in *Somatic Cell Mol. Genet.,* 12, 51 (1986) and the like.

As the lectin, any lectin can be used, so long as it is a lectin which recognizes a sugar chain structure in which 1-position of fucose is bound to 6-position of N-acetylglucosamine in the reducing end through α-bond in the N-glycoside-linked sugar chain. Examples include a *Lens culinaris* lectin LCA (lentil agglutinin derived from *Lens culinaris*), a pea lectin PSA (pea lectin derived from *Pisum sativum*), a broad bean lectin VFA (agglutinin derived from *Vicia faba*), an *Aleuria aurantia* lectin AAL (lectin derived from *Aleuria aurantia*) and the like.

Specifically, the clone of the present invention resistant to a lectin which recognizes a sugar chain structure in which 1-position of fucose is bound to 6-position of N-acetylglucosamine in the reducing end through α-bond in the N-glycoside-linked sugar chain can be selected by culturing cells by using a medium comprising the lectin at a concentration of 1 μg/ml to 1 mg/ml for 1 day to 2 weeks, preferably 1 day to 1 week, subculturing surviving cells or picking up a colony and transferring it into a culture vessel, and subsequently continuing the culturing using the lectin-containing medium.

The method for confirming that the cell is a lectin-resistant cell includes a method for confirming expression of the GDP-fucose synthase, α1,6-fucose modifying enzyme or the GDP-fucose transport protein, a method for culturing the cell in a medium to which lectin is directly added. Specifically, when the expression amount of the mRNA of α1,6-fucosyltransferase which is one of α1,6-fucose modifying enzymes in the cell is measured, a lectin-resistant cell decreases in an amount of the mRNA expressed.

2. Preparation of Transgenic Non-Human Animal or Plant or the Progenies

The cell used in the method of the present invention can be prepared by using a transgenic non-human animal or plant or the progenies thereof in which a genomic gene is modified in such a manner that the activity of the GDP-fucose synthase, the α1,6-fucose modifying enzyme or the GDP-fucose transport protein is decreased or deleted. The transgenic non-human animal or plant or the progenies thereof can be prepared by targeting a gene encoding the above protein according to the method similar to that in the item 1.

In a transgenic non-human animal, the embryonic stem cell used in the process of the present invention in which the activity of the GDP-fucose synthase, the α1,6-fucose modifying enzyme or the GDP-fucose transport protein is decreased or deleted can be prepared applying the method similar to that in the item 1 to an embryonic stem cell of the intended non-human animal such as cattle, sheep, goat, pig, horse, mouse, rat, fowl, monkey or rabbit.

Specifically, a mutant clone is prepared in which a gene encoding the GDP-fucose synthase, the α1,6-fucose modifying enzyme or the GDP-fucose transport protein is inactivated or substituted with any nucleotide sequence, by a known homologous recombination technique [e.g., *Nature,* 326, 6110, 295 (1987); *Cell,* 51, 3, 503 (1987); etc.]. Using the prepared mutant clone, a chimeric individual comprising an embryonic stem cell clone and a normal cell can be prepared by an injection chimera method into blastocyst of fertilized egg of an animal or by an aggregation chimera method. The chimeric individual is crossed with a normal individual, so that a transgenic non-human animal in which the activity of the GDP-fucose synthase, the α1,6-fucose modifying enzyme or the GDP-fucose transport protein is decreased or deleted in the whole body cells can be obtained.

The target vector for the homologous recombination of the target gene can be prepared in accordance with a method described in *Gene Targeting, A Practical Approach*, IRL Press at Oxford University Press (1993); *Preparation of Mutant Mice using ES Cells*, or the like. The target vector can be used as any of a replacement type, an insertion type and a gene trap type.

As the method for introducing the target vector into the embryonic stem cell, any method can be used, so long as it can introduce DNA into an animal cell. Examples include electroporation [*Cytotechnology,* 3, 133 (1990)], the calcium phosphate method (Japanese Published Unexamined Patent Application No. 227075/90), the lipofection method [*Proc. Natl. Acad. Sci. USA,* 84, 7413 (1987)], the injection method [*Manipulating the Mouse Embryo*, Second Edition], a method using particle gun (gene gun) (Japanese Patent No. 2606856, Japanese Patent No. 2517813), the DEAE-dextran method [*Biomanual Series 4-Gene Transfer and Expression Analysis* (Yodo-sha), edited by Takashi Yokota and Kenichi Arai (1994)], the virus vector method [*Manipulating Mouse Embryo*, Second Edition] and the like.

The method for efficiently selecting a homologous recombinant includes a method such as the positive selection, promoter selection, negative selection or poly A selection described in *Gene Targeting, A Practical Approach*, IRL Press at Oxford University Press (1993), *Preparation of Mutant Mice using ES Cells*, or the like. Specifically, in the case of the target vector containing hprt gene, it is introduced into the hprt gene-defected embryonic stem cell, the embryonic stem cell is cultured in a medium containing aminopterin, hypoxanthine and thymidine, and positive selection which selects the homologous recombinant of the hprt gene can be carried out by selecting an a homogenous recombinant containing an aminopterin-resistant clone. In the case of the target vector containing a neomycin-resistant gene, the vector-introduced embryonic stem cell is cultured in a medium containing G418, and positive selection which selects a homogenous recombinant containing a neomycin-resistant gene can be carried out by selecting a G418-resistant clone. In the case of the target vector containing DT gene, the vector-introduced embryonic stem cell is cultured, and negative selection selecting a DT gene-free homogenous recombinant can be carried out by selecting the grown clone (in the recombinants introduced into a chromosome at random rather than the homogenous recombination, since the DT gene is expressed while integrated in the chromosome, the recombinants cannot grow because of the toxicity of DT). The method for selecting the homogenous recombinant of interest among the selected clones include the Southern hybridization for genomic DNA (*Molecular Cloning*, Second Edition), PCR [*PCR Protocols*, Academic Press (1990)] and the like.

When the embryonic stem cell is introduced into a fertilized egg by using an aggregation chimera method, in general, a fertilized egg at the development stage before 8-cell stage is preferably used. When the embryonic stem cell is introduced into a fertilized egg by using an injection chimera method, in general, it is preferred that a fertilized egg at the development stage from 8-cell stage to blastocyst stage is preferably used.

When the fertilized egg is transplanted into a female mouse, it is preferred that a fertilized egg obtained from a pseudopregnant female mouse in which fertility is induced by mating with a male non-human mammal which is subjected to vasoligation is artificially transplanted or implanted. Although the pseudopregnant female mouse can be obtained by natural mating, the pseudopregnant female mouse in which fertility is induced can be obtained by mating with a male mouse after administration of a luteinizing hormone-releasing hormone (hereinafter referred to as "LHRH") or its analogue thereof. The analogue of LHRH includes [3,5-DilTyr5]-LHRH, [Gln8]-LHRH, [D-Ala6]-LHRH, des-Gly10-[D-His(Bzl)6]-LHRH ethylamide and the like.

Also, a fertilized egg cell of the present invention in which the activity of the GDP-fucose synthase, the α1,6-fucose modifying enzyme or the GDP-fucose transport protein is decreased or deleted can be prepared by applying the method similar to that in the item 1 to fertilized egg of a non-human animal of interest such as cattle, sheep, goat, pig, horse, mouse, rat, fowl, monkey, rabbit or the like.

A transgenic non-human animal in which the activity of the GDP-fucose synthase, the α1,6-fucose modifying enzyme or the GDP-fucose transport protein is decreased or deleted can be prepared by transplanting the prepared fertilized egg cell into the oviduct or uterus of a pseudopregnant female using the embryo transplantation method described in *Manipulating Mouse Embryo*, Second Edition or the like, followed by childbirth by the animal.

In a transgenic plant, the callus of the present invention in which the activity of the GDP-fucose synthase or the activity of an enzyme relating to modification of a sugar chain in which 1-position of fucose is bound to 6- or 3-position of N-acetylglucosamine in the reducing end in the N-glycoside-linked complex sugar chain is decreased or deleted can be prepared by applying the method similar to that in the item 1 to a callus or cell of the plant of interest.

A transgenic plant in which the activity of the GDP-fucose synthase, the α1,6-fucose modifying enzyme or the GDP-fucose transport protein is decreased or deleted can be prepared by culturing the prepared callus in a medium comprising auxin and cytokinin to rediffereniate it in accordance with conventional methods [*Tissue Culture (Soshiki Baiyo)*, 20 (1994); *Tissue Cultur (Soshiki Baiyo)e*, 21 (1995); *Trends in Biotechnology*, 15, 45 (1997)].

3. Method for Producing Antibody Composition

The antibody composition can be obtained by expressing it in a host cell by using the methods described in *Molecular Cloning*, Second Edition; *Current Protocols in Molecular Biology; Antibodies, A Laboratory Manual*, Cold Spring Harbor Laboratory, 1988 (hereinafter sometimes referred to as "*Antibodies*"); *Monoclonal Antibodies: Principles and Practice*, Third Edition, Acad. Press, 1996 (hereinafter sometimes referred to as "*Monoclonal Antibodies*"); and *Antibody Engineering, A Practical Approach*, IRL Press at Oxford University Press, 1996 (hereinafter sometimes referred to as "*Antibody Engineering*"), for example, as follows.

A full length cDNA of an antibody molecule is prepared, and a DNA fragment of an appropriate length comprising a DNA encoding the antibody molecule is prepared.

A recombinant vector is prepared by inserting the DNA fragment or the full length cDNA into downstream of the promoter of an appropriate expression vector.

A transformant which produces the antibody molecule can be obtained by introducing the recombinant vector into a host cell suitable for the expression vector.

As the host cell, the host cell of any cell such as yeast, an animal cell, an insect cell, a plant cell or the like can be used, so long as it can express the gene of interest.

A cell such as yeast, an animal cell, an insect cell, a plant cell or the like into which an enzyme relating to the modification of an N-glycoside-linked sugar chain which binds to the Fc region of the antibody molecule is introduced by a genetic engineering technique can also be used as the host cell.

As the expression vector, a vector which is autonomously replicable in the host cell or can be integrated into the chromosome and comprises a promoter at such a position that the DNA encoding the antibody molecule of interest can be transferred is used.

The cDNA can be prepared from a human or non-human tissue or cell by using a probe primer specific for the antibody molecule of interest and the like according to the methods described in "Preparation of DNA" in the item 1(1)(a).

When yeast is used as the host cell, the expression vector includes YEP13 (ATCC 37115), YEp24 (ATCC 37051), YCp50 (ATCC 37419) and the like.

As the promoter, any promoter can be used so long as it can function in yeast. Examples include a promoter of a gene relating to the glycolytic pathway such as a hexose kinase, PHOS promoter, PGK promoter, GAP promoter, ADH promoter, gal 1 promoter, gal 10 promoter, heat shock protein promoter, MFα1 promoter, CUP 1 promoter and the like.

The host cell includes yeast belonging to the genus *Saccharomyces*, the genus *Schizosaccharomyces*, the genus *Kluyveromyces*, the genus *Trichosporon*, the genus *Schwanniomyces* and the like, such as *Saccharomyces cerevisiae*, *Schizosaccharomyces pombe*, *Kluyveromyces lactis*, *Trichosporon pullulans* and *Schwanniomyces alluvius*.

As the method for introducing the recombinant vector, any method can be used, so long as it can introduce DNA into yeast. Examples include electroporation [*Methods in Enzymology*, 194, 182 (1990)], spheroplast method [*Proc. Natl. Acad. Sci. USA*, 84, 1929 (1978)], lithium acetate method [*J. Bacteriol.*, 153, 163 (1983)], a method described in *Proc. Natl. Acad. Sci. USA*, 75, 1929 (1978) and the like.

When an animal cell is used as the host cell, the expression vector includes pcDNAI, pcDM8 (available from Funakoshi), pAGE107 [Japanese Published Unexamined Patent Application No. 22979/91; *Cytotechnology*, 3, 133 (1990)], pAS3-3 (Japanese Published Unexamined Patent Application No. 227075/90), pCDM8 [*Nature*, 329, 840 (1987)], pcDNAI/Amp (manufactured by Invitrogen), pREP4 (manufactured by Invitrogen), pAGE103 [*J. Biochemistry*, 101, 1307 (1987)], pAGE210 and the like.

As the promoter, any promoter can be used, so long as it can function in an animal cell. Examples include a promoter of IE (immediate early) gene of cytomegalovirus (CMV), an early promoter of SV40, a promoter of retrovirus, a promoter of metallothionein, a heat shock promoter, an SRα promoter and the like. Also, an enhancer of the IE gene of human CMV may be used together with the promoter.

The host cell includes a human cell such as Namalwa cell, a monkey cell such as COS cell, a Chinese hamster cell such as CHO cell or HBT5637 (Japanese Published Unexamined Patent Application No. 299/88), a rat myeloma cell, a mouse myeloma cell, a cell derived from syrian hamster kidney, an embryonic stem cell, a fertilized egg cell and the like.

As the method for introducing the recombinant vector, any method can be used, so long as it can introduce DNA into an animal cell. Examples include electroporation [*Cytotechnology*, 3, 133 (1990)], the calcium phosphate method (Japanese Published Unexamined Patent Application No. 227075/90), the lipofection method [*Proc. Natl. Acad. Sci. USA*, 84, 7413 (1987)], the injection method [*Manipulating the Mouse Embryo, A Laboratory Manual*], a method using particle gun (gene gun) (Japanese Patent No. 2606856, Japanese Patent No. 2517813), the DEAE-dextran method [*Biomanual Series 4-Gene Transfer and Expression Analysis* (Yodo-sha), edited by Takashi Yokota and Kenichi Arai (1994)], the virus vector method [*Manipulating Mouse Embryo*, Second Edition] and the like.

When an insect cell is used as the host cell, the protein can be expressed by the method described in *Current Protocols in Molecular Biology, Baculovirus Expression Vectors, A Laboratory Manual*, W.H. Freeman and Company, New York (1992), *Bio/Technology*, 6, 47 (1988) or the like.

That is, the protein can be expressed by co-introducing a recombinant gene-introducing vector and a baculovirus into an insect cell to obtain a recombinant virus in an insect cell culture supernatant and then infecting the insect cell with the recombinant virus.

The gene introducing vector used in the method includes pVL1392, pVL1393, pBlueBacIII (all manufactured by Invitrogen) and the like.

The baculovirus includes *Autographa californica* nuclear polyhedrosis virus which is infected by an insect of the family Barathra.

The insect cell includes *Spodoptera frugiperda* oocytes Sf9 and Sf21 [*Current Protocols in Molecular Biology, Baculovirus Expression Vectors, A Laboratory Manual*, W.H. Freeman and Company, New York (1992)], a *Trichoplusia ni* oocyte High 5 (manufactured by Invitrogen) and the like.

The method for co-introducing the above recombinant gene-introducing vector and the baculovirus to the insect cells for preparing the above recombinant virus includes the calcium phosphate method (Japanese Published Unexamined Patent Application No. 227075/90), the lipofection method [*Proc. Natl. Acad. Sci. USA*, 84, 7413 (1987)] and the like.

When a plant cell is used as the host cell, the expression vector includes Ti plasmid, tobacco mosaic virus and the like.

As the promoter, any promoter can be used, so long as it can function in a plant cell. Examples include cauliflower mosaic virus (CaMV) 35S promoter, rice actin 1 promoter and the like.

The host cell includes plant cells of tobacco, potato, tomato, carrot, soybean, rape, alfalfa, rice, wheat, barley and the like.

As the method for introducing the recombinant vector, any method can be used, so long as it can introduce DNA into a plant cell. Examples include a method using *Agrobacterium* (Japanese Published Unexamined Patent Application No. 140885/84, Japanese Published Unexamined Patent Application No. 70080/85, WO94/00977), electroporation (Japanese Published Unexamined Patent Application No. 251887/85), a method using a particle gun (gene gun) (Japanese Patent No. 2606856, Japanese Patent No. 2517813) and the like.

As the method for expressing an antibody gene, secretion production, expression of a fusion protein of the Fc region with other protein and the like can be carried out in accordance with the method described in *Molecular Cloning*, Second Edition or the like, in addition to the direct expression.

When a gene is expressed by a microorganism, yeast, an animal cell, an insect cell or a plant cell into which a gene relating to the synthesis of a sugar chain is introduced, an antibody molecule to which a sugar or a sugar chain is added by the introduced gene can be obtained.

An antibody composition can be produced by culturing the obtained transformant in a medium to produce and accumulate the antibody molecule in the culture and then recovering it from the resulting culture. The method for culturing the transformant in a medium can be carried out in accordance with a general method which is used for the culturing of host cells.

As the medium for culturing a transformant obtained using yeast as the host cell, the medium may be either a natural medium or a synthetic medium, so long as it comprises materials such as a carbon source, a nitrogen source and an inorganic salt which can be assimilated by the organism and culturing of the transformant can be efficiently carried out.

As the carbon source, those which can be assimilated by the organism can be used. Examples include carbohydrates such as glucose, fructose, sucrose, molasses thereof, starch and starch hydrolysate; organic acids such as acetic acid and propionic acid; alcohols such as ethanol and propanol; and the like.

The nitrogen source includes ammonia; ammonium salts of inorganic acid or organic acid such as ammonium chloride, ammonium sulfate, ammonium acetate and ammonium phosphate; other nitrogen-containing compounds; peptone; meat extract; yeast extract; corn steep liquor; casein hydrolysate; soybean meal; soybean meal hydrolysate; various fermented cells and hydrolysates thereof; and the like.

The inorganic salt includes potassium dihydrogen phosphate, dipotassium hydrogen phosphate, magnesium phosphate, magnesium sulfate, sodium chloride, ferrous sulfate, manganese sulfate, copper sulfate, calcium carbonate, and the like.

The culturing is carried out generally under aerobic conditions such as a shaking culture or submerged-aeration stirring culture. The culturing temperature is preferably at 15 to 40° C., and the culturing time is generally 16 hours to 7 days. During the culturing, the pH is maintained at 3.0 to 9.0. The pH is adjusted using an inorganic or organic acid, an alkali solution, urea, calcium carbonate, ammonia or the like.

Furthermore, if necessary, an antibiotic such as ampicillin or tetracycline can be added to the medium during the culturing.

When yeast transformed with a recombinant vector obtained by using an inducible promoter as the promoter is cultured, an inducer can be added to the medium, if necessary. For example, when yeast transformed with a recombinant vector obtained by using lac promoter is cultured, isopropyl-$\beta$-D-thiogalactopyranoside and the like can be added to the medium, and when yeast transformed with a recombinant vector obtained by using trp promoter is cultured, indoleacrylic acid and the like can be added to the medium.

When a transformant obtained by using an animal cell as the host is cultured, the medium includes generally used RPMI 1640 medium [*The Journal of the American Medical Association*, 199, 519 (1967)], Eagle's MEM medium [*Science*, 122, 501 (1952)], Dulbecco's modified MEM medium [*Virology*, 8, 396 (1959)], 199 medium [*Proceeding of the Society for the Biological Medicine*, 73, 1 (1950)] and Whitten's medium [*Developmental Engineering Experimentation Manual-Preparation of Transgenic Mice* (Kodan-sha), edited by M. Katsuki (1987)], the media to which fetal calf serum, etc. are added, and the like.

The culturing is carried out generally at conditions under pH of 6 to 8 and 30 to 40° C. for 1 to 7 days in the presence of 5% $CO_2$ and the like, for 1 to 7 days.

Furthermore, if necessary, an antibiotic such as kanamycin or penicillin can be added to the medium during the culturing.

The medium for culturing a transformant obtained by using an insect cell as the host includes generally used TNM-FH medium (manufactured by Pharmingen), Sf-900 II SFM medium (manufactured by Life Technologies), ExCell 400 and ExCell 405 (both manufactured by JRH Biosciences), Grace's Insect Medium [*Nature*, 195, 788 (1962)] and the like.

The culturing is carried out generally at conditions under pH of 6 to 7 and 25 to 30° C. and the like, for 1 to 5 days.

Furthermore, if necessary, an antibiotic such as gentamicin can be added to the medium during the culturing.

A transformant obtained by using a plant cell as the host can be cultured as a cell or by differentiating it into a plant cell or organ. The medium for culturing the transformant includes generally used Murashige and Skoog (MS) medium and White medium, the media to which a plant hormone such as auxin or cytokinin is added, and the like.

The culturing is carried out generally at conditions under pH of 5 to 9 and 20 to 40° C. for 3 to 60 days.

Furthermore, if necessary, an antibiotic such as kanamycin or hygromycin can be added to the medium during the culturing.

As described above, an antibody composition can be produced by culturing a transformant derived from yeast, an animal cell, an insect cell or a plant cell, which comprises a recombinant vector into which a DNA encoding an antibody molecule is inserted, in accordance with a general culturing method, to thereby produce and accumulate the antibody composition, and then recovering the antibody composition from the culture.

As the method for expressing the gene encoding an antibody, secretion production, expression of a fusion protein and the like can be carried out in accordance with the method described in *Molecular Cloning*, Second Edition in addition to the direct expression.

The method for producing an antibody composition includes a method of intracellular expression in a host cell, a method of extracellular secretion from a host cell, and a method of production on a host cell membrane outer envelope. The method can be selected by changing the host cell used or the structure of the antibody composition produced.

The method for producing an antibody composition includes a method of intracellular expression in a host cell, a method of extracellular secretion from a host cell, and a method of production on a host cell membrane outer envelope. The method can be selected by changing the host cell used or the structure of the antibody composition produced.

When the antibody composition is produced in a host cell or on a host cell membrane outer envelope, it can be positively secreted extracellularly in accordance with the method of Paulson et al. [*J. Biol. Chem.*, 264, 17619 (1989)], the method of Lowe et al. [*Proc. Natl. Acad. Sci. USA*, 86, 8227 (1989), *Genes Develop.*, 4, 1288 (1990)], the methods described in Japanese Published Unexamined Patent Application No. 336963/93 and Japanese Published Unexamined Patent Application No. 823021/94 and the like.

That is, an antibody molecule of interest can be positively secreted extracellularly from a host cell by inserting a DNA encoding the antibody molecule and a DNA encoding a signal peptide suitable for the expression of the antibody molecule into an expression vector according to a gene recombination technique and then expressing the antibody molecule.

Also, its production amount can be increased in accordance with the method described in Japanese Published Unexamined Patent Application No. 227075/90 according to a gene amplification system using a dihydrofolate reductase gene.

In addition, the antibody composition can also be produced by using a gene-introduced animal individual (transgenic non-human animal) or a plant individual (transgenic plant) which is constructed by the redifferentiation of an animal or plant cell into which the gene is introduced.

When the transformant is an animal individual or a plant individual, an antibody composition can be produced in accordance with a general method by rearing or cultivating it to thereby produce and accumulate the antibody composition and then recovering the antibody composition from the animal or plant individual.

The method for producing an antibody composition using an animal individual includes a method in which the antibody composition of interest is produced in an animal constructed by introducing a gene in accordance with a known method [*American Journal of Clinical Nutrition*, 63, 639S (1996); *American Journal of Clinical Nutrition*, 63, 627S (1996); *Bio/Technology*, 9, 830 (1991)].

In the case of an animal individual, an antibody composition can be produced, for example, by rearing a transgenic non-human animal into which a DNA encoding an antibody molecule is introduced to thereby produce and accumulate the antibody composition in the animal, and then recovering the antibody composition from the animal. The place of the animal where the composition is produced and accumulated includes milk (Japanese Published Unexamined Patent Application No. 309192/88) and eggs of the animal. As the promoter used in this case, any promoter can be used, so long as it can function in an animal. Preferred examples include mammary gland cell-specific promoters such as α casein promoter, β casein promoter, β lactoglobulin promoter, whey acidic protein promoter and the like.

The method for producing an antibody composition using a plant individual includes a method in which an antibody composition is produced by cultivating a transgenic plant into which a DNA encoding an antibody molecule is introduced by a known method [*Tissue Culture (Soshiki Baiyo)*, 20 (1994); *Tissue Culture (Soshiki Baiyo)*, 21 (1995); *Trends in Biotechnology*, 15, 45 (1997)] to produce and accumulate the antibody composition in the plant, and then recovering the antibody composition from the plant.

Regarding purification of an antibody composition produced by a transformant into which a gene encoding an antibody molecule is introduced, for example, when the antibody composition is intracellularly expressed in a dissolved state, the cells after culturing are recovered by centrifugation, suspended in an aqueous buffer and then disrupted by using ultrasonic oscillator, French press, Manton Gaulin homogenizer, dynomill or the like to obtain a cell-free extract. A purified product of the antibody composition can be obtained from a supernatant obtained by centrifuging the cell-free extract according to a general enzyme isolation purification techniques such as solvent extraction; salting out or desalting with ammonium sulfate; precipitation with an organic solvent; anion exchange chromatography using a resin such as diethylaminoethyl (DEAE)-Sepharose or DIAION HPA-75 (manufactured by Mitsubishi Chemical); cation exchange chromatography using a resin such as S-Sepharose FF (manufactured by Pharmacia); hydrophobic chromatography using a resin such as butyl-Sepharose or phenyl-Sepharose, gel filtration using a molecular sieve; affinity chromatography; chromatofocusing; electrophoresis such as isoelectric focusing; and the like which may be used alone or in combination.

Also, when the antibody composition is expressed intracellularly by forming an insoluble body, the cells are recovered, disrupted and centrifuged in the same manner, and the insoluble body of the antibody composition is recovered as a precipitation fraction. The recovered insoluble body of the antibody composition is solubilized by using a protein denaturing agent. The antibody composition is made into a normal three-dimensional structure by diluting or dialyzing the solubilized solution, and then a purified product of the antibody composition is obtained by the same isolation purification method.

When the antibody composition is secreted extracellularly, the antibody composition or derivatives thereof can be recovered from the culture supernatant. That is, the culture is treated according to a technique such as centrifugation as described above to obtain a soluble fraction, and a purified preparation of the antibody composition can be obtained from the soluble fraction by the same isolation purification method as described above.

The thus obtained antibody composition includes an antibody, the fragment of the antibody, a fusion protein comprising the Fc region of the antibody, and the like.

As an example for obtaining the antibody composition, a method for producing a composition of a humanized antibody and Fc fusion protein is described below in detail, but other antibody compositions can also be obtained in a manner similar to the method.

A. Preparation of Humanized Antibody Composition (1) Construction of Vector for Expression of Humanized Antibody A vector for expression of humanized antibody is an expression vector for animal cell into which genes encoding CH and CL of a human antibody are inserted, which can be constructed by cloning each of genes encoding CH and CL of a human antibody into an expression vector for animal cell.

The C regions of a human antibody may be CH and CL of any human antibody. Examples include the C region belonging to IgG1 subclass in the H chain of a human antibody (hereinafter referred to as "hCγ1"), the C region belonging to κ class in the L chain of a human antibody (hereinafter referred to as "hCκ"), and the like.

As the genes encoding CH and CL of a human antibody, a chromosomal DNA comprising an exon and an intron can be used, and a cDNA can also be used.

As the expression vector for animal cell, any vector can be used, so long as a gene encoding the C region of a human antibody can be inserted thereinto and expressed therein. Examples include pAGE107 [*Cytotechnology*, 3, 133 (1990)], pAGE103 [*J. Biochem.*, 101, 1307 (1987)], pHSG274 [*Gene*, 27, 223 (1984)], pKCR [*Proc. Natl. Acad. Sci. USA*, 78, 1527 (1981), pSG1β d2-4 [*Cytotechnology*, 4, 173 (1990)] and the like. The promoter and enhancer in the expression vector for animal cell includes SV40 early promoter and enhancer [*J. Biochem.*, 101, 1307 (1987)], Moloney mouse leukemia virus LTR promoter [*Biochem. Biophys. Res. Commun.*, 149, 960 (1987)], immunoglobulin H chain promoter [*Cell*, 41, 479 (1985)] and enhancer [*Cell*, 33, 717 (1983)], and the like.

The vector for expression of humanized antibody may be either of a type in which genes encoding the H chain and L chain of an antibody exist on separate vectors or of a type in which both genes exist on the same vector (hereinafter referred to "tandem type"). In respect of easiness of construction of a vector for expression of humanized antibody, easiness of introduction into animal cells, and balance between the expression amounts of the H and L chains consisting of an antibody in animal cells, a tandem type of the vector for humanized antibody expression is more preferred [*J. Immunol. Methods*, 167, 271 (1994)].

The constructed vector for expression of humanized antibody can be used for expression of a human chimeric antibody and a human CDR-grafted antibody in animal cells.

(2) Preparation Method of cDNA Encoding V Region of Non-Human Animal Antibody cDNAs encoding VH and VL of a non-human animal antibody such as mouse antibody can be obtained in the following manner.

A cDNA is synthesized from mRNA extracted from a hybridoma cell which produces the mouse antibody of interest. The synthesized cDNA is cloned into a vector such as a phage or a plasmid to obtain a cDNA library. Each of a recombinant phage or recombinant plasmid comprising a cDNA encoding VH and a recombinant phage or recombinant plasmid comprising a cDNA encoding VL is isolated from the library by using a C region part or a V region part of an existing mouse antibody as the probe. Full nucleotide sequences of VH and VL of the mouse antibody of interest on the recombinant phage or recombinant plasmid are determined, and full length amino acid sequences of VH and VL are deduced from the nucleotide sequences.

As the non-human animal, any animal such as mouse, rat, hamster or rabbit can be used, so long as a hybridoma cell can be produced therefrom.

The method for preparing a total RNA from a hybridoma cell includes the guanidine thiocyanate-cesium trifluoroacetate method [*Methods in Enzymology*, 154, 3 (1987)] and the like, and the method for preparing mRNA from total RNA includes an oligo(dT)-immobilized cellulose column method (*Molecular Cloning*, Second Edition) and the like. In addition, a kit for preparing mRNA from a hybridoma cell includes Fast Track mRNA Isolation Kit (manufactured by Invitrogen), Quick Prep mRNA Purification Kit (manufactured by Pharmacia) and the like.

The method for synthesizing a cDNA and preparing a cDNA library includes the usual methods (*Molecular Cloning*, Second Edition, *Current Protocols in Molecular Biology*, Supplement 1-34), methods using a commercially available kit such as SuperScript™, Plasmid System for cDNA Synthesis and Plasmid Cloning (manufactured by GIBCO BRL) or ZAP-cDNA Synthesis Kit (manufactured by Stratagene), and the like.

In preparing the cDNA library, the vector into which a cDNA synthesized by using mRNA extracted from a hybridoma cell as the template is inserted may be any vector, so long as the cDNA can be inserted. Examples include ZAP Express [*Strategies*, 5, 58 (1992)], pBluescript II SK(+) [*Nucleic Acids Research*, 17, 9494 (1989)], λzapII (manufactured by Stratagene), λgt10 and λgt11 [*DNA Cloning, A Practical Approach*, I, 49 (1985)], Lambda BlueMid (manufactured by Clontech), λExCell, pT7T3 18U (manufactured by Pharmacia), pcD2 [*Mol. Cell. Biol.*, 3, 280 (1983)], pUC18 [*Gene*, 33, 103 (1985)] and the like.

As *Escherichia coli* into which the cDNA library constructed from a phage or plasmid vector is introduced, any *Escherichia coli* can be used, so long as the cDNA library can be introduced, expressed and maintained. Examples include XL1-Blue MRF' [*Strategies*, 5, 81 (1992)], C600 [*Genetics*, 39, 440 (1954)], Y1088 and Y1090 [*Science*, 222, 778 (1983)], NM522 [*J. Mol. Biol.*, 166, 1 (1983)], K802 [*J. Mol. Biol.*, 16, 118 (1966)], JM105 [*Gene*, 38, 275 (1985)] and the like.

As the method for selecting a cDNA clone encoding VH and VL of a non-human animal antibody from the cDNA library, a colony hybridization or a plaque hybridization using an isotope- or fluorescence-labeled probe can be used (*Molecular Cloning*, Second Edition). The cDNA encoding VH and VL can also be prepared by preparing primers and carrying out polymerase chain reaction (hereinafter referred to as "PCR"; *Molecular Cloning*, Second Edition; *Current Protocols in Molecular Biology*, Supplement 1-34) using a cDNA synthesized from mRNA or a cDNA library as the template.

The nucleotide sequences of the cDNAs can be determined by digesting the selected cDNAs with appropriate restriction enzymes, cloning the fragments into a plasmid such as pBluescript SK(-) (manufactured by Stratagene), carrying out the reaction of a generally used nucleotide sequence analyzing method such as the dideoxy method of Sanger et al. [*Proc. Natl. Acad. Sci., USA*, 74, 5463 (1977)], and then analyzing the clones using an automatic nucleotide sequence analyzer such as A.L.F. DNA Sequencer (manufactured by Pharmacia).

Whether or not the obtained cDNAs encode the full length amino acid sequences of VH and VL of the antibody comprising a secretory signal sequence can be confirmed by deducing the full length amino acid sequences of VH and VL from the determined nucleotide sequence and comparing them with the full length amino acid sequences of VH and VL of known antibodies [*Sequences of Proteins of Immunological Interest*, US Dep. Health and Human Services (1991), hereinafter referred to as "*Sequences of Proteins of Immunological Interest*"].

(3) Analysis of Amino Acid Sequence of V Region of Non-Human Animal Antibody

Regarding the full length amino acid sequences of VH and VL of the antibody comprising a secretory signal sequence, the length of the secretory signal sequence and the N-terminal amino acid sequences can be deduced and subgroups to which they belong can also be found, by comparing them with the full length amino acid sequences of VH and VL of known antibodies (*Sequences of Proteins of Immunological Interest*). In addition, the amino acid sequences of each CDR of VH and VL can also be found by comparing them with the amino acid sequences of VH and VL of known antibodies (*Sequences of Proteins of Immunological Interest*).

(4) Construction of Human Chimeric Antibody Expression Vector

A human chimeric antibody expression vector can be constructed by cloning cDNAs encoding VH and VL of a non-human animal antibody into upstream of genes encoding CH and CL of a human antibody in the vector for expression of humanized antibody constructed described in the item 3(1). For example, a human chimeric antibody expression vector can be constructed by linking each of cDNAs encoding VH and VL of a non-human animal antibody to a synthetic DNA comprising nucleotide sequences at the 3'-terminals of VH and VL of a non-human animal antibody and nucleotide sequences at the 5'-terminals of CH and CL of a human antibody and also having a recognition sequence of an appropriate restriction enzyme at both terminals, and by cloning them into upstream of genes encoding CH and CL of a human antibody contained in the vector for expression of humanized antibody constructed described in the item 3(1) in such a manner that they can be expressed in a suitable form.

(5) Construction of cDNA Encoding V Region of Human CDR-Grafted Antibody cDNAs encoding VH and VL of a human CDR-grafted antibody can be obtained as follows. First, amino acid sequences of the frameworks (hereinafter referred to as "FR") of VH and VL of a human antibody for grafting CDR of VH and VL of a non-human animal antibody is selected. As the amino acid sequences of FRs of VH and VL of a human antibody, any amino acid sequences can be used so long as they are derived from a human antibody. Examples include amino acid sequences of FRs of VH and VL of human antibodies registered at databases such as Protein Data Bank, amino acid sequences common in each subgroup of FRs of VH and VL of human antibodies (*Sequences of Proteins of Immunological Interest*) and the like. In order to produce a human CDR-grafted antibody having enough activities, it is preferred to select an amino acid sequence having homology as high as possible (at least 60% or more) with amino acid sequences of VH and VL of a non-human animal antibody of interest.

Next, the amino acid sequences of CDRs of VH and VL of the non-human animal antibody of interest are grafted to the selected amino acid sequences of FRs of VH and VL of a human antibody to design amino acid sequences of VH and VL of the human CDR-grafted antibody. The designed amino acid sequences are converted into DNA sequences by considering the frequency of codon usage found in nucleotide sequences of antibody genes (*Sequences of Proteins of Immunological Interest*), and the DNA sequences encoding the amino acid sequences of VH and VL of the human CDR-grafted antibody are designed. Based on the designed DNA sequences, several synthetic DNAs having a length of about 100 bases are synthesized, and PCR is carried out by using them. In this case, it is preferred in each of the H chain and the L chain that 6 synthetic DNAs are designed in view of the reaction efficiency of PCR and the lengths of DNAs which can be synthesized.

Also, they can be easily cloned into the vector for expression of humanized antibody described in the item 3(1) by introducing recognition sequences of an appropriate restriction enzyme into the 5'-terminals of the synthetic DNA on both terminals. After the PCR, the amplified product is cloned into a plasmid such as pBluescript SK(-) (manufactured by Stratagene) and the nucleotide sequences are determined by the method in the item 3(2) to thereby obtain a plasmid having DNA sequences encoding the amino acid sequences of VH and VL of the desired human CDR-grafted antibody.

(6) Construction of Human CDR-Grafted Antibody Expression Vector

A human CDR-grafted antibody expression vector can be constructed by cloning the cDNAs encoding VH and VL of the human CDR-grafted antibody constructed in the item 3(5) into upstream of the gene encoding CH and CL of a human antibody in the vector for expression of humanized antibody described in the item 3(1). For example, recognizing sequences of an appropriate restriction enzyme are introduced into the 5'-terminals of both terminals of a synthetic DNA fragment, among the synthetic DNA fragments which are used in the item 3(5) for constructing the VH and VL of the human CDR-grafted antibody, so that they are cloned into upstream of the genes encoding CH and CL of a human antibody in the vector for expression of humanized antibody described in the item 3(1) in such a manner that they can be expressed in a suitable form, to thereby construct the human CDR-grafted antibody expression vector.

(7) Stable Production of Humanized Antibody

A transformant capable of stably producing a human chimeric antibody and a human CDR-grafted antibody (both hereinafter referred to as "humanized antibody") can be obtained by introducing the vectors for humanized antibody expression described in the items 3(4) and (6) into an appropriate animal cell.

The method for introducing a humanized antibody expression vector into an animal cell includes electroporation [Japanese Published Unexamined Patent Application No. 257891/90, *Cytotechnology*, 3, 133 (1990)] and the like.

As the animal cell into which a humanized antibody expression vector is introduced, any cell can be used so long as it is an animal cell which can produce the humanized antibody.

Examples include mouse myeloma cells such as NS0 cell and SP2/0 cell, Chinese hamster ovary cells such as CHO/dhfr$^-$ cell and CHO/DG44 cell, rat myeloma such as YB2/0 cell and IR983F cell, BHK cell derived from a syrian hamster kidney, a human myeloma cell such as Namalwa cell, and the like, and a Chinese hamster ovary cell CHO/DG44 cell, a rat myeloma YB2/0 cell and the host cells of the present invention described in the item 5 are preferred.

After introduction of the humanized antibody expression vector, a transformant capable of stably producing the humanized antibody can be selected by using a medium for animal cell culture comprising an agent such as G418 sulfate (hereinafter referred to as "G418"; manufactured by SIGMA) and the like in accordance with the method described in Japanese Published Unexamined Patent Application No. 257891/90. The medium to culture animal cells includes RPMI 1640 medium (manufactured by Nissui Pharmaceutical), GIT medium (manufactured by Nihon Pharmaceutical), EX-CELL 302 medium (manufactured by JRH), IMDM medium (manufactured by GIBCO BRL), Hybridoma-SFM medium (manufactured by GIBCO BRL), media obtained by adding various additives such as fetal bovine serum (hereinafter referred to as "FBS") to these media, and the like. The humanized antibody can be produced and accumulated in the culture supernatant by culturing the obtained transformant in a medium. The amount pf production and antigen binding activity of the humanized antibody in the culture supernatant can be measured by a method such as enzyme-linked immunosorbent assay (hereinafter referred to as "ELISA"; *Antibodies, Monoclonal Antibodies*) or the like. Also, the amount of the humanized antibody produced by the transformant can be increased by using a DHFR gene amplification system in accordance with the method described in Japanese Published Unexamined Patent Application No. 257891/90.

The humanized antibody can be purified from a culture supernatant culturing the transformant by using a protein A column (*Antibodies*, Chapter 8; *Monoclonal Antibodies*). In addition, purification methods generally used for the purification of proteins can also be used. For example, the purification can be carried out through the combination of gel filtration, ion exchange chromatography and ultrafiltration. The molecular weight of the H chain, L chain or antibody molecule as a whole of the purified humanized antibody can be measured, e.g., by polyacrylamide gel electrophoresis [hereinafter referred to as "SDS-PAGE"; *Nature*, 227, 680 (1970)], Western blotting (*Antibodies, Monoclonal Antibodies*) or the like.

B. Preparation of Fc Fusion Protein (1) Construction of Fc Fusion Protein Expression Vector An Fc fusion protein expression vector is an expression vector for animal cells into which genes encoding the Fc region of a human antibody and a protein to be fused are inserted, which can be constructed by cloning each of genes encoding the Fc region of a human antibody and the protein to be fused into an expression vector for animal cell.

The Fc region of a human antibody includes those containing a part of a hinge region and/or CH1 in addition to regions containing CH2 and CH3 regions. Also, it can be any Fc region, so long as at least one amino acid of CH2 or CH3 may be deleted, substituted, added or inserted, and substantially has the binding activity to the Fcγ receptor.

As the genes encoding the Fc region of a human antibody and the protein to be fused, a chromosomal DNA comprising an exon and an intron can be used, and a cDNA can also be used. The method for linking the genes and the Fc region includes PCR using each of the gene sequences as the template (*Molecular Cloning*, Second Edition; *Current Protocols in Molecular Biology*, Supplement 1-34).

As the expression vector for animal cell, any vector can be used, so long as a gene encoding the C region of a human antibody can be inserted thereinto and expressed therein. Examples include pAGE107 [*Cytotechnology*, 3, 133 (1990)], pAGE103 [*J. Biochem.*, 101, 1307 (1987)], pHSG274 [*Gene*, 27, 223 (1984)], pKCR [*Proc. Natl. Acad. Sci. USA*, 78, 1527 (1981), pSG1β d2-4 [*Cytotechnology*, 4, 173 (1990)] and the like. The promoter and enhancer in the expression vector for animal cell include SV40 early promoter and enhancer [*J. Biochem.*, 101, 1307 (1987)], Moloney mouse leukemia virus LTR [*Biochem. Biophys. Res. Commun.*, 149, 960 (1987)], immunoglobulin H chain promoter [*Cell*, 41, 479 (1985)] and enhancer [*Cell*, 33, 717 (1983)], and the like.

(2) Preparation of DNA Encoding Fc Region of Human Antibody and Protein to be Fused A DNA encoding the Fc region of a human antibody and the protein to be fused can be obtained in the following manner.

A cDNA is synthesized from mRNA extracted from a cell or tissue which expresses the protein of interest to be fused with Fc. The synthesized cDNA is cloned into a vector such as a phage or a plasmid to obtain a cDNA library. A recombinant phage or recombinant plasmid comprising cDNA encoding the protein of interest is isolated from the library using the gene sequence part of the protein of interest as the probe. A full nucleotide sequence of the antibody of interest on the recombinant phage or recombinant plasmid is determined, and a full length amino acid sequence is deduced from the nucleotide sequence.

As the non-human animal, any animal such as mouse, rat, hamster or rabbit can be used, so long as a cell or tissue can be removed therefrom.

The method for preparing a total RNA from a cell or tissue includes the guanidine thiocyanate-cesium trifluoroacetate method [*Methods in Enzymology*, 154, 3 (1987)] and the like, and the method for preparing mRNA from total RNA includes an oligo (dT)-immobilized cellulose column method (*Molecular Cloning*, Second Edition) and the like. In addition, a kit for preparing mRNA from a cell or tissue includes Fast Track mRNA Isolation Kit (manufactured by Invitrogen), Quick Prep mRNA Purification Kit (manufactured by Pharmacia) and the like.

The method for synthesizing a cDNA and preparing a cDNA library includes the usual methods (*Molecular Cloning*, Second Edition; *Current Protocols in Molecular Biology*, Supplement 1-34); methods using a commercially available kit such as SuperScript™, Plasmid System for cDNA Synthesis and Plasmid Cloning (manufactured by GIBCO BRL) or ZAP-cDNA Synthesis Kit (manufactured by Stratagene); and the like.

In preparing the cDNA library, the vector into which a cDNA synthesized by using mRNA extracted from a cell or tissue as the template is inserted may be any vector so long as the cDNA can be inserted. Examples include ZAP Express [*Strategies*, 5, 58 (1992)], pBluescript II SK(+) [*Nucleic Acids Research*, 17, 9494 (1989)], λzapII (manufactured by Stratagene), λgt10 and λgt11 [*DNA Cloning, A Practical Approach*, I, 49 (1985)], Lambda BlueMid (manufactured by Clontech), λExCell, pT7T3 18U (manufactured by Pharmacia), pcD2 [*Mol. Cell. Biol.*, 3, 280 (1983)], pUC18 [*Gene*, 33, 103 (1985)] and the like.

As *Escherichia coli* into which the cDNA library constructed from a phage or plasmid vector is introduced, any *Escherichia coli* can be used, so long as the cDNA library can be introduced, expressed and maintained. Examples include XL1-Blue MRF' [*Strategies*, 5, 81 (1992)], C600 [*Genetics*, 39, 440 (1954)], Y1088 and Y1090 [*Science*, 222, 778 (1983)], NM522 [*J. Mol. Biol.*, 166, 1 (1983)], K802 [*J. Mol. Biol.*, 16, 118 (1966)], JM105 [*Gene*, 38, 275 (1985)] and the like.

As the method for selecting a cDNA clone encoding the protein of interest from the cDNA library, a colony hybridization or a plaque hybridization using an isotope- or fluorescence-labeled probe can be used (*Molecular Cloning*, Second Edition). The cDNA encoding the protein of interest can also be prepared by preparing primers and using a cDNA synthesized from mRNA or a cDNA library as the template according to PCR.

The method for fusing the protein of interest with the Fc region of a human antibody includes PCR. For example, synthesized oligo DNAs (primers) are designed at the 5'-terminal and 3'-terminal of the gene sequence encoding the protein of interest, and PCR is carried out to prepare a PCR product. In the same manner, primers are designed for the gene sequence encoding the Fc region of a human antibody to be fused to prepare a PCR product. At this time, the primers are designed in such a manner that the same restriction enzyme site or the same gene sequence is present between the 3'-terminal of the PCR product of the protein to be fused and the 5'-terminal of the PCR product of the Fc region. When it is necessary to modify the amino acids around the linked site, mutation is introduced by using the primer into which the mutation is introduced. PCR is further carried out by using the two kinds of the obtained PCR fragments to link the genes. Also, they can be linked by carrying out ligation after treatment with the same restriction enzyme.

The nucleotide sequence of the DNA can be determined by digesting the gene sequence linked by the above method with appropriate restriction enzymes, cloning the fragments into a plasmid such as pBluescript SK(−) (manufactured by Stratagene), carrying out analysis by using a generally used nucleotide sequence analyzing method such as the dideoxy method of Sanger et al. [*Proc. Natl. Acad. Sci. USA*, 74, 5463 (1977)] or an automatic nucleotide sequence analyzer such as ABI PRISM 377 DNA Sequencer (manufactured by Pharmacia).

Whether or not the obtained cDNA encodes the full length amino acid sequences of the Fc fusion protein containing a secretory signal sequence can be confirmed by deducing the full length amino acid sequence of the Fc fusion protein from the determined nucleotide sequence and comparing it with the amino acid sequence of interest.

(3) Stable Production of Fc Fusion Protein

A transformant capable of stably producing an Fc fusion protein can be obtained by introducing the Fc fusion protein expression vector described in the item (1) into an appropriate animal cell.

The method for introducing the Fc fusion protein expression vector into an animal cell include electroporation [Japanese Published Unexamined Patent Application No. 257891/90, *Cytotechnology*, 3, 133 (1990)] and the like.

As the animal cell into which the Fc fusion protein expression vector is introduced, any cell can be used, so long as it is an animal cell which can produce the Fc fusion protein.

Examples include mouse myeloma cells such as NS0 cell and SP2/0 cell, Chinese hamster ovary cells such as CHO/dhfr− cell and CHO/DG44 cell, rat myeloma such as YB2/0 cell and IR983F cell, BHK cell derived from a syrian hamster kidney, a human myeloma cell such as Namalwa cell, and the like, and preferred are a Chinese hamster ovary cell CHO/DG44 cell, a rat myeloma YB2/0 cell and the host cells used in the method of the present invention described in the item 1.

After introduction of the Fc fusion protein expression vector, a transformant capable of stably producing the Fc fusion protein expression vector can be selected by using a medium for animal cell culture comprising an agent such as G418 and the like in accordance with the method described in Japanese Published Unexamined Patent Application No. 257891/90. The medium to culture animal cells includes RPMI 1640 medium (manufactured by Nissui Pharmaceutical), GIT medium (manufactured by Nihon Pharmaceutical), EX-CELL 302 medium (manufactured by JRH), IMDM medium (manufactured by GIBCO BRL), Hybridoma-SFM medium (manufactured by GIBCO BRL), media obtained by adding various additives such as fetal bovine serum to these media, and the like. The Fc fusion protein can be produced and accumulated in the culture medium by culturing the obtained transformant in a medium. The production amount and antigen binding activity of the Fc fusion protein in the culture medium can be measured by a method such as ELISA. Also, the amount of the Fc fusion protein produced by the transformant can be increased by using a dhfr gene amplification system in accordance with the method described in Japanese Published Unexamined Patent Application No. 257891/90.

The Fc fusion protein can be purified from a culture supernatant culturing the transformant using a protein A column (*Antibodies*, Chapter 8; *Monoclonal Antibodies*). In addition, purification methods generally used for purifying proteins can also be used. For example, the purification can be carried out through the combination of a gel filtration, an ion exchange chromatography and an ultrafiltration. The molecular weight as a whole of the purified Fc fusion protein molecule can be measured by SDS-PAGE [*Nature*, 227, 680 (1970)], Western blotting (*Antibodies*, Chapter 12; *Monoclonal Antibodies*) or the like.

Thus, methods for producing an antibody composition using an animal cell as the host cell have been described, but, as described above, it can also be produced by yeast, an insect cell, a plant cell, an animal individual or a plant individual by the same methods on the animal cell.

When the host cell is capable of preparing the antibody molecule, the antibody composition of the present invention can be prepared by culturing the cell capable of expressing an antibody molecule according to the method described in the above item 1, culturing the cell, and recovering the antibody composition of interest.

4. Measurement of Binding Activity to Human FcγRIIIa

Binding activity of the antibody composition to FcγRIIIa can be measured by the following technique.

(1) Preparation of Human FcγRIIIa

FcγRIIIa which can be used includes FcγIIIa present on the cell surface of peripheral blood lymphocyte of a human or non-human animal, FcγIIIa obtained by preparing a gene encoding FcγRIIIa and introducing the gene into a host cell and expressing the FcγR on the cell surface, FcγRIIIa secreted from the cell, and the like.

A method for preparing a gene encoding FcγRIIIa, introducing the gene into a host cell and expressing the FcγRIIIa on the cell surface, and a method obtaining FcγRIIIa by secreting it from the cell are described below.

A total RNA or mRNA is prepared from human or non-human animal tissues or cells.

A commercially available product (e.g., manufactured by Clontech) can be used as the mRNA of human or non-human animal tissues or cells, or it may be prepared from human or non-human animal tissues or cells as follows. The method for preparing a total RNA from human or non-human animal tissues or cells includes the guanidine thiocyanate-cesium trifluoroacetate method [*Methods in Enzymology*, 154, 3 (1987)], the acidic guanidine thiocyanate phenol chloroform (AGPC) method [*Analytical Biochemistry*, 162, 156 (1987); *Experimental Medicine (Jikken Igaku)*, 9, 1937 (1991)] and the like.

Also, the method for preparing mRNA as poly(A)$^+$ RNA from a total RNA includes an oligo(dT)-immobilized cellulose column method (*Molecular Cloning*, Second Edition) and the like.

In addition, mRNA can be prepared by using a kit such as Fast Track mRNA Isolation Kit (manufactured by Invitrogen) or Quick Prep mRNA Purification Kit (manufactured by Pharmacia).

A cDNA library is prepared from a full RNA or mRNA of the prepared human or non-human animal tissue or cell.

The method for preparing a cDNA library include methods described in *Molecular Cloning*, Second Edition; *Current Protocols in Molecular Biology*; and the like, methods using a commercially available kit such as SuperScript Plasmid System for cDNA Synthesis and Plasmid Cloning (manufactured by Life Technologies) or ZAP-cDNA Synthesis Kit (manufactured by STRATAGENE), and the like.

As the cloning vector for the preparation of the cDNA library, any vector such as a phage vector or a plasmid vector can be used, so long as it is autonomously replicable in *Escherichia coli* K12. Examples include ZAP Express [manufactured by STRATAGENE, *Strategies*, 5, 58 (1992)], pBluescript II SK(+) [*Nucleic Acids Research*, 17, 9494

(1989)], Lambda ZAP II (manufactured by STRATAGENE), λgt10 and λgt11 [DNA Cloning, A Practical Approach, 1, 49 (1985)], λTriplEx (manufactured by Clontech), λExCell (manufactured by Pharmacia), pcD2 [*Mol. Cell. Biol.*, 3, 280 (1983)], pUC18 [*Gene*, 33, 103 (1985)] and the like.

Any microorganism can be used as the host microorganism, and *Escherichia coli* is preferably used. Examples include *Escherichia coli* XL1-Blue MRF' [manufactured by STRATAGENE, *Strategies*, 5, 81 (1992)], *Escherichia coli* C600 [*Genetics*, 39, 440 (1954)], *Escherichia coli* Y1088 [*Science*, 222, 778 (1983)], *Escherichia coli* Y1090 [*Science*, 222, 778 (1983)], *Escherichia coli* NM522 [*J. Mol. Biol.*, 166, 1 (1983)], *Escherichia coli* K802 [*J. Mol. Biol.*, 16, 118 (1966)], *Escherichia coli* JM105 [*Gene*, 38, 275 (1985)] and the like.

The cDNA library may be used as such in the succeeding analysis, and in order to obtain a full length cDNA as efficient as possible by decreasing the ratio of an infull length cDNA, a cDNA library prepared using the oligo cap method developed by Sugano et al. [*Gene*, 138, 171 (1994); *Gene*, 200, 149 (1997); *Protein, Nucleic Acid and Enzyme*, 41, 603 (1996); *Experimental Medicine*, 11, 2491 (1993); cDNA Cloning (Yodo-sha) (1996); *Methods for Preparing Gene Libraries* (Yodo-sha) (1994)] may be used in the following analysis.

A gene encoding FcγR can be obtained by preparing primers specific for 5'-terminal and 3'-terminal nucleotide sequences based on the nucleotide sequences of various FcγRIIIa, and amplifying DNA by PCR [*PCR Protocols*, Academic Press (1990)] using a prepared cDNA library as the template.

Whether the thus obtained gene is a DNA encoding FcγRIIIa can be confirmed by analyzing it according to the generally used nucleotide sequence analyzing method such as the dideoxy method of Sanger et al. [*Proc. Natl. Acad. Sci. U.S.A.*, 74, 5463 (1977)] or by using a nucleotide sequence analyzer such as ABI PRISM 377 DNA Sequencer (manufactured by PE Biosystems).

The nucleotide sequence of a gene encoding FcγRIIIa obtained by the above method includes the nucleotide sequence of FcγRIIIa represented by SEQ ID NO:27.

The gene encoding FcγRIIIa can also be obtained based on the determined DNA nucleotide sequence by carrying out chemical synthesis by a DNA synthesizer such as DNA Synthesizer Model 392 manufactured by Perkin Elmer using a phosphoamidite method.

A recombinant vector is prepared by inserting the thus obtained cDNA encoding FcγRIIIa into downstream of the promoter of an appropriate expression vector.

A transformant which produces an antibody molecule can be obtained by introducing the recombinant vector into a host cell suitable for the expression vector.

As the host cell, any of yeast, an animal cell, an insect cell, a plant cell or the like can be used, so long as it can express the gene of interest.

As the expression vector, a vector which is autonomously replicable in the above host cell or can be integrated into the chromosome and comprises a promoter at such a position that the DNA encoding the FcγRIIIa of interest can be transferred is used.

When a yeast is used as the host cell, the expression vector includes YEP13 (ATCC 37115), YEp24 (ATCC 37051), YCp50 (ATCC 37419) and the like.

Any promoter can be used, so long as it can function in yeast. Examples include a promoter of a gene of the glycolytic pathway such as a hexose kinase gene, PHOS promoter, PGK promoter, GAP promoter, ADH promoter, gal 1 promoter, gal 10 promoter, heat shock protein promoter, MF α1 promoter, CUP 1 promoter and the like.

The host cell includes microorganisms belonging to the genus *Saccharomyces*, the genus *Schizosaccharomyces*, the genus *Kluyveromyces*, the genus *Trichosporon*, the genus *Schwanniomyces* and the like, such as *Saccharomyces cerevisiae*, *Schizosaccharomyces pombe*, *Kluyveromyces lactis*, *Trichosporon pullulans* and *Schwanniomyces alluvius*.

As the method for introducing the recombinant vector, any method can be used, so long as it can introduce DNA into yeast. Examples include electroporation [*Methods in Enzymology*, 194, 182 (1990)], spheroplast method [*Proc. Natl. Acad. Sci. USA*, 84, 1929 (1978)], lithium acetate method [*J. Bacteriol.*, 153, 163 (1983)], a method described in *Proc. Natl. Acad. Sci. USA*, 75, 1929 (1978) and the like.

When an animal cell is used as the host, the expression vector includes pcDNAI, pcDM8 (available from Funakoshi), pAGE107 [Japanese Published Unexamined Patent Application No. 22979/91; *Cytotechnology*, 3, 133 (1990)], pAS3-3 (Japanese Published Unexamined Patent Application No. 227075/90), pCDM8 [*Nature*, 329, 840 (1987)], pcDNAI/Amp (manufactured by Invitrogen), pREP4 (manufactured by Invitrogen), pAGE103 [*J. Biochemistry*, 101, 1307 (1987)], pAGE210 and the like.

Any promoter can be used, so long as it can function in an animal cell. Examples include a promoter of IE (immediate early) gene of cytomegalovirus (CMV), an early promoter of SV40, a promoter of retrovirus, a promoter of metallothionein, a heat shock promoter, an SRα promoter and the like. Also, an enhancer of the IE gene of human CMV may be used together with the promoter.

The host cell includes a human cell such as Namalwa cell, a monkey cell such as COS cell, a Chinese hamster cell such as CHO cell or HBT5637 (Japanese Published Unexamined Patent Application No. 299/88), a rat myeloma cell, a mouse myeloma cell, a cell derived from syrian hamster kidney, an embryonic stem cell, a fertilized egg cell and the like.

As the method for introducing the recombinant vector, any method can be used, so long as it can introduce DNA into an animal cell. Examples include electroporation [*Cytotechnology*, 3, 133 (1990)], the calcium phosphate method (Japanese Published Unexamined Patent Application No. 227075/90), the lipofection method [*Proc. Natl. Acad. Sci. USA*, 84, 7413 (1987)], the injection method (*Manipulating the Mouse Embryo, A Laboratory Manual*), a method using particle gun (gene gun) (Japanese Patent No. 2606856, Japanese Patent No. 2517813), the DEAE-dextran method [*Biomanual Series 4-Gene Transfer and Expression Analysis* (Yodo-sha), edited by Takashi Yokota and Kenichi Arai (1994)], the virus vector method (*Manipulating Mouse Embryo*, Second Edition) and the like.

When an insect cell is used as the host, the protein can be expressed by the method described in *Current Protocols in Molecular Biology, Baculovirus Expression Vectors, A Laboratory Manual*, W.H. Freeman and Company, New York (1992), *Bio/Technology*, 6, 47 (1988) or the like.

That is, the protein can be expressed by co-introducing a recombinant gene-introducing vector and a baculovirus into an insect cell to obtain a recombinant virus in an insect cell culture supernatant and then infecting the insect cell with the recombinant virus.

The gene introducing vector used in the method includes pVL1392, pVL1393, pBlueBacIII (all manufactured by Invitrogen) and the like.

The baculovirus includes *Autographa californica* nuclear polyhedrosis virus which is infected by an insect of the family Barathra.

The insect cell includes *Spodoptera frugiperda* oocytes Sf9 and Sf21 [*Current Protocols in Molecular Biology, Baculovirus Expression Vectors, A Laboratory Manual*, W.H. Freeman and Company, New York (1992)], a *Trichoplusia ni* oocyte High 5 (manufactured by Invitrogen) and the like.

The method for co-introducing the recombinant gene-introducing vector and the baculovirus for preparing the recombinant virus includes the calcium phosphate method (Japanese Published Unexamined Patent Application No. 227075/90), the lipofection method [*Proc. Natl. Acad. Sci. USA*, 84, 7413 (1987)] and the like.

When a plant cell is used as the host, the expression vector includes Ti plasmid, tobacco mosaic virus and the like.

As the promoter, any promoter can be used, so long as it can function in a plant cell. Examples include cauliflower mosaic virus (CaMV) 35S promoter, rice actin 1 promoter and the like.

The host cell includes plant cells of tobacco, potato, tomato, carrot, soybean, rape, alfalfa, rice, wheat, barley and the like.

As the method for introducing the recombinant vector, any method can be used, so long as it can introduce DNA into a plant cell. Examples include a method using *Agrobacterium* (Japanese Published Unexamined Patent Application No. 140885/84, Japanese Published Unexamined Patent Application No. 70080/85, WO94/00977), electroporation (Japanese Published Unexamined Patent Application No. 251887/85), a method using a particle gun (gene gun) (Japanese Patent No. 2606856, Japanese Patent No. 2517813) and the like.

As the method for expressing a gene, secretion production, expression of a fusion protein with other protein and the like can be carried out in accordance with the method described in *Molecular Cloning*, Second Edition or the like, in addition to the direct expression.

FcγRIIIa can be produced by culturing the thus obtained transformant in a medium to produce and accumulate FcγRIIIa in the culture and then recovering it from the resulting culture. The method for culturing the transformant using a medium can be carried out in accordance with a general method which is used for culturing host cells.

As the medium for culturing a transformant obtained by using yeast as the host, the medium may be either a natural medium or a synthetic medium, so long as it comprises materials such as a carbon source, a nitrogen source and an inorganic salt which can be assimilated by the yeast and culturing of the transformant can be efficiently carried out.

As the carbon source, those which can be assimilated by the yeast can be used. Examples include carbohydrates such as glucose, fructose, sucrose, molasses containing them, starch and starch hydrolysate; organic acids such as acetic acid and propionic acid; alcohols such as ethanol and propanol; and the like.

The nitrogen source includes ammonia; ammonium salts of inorganic acid or organic acid such as ammonium chloride, ammonium sulfate, ammonium acetate and ammonium phosphate; other nitrogen-containing compounds; peptone; meat extract; yeast extract; corn steep liquor; casein hydrolysate; soybean meal; soybean meal hydrolysate; various fermented cells and hydrolysates thereof; and the like.

The inorganic salt includes potassium dihydrogen phosphate, dipotassium hydrogen phosphate, magnesium phosphate, magnesium sulfate, sodium chloride, ferrous sulfate, manganese sulfate, copper sulfate, calcium carbonate, and the like.

The culturing is carried out generally under aerobic conditions such as shaking culture or submerged-aeration stirring culture. The culturing temperature is preferably 15 to 40° C., and the culturing time is generally 16 hours to 7 days. During the culturing, the pH is maintained at 3.0 to 9.0. The pH is adjusted with an inorganic or organic acid, an alkali solution, urea, calcium carbonate, ammonia or the like.

If necessary, an antibiotic such as ampicillin or tetracycline can be added to the medium during the culturing.

When yeast transformed with a recombinant vector obtained by using an inducible promoter as the promoter is cultured, an inducer can be added to the medium, if necessary. For example, when yeast transformed with a recombinant vector obtained using lac promoter is cultured, isopropyl-β-D-thiogalactopyranoside can be added to the medium, and when yeast transformed with a recombinant vector obtained using trp promoter is cultured, indoleacrylic acid and the like can be added to the medium.

When a transformant obtained by using an animal cell as the host cell is cultured, the medium includes generally used RPMI 1640 medium [*The Journal of the American Medical Association*, 199, 519 (1967)], Eagle's MEM medium [*Science*, 122, 501 (1952)], Dulbecco's modified MEM medium [*Virology*, 8, 396 (1959)], 199 medium [*Proceeding of the Society for the Biological Medicine*, 73, 1 (1950)] and Whitten's medium [*Developmental Engineering Experimentation Manual (Hassei Kogaku Jikken Manual)-Preparation of Transgenic Mice* (Kodan-sha), edited by M. Katsuki (1987)], the media to which fetal calf serum, etc. is added, and the like.

The culturing is carried out generally at a pH of 6.0 to 8.0 and 30 to 40° C. for 1 to 7 days in the presence of 5% $CO_2$. If necessary, an antibiotic such as kanamycin or penicillin can be added to the medium during the culturing.

The medium for the culturing of a transformant obtained by using an insect cell as the host includes generally used TNM-FH medium (manufactured by Pharmingen), Sf-900 II SFM medium (manufactured by Life Technologies), ExCell 400 and ExCell 405 (both manufactured by JRH Biosciences), Grace's Insect Medium [*Nature*, 195, 788 (1962)] and the like.

The culturing is carried out generally at a medium pH of 6.0 to 7.0 and 25 to 30° C. for 1 to 5 days.

In addition, antibiotics such as gentamicin can be added to the medium during the culturing, if necessary.

A transformant obtained by using a plant cell as the host cell can be cultured as a cell or by differentiating it into a plant cell or organ. The medium for culturing the transformant includes generally used Murashige and Skoog (MS) medium and White medium, the media to which a plant hormone such as auxin or cytokinin is added, and the like.

The culturing is carried out generally at a pH of 5.0 to 9.0 and 20 to 40° C. for 3 to 60 days.

If necessary, an antibiotic such as kanamycin or hygromycin can be added to the medium during the culturing.

As discussed above, FcγRIIIa can be produced by culturing a transformant derived from a microorganism, an animal cell, an insect cell or a plant cell which comprises a recombinant vector into which a DNA encoding FcγRIIIa is inserted, in accordance with the general culturing method to thereby produce and accumulate FcγRIIIa, and then recovering FcγRIIIa from the culture.

As the method for expressing FcγRIIIa, secretion production, expression of a fusion protein and the like can be carried out in accordance with the method described in *Molecular Cloning*, Second Edition in addition to the direct expression.

The method for producing FcγRIIIa includes a method of intracellular expression in a host cell, a method of extracellular secretion from a host cell, and a method of production on a host cell membrane outer envelope. The method can be selected by changing the host cell used or the structure of FcγRIIIa produced.

When FcγRIIIa is produced in a host cell or on a host cell membrane outer envelope, it can be positively secreted extracellularly in accordance with the method of Paulson et al. [*J. Biol. Chem.*, 264, 17619 (1989)], the method of Lowe et al. [*Proc. Natl. Acad. Sci. USA*, 86, 8227 (1989), *Genes Develop.*, 4, 1288 (1990)], the methods described in Japanese Published Unexamined Patent Application No. 336963/93 and Japanese Published Unexamined Patent Application No. 823021/94 and the like.

That is, FcγRIIIa of interest can be positively secreted extracellularly from a host cell by inserting a DNA encoding FcγRIIIa and a signal peptide suitable for the expression of FcγRIIIa into an expression vector by using a gene recombination technique, and then expressing the vector.

Also, its production amount can be increased in accordance with the method described in Japanese Published Unexamined Patent Application No. 227075/90 based on a gene amplification system using a dihydrofolate reductase gene.

In addition, FcγR can also be produced by using a gene-introduced animal individual (transgenic non-human animal) or a plant individual (transgenic plant) which is constructed by the redifferentiation of an animal or plant cell into which the gene is introduced.

When the transformant is an animal individual or a plant individual, FcγRIIIa can be produced in accordance with a general method by rearing or cultivating it to thereby produce and accumulate FcγR and then recovering FcγRIIIa from the animal or plant individual.

The method for producing FcγRIIIa by using an animal individual includes a method in which FcγRIIIa of interest is produced in an animal constructed by introducing a gene in accordance with a known method [*American Journal of Clinical Nutrition*, 63, 639 (1996); *American Journal of Clinical Nutrition*, 63, 627S (1996); *Bio/Technology*, 9, 830 (1991)].

In the case of an animal individual, FcγRIIIa can be produced by rearing a transgenic non-human animal into which a DNA encoding FcγRIIIa is introduced to thereby produce and accumulate FcγRIIIa in the animal, and then recovering FcγRIIIa from the animal. The place of the animal where FcγRIIIa is produced and accumulated includes milk (Japanese Published Unexamined Patent Application No. 309192/88) and eggs of the animal. As the promoter used in this case, any promoter can be used, so long as it can function in an animal. Preferred examples include mammary gland cell-specific promoters such as α casein promoter, β casein promoter, β lactoglobulin promoter and whey acidic protein promoter.

The method for producing FcγRIIIa by using a plant individual includes a method in which FcγRIIIa is produced by cultivating a transgenic plant into which a DNA encoding FcγR is introduced by a known method [*Tissue Culture (Soshiki Baiyo)*, (1994); *Tissue Culture (Soshiki Baiyo)*, 21 (1995); *Trends in Biotechnology*, 15, 45 (1997)] to produce and accumulate FcγR in the plant, and then recovering FcγRIIIa from the plant.

Regarding purification of FcγRIIIa produced by a transformant into which a gene encoding FcγRIIIa is introduced, for example, when FcγRIIIa is intracellularly expressed in a dissolved state, the cells after culturing are recovered by centrifugation, suspended in an aqueous buffer and then disrupted using ultrasonic oscillator, French press, Manton Gaulin homogenizer, dynomill or the like to obtain a cell-free extract. A purified product of FcγRIIIa can be obtained from a supernatant obtained by centrifuging the cell-free extract, by using an ordinary enzyme isolation purification technique such as solvent extraction; salting out and desalting with ammonium sulfate, etc.; precipitation with an organic solvent; anion exchange chromatography using a resin such as diethylaminoethyl (DEAE)-Sepharose or DIAION HPA-75 (manufactured by Mitsubishi Chemical); cation exchange chromatography using a resin such as S-Sepharose FF (manufactured by Pharmacia); hydrophobic chromatography using a resin such as butyl-Sepharose or phenyl-Sepharose; gel filtration using a molecular sieve; affinity chromatography; chromatofocusing; electrophoresis such as isoelectric focusing; and the like which may be used alone or in combination.

Also, when FcγRIIIa is expressed intracellularly by forming an insoluble body, the cells are recovered, disrupted and centrifuged in the same manner, and the insoluble body of FcγRIIIa is recovered as a precipitation fraction. The recovered insoluble body of FcγRIIIa is solubilized by using a protein denaturing agent. FcγRIIIa is made into a normal three-dimensional structure by diluting or dialyzing the solubilized solution, and then a purified product of FcγRIIIa is obtained by the same isolation purification method.

When FcγRIIIa is secreted extracellularly, FcγRIIIa or derivatives thereof can be recovered from the culture supernatant. That is, the culture is treated by a similar technique such as centrifugation to obtain a soluble fraction, and a purified preparation of FcγRIIIa can be obtained from the soluble fraction by the same isolation purification method.

(2) Measurement of Binding Activity to FcγRIIIa

Binding activity of the antibody composition to FcγRIIIa expressed on the cell membrane can be measured by the immunofluorescent method [*Cancer Immunol. Immunother.*, 36, 373 (1993)] or the like. Also, binding activity to the purified FcγRIIIa prepared by the method described in the item 4(1) can be measured according to the immunological determination method such as Western staining described in literatures [*Monoclonal Antibodies: Principles and Applications*, Wiley-Liss, Inc., (1995); *Enzyme Immunoassay (Koso Men-eki Sokutei Ho)*, 3rd edition, Igaku Shoin (1987), reversed edition; *Enzyme Antibody Method (Koso Kotai Ho)*, Gakusai Kikaku (1985)], RIA (radioimmunoassay), VIA (viroimmunoassay), EIA (enzyme immunoassay), FIA (fluoroimmunoassay) or MIA (metalloimmunoassay), for example, as follows.

FcγRIIIa is immobilized on a plastic plate for EIA and is allowed to react with a sample containing an antibody composition. Next, an amount of the bound antibody composition is measured by using an appropriate secondary antibody.

In addition, binding activity to the purified FcγRIIIa can also be measured by a measuring method using biosensor [e.g., BIAcore (manufactured by BIACORE)] [*J. Immunol. Methods*, 200, 121 (1997)], isothermal titration calorimetry [*Proc. Natl. Acad. Sci. U.S.A.*, 97, 9026 (2000)] or the like.

5. Activity Evaluation of Antibody Composition

As the method for measuring the amount of the purified antibody composition, its binding activity to an antigen, its binding activity to FcγRIIIa and its effector function, the known method described in *Monoclonal Antibodies, Antibody Engineering* and the like can be used.

For example, when the antibody composition is a humanized antibody, the binding activity to an antigen, binding activity to an antigen-positive cultured clone and binding activity to FcγRIIIa can be measured by methods such as ELISA and the immunofluorescent method [*Cancer Immunol. Immunother.*, 36, 373 (1993)], measurement using biosensor [for example, using BIAcore (manufactured by BIACORE)] [*J. Immunol. Methods*, 200, 121 (1997)], isothermal titration calorimetry method [*Proc. Natl. Acad. Sci. U.S.A.*, 97, 9026 (2000)] and the like. Among the effector functions, the cytotoxic activity against an antigen-positive cultured clone can be evaluated by measuring CDC activity, ADCC activity [*Cancer Immunol. Immunother.*, 36, 373 (1993)] and the like.

6. Analysis of Sugar Chains of Antibody Molecule Expressed in Various Cells

The sugar chain structure binding to an antibody molecule expressed in various cells can be analyzed in accordance with the general analysis of the sugar chain structure of a glycoprotein. For example, the sugar chain which is bound to IgG molecule comprises a neutral sugar such as galactose, mannose, fucose, an amino sugar such as N-acetylglucosamine and an acidic sugar such as sialic acid, and can be analyzed by a method such as a sugar chain structure analysis using sugar composition analysis, two dimensional sugar chain mapping or the like.

(1) Analysis of Neutral Sugar and Amino Sugar Compositions

The composition analysis of the sugar chain of an antibody molecule can be carried out by acid hydrolysis of sugar chains with trifluoroacetic acid or the like to release a neutral sugar or an amino sugar and measuring the composition ratio.

Examples include a method using a sugar composition analyzer (BioLC) manufactured by Dionex. The BioLC is an apparatus which analyzes a sugar composition by HPAEC-PAD (high performance anion-exchange chromatography-pulsed amperometric detection) [*J. Liq. Chromatogr.*, 6, 1577 (1983)].

The composition ratio can also be analyzed by a fluorescence labeling method using 2-aminopyridine. Specifically, the composition ratio can be calculated in accordance with a known method [*Agric. Biol. Chem.*, 55(1), 283 (1991)] by labeling an acid-hydrolyzed sample with a fluorescence by 2-aminopyridylation and then analyzing the composition by HPLC.

(2) Analysis of Sugar Chain Structure

The sugar chain structure binding to an antibody molecule can be analyzed by the two dimensional sugar chain mapping method [*Anal. Biochem.*, 171, 73 (1988), *Biochemical Experimentation Methods* 23-*Methods for Studying Glycoprotein Sugar Chains* (Japan Scientific Societies Press) edited by Reiko Takahashi (1989)]. The two dimensional sugar chain mapping method is a method for deducing a sugar chain structure by, e.g., plotting the retention time or elution position of a sugar chain by reverse phase chromatography as the X axis and the retention time or elution position of the sugar chain by normal phase chromatography as the Y axis, respectively, and comparing them with those of known sugar chains.

Specifically, sugar chains are released from an antibody by subjecting the antibody to hydrazinolysis, and the released sugar chains are subjected to fluorescence labeling with 2-aminopyridine (hereinafter referred to as "PA") [*J. Biochem.*, 95, 197 (1984)], and then the sugar chains are separated from an excess PA-treating reagent by gel filtration, and subjected to reverse phase chromatography. Thereafter, each peak of the separated sugar chains are subjected to normal phase chromatography. From these results, the sugar chain structure can be deduced by plotting the results on a two dimensional sugar chain map and comparing them with the spots of a sugar chain standard (manufactured by Takara Shuzo) or a literature [*Anal. Biochem.*, 171, 73 (1988)].

The structure deduced by the two dimensional sugar chain mapping method can be confirmed by further carrying out mass spectrometry such as MALDI-TOF-MS of each sugar chain.

7. Immunological Determination Method for Identifying Sugar Chain Structure of Antibody Molecule An antibody composition comprises an antibody molecule in which sugar chains binding to the Fc region of the antibody are different in structure. The antibody composition comprising a sugar chain in which fucose is not bound to N-acetylglucosamine in the reducing end in the sugar chain among the total complex N-glycoside-linked sugar chains binding to the Fc region in the antibody composition reducing end can be identified by using the method for analyzing the sugar chain structure binding to an antibody molecule described in the item 6. Also, it can also be identified by an immunological determination method using a lectin.

The sugar chain structure binding to an antibody molecule can be identified by the immunological determination method using a lectin in accordance with the known immunological determination method such as Western staining, IRA (radioimmunoassay), VIA (viroimmunoassay), EIA (enzymoimmunoassay), FIA (fluoroimmunoassay) or MIA (metalloimmunoassay) described in literatures [*Monoclonal Antibodies: Principles and Applications*, Wiley-Liss, Inc. (1995); *Immunoassay* (*Koso Meneki Sokuteiho*), 3rd Ed., Igakushoin (1987); Revised Edition, *Enzyme Antibody Method* (*Koso Kotaiho*), Gakusai Kikaku (1985)] and the like.

A lectin which recognizes the sugar chain structure binding to an antibody molecule comprised in an antibody composition is labeled, and the labeled lectin is allowed to react with a sample antibody composition. Then, the amount of the complex of the labeled lectin with the antibody molecule is measured.

The lectin used for identifying the sugar chain structure binding to an antibody molecule includes WGA (wheat-germ agglutinin derived from T vulgaris), ConA (cocanavalin A derived from *C. ensiformis*), RIC (toxin derived from *R. communis*), L-PHA (leucoagglutinin derived from *P. vulgaris*), LCA (lentil agglutinin derived from *L. culinaris*), PSA (pea lectin derived from *P. sativum*), AAL (*Aleuria aurantia* lectin), ACL (*Amaranthus caudatus* lectin), BPL (*Bauhinia purpurea* lectin), DSL (*Datura stramonium* lectin), DBA (*Dolichos biflorus* agglutinin), EBL (elderberry balk lectin), ECL (*Erythrina cristagalli* lectin), EEL (*Euonymus eoropaeus* lectin), GNL (*Galanthus nivalis* lectin), GSL (*Griffonia simplicifolia* lectin), HPA (*Helix pomatia* agglutinin), HHL (*Hippeastrum* hybrid lectin), Jacalin, LTL (*Lotus tetragonolobus* lectin), LEL (*Lycopersicon esculentum* lectin), MAL (*Maackia amurensis* lectin), MPL (*Madura pomifera* lectin), NPL (*Narcissus pseudonarcissus* lectin), PNA (peanut agglutinin), E-PHA (*Phaseolus vulgaris* erythroagglutinin), PTL (*Psophocarpus tetragonolobus* lectin), RCA (*Ricinus communis* agglutinin), STL (*Solanum tuberosum* lectin), SJA (*Sophora japonica* agglutinin), SBA (soybean agglutinin), UEA (*Ulex europaeus* agglutinin), VVL (*Vicia villosa* lectin) and WFA (*Wisteria floribunda* agglutinin).

It is preferable to use a lectin which specifically recognizes a sugar chain structure wherein fucose binds to the N-acetylglucosamine in the reducing end in the complex N-glycoside-linked sugar chain. Examples include *Lens culinaris* lectin LCA (lentil agglutinin derived from *Lens culinaris*), pea lectin PSA (pea lectin derived from *Pisum sativum*), broad bean lectin VFA (agglutinin derived from *Vicia faba*) and *Aleuria aurantia* lectin AAL (lectin derived from *Aleuria aurantia*).

8. Method for Measuring Binding Activity of Antibody Composition to FcγRIIIa

The present invention relates to a method for detecting the ratio of a sugar chain in which fucose is not bound to N-acetylglucosamine in the reducing end in an antibody composition by using a measuring method which comprises reacting an antigen with a tested antibody composition to form a complex of the antigen and the antibody composition; contacting the complex with an Fcγ receptor IIIa. Furthermore, the present invention relates to a method for detecting the antibody-dependent cell-mediated cytotoxic activity.

The measuring method used in the present invention is described below in detail.

First, an antigen is fixed on a plate, and a sample of antibody composition is allowed to react with it. The resulting complex after the antigen-antibody reaction is allowed to react with human FcγIIIa.

The human FcγRIIIa to be allowed to react is labeled with a label such as an enzyme, a radioisotope or an fluorescent, and the binding activity of the antibody bound to the antigen can be measured by an immunological measuring method.

The immunological measuring method includes any method which uses an antigen-antibody reaction such as an immunoassay, an immunoblotting, a coagulation reaction, a complement binding reaction, a hemolysis reaction, a precipitation reaction, a colloidal gold method, a chromatography or an immune staining method. Among these, the immunoassay is preferred.

Also, human FcγRIIIa having a tag can be obtained by ligating a nucleotide sequence encoding a short peptide to a gene encoding the human FcγRIIIa, and expressing the product by genetic engineering techniques. The tag includes histidine and the like.

Accordingly, when the above reaction is carried out by using the human FcγRIIIa having a tag, an immunoassay having high sensitivity can be carried out by applying an antibody against the tag after the reaction and labeling the antibody against the tag as described above, or using a labeled antibody which binds to the antibody against the tag.

Also, human FcγRIIIa having a tag can be obtained by ligating a nucleotide sequence encoding a short peptide to a gene encoding the human FcγRIIIa, and expressing the product by genetic engineering techniques. The tag includes histidine and the like.

Accordingly, when the above reaction is carried out by using the human FcγRIIIa having a tag, an immunoassay having high sensitivity can be carried out by applying an antibody against the tag after the reaction and labeling the antibody against the tag as described above, or using a labeled antibody which binds to the antibody against the tag.

The detection method of the present invention can also be carried out by directly contacting a sample of antibody composition with FcγRIIIa, without reacting an antigen with the sample of antibody component. For example, a labeled antibody which recognizes the human Fc region can be detected by solid-phasing an antibody against the tag and reacting the antibody with tag-containing FcγRIIIa, followed by reaction with a tested antibody composition.

The method for detecting the ratio of a sugar chain in which fucose is not bound to N-acetylglucosamine in the reducing end of an antibody composition can be carried out according to the following method.

First, antibody compositions (standards) necessary for the preparation of a standard curve having a different ratio of a sugar chain in which fucose is not bound to N-acetylglucaomine in the sugar chain reducing end are prepared and the sugar chain analysis of an antibody composition is carried out. In this case, the concentrations of the antibody compositions are adjusted to the same. Each of the binding activities of the prepared antibody composition samples to FcγRIIIa is measured, and a standard curve between the ratio of sugar chain and the binding activity to FcγRIIIa is prepared.

Based on the above standard curve, the binding activity of the antibody composition sample to be measured to FcγRIIIa is measured while keeping the definite concentration of the antibody composition according to a measuring method similar to the above, Based on the above standard curve, the binding activity of the antibody composition to FcγRIIIa is measured with the same concentration of the sample to be measured according to the measuring method similar to the above, so that the ratio of a sugar chain in which fucose is not bound to N-acetylglucosamine in the sugar chain reducing end in the antibody composition sample can be obtained.

Furthermore, detection of ADCC activity can be carried out by the following method.

ADCC activities of the standards used for the preparation of the standard curve in the method for detecting the ratio of a sugar chain in which fucose is not bound to N-acetylglucosamine in the sugar chain reducing end of the above antibody composition are measured. The measuring method includes the method for measuring ADCC described below. Each of binding activities of the prepared antibody composition samples is measured by the above measuring method, and a standard curve between the ADCC activity and the binding activity to FcγRIIIa is prepared.

Based on the above standard curve, the binding activity of the antibody composition sample to be measured to FcγRIIIa is measured while keeping the definite concentration of the antibody composition according to the measuring method used above, so that the ADCC activity can be obtained.

8 Screening Method for Antibody Composition

The present invention relates to a method for screening an antibody composition having a higher binding activity to FcRIIIa, which comprises reacting an antigen with a tested antibody, followed by treatment with FcγRIIIa.

The screening method of the present invention is described below in detail.

An antigen is fixed on a plate and allowed to react with an antibody to be tested. Human FcγRIIIa is allowed to react with the complex of the antigen-antibody reaction.

The human FcγRIIIa to be allowed to react is labeled with a label such as an enzyme, a radioisotope or an fluorescent, and the binding activity of the antibody bound to the antigen can be measured by an immunological measuring method.

The immunological measuring method includes any method which uses an antigen-antibody reaction such as an immunoassay, an immunoblotting, a coagulation reaction, a complement binding reaction, a hemolysis reaction, a precipitation reaction, a colloidal gold method, a chromatography or an immune staining method. Among these, the immunoassay is preferred.

Also, human FcγRIIIa having a tag can be obtained by ligating a nucleotide sequence encoding a short peptide to a gene encoding the human FcγRIIIa, and expressing the product by genetic engineering techniques. The tag includes histidine and the like.

Accordingly, when the above reaction is carried out by using the human FcγRIIIa having a tag, an immunoassay having high sensitivity can be carried out by applying an antibody against the tag after the above reaction and labeling the antibody against the tag as described above, or using a labeled antibody which binds to the antibody against the tag.

10. Application of Antibody Composition of the Present Invention

The antibody composition obtained by the screening method of the present invention has high ADCC activity.

An antibody having high ADCC activity is useful for preventing and treating various diseases including cancers, inflammatory diseases, immune diseases such as autoimmune diseases and allergies, cardiovascular diseases and viral or bacterial infections.

In the case of cancers, namely malignant tumors, cancer cells grow. General anti-tumor agents are characterized by inhibiting the growth of cancer cells. In contrast, an antibody having high ADCC activity can treat cancers by injuring cancer cells through its cell killing effect, and therefore, it is more effective as a therapeutic agent than the general anti-tumor agents. At present, in regard to therapeutic agents for cancers, an anti-tumor effect of an antibody medicament alone is insufficient, so that it has been taken to chemotherapy [*Science*, 280, 1197 (1998)]. If higher anti-tumor effect is found by the antibody composition of the present invention alone, the dependency on chemotherapy will be decreased and side effects will be reduced.

In immune diseases such as inflammatory diseases, autoimmune diseases and allergies, in vivo reactions of the diseases are induced by the release of a mediator molecule by immunocytes, so that the allergy reaction can be inhibited by eliminating immunocytes using an antibody having high ADCC activity.

The cardiovascular diseases include arteriosclerosis and the like. The arteriosclerosis is treated by using balloon catheter at present, but cardiovascular diseases can be prevented and treated by using an antibody having high ADCC activity because growth of arterial cells in restricture after above treatment can be inhibited by using the antibody.

Various diseases including viral and bacterial infections can be prevented and treated by inhibiting proliferation of cells infected with a virus or bacterium using an antibody having high ADCC activity.

Specific examples of an antibody which recognizes a tumor-related antigen, an antibody which recognizes an allergy- or inflammation-related antigen, an antibody which recognizes cardiovascular disease-related antigen and an antibody which recognizes a viral or bacterial infection-related antigen are described below.

The antibody which recognizes a tumor-related antigen includes anti-GD2 antibody [*Anticancer Res.*, 13, 331 (1993)], anti-GD3 antibody [*Cancer Immunol. Immunother.*, 36, 260 (1993)], anti-GM2 antibody [*Cancer Res.*, 54, 1511 (1994)], anti-HER2 antibody [*Proc. Natl. Acad. Sci. USA*, 89, 4285 (1992)], anti-CD52 antibody [*Proc. Natl. Acad. Sci. USA*, 89, 4285 (1992)], anti-MAGE antibody [*British J. Cancer*, 83, 493 (2000)], anti-HM1.24 antibody [*Molecular Immunol.*, 36, 387 (1999)], anti-parathyroid hormone-related protein (PTHrP) antibody [*Cancer*, 88, 2909 (2000)], anti-basic fibroblast growth factor antibody and anti-FGF8 antibody [*Proc. Natl. Acad. Sci. USA*, 86, 9911 (1989)], anti-basic fibroblast growth factor receptor antibody and anti-FGF8 receptor antibody [*J. Biol. Chem.*, 265, 16455 (1990)], anti-insulin-like growth factor antibody [*J. Neurosci. Res.*, 40, 647 (1995)], anti-insulin-like growth factor receptor antibody [*J. Neurosci. Res.*, 40, 647 (1995)], anti-PMSA antibody [*J. Urology*, 160, 2396 (1998)], anti-vascular endothelial cell growth factor antibody [*Cancer Res.*, 57, 4593 (1997)], anti-vascular endothelial cell growth factor receptor antibody [*Oncogene*, 19, 2138 (2000)] and the like.

The antibody which recognizes an allergy- or inflammation-related antigen includes anti-interleukin 6 antibody [*Immunol. Rev.*, 127, 5 (1992)], anti-interleukin 6 receptor antibody [*Molecular Immunol.*, 31, 371 (1994)], anti-interleukin 5 antibody [*Immunol. Rev.*, 127, 5 (1992)], anti-interleukin 5 receptor antibody and anti-interleukin 4 antibody [*Cytokine*, 3, 562 (1991)], anti-interleukin 4 receptor antibody [*J. Immunol. Methods*, 217, 41 (1998)], anti-tumor necrosis factor antibody [*Hybridoma*, 13, 183 (1994)], anti-tumor necrosis factor receptor antibody [*Molecular Pharmacol.*, 58, 237 (2000)], anti-CCR4 antibody [*Nature*, 400, 776 (1999)], anti-chemokine antibody [*J. Immuno. Meth.*, 174, 249 (1994)], anti-chemokine receptor antibody [*J. Exp. Med.*, 186, 1373 (1997)] and the like. The antibody which recognizes a cardiovascular disease-related antigen includes anti-GpIIb/IIIa antibody [*J. Immunol.*, 152, 2968 (1994)], anti-platelet-derived growth factor antibody [*Science*, 253, 1129 (1991)], anti-platelet-derived growth factor receptor antibody [*J. Biol. Chem.*, 272, 17400 (1997)] and anti-blood coagulation factor antibody [*Circulation*, 101, 1158 (2000)] and the like.

The antibody which recognizes a viral or bacterial infection-related antigen includes anti-gp120 antibody [*Structure*, 8, 385 (2000)], anti-CD4 antibody [*J. Rheumatology*, 25, 2065 (1998)], anti-CCR5 antibody and anti-Vero toxin antibody [*J. Clin. Microbiol.*, 37, 396 (1999)] and the like.

These antibodies can be obtained from public organizations such as ATCC (The American Type Culture Collection), RIKEN Gene Bank at The Institute of Physical and Chemical Research and National Institute of Bioscience and Human Technology, Agency of Industrial Science and Technology, or private reagent sales companies such as Dainippon Pharmaceutical, R & D SYSTEMS, PharMingen, Cosmo Bio and Funakoshi Co., Ltd.

The antibody composition obtained by the process of the present invention can be administered as various therapeutic agents alone, but generally, it is preferable to provide it as a pharmaceutical formulation produced by an appropriate method well known in the technical field of pharmaceutical, by mixing it with one or more pharmaceutically acceptable carriers.

It is preferable to select a route of administration which is most effective in treatment. Examples include oral administration and parenteral administration, such as buccal, tracheal, rectal, subcutaneous, intramuscular and intravenous. In the case of an antibody preparation, intravenous administration is preferred.

The dosage form includes sprays, capsules, tablets, granules, syrups, emulsions, suppositories, injections, ointments, tapes and the like.

The pharmaceutical preparation suitable for oral administration include emulsions, syrups, capsules, tablets, powders, granules and the like.

Liquid preparations such as emulsions and syrups can be produced by using, as additives, water; sugars such as sucrose, sorbitol and fructose; glycols such as polyethylene glycol and propylene glycol; oils such as sesame oil, olive oil and soybean oil; antiseptics such as p-hydroxybenzoic acid esters; flavors such as strawberry flavor and peppermint; and the like.

Capsules, tablets, powders, granules and the like can be prepared by using, as additives, excipients such as lactose, glucose, sucrose and mannitol; disintegrating agents such as starch and sodium alginate; lubricants such as magnesium stearate and talc; binders such as polyvinyl alcohol, hydroxypropylcellulose and gelatin; surfactants such as fatty acid ester; plasticizers such as glycerine; and the like.

The pharmaceutical preparation suitable for parenteral administration includes injections, suppositories, sprays and the like.

Injections may be prepared by using a carrier such as a salt solution, a glucose solution or a mixture thereof. Also, powdered injections can be prepared by freeze-drying the antibody composition in the usual way and adding sodium chloride thereto.

Suppositories may be prepared by using a carrier such as cacao butter, hydrogenated fat or carboxylic acid.

Also, sprays may be prepared by using the antibody composition as such or using a carrier, etc. which do not stimulate the buccal or airway mucous membrane of the patient and can facilitate absorption of the antibody composition by dispersing it as fine particles.

The carrier includes lactose, glycerine and the like. Depending on the properties of the antibody composition and the carrier, it is possible to produce pharmaceutical preparations such as aerosols and dry powders. In addition, the components exemplified as additives for oral preparations can also be added to the parenteral preparations.

Although the clinical dose or the frequency of administration varies depending on the objective therapeutic effect, administration method, treating period, age, body weight and the like, it is usually 10 µg/kg to 20 mg/kg per day and per adult.

Also, as the method for examining antitumor effect of the antibody composition against various tumor cells, in vitro tests include CDC activity measuring method, ADCC activity measuring method and the like, and in vivo tests include antitumor experiments using a tumor system in an experimental animal such as a mouse, and the like.

CDC activity and ADCC activity measurements and antitumor experiments can be carried out in accordance with the methods described in *Cancer Immunology Immunotherapy*, 36, 373 (1993); *Cancer Research*, 54, 1511 (1994) and the like.

The present invention will be described below in detail based on Examples; however, Examples are only simple illustrations, and the scope of the present invention is not limited thereto.

BEST MODE FOR CARRYING OUT THE INVENTION

EXAMPLE 1

Preparation of Anti-Ganglioside GD3 Human Chimeric Antibody

1. Construction of Tandem Expression Vector pChi641LHGM4 for Anti-Ganglioside GD3 Human Chimeric Antibody A plasmid pChi641LGM40 was constructed by ligating a fragment of about 4.03 kb containing an L chain cDNA, obtained by digesting an L chain expression vector pChi641LGM4 [*J. Immunol. Methods*, 167, 271 (1994)] for anti-ganglioside GD3 human chimeric antibody (hereinafter referred to as "anti-GD3 chimeric antibody") with restriction enzymes MluI (manufactured by Takara Shuzo) and SalI (manufactured by Takara Shuzo) with a fragment of about 3.40 kb containing a G418-resistant gene and a splicing signal, obtained by digesting an expression vector pAGE107 [*Cytotechnology*, 3, 133 (1990)] for animal cell with restriction enzymes MluI (manufactured by Takara Shuzo) and SalI (manufactured by Takara Shuzo) using DNA Ligation Kit (manufactured by Takara Shuzo), and then transforming *E. coli* HB101 (*Molecular Cloning*, Second Edition) with the ligated product.

Next, a fragment of about 5.68 kb containing an L chain cDNA, obtained by digesting the constructed plasmid pChi641LGM40 with a restriction enzyme ClaI (manufactured by Takara Shuzo), changing it to blunt-end using DNA Blunting Kit (manufactured by Takara Shuzo) and further digesting it with MluI (manufactured by Takara Shuzo), was ligated with a fragment of about 8.40 kb containing an H chain cDNA, obtained by digesting an anti-GD3 chimeric antibody H chain expression vector pChi641HGM4 [*J. Immunol. Methods*, 167, 271 (1994)] with a restriction enzyme XhoI (manufactured by Takara Shuzo), changing it to blunt-end using DNA Blunting Kit (manufactured by Takara Shuzo) and further digesting it with MluI (manufactured by Takara Shuzo) using DNA Ligation Kit (manufactured by Takara Shuzo), and then *E. coli* HB101 (*Molecular Cloning*, Second Edition) was transformed with the ligated product to thereby construct a tandem expression vector pChi641LHGM4 for anti-GD3 chimeric antibody.

2. Preparation of Cell Stably Producing Anti-GD3 Chimeric Antibody

Cells capable of stably producing an anti-GD3 chimeric antibody were prepared by introducing the tandem expression vector pChi641LHGM4 for anti-GD3 chimeric antibody constructed in the item 1 of Example 1 and selecting suitable clones, as described below.

(1) Preparation of Producing Cell Using Rat Myeloma YB2/0 Cell

After introducing 5 µg of the anti-GD3 chimeric antibody expression vector pChi641LHGM4 into $4\times10^6$ cells of rat myeloma YB2/0 [ATCC CRL-1662, *J. Cell. Biol.*, 93, 576 (1982)] by electroporation [*Cytotechnology*, 3, 133 (1990)], the cells were suspended in 40 ml of RPMI1640-FBS(10) (RPMI1640 medium comprising 10% (fetal bovine serum (hereinafter referred to as "FBS") (manufactured by GIBCO BRL)) and dispensed at 200 µl/well into a 96 well culture plate (manufactured by Sumitomo Bakelite). After culturing at 37° C. for 24 hours in a 5% $CO_2$ incubator, G418 was added to give a concentration of 0.5 mg/ml, followed by culturing for 1 to 2 weeks. The culture supernatant was recovered from wells in which colonies of transformants showing G418 resistance were formed and growth of colonies was observed, and the antigen binding activity of the anti-GD3 chimeric antibody in the supernatant was measured by the ELISA shown in the item 3 of Example 1.

Regarding the transformants in wells in which production of the anti-GD3 chimeric antibody was observed in culture supernatants, in order to increase the amount of the antibody production using a DHFR gene amplification system, each of them was suspended in the RPMI1640-FBS(10) medium comprising 0.5 mg/ml G418 and 50 nmol/L DHFR inhibitor, methotrexate (hereinafter referred to as "MTX"; manufactured by SIGMA) to give a density of 1 to $2\times10^5$ cells/ml, and the suspension was dispensed at 2 ml into each well of a 24 well plate (manufactured by Greiner). Transformants showing 50 nmol/L MTX resistance were induced by culturing at 37° C. for 1 to 2 weeks in a 5% $CO_2$ incubator. The antigen binding activity of the anti-GD3 chimeric antibody in culture supernatants in wells in which growth of transformants was observed was measured by the ELISA shown in the item 3 of Example 1. Regarding the transformants in wells in which production of the anti-GD3 chimeric antibody was observed in culture supernatants, the MTX concentration was increased to 100 nmol/L and then to 200 nmol/L, and transformants capable of growing in the RPMI1640-FBS(10) medium comprising 0.5 mg/ml G418 and 200 nmol/L MTX and capable of producing the anti-GD3 chimeric antibody in a large amount were finally obtained by the same method as described above. Among the obtained transformants, suitable clones were selected and were made into a single cell (cloning) by limiting dilution twice.

The obtained anti-GD3 chimeric antibody-producing transformed cell clone 7-9-51 has been deposited on Apr. 5, 1999, as FERM BP-6691 in National Institute of Bioscience and Human Technology, Agency of Industrial Science and Technology (Higashi 1-1-3, Tsukuba, Ibaraki, Japan) (present name: International Patent Organism Depositary, National Institute of Advanced Industrial Science and Technology (Tsukuba Central 6, 1, Higashi 1-Chome Tsukubashi, Ibaraki-ken, Japan)).

(2) Preparation of Producing Cell Using CHO/DG44 Cell

After introducing 4 µg of the anti-GD3 chimeric antibody expression vector pChi641LHGM4 into $1.6 \times 10^6$ cells of CHO/DG44 cell [*Proc. Natl. Acad. Sci. USA*, 77, 4216 (1980)] by electroporation [*Cytotechnology*, 3, 133 (1990)], the cells were suspended in 10 ml of IMDM-FBS(10)-HT(1) [IMDM medium comprising 10% FBS and 1× concentration of HT supplement (manufactured by GIBCO BRL)] and dispensed at 200 µl/well into a 96 well culture plate (manufactured by Iwaki Glass). After culturing at 37° C. for 24 hours in a 5% $CO_2$ incubator, G418 was added to give a concentration of 0.5 mg/ml, followed by culturing for 1 to 2 weeks. The culture supernatant was recovered from wells in which colonies of transformants showing G418 resistance were formed and growth of colonies was observed, and the antigen binding activity of the anti-GD3 chimeric antibody in the supernatant was measured by the ELISA shown in the item 3 of Example 1.

Regarding the transformants in wells in which production of the anti-GD3 chimeric antibody was observed in culture supernatants, in order to increase the amount of the antibody production using a DHFR gene amplification system, each of them was suspended in an IMDM-dFBS(10) medium [IMDM medium comprising 10% dialyzed fetal bovine serum (hereinafter referred to as "dFBS"; manufactured by GIBCO BRL)] comprising 0.5 mg/ml G418 and 10 nmol/L MTX to give a density of 1 to $2 \times 10^5$ cells/ml, and the suspension was dispensed at 0.5 ml into each well of a 24 well plate (manufactured by Iwaki Glass). Transformants showing 10 nmol/L MTX resistance were induced by culturing at 37° C. for 1 to 2 weeks in a 5% $CO_2$ incubator. Regarding the transformants in wells in which their growth was observed, the MTX concentration was increased to 100 nmol/L, and transformants capable of growing in the IMDM-dFBS(10) medium comprising 0.5 mg/ml G418 and 100 nmol/L MTX and of producing the anti-GD3 chimeric antibody in a large amount were finally obtained by the same method as described above. Among the obtained transformants, suitable clones were selected and were made into a single cell (cloning) by limiting dilution twice.

(3) Preparation of Producing Cell Using Mouse Myeloma NS0 Cell

After introducing 5 µg of the anti-GD3 chimeric antibody expression vector pChi641LHGM4 into $4 \times 10^6$ cells of mouse myeloma NS0 by electroporation [*Cytotechnology*, 3, 133 (1990)], the cells were suspended in 40 ml of EX-CELL302-FBS(10) [EX-CELL302 medium comprising 10% FBS and 2 mmol/L L-glutamine (hereinafter referred to as "L-Gln"; manufactured by GIBCO BRL)] and dispensed at 200 µl/well into a 96 well culture plate (manufactured by Sumitomo Bakelite). After culturing at 37° C. for 24 hours in a 5% $CO_2$ incubator, G418 was added to give a concentration of 0.5 mg/ml, followed by culturing for 1 to 2 weeks. The culture supernatant was recovered from wells in which colonies of transformants showing G418 resistance were formed and growth of colonies was observed, and the antigen binding activity of the anti-GD3 chimeric antibody in the supernatant was measured by the ELISA shown in the item 3 of Example 1.

Regarding the transformants in wells in which production of the anti-GD3 chimeric antibody was observed in culture supernatants, in order to increase the amount of the antibody production using a DHFR gene amplification system, each of them was suspended in an EX-CELL302-dFBS(10) medium (EX-CELL302 medium comprising 10% dFBS and 2 mmol/L L-Gln) comprising 0.5 mg/ml G418 and 50 nmol/L MTX to give a density of 1 to $2 \times 10^5$ cells/ml, and the suspension was dispensed at 2 ml into each well of a 24 well plate (manufactured by Greiner). Transformants showing 50 nmol/L MTX resistance were induced by culturing at 37° C. for 1 to 2 weeks in a 5% $CO_2$ incubator. The antigen binding activity of the anti-GD3 chimeric antibody in culture supernatants in wells in which growth of transformants was observed was measured by the ELISA shown in the item 3 of Example 1. Regarding the transformants in wells in which production of the anti-GD3 chimeric antibody was observed in culture supernatants, the MTX concentration was increased to 100 nmol/L and then to 200 nmol/L, and transformants capable of growing in the EX-CELL302-dFBS(10) medium comprising 0.5 mg/ml G418 and 200 nmol/L MTX and of producing the anti-GD3 chimeric antibody in a large amount was finally obtained by the same method as described above. Among the obtained transformants, suitable clones were selected and were made into a single cell (cloning) by limiting dilution twice. Also, using the method for determining the transcription product of an α1,6-fucosyltransferase gene shown in Example 9, a clone producing a relatively small amount of the transcription product was selected and used as a suitable clone.

3. Measurement of Binding Activity of Antibody to GD3 (ELISA)

The binding activity of the antibody to GD3 was measured as described below.

In 2 ml of an ethanol solution containing 10 µg of dipalmitoylphosphatidylcholine (manufactured by SIGMA) and 5 µg of cholesterol (manufactured by SIGMA), 4 nmol of GD3 (manufactured by Snow Brand Milk Products) was dissolved. Into each well of a 96 well plate for ELISA (manufactured by Greiner), 20 µl of the solution (40 µmol/well in final concentration) was dispensed, followed by air-drying, 1% bovine serum albumin (hereinafter referred to as "BSA"; manufactured by SIGMA)-containing PBS (hereinafter referred to as "1% BSA-PBS") was dispensed at 100 µl/well, and then the reaction was carried out at room temperature for 1 hour to block remaining active groups. After discarding 1% BSA-PBS, a culture supernatant of a transformant or a diluted solution of a human chimeric antibody was dispensed at 50 µl/well to carry out the reaction at room temperature for 1 hour. After the reaction, each well was washed with 0.05% Tween 20 (manufactured by Wako Pure Chemical Industries)-containing PBS (hereinafter referred to as "Tween-PBS"), a peroxidase-labeled goat anti-human IgG (H & L) antibody solution (manufactured by American Qualex) diluted 3,000 times with 1% BSA-PBS was dispensed at 50 µl/well as a secondary antibody solution, and then the reaction was carried out at room temperature for 1 hour. After the reaction and subsequent washing with Tween-PBS, ABTS substrate solution [solution prepared by dissolving 0.55 g of 2,2'-azino-bis(3-ethylbenzothiazoline-6-sulfonic acid) ammonium salt in 1 liter of 0.1 mol/L citrate buffer (pH 4.2) and adding 1 µl/ml of hydrogen peroxide to the solution just before use (hereinafter the same solution was used)] was dispensed at 50 µl/well for color development, and then absorbance at 415 nm (hereinafter referred to as "OD415") was measured.

4. Purification of Anti-GD3 Chimeric Antibody (1) Culturing of Producing Cell Derived from YB2/0 Cell and Purification of Antibody The anti-GD3 chimeric antibody-producing transformed cell clone obtained in the item 2(1) of Example 1 was suspended in the Hybridoma-SFM medium comprising 0.2% BSA, 200 nmol/L MTX and 100 nmol/L triiodothyronine (hereinafter referred to as "T3"; manufactured by SIGMA) to give a density of $3\times10^5$ cells/ml and cultured in a 2.0 liter bottle (manufactured by Iwaki Glass) under stirring at a rate of 50 rpm. After culturing at 37° C. for 10 days in a temperature-controlling room, the culture supernatant was recovered. The anti-GD3 chimeric antibody was purified from the culture supernatant using a Prosep-A (manufactured by Bioprocessing) column in accordance with the manufacture's instructions. The purified anti-GD3 chimeric antibody was named YB2/0-GD3 chimeric antibody.

(2) Culturing of Producing Cell Derived from CHO/DG44 Cell and Purification of Antibody The anti-GD3 chimeric antibody-producing transformed cell clone obtained in the item 2(2) of Example 1 was suspended in the EX-CELL302 medium comprising 3 mmol/L L-Gln, 0.5% fatty acid concentrated solution (hereinafter referred to as "CDLC"; manufactured by GIBCO BRL) and 0.3% Pluronic F68 (hereinafter referred to as "PF68"; manufactured by GIBCO BRL) to give a density of $1\times10^6$ cells/ml, and the suspension was dispensed at 50 ml into 175 mm² flasks (manufactured by Greiner). After culturing at 37° C. for 4 days in a 5% $CO_2$ incubator, the culture supernatant was recovered. The anti-GD3 chimeric antibody was purified from the culture supernatant using a Prosep-A (manufactured by Bioprocessing) column in accordance with the manufacture's instructions. The purified anti-GD3 chimeric antibody was named CHO/DG44-GD3 chimeric antibody.

(3) Culturing of Producing Cell Derived from NS0 Cell and Purification of Antibody The anti-GD3 chimeric antibody-producing transformed cell clone obtained in the item 2(3) of Example 1 was suspended in the EX-CELL302 medium comprising 2 mmol/L L-Gln, 0.5 mg/ml G418, 200 nmol/L MTX and 1% FBS, to give a density of $1\times10^6$ cells/ml, and the suspension was dispensed at 200 ml into 175 mm² flasks (manufactured by Greiner). After culturing at 37° C. for 4 days in a 5% $CO_2$ incubator, the culture supernatant was recovered. The anti-GD3 chimeric antibody was purified from the culture supernatant using a Prosep-A (manufactured by Bioprocessing) column in accordance with the manufacture's instructions. The purified anti-GD3 chimeric antibody was named NS0-GD3 chimeric antibody (302).

Also, the transformed cell clone was suspended in the GIT medium comprising 0.5 mg/ml G418 and 200 nmol/L MTX to give a density of $3\times10^5$ cells/ml, and the suspension was dispensed at 200 ml into 175 mm² flasks (manufactured by Greiner). After culturing at 37° C. for 10 days in a 5% $CO_2$ incubator, the culture supernatant was recovered. The anti-GD3 chimeric antibody was purified from the culture supernatant using a Prosep-A (manufactured by Bioprocessing) column in accordance with the manufacture's instructions. The purified anti-GD3 chimeric antibody was named NS0-GD3 chimeric antibody (GIT).

(4) Culturing of Producing Cell Derived from SP2/0 Cell and Purification of Antibody The anti-GD3 chimeric antibody-producing transformed cell clone (KM-871 (FERM BP-3512)) described in Japanese Published Unexamined Patent Application No. 304989/93 (EP 533199) was suspended in the GIT medium comprising 0.5 mg/ml G418 and 200 nmol/L MTX to give a density of $3\times10^5$ cells/ml, and the suspension was dispensed at 200 ml into 175 mm² flasks (manufactured by Greiner). After culturing at 37° C. for 8 days in a 5% $CO_2$ incubator, the culture supernatant was recovered. The anti-GD3 chimeric antibody was purified from the culture supernatant using a Prosep-A (manufactured by Bioprocessing) column in accordance with the manufacture's instructions. The purified anti-GD3 chimeric antibody was named SP2/0-GD3 chimeric antibody.

5. Analysis of Purified Anti-GD3 Chimeric Antibody

Figure 1A:
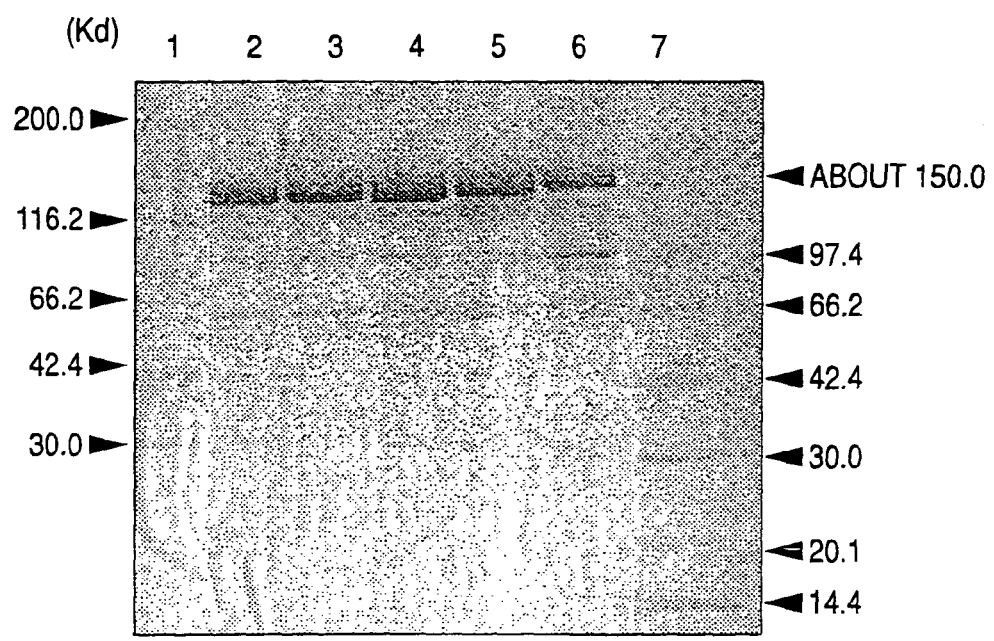
FIG. 1A and FIG. 1B show results of the electrophoresis under non-reducing conditions and under reducing conditions, respectively. Lanes 1 to 7 show electrophoresis patterns of high molecular weight markers, YB2/0-GD3 chimeric antibody, CHO/DG44-GD3 chimeric antibody, SP2/0-GD3 chimeric antibody, NS0-GD3 chimeric antibody (302), NS0-GD3 chimeric antibody (GIT) and low molecular weight markers, respectively.
Figure 1B:
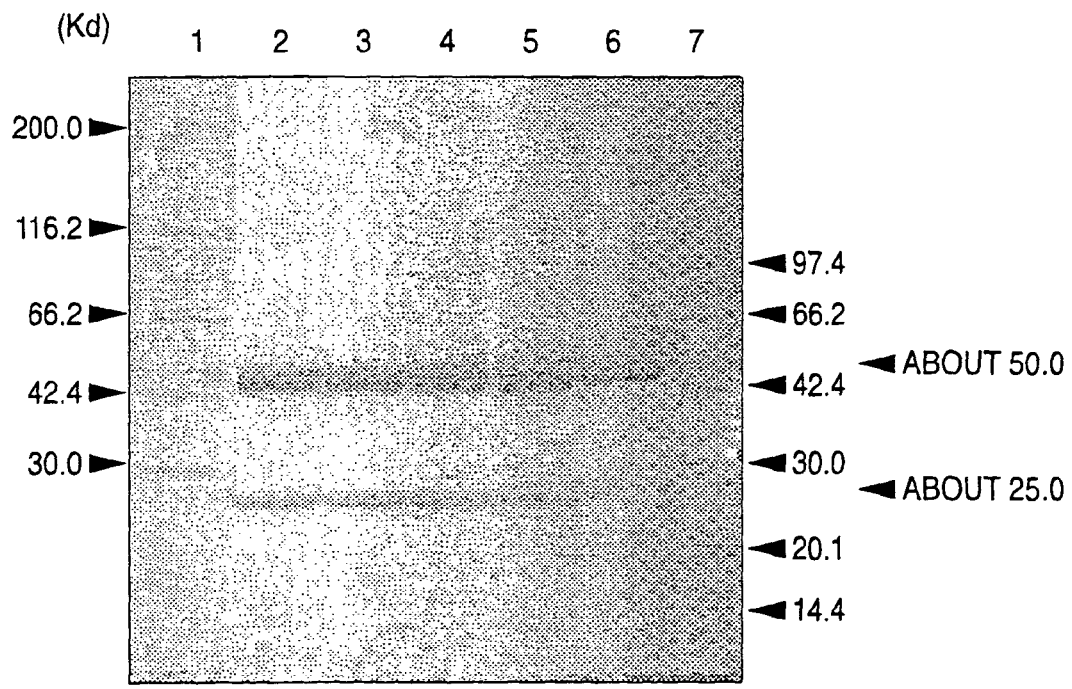

In accordance with a known method [*Nature*, 227, 680 (1970)], 4 μg of each of the five kinds of the anti-GD3 chimeric antibodies produced by and purified from respective animal cells, obtained in the item 4 of Example 1, was subjected to SDS-PAGE to analyze the molecular weight and purity. The results are shown in FIG. 1. As shown in FIG. 1, a single band of about 150 kilodaltons (hereinafter referred to as "Kd") in molecular weight was found under non-reducing conditions, and two bands of about 50 Kd and about 25 Kd under reducing conditions, in each of the purified anti-GD3 chimeric antibodies. The molecular weights almost coincided with the molecular weights deduced from the cDNA nucleotide sequences of H chain and L chain of the antibody (H chain: about 49 Kd, L chain: about 23 Kd, whole molecule: about 144 Kd), and also coincided with the reports stating that the IgG antibody has a molecular weight of about 150 Kd under non-reducing conditions and is degraded into H chains having a molecular weight of about 50 Kd and L chains having a molecular weight of about 25 Kd under reducing conditions due to cutting of the disulfide bond (hereinafter referred to as "S—S bond") in the molecule (*Antibodies*, Chapter 14; *Monoclonal Antibodies*), so that it was confirmed that each anti-GD3 chimeric antibody was expressed and purified as an antibody molecule having the true structure.

EXAMPLE 2

Activity Evaluation of Anti-GD3 Chimeric Antibody

1. Binding Activity of Anti-GD3 Chimeric Antibody to GD3 (ELISA)

Figure 2:
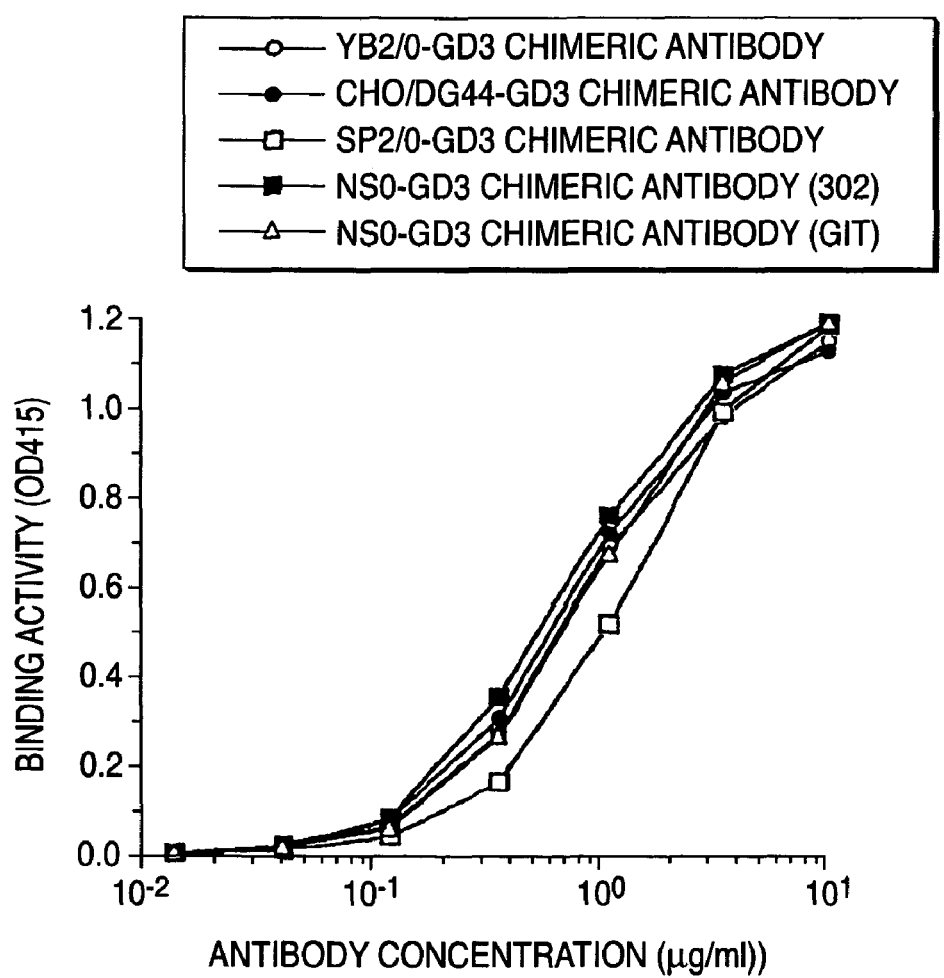
FIG. 2 shows binding activities of five kinds of purified anti-GD3 chimeric antibodies to GD3, measured by changing the antibody concentration. The ordinate and the abscissa show the binding activity to GD3 and the antibody concentration, respectively. "○", "●", "□", "■" and "Δ" show the activities of YB2/0-GD3 chimeric antibody, CHO/DG44-GD3 chimeric antibody, SP2/0-GD3 chimeric antibody, NS0-GD3 chimeric antibody (302) and NS0-GD3 chimeric antibody (GIT), respectively.

Binding activities of the five kinds of the purified anti-GD3 chimeric antibodies obtained in the item 4 of Example 1 to GD3 were measured by the ELISA shown in the item 3 of Example 1. FIG. 2 shows results of the examination of the binding activity measured by changing the concentration of the anti-GD3 chimeric antibody to be added. As shown in FIG. 2, the five kinds of the anti-GD3 chimeric antibodies showed almost the same binding activity to GD3. The result shows that antigen binding activities of these antibodies are constant independently of the antibody-producing animal cells and their culturing methods. Also, it was suggested from the comparison of the NS0-GD3 chimeric antibody (302) with the NS0-GD3 chimeric antibody (GIT) that the antigen binding activities are constant independently of the media used in the culturing.

2. ADCC Activity of Anti-GD3 Chimeric Antibody

ADCC activities of the five kinds of the purified anti-GD3 chimeric antibodies obtained in the item 4 of Example 1 were measured in accordance with the following method.

(1) Preparation of Target Cell Solution

A human melanoma cell line G-361 (ATCC CRL 1424) was cultured in the RPMI1640-FBS(10) medium to prepare $1\times10^6$ cells, and the cells were radioisotope-labeled by reacting them with 3.7 MBq equivalents of a radioactive substance $Na_2^{51}CrO_4$ at 37° C. for 1 hour. After the reaction, the cells were washed three times through their suspension in the RPMI1640-FBS(10) medium and centrifugation, re-suspended in the medium and then allowed to react at 4° C. for 30 minutes on ice for spontaneous dissolution of the radioactive substance. After centrifugation, the precipitate was adjusted to $2\times10^5$ cells/ml by adding 5 ml of the RPMI1640-FBS(10) medium and used as the target cell solution.

(2) Preparation of Effector Cell Solution

From a healthy donor, 50 ml of venous blood was collected, and gently mixed with 0.5 ml of heparin sodium (manufactured by Takeda Pharmaceutical). The mixture was centrifuged to isolate a mononuclear cell layer using Lymphoprep (manufactured by Nycomed Pharma AS) in accordance with the manufacture's instructions. After washing with the RPMI1640-FBS(10) medium by centrifugation three times, the resulting precipitate was re-suspended to give a density of $2 \times 10^6$ cells/ml by using the medium and used as the effector cell solution.

(3) Measurement of ADCC Activity

Into each well of a 96 well U-shaped bottom plate (manufactured by Falcon), 50 μl of the target cell solution prepared in the above (1) ($1 \times 10^4$ cells/well) was dispensed. Next, 100 μl of the effector cell solution prepared in the above (2) was added thereto ($2 \times 10^5$ cells/well, the ratio of effector cells to target cells becomes 20:1). Subsequently, each of the anti-GD3 chimeric antibodies was added at various concentrations, followed by reaction at 37° C. for 4 hours. After the reaction, the plate was centrifuged, and the amount of $^{51}Cr$ in the supernatant was measured with a γ-counter. The amount of spontaneously released $^{51}Cr$ was calculated by the same operation using only the medium instead of the effector cell solution and the antibody solution, and measuring the amount of $^{51}Cr$ in the supernatant. The amount of total released $^{51}Cr$ was calculated by the same operation as above using only the medium instead of the antibody solution and adding 1 N hydrochloric acid instead of the effector cell solution, and measuring the amount of $^{51}Cr$ in the supernatant. The ADCC activity was calculated from the following equation (I):

$$ADCC\ activity\ (\%) = \frac{^{51}Cr\ in\ sample\ supernatant - spontaneously\ released\ ^{51}Cr}{total\ released\ ^{51}Cr - spontaneously\ released\ ^{51}Cr} \times 100 \quad (1)$$

Figure 3:
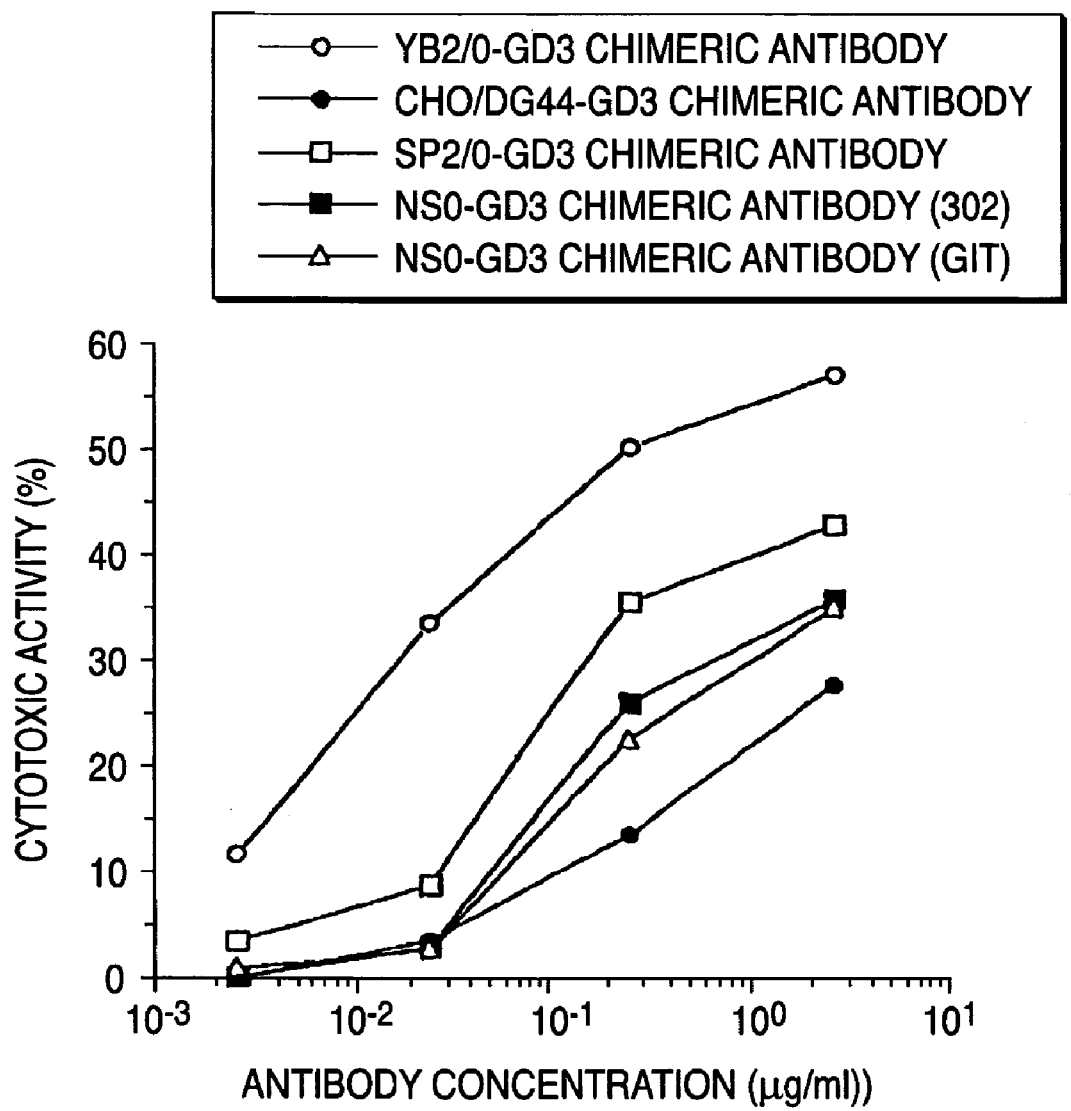
FIG. 3 shows ADCC activities of five kinds of purified anti-GD3 chimeric antibodies to a human melanoma cell line G-361. The ordinate and the abscissa show the cytotoxic activity and the antibody concentration, respectively. "○", "●", "□", "■" and "Δ" show the activities of YB2/0-GD3 chimeric antibody, CHO/DG44-GD3 chimeric antibody, SP2/0-GD3 chimeric antibody, NS0-GD3 chimeric antibody (302) and NS0-GD3 chimeric antibody (GIT), respectively.

The results are shown in FIG. 3. As shown in FIG. 3, among the five kinds of the anti-GD3 chimeric antibodies, the YB2/0-GD3 chimeric antibody showed the highest ADCC activity, followed by the SP2/0-GD3 chimeric antibody, NS0-GD3 chimeric antibody and CHO-GD3 chimeric antibody in that order. No difference in the ADCC activity was found between the NS0-GD3 chimeric antibody (302) and NS0-GD3 chimeric antibody (GIT) prepared by using different media in the culturing. The above results show that the ADCC activity of antibodies greatly varies depending on the kind of the animal cells to be used in their production. As its mechanism, since their antigen binding activities were equal, it was considered that ADCC activity depends on a difference in the structure of the Fc region of the antibody.

EXAMPLE 3

Activity Evaluation of Anti-GD3 Chimeric Antibodies Having a Different Ratio of a Sugar Chain in which 1-Position of Fucose is not Bound to 6-Position of N-acetylglucosamine in the Reducing End 1. Preparation of Anti-GD3 Chimeric Antibodies Having a Different Ratio of a Sugar Chain in which 1-Position of Fucose is not Bound to 6-Position of N-acetylglucosamine in the Reducing End Through α-Bond In accordance with the method described in the item 2(1) of Example 1, some transformed clones derived from YB2/0 cell capable of producing an anti-GD3 chimeric antibody was obtained. Antibodies were prepared from the transformed clones derived from YB2/0 cell and named lot 1, lot 2 and lot 3. Sugar chain analysis of the anti-GD3 chimeric antibodies of lot 1, lot 2 and lot 3 was carried out by the following method.

The solution of each purified antibody was exchanged to 10 mmol/L $KH_2PO_4$ using Ultra Free 0.5-10K (manufactured by Millipore). The exchange was carried out in such a manner that the exchanging ratio became 80-fold or more.

Into Hydraclub S-204 test tube, 100 μg of each antibody was put and dried with a centrifugal evaporator. The dried sample was subjected to hydrazinolysis using Hydraclub manufactured by Hohnen. The sample was allowed to react with hydrazine at 110° C. for 1 hour using a hydrazinolysis reagent manufactured by Hohnen [*Method of Enzymology*, 83, 263 (1982)]. After the reaction, hydrazine was evaporated under a reduced pressure, and the reaction tube was returned to room temperature by allowing it to stand for 30 minutes. Next, 250 μl of an acetylation reagent manufactured by Hohnen and 25 μl of acetic anhydride were added thereto, followed by thoroughly stirred for reaction at room temperature for 30 minutes. Then, 250 μl of the acetylation reagent and 25 μl of acetic anhydride were further added thereto, followed by thoroughly stirring for reaction at room temperature for 1 hour. The sample was frozen at −80° C. in a freezer and freeze-dried for about 17 hours. Sugar chains were recovered from the freeze-dried sample by using Cellulose Cartridge Glycan Preparation Kit Manufactured by Takara Shuzo. The Sample Sugar Chain Solution was dried with a centrifugal evaporator and then subjected to fluorescence labeling with 2-aminopyridine [*J. Biochem.*, 95, 197 (1984)]. The 2-aminopyridine solution was prepared by adding 760 μl of HCl per 1 g of 2-aminopyridine (1×PA solution) and diluting the solution 10-fold with reverse osmosis purified water (10-fold diluted PA solution). The sodium cyanoborohydride solution was prepared by adding 20 μl of 1×PA solution and 430 μl of reverse osmosis purified water per 10 mg of sodium cyanoborohydride. To the sample, 67 μl of a 10 fold-diluted PA solution was added, followed by reaction at 100° C. for 15 minutes and spontaneously cooled, and 2 μl of sodium cyanoborohydride was further added thereto, followed by reaction at 90° C. for 12 hours for fluorescence labeling of the sample sugar chains. The fluorescence-labeled sugar chain group (PA-treated sugar chain group) was separated from excess reagent by using Superdex Peptide HR 10/30 column (manufactured by Pharmacia). This step was carried out by using 10 mmol/L ammonium bicarbonate as the eluent at a flow rate of 0.5 ml/min and at a column temperature of room temperature, and using a fluorescence detector of 320 nm excitation wavelength and 400 nm fluorescence wavelength. The eluate was recovered 20 to 30 minutes after addition of the sample and dried with a centrifugal evaporator to be used as purified PA-treated sugar chains.

Figure 4:
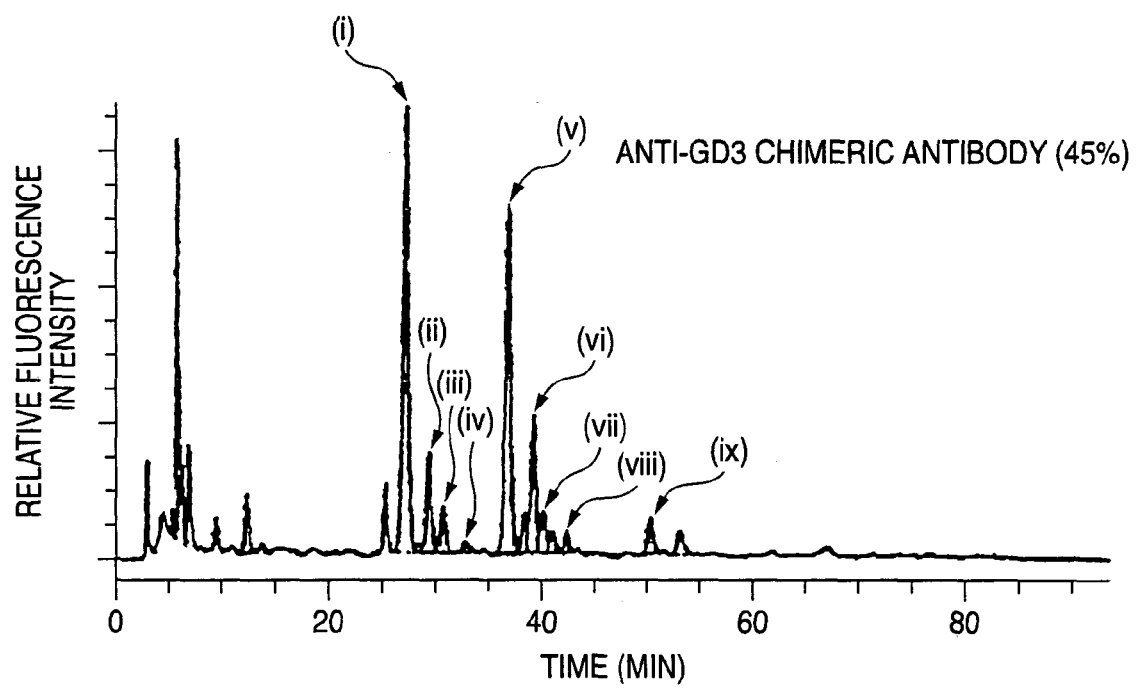
FIG. 4 shows elution patterns of PA-treated sugar chains prepared from the anti-GD3 chimeric antibody of lot 2, obtained by analyzing them with reverse phase HPLC. The ordinate and the abscissa show the relative fluorescence intensity and the elution time, respectively.

Next, reverse phase HPLC analysis of the purified PA-treated sugar chains was carried out by using CLC-ODS column (manufactured by Shimadzu, φ6.0 nm×159 nm). The step was carried out at a column temperature of 55° C. and at a flow rate of 1 ml/min and using a fluorescence detector of 320 nm excitation wavelength and 400 nm fluorescence wavelength. The column was equilibrated with a 10 mmol/L sodium phosphate buffer (pH 3.8) and elution was carried out for 80 minutes by a 0.5% 1-butanol linear density gradient. FIG. 4 shows elution patterns of the purified PA-treated sugar chains of the anti-GD3 antibody of lot 2. Each of the PA-treated sugar chain was identified by post source decay analysis of each peak of the separated PA-treated sugar chains using matrix-assisted laser ionization type of flight mass spectrometry (MALDI-TOF-MS analysis), comparison of elution positions with standards of PA-treated sugar chain manufactured by Takara Shuzo, and reverse phase HPLC analysis after digestion of each PA-treated sugar chain using various enzymes.

The sugar chain content was calculated from each of the peak area of PA-treated sugar chain by reverse HPLC analysis. A PA-treated sugar chain whose reducing end is not N-acetylglucosamine was excluded from the peak area calculation, because it is an impurity or a by-product during preparation of PA-treated sugar chain. Peaks (i) to (ix) in the figure show the following structures (1) to (9), respectively.

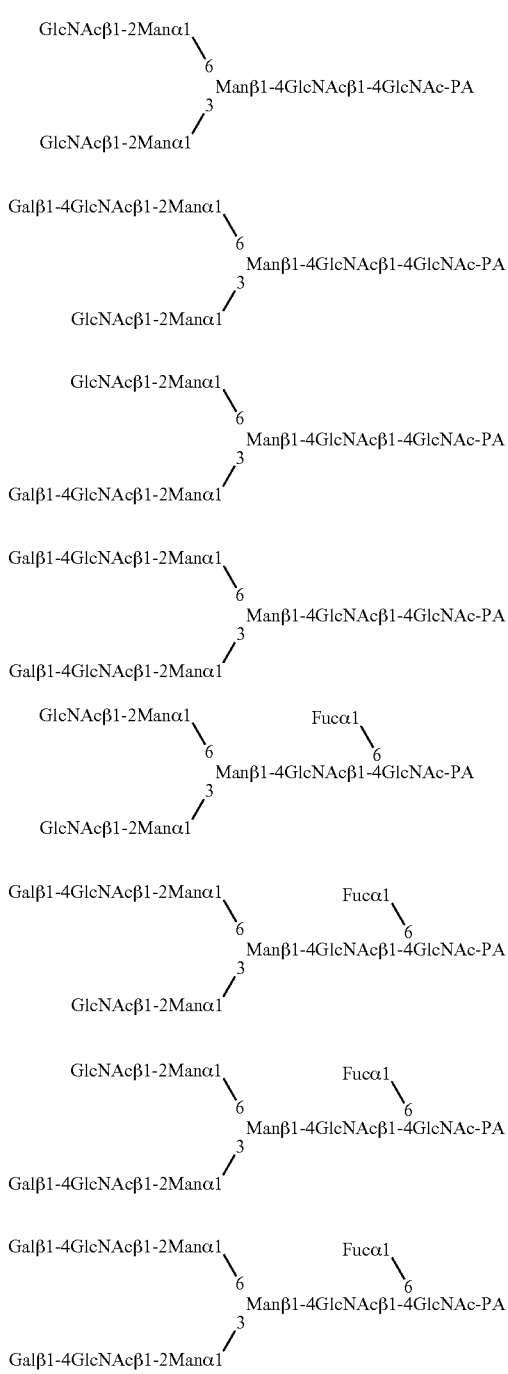

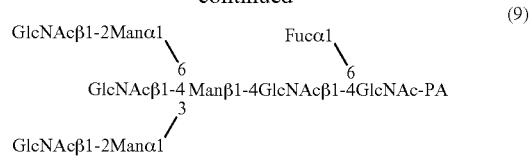

GlcNAc, Gal, Man, Fuc and PA indicate N-acetylglucosamine, galactose, mannose, fucose and a pyridylamino group, respectively. In FIG. 4, the ratio of a sugar chain in which 1-position of fucose was not bound to 6-position of N-acetylglucosaminethe in the reducing end through α-bond was calculated from the area occupied by the peaks (i) to (iv) among (i) to (ix), and the ratio of a sugar chain in which 1-position of fucose was bound to 6-position of N-acetylglucosaminethe in the reducing end through α-bond was calculated from the area occupied by the peaks (v) to (ix) among (i) to (ix). Each ratio of a sugar chain was shown as an average value of the result of two sugar chain analyses.

As a result, the ratios of a sugar chain in which 1-position of fucose was not bound to 6-position of N-acetylglucosamine in the reducing end through α-bond were 50%, 45% and 29% in lot 1, lot 2 and lot 3, respectively. Herein, these samples were named anti-GD3 chimeric antibody (50%), anti-GD3 chimeric antibody (45%) and anti-GD3 chimeric antibody (29%).

Also, sugar chains of the anti-GD3 chimeric antibody derived from the CHO/DG44 cell prepared in the item 2(2) of Example 1 were analyzed in accordance with the above-described method, and it was found that the ratio of a sugar chain in which 1-position of fucose was not bound to 6-position of N-acetylglucosamine in the reducing end through α-bond was 7%. Herein, the sample was named anti-GD3 chimeric antibody (7%).

Further, the anti-GD3 chimeric antibody (45%) and anti-GD3 chimeric antibody (7%) were mixed at a ratio of anti-GD3 chimeric antibody (45%):anti-GD3 chimeric antibody (7%)=5:3 and 1:7, respectively. Sugar chains of the samples were analyzed in accordance with the above-described method, and the ratios of a sugar chain in which 1-position of fucose was not bound to 6-position of N-acetylglucosamine in the reducing end through α-bond were 24% and 13%. Herein, they were named anti-GD3 chimeric antibody (24%) and anti-GD3 chimeric antibody (13%).

2. Evaluation of Binding Activity to GD3 (ELISA)

Figure 5:
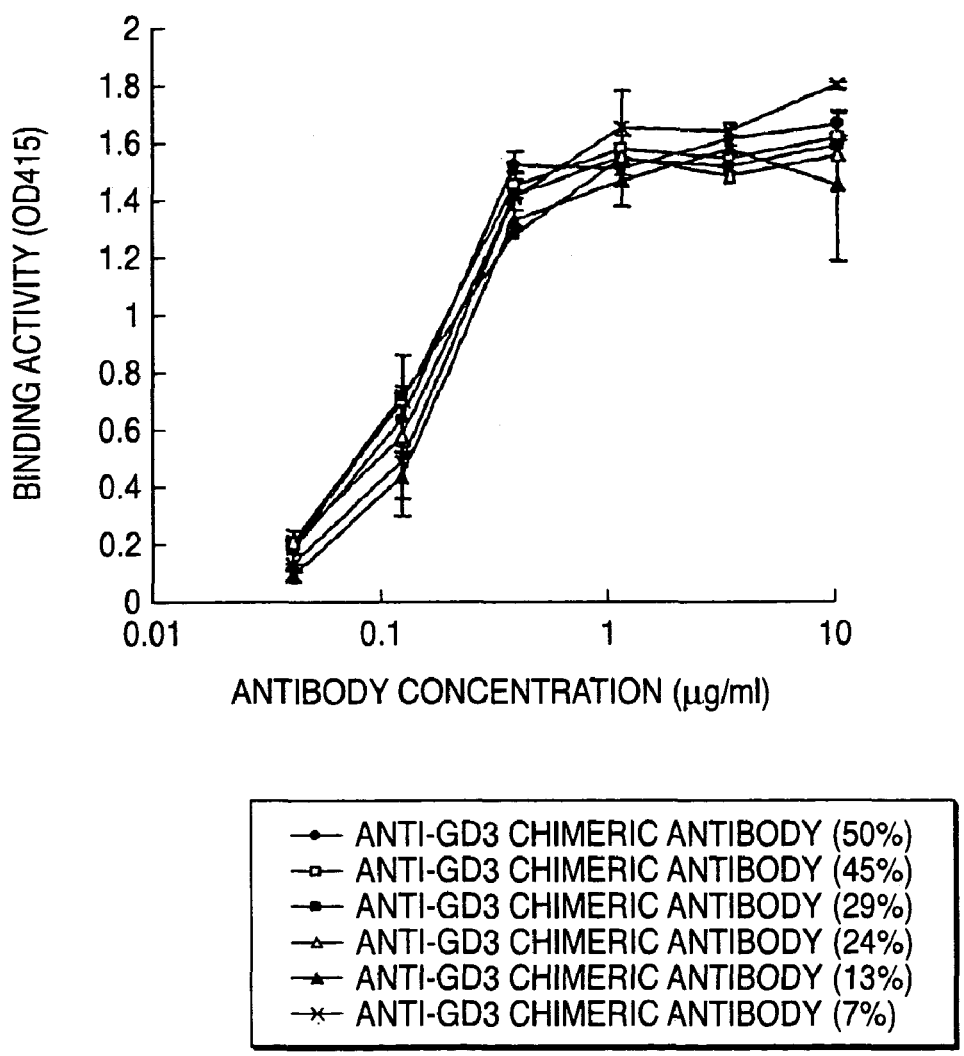
FIG. 5 shows binding activities of six kinds of anti-GD3 chimeric antibodies having a different ratio of a sugar chain in which 1-position of fucose is not bound to 6-position of N-acetylglucosaminethe in the reducing end through α-bond to GD3, measured by changing the antibody concentration. The ordinate and the abscissa show the binding activity to GD3 and the antibody concentration, respectively. "●", "□", "■", "Δ", "▲" and "x" show the activities of anti-GD3 chimeric antibody (50%), anti-GD3 chimeric antibody (45%), anti-GD3 chimeric antibody (29%), anti-GD3 chimeric antibody (24%), anti-GD3 chimeric antibody (13%) and anti-GD3 chimeric antibody (7%), respectively.

The binding activities of the six kinds of the anti-GD3 chimeric antibodies having a different ratio of a sugar chain in which 1-position of fucose was not bound to 6-position of N-acetylglucosamine in the reducing end through α-bond prepared in the item 1 of Example 3 to GD3 were measured by the ELISA shown in the item 3 of Example 1. As a result, all of the six kinds of the anti-GD3 chimeric antibodies showed almost the same GD3-binding activity as shown in FIG. 5, and it was found that the ratio of a sugar chain in which 1-position of fucose was not bound to 6-position of N-acetylglucosamine in the reducing end through α-bond does not have influence on the antigen binding activity of the antibody.

3. Evaluation of ADCC Activity on Human Melanoma Cell Line

ADCC activities of six kinds of the anti-GD3 chimeric antibodies having a different ratio of a sugar chain in which 1-position of fucose was not bound to 6-position of N-acetylglucosamine in the reducing end through α-bond prepared in the item 1 of Example 3 to human melanoma cell line G-361

(ATCC CRL1424) were measured according to the method described in the item 2 of Example 2.

Figure 6A:
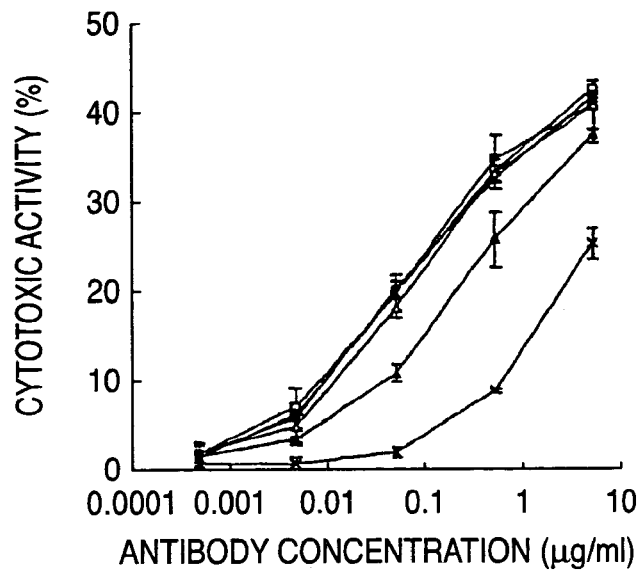
FIG. 6A and FIG. 6B show ADCC activities of six kinds of anti-GD3 chimeric antibodies having a different ratio of a sugar chain in which 1-position of fucose is not bound to 6-position of N-acetylglucosaminethe in the reducing end through α-bond against a human melanoma cell line G-361, using effector cells of the donor A and the donor B, respectively. The ordinate and the abscissa show the cytotoxic activity and the antibody concentration, respectively. "●", "□", "■", "Δ", "▲" and "x" show the activities of anti-GD3 chimeric antibody (50%), anti-GD3 chimeric antibody (45%), anti-GD3 chimeric antibody (29%), anti-GD3 chimeric antibody (24%), anti-GD3 chimeric antibody (13%) and anti-GD3 chimeric antibody (7%), respectively.
Figure 6B:
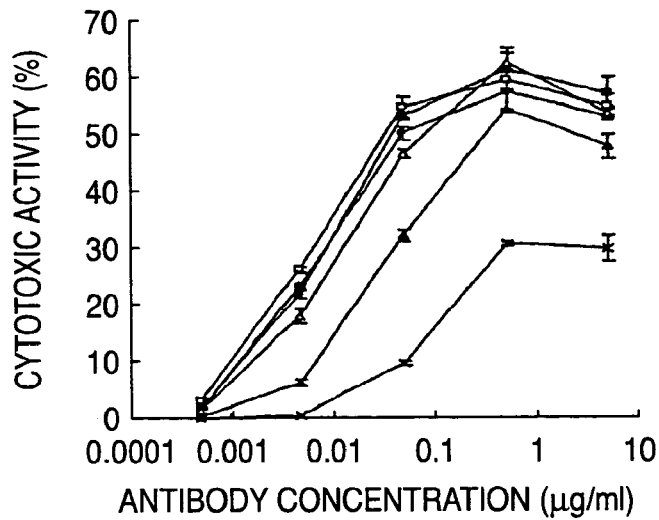
Figure 7:
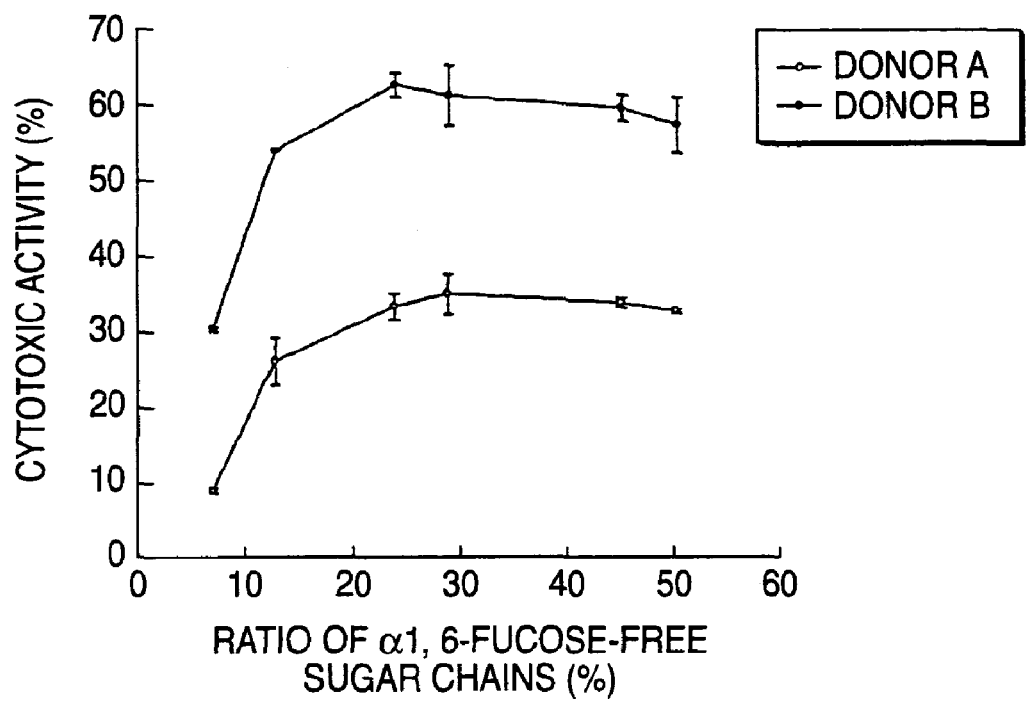
FIG. 7 shows the relationship between sugar chain contents in which 1-fucose is not bound to N-acetylglucosamine at the reduced end in the donor A and the donor B and the ADCC activities.

FIGS. 6 and 7 show results of the measurement of ADCC activity of the six kinds of the anti-GD3 chimeric antibodies having a different ratio of a sugar chain in which 1-position of fucose was bound to 6-position of N-acetylglucosamine in the reducing end through α-bond at various concentrations (0.0005 to 5 μg/ml) using effector cells of two healthy donors (A and B). As shown in FIGS. 6 and 7, the ADCC activity of the anti-GD3 chimeric antibodies showed a tendency to increase in proportion to the ratio of a sugar chain in which 1-position of fucose was not bound to 6-position of N-acetylglucosamine in the reducing end through α-bond at each antibody concentration. The ADCC activity decreases when the antibody concentration is low.

At an antibody concentration of 0.05 μg/ml, the antibody in which the ratio of a sugar chain in which 1-position of fucose was not bound to 6-position of N-acetylglucosamine in the reducing end through α-bond was 24%, 29%, 45% or 50% showed almost the same high ADCC activity, but the antibody (13%) or (7%) in which the ratio of a sugar chain in which 1-position of fucose was bound to 6-position of N-acetylglucosamine in the reducing end through α-bond is less than 20%, 13% or 7% showed the low ADCC activity. These results did not change even if the effector cell having donor was different.

EXAMPLE 4

Activity Evaluation of Anti-CCR4 Chimeric Antibodies Having a Different Ratio of a Sugar Chain in which 1-Position of Fucose was not Bound to 6-Position of N-acetylglucosamine in the Reducing End Through α-Bond 1. Preparation of Cells Stably Producing Anti-CCR4 Chimeric Antibody Cells which are capable of stably producing an anti-CCR4 chimeric antibody were prepared as follows by using a tandem type expression vector pKANTEX2160 for an anti-CCR4 chimeric antibody described in WO01/64754.

(1) Preparation of Producing Cell Using Rat Myeloma YB2/0 Cell

After introducing 10 μg of the anti-CCR4 chimeric antibody expression vector pKANTEX2160 into $4\times10^6$ cells of rat myeloma YB2/0 cell (ATCC CRL 1662) by electroporation [*Cytotechnology*, 3, 133 (1990)], the cells were suspended in 40 ml of Hybridoma-SFM-FBS(5) [Hybridoma-SFM medium (manufactured by Invitrogen) comprising 5% FBS (manufactured by PAA Laboratories)] and dispensed at 200 μl/well into a 96 well culture plate (manufactured by Sumitomo Bakelite). After culturing at 37° C. for 24 hours in a 5% $CO_2$ incubator, G418 was added to give a concentration of 1 mg/ml, followed by culturing for 1 to 2 weeks. Culture supernatant was recovered from wells in which growth of transformants showing G418 resistance was observed by the formation of colonies, and antigen binding activity of the anti-CCR4 chimeric antibody in the supernatant was measured by the ELISA described in the item 2 of Example 4.

Regarding the transformants in wells in which production of the anti-CCR4 chimeric antibody was observed in culture supernatants, in order to increase an amount of the antibody production using a DHFR gene amplification system, each of them was suspended in the Hybridoma-SFM-FBS(5) medium comprising 1 mg/ml G418 and 50 nmol/L DHFR inhibitor MTX (manufactured by SIGMA) to give a density of 1 to $2\times10^5$ cells/ml, and the suspension was dispensed at 1 ml into each well of a 24 well plate (manufactured by Greiner). After culturing at 37° C. for 1 to 2 weeks in a 5% $CO_2$ incubator, transformants showing 50 nmol/L MTX resistance were induced. Antigen binding activity of the anti-CCR4 chimeric antibody in culture supernatants in wells in which growth of transformants was observed was measured by the ELISA described in the item 2 of Example 4.

Regarding the transformants in wells in which production of the anti-CCR4 chimeric antibody was observed in culture supernatants, the MTX concentration was increased by the same method, and a transformant capable of growing in the Hybridoma-SFM-FBS(5) medium comprising 200 nmol/L MTX and of producing the anti-CCR4 chimeric antibody in a large amount was finally obtained. The obtained transformant was made into a single cell (cloning) by limiting dilution twice, and the obtained clone was named KM2760#58-35-16.

(2) Preparation of Producing Cell Using CHO/DH44 Cell

After introducing 4 μg of the anti-CCR4 chimeric antibody expression vector pKANTEX2160 into $1.6\times10^6$ cells of CHO/DG44 cell by electroporation [*Cytotechnology*, 3, 133 (1990)], the cells were suspended in 10 ml of IMDM-dFBS (10)-HT(1) [IMDM medium (manufactured by Invitrogen) comprising 10% dFBS (manufactured by Invitrogen) and 1× concentration of HT supplement (manufactured by Invitrogen)] and dispensed at 100 μl/well into a 96 well culture plate (manufactured by Iwaki Glass). After culturing at 37° C. for 24 hours in a 5% $CO_2$ incubator, the medium was changed to IMDM-dFBS(10) (IMDM medium comprising 10% of dialyzed FBS), followed by culturing for 1 to 2 weeks. Culture supernatant was recovered from wells in which the growth was observed due to formation of a transformant showing HT-independent growth, and an expression amount of the anti-CCR4 chimeric antibody in the supernatant was measured by the ELISA described in the item 2 of Example 4.

Regarding the transformants in wells in which production of the anti-CCR4 chimeric antibody was observed in culture supernatants, in order to increase an amount of the antibody production using a DHFR gene amplification system, each of them was suspended in the IMDM-dFBS(10) medium comprising 50 nmol/L MTX to give a density of 1 to $2\times10^5$ cells/ml, and the suspension was dispensed at 0.5 ml into each well of a 24 well plate (manufactured by Iwaki Glass). After culturing at 37° C. for 1 to 2 weeks in a 5% $CO_2$ incubator, transformants showing 50 nmol/L MTX resistance were induced. Regarding the transformants in wells in which the growth was observed, the MTX concentration was increased to 200 nmol/L by the similar method as above, and a transformant capable of growing in the IMDM-dFBS(10) medium comprising 200 nmol/L MTX and of producing the anti-CCR4 chimeric antibody in a large amount was finally obtained. The obtained transformant was named clone 5-03.

2. Binding Activity of Antibody to CCR4 Partial Peptide (ELISA)

Compound 1 (SEQ ID NO:25) was selected as a human CCR4 extracellular region peptide capable of reacting with the anti-CCR4 chimeric antibody. In order to use it in the activity measurement by ELISA, a conjugate with BSA (manufactured by Nacalai Tesque) was prepared by the following method and used as the antigen. That is, 100 ml of a DMSO solution comprising 25 mg/ml SMCC [4-(N-maleimidomethyl)-cyclohexane-1-carboxylic acid N-hydroxysuccinimide ester] (manufactured by Sigma) was added dropwise to 900 ml of a 10 mg BSA-containing PBS solution under stirring with a vortex, followed by gently stirring for 30 minutes. To a gel filtration column such as NAP-10 column equilibrated with 25 ml of PBS, 1 ml of the reaction solution was applied and then eluted with 1.5 ml of PBS and the resulting eluate was used as a BSA-SMCC solution (BSA concentration was calculated based on $A_{280}$ measurement). Next, 250 ml of PBS was added to 0.5 mg of Compound 1 and then completely dissolved by adding 250 ml of DMF, and the BSA-SMCC solution was added thereto under vortex, followed by gently stirring for 3 hours. The reaction solution was dialyzed against PBS at 4° C. overnight, sodium azide was added thereto to give a final concentration of 0.05%, and the mixture was filtered through a 0.22 mm filter to be used as a BSA-compound 1 solution.

The prepared conjugate was dispensed at 0.05 µg/ml and 50 µl/well into a 96 well EIA plate (manufactured by Greiner) and incubated for adhesion at 4° C. overnight. After washing each well with PBS, 1% BSA-PBS was added thereto in 100 µl/well and allowed to react at room temperature to block the remaining active groups. After washing each well with Tween-PBS, a culture supernatant of a transformant was added at 50 µl/well and allowed to react at room temperature for 1 hour. After the reaction, each well was washed with Tween-PBS, and then a peroxidase-labeled goat anti-human IgG(γ) antibody solution (manufactured by American Qualex) diluted 6000 times with 1% BSA-PBS as the secondary antibody solution was added at 50 µl/well and allowed to react at room temperature for 1 hour. After the reaction and subsequent washing with Tween-PBS, the ABTS substrate solution was added at 50 µl/well for color development, and 20 minutes thereafter, the reaction was stopped by adding a 5% SDS solution at 50 µl/well. Thereafter, the absorbance at $OD_{415}$ was measured. The anti-CCR4 chimeric antibody obtained in the item 1 of Example 4 showed the binding activity to CCR4.

3. Purification of Anti-CCR4 Chimeric Antibody (1) Culturing of Producing Cell Derived from YB2/0 Cell and Purification of Antibody The anti-CCR4 chimeric antibody-expressing transformant cell clone KM2760#58-35-16 obtained in the item 1(1) of Example 4 was suspended in Hybridoma-SFM (manufactured by Invitrogen) medium comprising 200 nmol/L MTX and 5% of Daigo's GF21 (manufactured by Wako Pure Chemical Industries) to give a density of $2\times10^5$ cells/ml and subjected to fed-batch shaking culturing with a spinner bottle (manufactured by Iwaki Glass) in a constant temperature chamber of 37° C. After culturing for 8 to 10 days and recovering the culture supernatant, the anti-CCR4 chimeric antibody was purified using Prosep-A (manufactured by Millipore) column and gel filtration. The purified anti-CCR4 chimeric antibody was named KM2760-1.

(2) Culturing of Producing Cell Derived from CHO-DG44 Cell and Purification of Antibody The anti-CCR4 chimeric antibody-producing transformant clone 5-03 obtained in the item 1(2) of Example 4 was cultured at 37° C. in a 5% $CO_2$ incubator using IMDM-dFBS(10) medium in a 182 cm² flask (manufactured by Greiner). When the cell density reached confluent after several days, the culture supernatant was discarded, and the cells were washed with 25 ml of PBS buffer and then mixed with 35 ml of EXCELL 301 medium (manufactured by JRH). After culturing at 37° C. for 7 days in a 5% $CO_2$ incubator, the culture supernatant was recovered. The anti-CCR4 chimeric antibody was purified from the culture supernatant using Prosep-A (manufactured by Millipore) column in accordance with the manufacture's instructions. The purified anti-CCR4 chimeric antibody was named KM3060.

When the binding activity to CCR4 of KM2760-1 and KM3060 was measured by the ELISA described in the item 2 of Example 4, they showed equivalent binding activity.

4. Analysis of Purified Anti-CCR4 Chimeric Antibodies

Each 4 µg of the two kinds of the anti-CCR4 chimeric antibodies produced by and purified from various animal cells, obtained in the item 3 of Example 4 was subjected to SDS-PAGE in accordance with a known method [*Nature*, 227, 680 (1970)], and the molecular weight and purity were analyzed. In each of the purified anti-CCR4 chimeric antibodies, a single band corresponding to the molecular weight of about 150 Kd was found under non-reducing conditions, and two bands of about 50 Kd and about 25 Kd were found under reducing conditions. The molecular weights almost coincided with the molecular weights deduced from the cDNA nucleotide sequences of antibody H chain and L chain (H chain: about 49 Kd, L chain: about 23 Kd, whole molecule: about 144 Kd) and further coincided with reports stating that an IgG type antibody has a molecular weight of about 150 Kd under non-reducing conditions and is degraded into H chain having a molecular weight of about 50 Kd and L chain having a molecular weight of about 25 Kd under reducing conditions caused by cutting an S—S bond in the molecule (*Antibodies*, Chapter 14 (1988), *Monoclonal Antibodies*), thus confirming that the anti-CCR4 chimeric antibody was expressed and purified as an antibody molecule having a correct structure.

5. Preparation of Anti-CCR4 Chimeric Antibody Having a Different Ratio of a Sugar Chain in which 1-Position of Fucose was not Bound to 6-Position of N-acetylglucosamine in the Reducing End Through α-Bond Sugar chains of the anti-CCR4 chimeric antibody KM2760-1 derived from YB2/0 cell and the anti-CCR4 chimeric antibody KM3060 derived from CHO/DG44 cell prepared in the item 3 of Example 4 were analyzed in accordance with the method in the item 1 of Example 3. The ratios of a sugar chain in which 1-position of fucose was not bound to 6-position of N-acetylglucosamine in the reducing end through α-bond were 87% and 8% in KM2760-1 and KM3060, respectively. Herein, the samples were named anti-CCR4 chimeric antibody (87%) and anti-CCR4 chimeric antibody (8%).

Furthermore, the anti-CCR4 chimeric antibody (87%) and anti-CCR4 chimeric antibody (8%) were mixed at a ratio of anti-CCR4 chimeric antibody (87%):anti-CCR4 chimeric antibody (8%)=1:39, 16:67, 22:57, 32:47 and 42:37, respectively. Sugar chains of these samples were analyzed in accordance with the method of the item 1 of Example 3. The ratios of a sugar chain in which 1-position of fucose was not bound to 6-position of N-acetylglucosamine in the reducing end through α-bond were 9%, 18%, 27%, 39% and 46%, respectively. Herein, these samples were named anti-CCR4 chimeric antibody (9%), anti-CCR4 chimeric antibody (18%), anti-CCR4 chimeric antibody (27%), anti-CCR4 chimeric antibody (39%) and anti-CCR4 chimeric antibody (46%).

Figure 8:
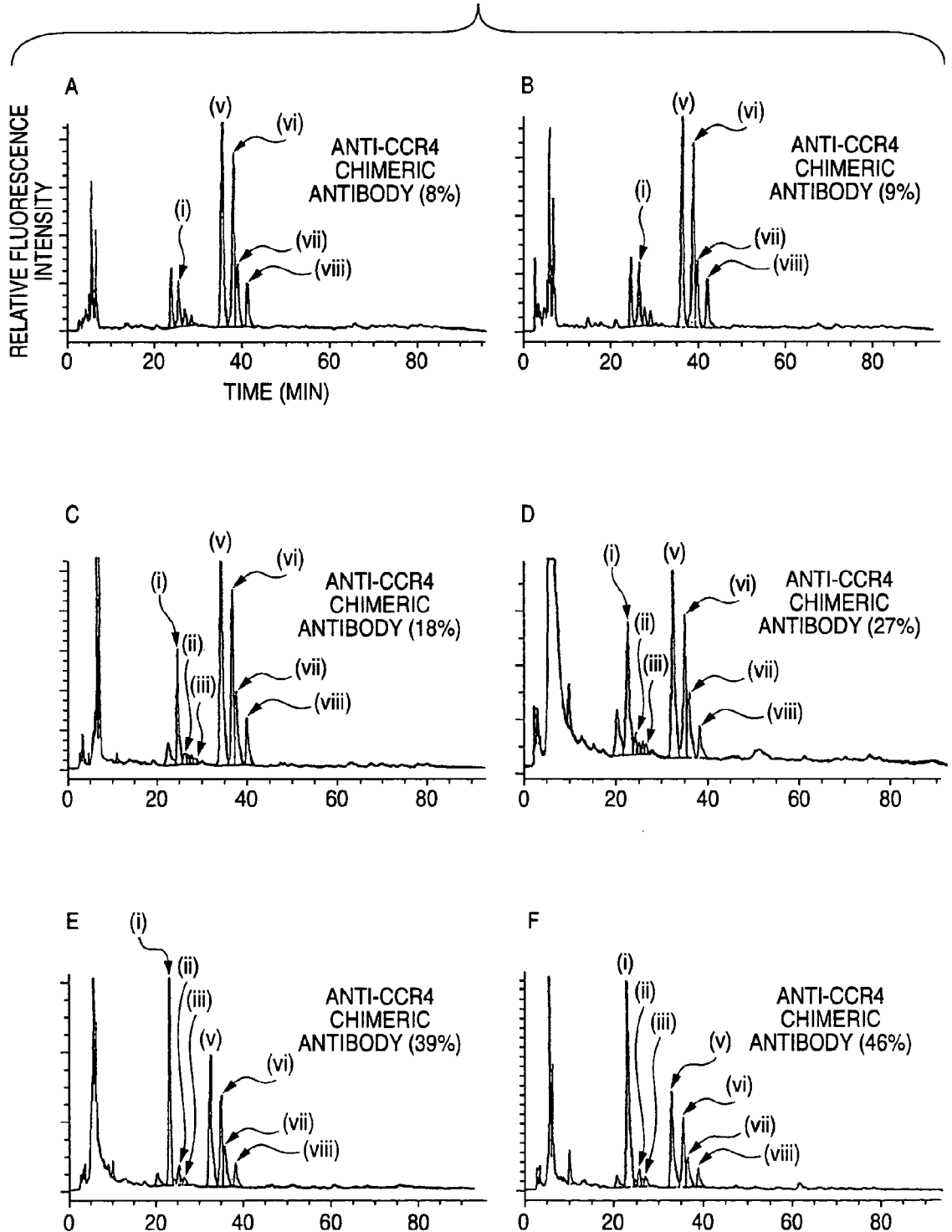
FIG. 8 shows elution patterns of PA-treated sugar chains prepared from six kinds of anti-GD3 chimeric antibodies, obtained by analyzing them with reverse phase HPLC. The ordinate and the abscissa show the relative fluorescence intensity and the elution time, respectively.

Results of the sugar chain analysis of each of the samples are shown in FIG. 8. The ratio of a sugar chain in which 1-position of fucose was not bound to 6-position of N-acetylglucosamine in the reducing end through α-bond was shown as an average value of the result of two sugar chain analyses.

6. Evaluation of Binding Activity of Antibody to CCR4 Partial Peptide (ELISA)

Binding activities of the six kinds of the anti-CCR4 chimeric antibodies having a different ratio of a sugar chain in which 1-position of fucose was not bound to 6-position of N-acetylglucosamine in the reducing end through α-bond prepared in the item 5 of Example 4 to a CCR4 partial peptide were measured in accordance with the method described in the item 2 of Example 4.

Figure 9:
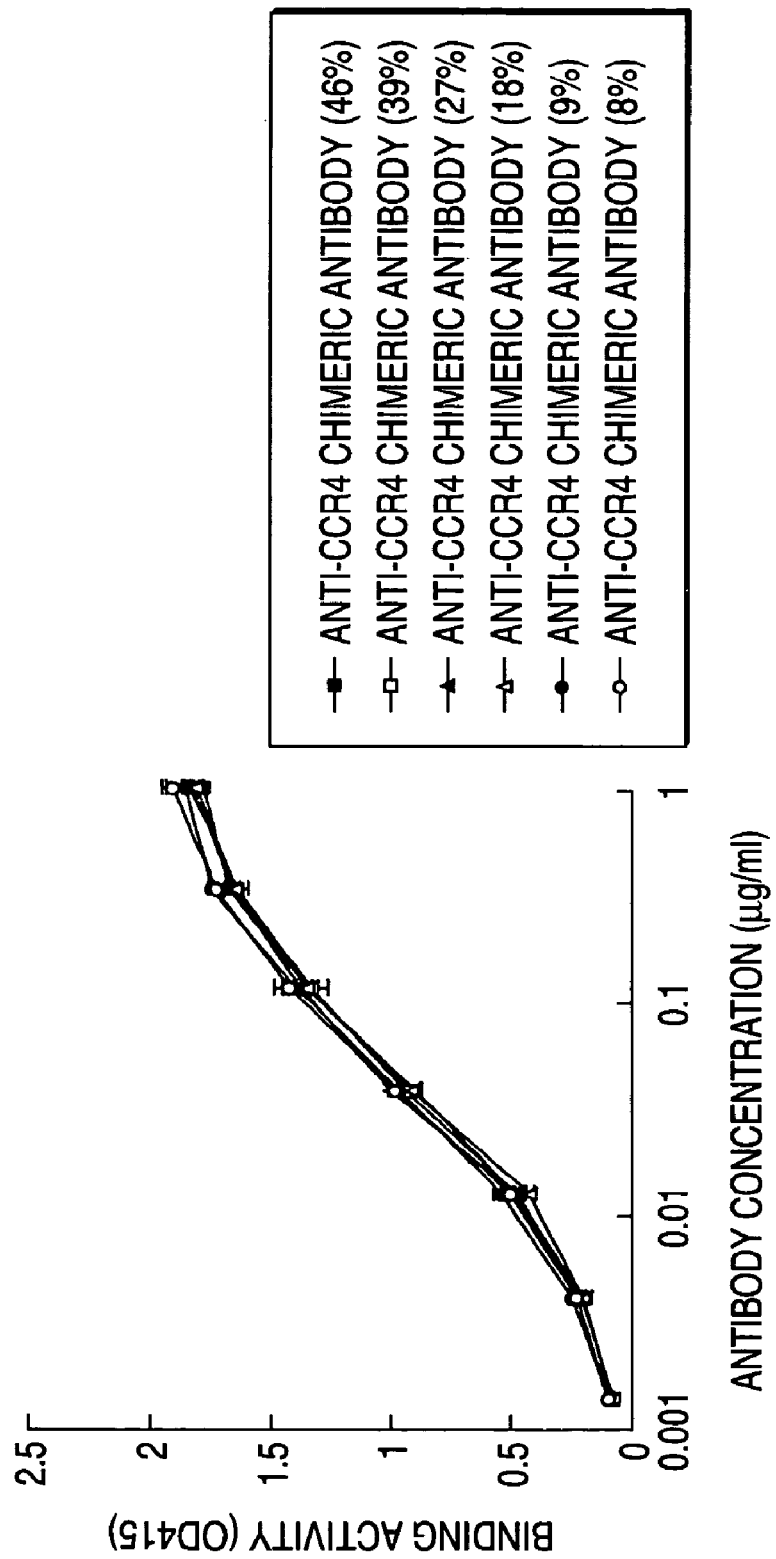
FIG. 9 shows binding activities of six kinds of anti-CCR4 chimeric antibodies having a different ratio of a sugar chain in which 1-position of fucose is not bound to 6-position of N-acetylglucosaminethe in the reducing end through α-bond measured by changing the antibody concentration to CCR4. The ordinate and the abscissa show the binding activity to CCR4 and the antibody concentration, respectively. "■", "□", "▲", "Δ", "●" and "○" show the activities of anti-CCR4 chimeric antibody (46%), anti-CCR4 chimeric antibody (39%), anti-CCR4 chimeric antibody (27%), anti-CCR4 chimeric antibody (18%), anti-CCR4 chimeric antibody (9%) and anti-CCR4 chimeric antibody (8%), respectively.

As a result, as shown in FIG. 9, the six kinds of the anti-CCR4 chimeric antibodies showed almost the same CCR4- binding activity, and it was found that the ratio of a sugar chain in which 1-position of fucose was not bound to 6-position of N-acetylglucosamine in the reducing end through α-bond does not have influence on the antigen-binding activity of the antibody.

7. Evaluation of ADCC Activity on Human CCR4-High Expressing Clone

The ADCC activity of the anti-CCR4 chimeric antibodies against a human CCR4-high highly expressing cell was measured as follows.

(1) Preparation of Target Cell Suspension

Cells ($1.5\times10^6$) of a human CCR4-highly expressing cell, CCR4/EL-4 cell, described in WO01/64754 were prepared and a 5.55 MBq equivalent of a radioactive substance $Na_2^{51}CrO_4$ was added thereto, followed by reaction at 37° C. for 1.5 hours to thereby label the cells with a radioisotope. After the reaction, the cells were washed three times by suspension in a medium and subsequent centrifugation, resuspended in the medium and then incubated at 4° C. for 30 minutes on ice for spontaneous dissociation of the radioactive substance. After centrifugation, the cells were adjusted to give a density of $2\times10^5$ cells/ml by adding 7.5 ml of the medium and used as a target cell suspension.

(2) Preparation of Human Effector Cell Suspension

From a healthy donor, 60 ml of peripheral blood was collected, 0.6 ml of heparin sodium (manufactured by Shimizu Pharmaceutical) was added thereto, followed by gently mixing. The mixture was centrifuged (800 g, 20 minutes) to isolate a mononuclear cell layer using Lymphoprep (manufactured by AXIS SHIELD) in accordance with the manufacture's instructions. The cells were washed by centrifuging (1,400 rpm, 5 minutes) three times in a medium and then re-suspended in the medium to give a density of $5\times10^6$ cells/ml and used as a human effector cell suspension.

(3) Measurement of ADCC Activity

The target cell suspension prepared in the above item (1) was dispensed at 50 µl ($1\times10^4$ cells/well) into each well of a 96 well U-bottom plate (manufactured by Falcon). Next, 100 µl of the effector cell suspension prepared in the above item (2) was added thereto ($5\times10^5$ cells/well, ratio of the human effector cells to the target cells was 50:1). Furthermore, each of the anti-CCR4 chimeric antibodies was added thereto to give a final concentration of 0.0001 to 10 µg/ml, followed by reaction at 37° C. for 4 hours. After the reaction, the plate was centrifuged and the amount of $^{51}Cr$ in the supernatant was measured with a γ-counter. An amount of the spontaneously dissociated $^{51}Cr$ was calculated by carrying out the same procedure as above using the medium alone instead of the human effector cell suspension and antibody solution, and measuring the amount of $^{51}Cr$ in the supernatant. An amount of the total dissociated $^{51}Cr$ was calculated by carrying out the same procedure as above using a 1 mol/L hydrochloric acid solution instead of the antibody solution and human effector cell suspension, and measuring the amount of $^{51}Cr$ in the supernatant. The ADCC activity (%) was calculated based on the above-mentioned equation (I).

Figure 10:
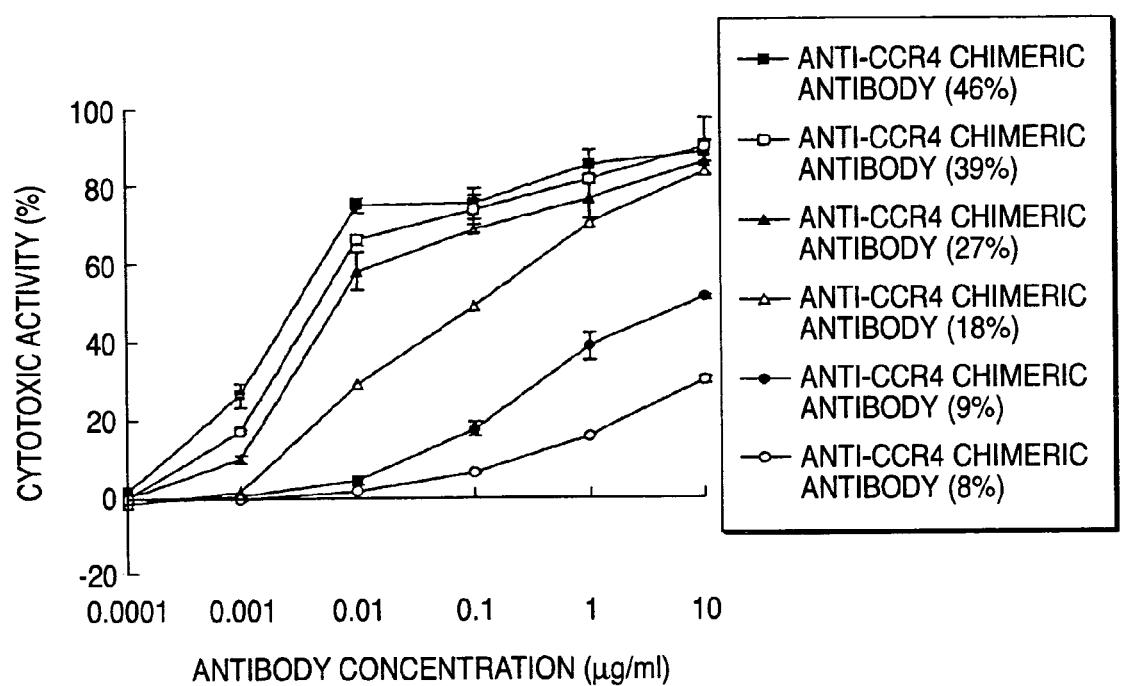
FIG. 10 shows ADCC activities of anti-CCR4 chimeric antibodies having a different ratio of a sugar chain in which 1-position of fucose is not bound to 6-position of N-acetylglucosaminethe in the reducing end through α-bond against CCR4/EL-4 cell, using an effector cell of the donor A. As effector cells, the effector cells derived from donor A were used. The ordinate and the abscissa show the cytotoxic activity and the antibody concentration, respectively. "■", "□", "▲", "Δ", "●" and "○" show the activities of anti-CCR4 chimeric antibody (46%), anti-CCR4 chimeric antibody (39%), anti-CCR4 chimeric antibody (27%), anti-CCR4 chimeric antibody (18%), anti-CCR4 chimeric antibody (9%) and anti-CCR4 chimeric antibody (8%), respectively.
Figure 11:
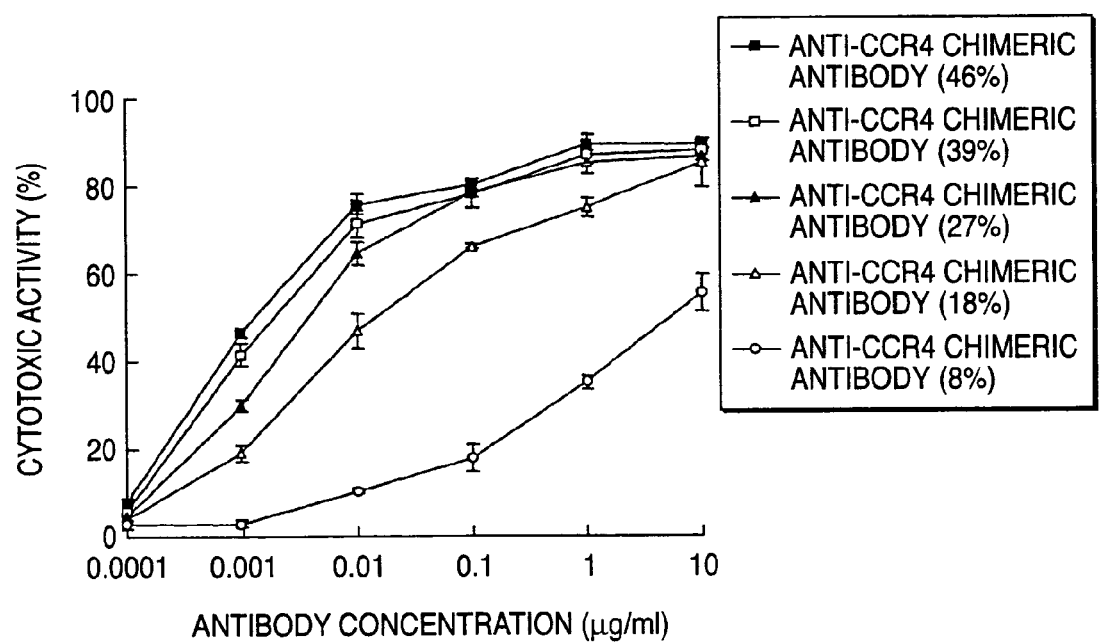
FIG. 11 shows ADCC activities of anti-CCR4 chimeric antibodies having a different ratio of a sugar chain in which 1-position of fucose is not bound to 6-position of N-acetylglucosaminethe in the reducing end through α-bond against CCR4/EL-4 cell, using an effector cell of the donor B. As effector cells, the effector cells derived from donor B were used. The ordinate and the abscissa show the cytotoxic activity and the antibody concentration, respectively. "■", "□", "▲", "Δ", "●" and "○" show the activities of anti-CCR4 chimeric antibody (46%), anti-CCR4 chimeric antibody (39%), anti-CCR4 chimeric antibody (27%), anti-CCR4 chimeric antibody (18%), anti-CCR4 chimeric antibody (9%) and anti-CCR4 chimeric antibody (8%), respectively.

FIGS. 10 and 11 show results of the measurement of ADCC activity of the anti-CCR4 chimeric antibodies having a different ratio of a sugar chain in which 1-position of fucose was not bound to 6-position of N-acetylglucosamine in the reducing end through α-bond at various concentrations (0.001 to 10 µg/ml) using effector cells of two healthy donors (A and B), respectively. As shown in FIGS. 10 and 11, the ADCC activity of the anti-CCR4 chimeric antibodies showed a tendency to increase in proportion to the ratio of a sugar chain in which 1-position of fucose was not bound to 6-position of N-acetylglucosamine in the reducing end through α-bond at each antibody concentration. The ADCC activity decreases when the antibody concentration is low. At an antibody concentration of 0.01 µg/ml, the antibody in which the ratios of a sugar chain in which 1-position of fucose was not bound to 6-position of N-acetylglucosamine in the reducing end through α-bond was 27%, 39% and 46%, respectively, showed almost the same high ADCC activity but the ADCC activity was low in the antibody in which the ratio of a sugar chain in which 1-position of fucose was not bound to 6-position of N-acetylglucosamine in the reducing end through α-bond is less than 20%. These results did not change even if the effector cell having donor was different.

EXAMPLE 5

Determination of Transcription Product of α1,6-Fucosyltransferase (FUT8) Gene in Host Clone 1. Preparation of Single-Stranded cDNA from Various Clones Single-stranded cDNAs were prepared from dhfr-deleted CHO/DG44 cells and rat myeloma YB2/0 cells by the following procedure.

The CHO/DG44 cells were suspended in IMDM medium (manufactured by Life Technologies) supplemented with 10% FBS (manufactured by Life Technologies) and 1× concentration HT supplement (manufactured by Life Technologies), and 15 ml of the suspension was inoculated into T75 flask for adhesion cell culture use (manufactured by Greiner) at a density of $2\times10^5$ cells/ml. Also, the YB2/0 cells were suspended in RPMI 1640 medium (manufactured by Life Technologies) supplemented with 10% FBS (manufactured by Life Technologies) and 4 mmol/l L-GLN (manufactured by Life Technologies), and 15 ml of the suspension was inoculated into T75 flask for suspension cell culture (manufactured by Greiner) at a density of $2\times10^5$ cells/ml. They were cultured at 37° C. in a 5% $CO_2$ incubator, and $1\times10^7$ of respective host cells were recovered on the 1st, 2nd, 3rd, 4th and 5th days of the culturing to extract total RNA using RNAeasy (manufactured by QIAGEN) in accordance with the manufacture's instructions.

The total RNA was dissolved in 45 µl of sterile water, 1 µl of RQ1 RNase-Free DNase (manufactured by Promega), 5 µl of the attached 10× DNase buffer and 0.5 µl of RNasin Ribonuclease Inhibitor (manufactured by Promega) were added thereto, followed by reaction at 37° C. for 30 minutes to degrade genomic DNA contaminated in the sample. After the reaction, the total RNA was purified again using RNAeasy (manufactured by QIAGEN) and dissolved in 50 µl of sterile water.

In a 20 µl of the reaction mixture using oligo(dT) as a primer, single-stranded cDNA was synthesized from 3 µg of each of the obtained total RNA samples by reverse transcription reaction using SUPERSCRIPT™ Preamplification System for First Strand cDNA Synthesis (manufactured by Life Technologies) in accordance with the manufacture's instructions. For the cloning of FUT8 and β-actin derived from respective host cells, 1× concentration solution of the reaction solution was used, and for the determination of each gene transcription amount by competitive PCR, 50 fold-diluted aqueous solution of the reaction solution were used. The solutions were stored at −80° C. until use.

2. Preparation Method of cDNA Partial Fragments of Chinese Hamster FUT8 and Rat FUT8

Figure 12:
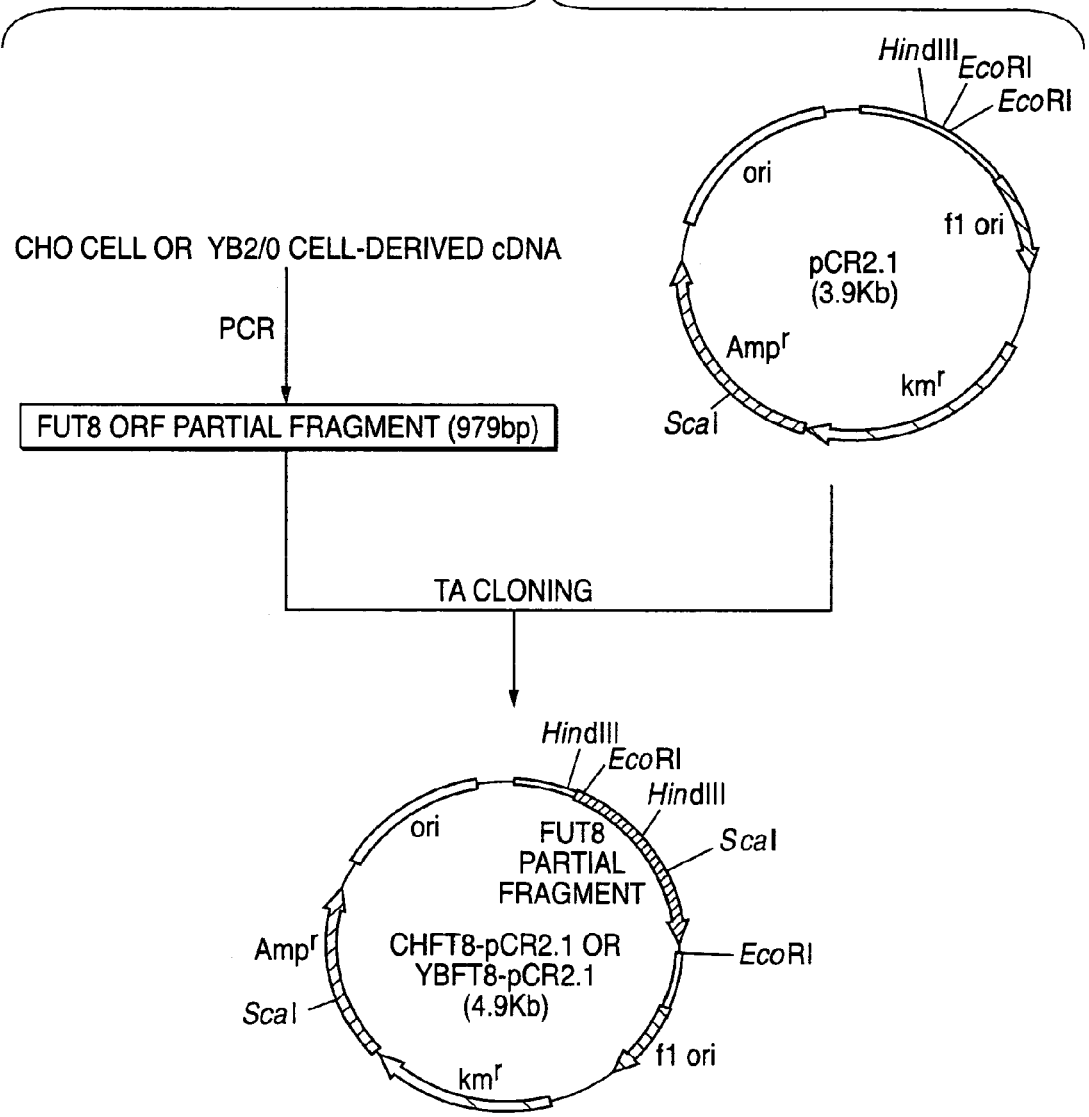
FIG. 12 shows construction of plasmids CHFT8-pCR2.1 and YBFT8-pCR2.1.

Each cDNA partial fragment of Chinese hamster FUT8 and rat FUT8 was prepared by the following procedure (FIG. 12).

First, primers (represented by SEQ ID NOs:4 and 5) specific for nucleotide sequences common to human FUT8 cDNA [*J. Biochem.*, 121, 626 (1997)] and swine FUT8 cDNA [*J. Biol. Chem.*, 271, 27810 (1995)] were designed.

Next, 25 μl of a reaction solution [ExTaq buffer (manufactured by Takara Shuzo), 0.2 mmol/l dNTPs and 0.5 μmol/l of the above gene-specific primers (SEQ ID NOs:4 and 5)] containing 1 μl of each of the cDNA prepared from CHO cell and cDNA prepared from YB2/0 cell, both obtained in the item 1 of Example 5 on the second day after culturing, and polymerase chain reaction (hereinafter referred to as "PCR") was carried out by using a DNA polymerase ExTaq (manufactured by Takara Shuzo). The PCR was carried out by heating at 94° C. for 1 minute, subsequent 30 cycles of heating at 94° C. for 30 seconds, 55° C. for 30 seconds and 72° C. for 2 minutes as one cycle, and further heating at 72° C. for 10 minutes.

After the PCR, the reaction solution was subjected to 0.8% agarose gel electrophoresis, and a specific amplified fragment of 979 bp was purified using GENECLEAN Spin Kit (manufactured by BIO 101) and eluted with 10 μl of sterile water (hereinafter, the method was used for the purification of DNA fragments from agarose gel). Into a plasmid pCR2.1, 4 μl of the amplified fragment was employed to insert in accordance with the manufacture's instructions of TOPO TA Cloning Kit (manufactured by Invitrogen), and *E. coli* XL1-Blue was transformed with the reaction solution by the method of Cohen et al. [*Proc. Natl. Acad. Sci. USA*, 69, 2110 (1972)] (hereinafter, the method was used for the transformation of *E. coli*). Plasmid DNA samples were isolated in accordance with a known method [*Nucleic Acids Research*, 7, 1513 (1979)] (hereinafter, the method was used for the isolation of plasmid) from cDNA-inserted six clones among the obtained kanamycin-resistant colonies.

The nucleotide sequences of cDNAs inserted into the plasmids were determined by using DNA Sequencer 377 (manufactured by Parkin Elmer) and BigDye Terminator Cycle Sequencing FS Ready Reaction kit (manufactured by Parkin Elmer) in accordance with the method of the manufacture's instructions. It was confirmed that all of the inserted cDNAs of which sequences were determined by the method encode the open reading frame (ORF) partial sequences of Chinese hamster FUT8 and rat FUT8 (represented by SEQ ID NOs:6 and 7). Among these, plasmid DNA samples containing absolutely no reading error by the PCR in the sequences were selected. Herein, these plasmids were named CHFT8-pCR2.1 and YBFT8-pCR2.1.

3. Preparation of Chinese Hamster β-Actin and Rat β-Actin cDNA

Figure 13:
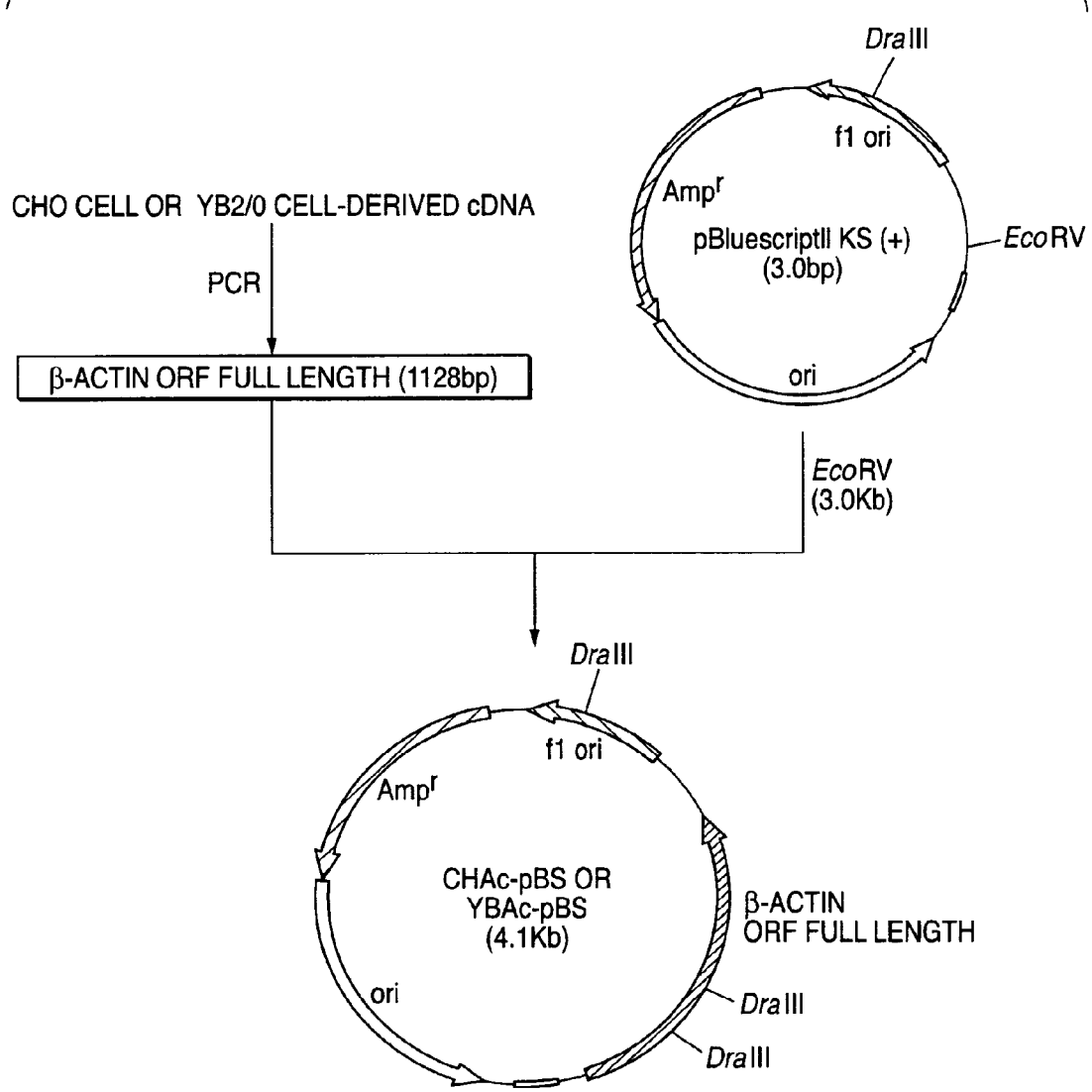
FIG. 13 shows construction of plasmids CHAc-pBS and YBAc-pBS.

Chinese hamster β-actin and rat β-actin were prepared by the following procedure (FIG. 13).

First, a forward primer specific for a common sequence containing translation initiation codon (represented by SEQ ID NO:8) and reverse primers specific for respective sequences containing translation termination codon (represented by SEQ ID NOs:9 and 10) were designed from Chinese hamster β-actin genomic sequence (GenBank, U20114) and rat β-actin genomic sequence [*Nucleic Acids Research*, 11, 1759 (1983).

Next, 25 μl of a reaction solution [1× concentration KOD buffer #1 (manufactured by Toyobo), 0.2 mmol/l dNTPs, 1 mmol/l MgCl$_2$, 0.4 μmol/l of the above gene-specific primers (SEQ ID NOs:8 and 9, or SEQ ID NOs:8 and 10) and 5% DMSO] containing 1 μl of each of the cDNA prepared from CHO cell and cDNA prepared from YB2/0 cell, both obtained in the item 1 of Example 5 on the second day after culturing was prepared, and PCR was carried out by using a DNA polymerase KOD (manufactured by Toyobo). The PCR was carried out by heating at 94° C. for 4 minutes and subsequent 25 cycles of heating at 98° C. for 15 seconds, 65° C. for 2 seconds and 74° C. for 30 seconds as one cycle.

After the PCR, the reaction solution was subjected to 0.8% agarose gel electrophoresis, and a specific amplified fragment of 1128 bp was purified. The DNA fragment was subjected to 5'-terminal phosphorylation using MEGALABEL (manufactured by Takara Shuzo) in accordance with the manufacture's instructions. The DNA fragment was recovered from the reaction solution using an ethanol precipitation method and dissolved in 10 μl of sterile water.

Separately, 3 μg of a plasmid pBluescript II KS(+) (manufactured by Stratagene) was dissolved in 35 μl of NEBuffer 2 (manufactured by New England Biolabs), and 16 units of a restriction enzyme EcoRV (manufactured by Takara Shuzo) were added thereto for digestion reaction at 37° C. for 3 hours. To the reaction solution, 35 μl of 1 mol/l Tris-HCl buffer (pH 8.0) and 3.5 μl of *E. coli* C15-derived alkaline phosphatase (manufactured by Takara Shuzo) were added thereto, followed by reaction at 65° C. for 30 minutes to thereby dephosphorylate the DNA terminus. The reaction solution was extracted with phenol/chloroform, followed by ethanol precipitation, and the recovered DNA fragment was dissolved in 100 μl of sterile water.

Each 4 μl of the amplified fragment prepared from Chinese hamster cDNA and the amplified fragment (1192 bp) prepared from rat cDNA was mixed with 1 μl of the EcoRV-EcoRV fragment (about 3.0 Kb) prepared from plasmid pBluescript II KS(+) and 5 μl of Ligation High (manufactured by Toyobo) for ligation reaction at 16° C. for 30 minutes. Using the reaction solution, *E. coli* XL1-Blue was transformed, and plasmid DNA samples were isolated respectively from the obtained ampicillin-resistant clones in accordance with a known method.

The nucleotide sequence of each cDNA inserted into the plasmid was determined by using DNA Sequencer 377 (manufactured by Parkin Elmer) and BigDye Terminator Cycle Sequencing FS Ready Reaction kit (manufactured by Parkin Elmer) in accordance with the method of the manufacture's instructions. It was confirmed that all of the inserted cDNAs of which sequences were determined by the method encode the ORF full sequences of Chinese hamster β-actin or rat β-actin. Among these, plasmid DNA samples containing absolutely no reading error of bases by the PCR in the sequences were selected. Herein, the plasmids are called CHAc-pBS and YBAc-pBS.

4. Preparation of FUT8 Standard and Internal Control

In order to measure a transcription amount of mRNA derived from FUT8 gene in each cell, CHFT8-pCR2.1 or YBFT8-pCR2.1, as plasmids in which cDNA partial fragments prepared in the item 2 of Example 5 from Chinese hamster FUT8 or rat FUT8 were inserted into pCR2.1, respectively, were digested with a restriction enzyme EcoRI, and the obtained linear DNAs were used as the standards for the preparation of a calibration curve. CHFT8d-pCR2.1 and YBFT8d-pCR2.1, which were obtained from the CHFT8-pCR2.1 and YBFT8-pCR2.1, by deleting 203 bp between ScaI and HindIII, an inner nucleotide sequence of Chinese hamster FUT8 and rat FUT8, respectively, were digested with a restriction enzyme EcoRI, and the obtained linear DNAs were used as the internal standards for FUT8 amount determination. Details thereof are described below.

Chinese hamster FUT8 and rat FUT8 standards were prepared as follows. In 40 μl of NEBuffer 2 (manufactured by New England Biolabs), 2 μg of the plasmid CHFT8-pCR2.1 was dissolved, 24 units of a restriction enzyme EcoRI (manufactured by Takara Shuzo) were added thereto, followed by digestion reaction at 37° C. for 3 hours. Separately, 2 μg of the plasmid YBFT8-pCR2.1 was dissolved in 40 µl of NEBuffer 2 (manufactured by New England Biolabs), and 24 units of a restriction enzyme EcoRI (manufactured by Takara Shuzo) were added thereto, followed by digestion reaction at 37° C. for 3 hours. By subjecting a part of each of the reaction solutions to 0.8% agarose gel electrophoresis, it was confirmed that an EcoRI-EcoRI fragment (about 1 Kb) containing each of cDNA partial fragments of Chinese hamster FUT8 and rat FUT8 was separated from the plasmids CHFT8-pCR2.1 and YBFT8-pCR2.1 bp the above restriction enzyme digestion reactions. Each of the reaction solutions was diluted with 1 µg/ml of baker's yeast t-RNA (manufactured by SIGMA) to give a concentration of 0.02 fg/µl, 0.2 fg/µl, 1 fg/µl, 2 fg/µl, 10 fg/µl, 20 fg/µl and 100 fg/µl and used as the Chinese hamster FUT8 and rat FUT8 standards.

Controls of Chinese hamster FUT8 and rat FUT8 were prepared as follows (FIG. 14). By using a DNA polymerase KOD (manufactured by Toyobo), 25 µl of a reaction solution [1× concentration KOD buffer #1 (manufactured by Toyobo), 0.2 mmol/l dNTPs, 1 mmol/l MgCl$_2$, 0.4 µmol/l gene-specific primers (SEQ ID NOs:11 and 12) and 5% DMSO] containing 5 ng of CHFT8-pCR2.1 or YBFT8-pCR2.1 was prepared, and PCR was carried out. The PCR was carried out by heating at 94° C. for 4 minutes and subsequent 25 cycles of heating at 98° C. for 15 seconds, 65° C. for 2 seconds and 74° C. for 30 seconds as one cycle. After the PCR, the reaction solution was subjected to 0.8% agarose gel electrophoresis, and a specific amplified fragment of about 4.7 Kb was purified. The DNA fragment was subjected to 5'-terminal phosphorylation using MEGALABEL (manufactured by Takara Shuzo) in accordance with the manufacture's instructions, and then the DNA fragment was recovered from the reaction solution by ethanol precipitation and dissolved in 50 µl of sterile water. The above obtained DNA fragment (5 µl, about 4.7 kb) and 5 µl of Ligation High (manufactured by Toyobo) were mixed, followed by self-cyclization reaction at 16° C. for 30 minutes.

Using the reaction solution, *E. coli* DH5α was transformed, and plasmid DNA samples were isolated in accordance with a known method from the obtained ampicillin-resistant clones. The nucleotide sequence of each plasmid DNA was determined by using DNA Sequencer 377 (manufactured by Parkin Elmer) and BigDye Terminator Cycle Sequencing FS Ready Reaction kit (manufactured by Parkin Elmer), and it was confirmed that a 203 bp inner nucleotide sequence between ScaI and HindIII of Chinese hamster FUT8 or rat FUT8 was deleted. The obtained plasmids were named CHFT8d-pCR2.1 or YBFT8d-pCR2.1, respectively.

Next, 2 µg of the plasmid CHFT8d-pCR2.1 was dissolved in 40 µl of NEBuffer 2 (manufactured by New England Biolabs), and 24 units of a restriction enzyme EcoRI (manufactured by Takara Shuzo) were added thereto, followed by digestion reaction at 37° C. for 3 hours. Separately, 2 µg of the plasmid YBFT8d-pCR2.1 was dissolved in 40 µl of NEBuffer 2 (manufactured by New England Biolabs), and 24 units of a restriction enzyme EcoRI (manufactured by Takara Shuzo) were added thereto, followed by digestion reaction at 37° C. for 3 hours. A part of each of the reaction solutions was subjected to 0.8% agarose gel electrophoresis, and it was confirmed that an EcoRI-EcoRI fragment (about 800 bp) containing a fragment from which 203 bp of the inner nucleotide sequences of Chinese hamster FUT8 or rat FUT8 partial fragments was deleted was separated from the plasmids CHFT8d-pCR2.1 or YBFT8d-pCR2.1 bp the above restriction enzyme digestion reactions. Dilutions of 2 fg/µl were prepared from the reaction solutions using 1 µg/ml baker's yeast t-RNA (manufactured by SIGMA) and used as the Chinese hamster FUT8 or rat FUT8 internal controls.

5. Preparation of β-Actin Standard and Internal Control

In order to measure a transcription amount of mRNA derived from β-actin gene in various host cells, CHAc-pBS and YBAc-pBS, as plasmids in which the ORF full length of each cDNA of Chinese hamster β-actin and rat β-actin prepared in the item 3 of Example 5 was inserted into pBluescript II KS(+), respectively, were digested with restriction enzymes HindIII and PstI and restriction enzymes HindIII and KpnI, respectively, and the digested linear DNAs were used as the standards for the preparation of a calibration curve. CHAcd-pBS and YBAcd-pBS which were obtained from the CHAc-pBS and YBAc-pBS by deleting 180 bp between DraIII and DraIII of an inner nucleotide sequence of Chinese hamster β-actin and rat β-actin were digested with restriction enzymes HindIII and PstI and restriction enzymes HindIII and KpnI, respectively, and the digested linear DNAs were used as the internal controls for β-actin amount determination. Details thereof are described below.

Chinese hamster β-actin and rat β-actin standards were prepared as follows. In 40 µl of NEBuffer 2 (manufactured by New England Biolabs), 2 µg of the plasmid CHAc-pBS was dissolved, and 25 units of a restriction enzyme HindIII (manufactured by Takara Shuzo) and 20 units of PstI (manufactured by Takara Shuzo) were added thereto, followed by digestion reaction at 37° C. for 3 hours. Separately, 2 µg of the plasmid YBAc-pBS was dissolved in 40 µl of NEBuffer 2 (manufactured by New England Biolabs), and 25 units of a restriction enzyme HindIII (manufactured by Takara Shuzo) and 24 units of KpnI (manufactured by Takara Shuzo) were added thereto, followed by digestion reaction at 37° C. for 3 hours. A part of each of the reaction solutions was subjected to 0.8% agarose gel electrophoresis, and it was confirmed that a HindIII-PstI fragment and a HindIII-KpnI fragment (about 1.2 Kb) containing the full length ORF of each cDNA of Chinese hamster β-actin and rat β-actin were separated from the plasmids CHAc-pBS and YBAc-pBS by the above restriction enzyme digestion reactions. Each of the reaction solutions was diluted with 1 µg/ml baker's yeast t-RNA (manufactured by SIGMA) to give a concentration 2 pg/µl, 1 pg/µl, 200 fg/µl, 100 fg/µl and 20 fg/µl and used as the Chinese hamster β-actin or rat β-actin standards.

Figure 15:
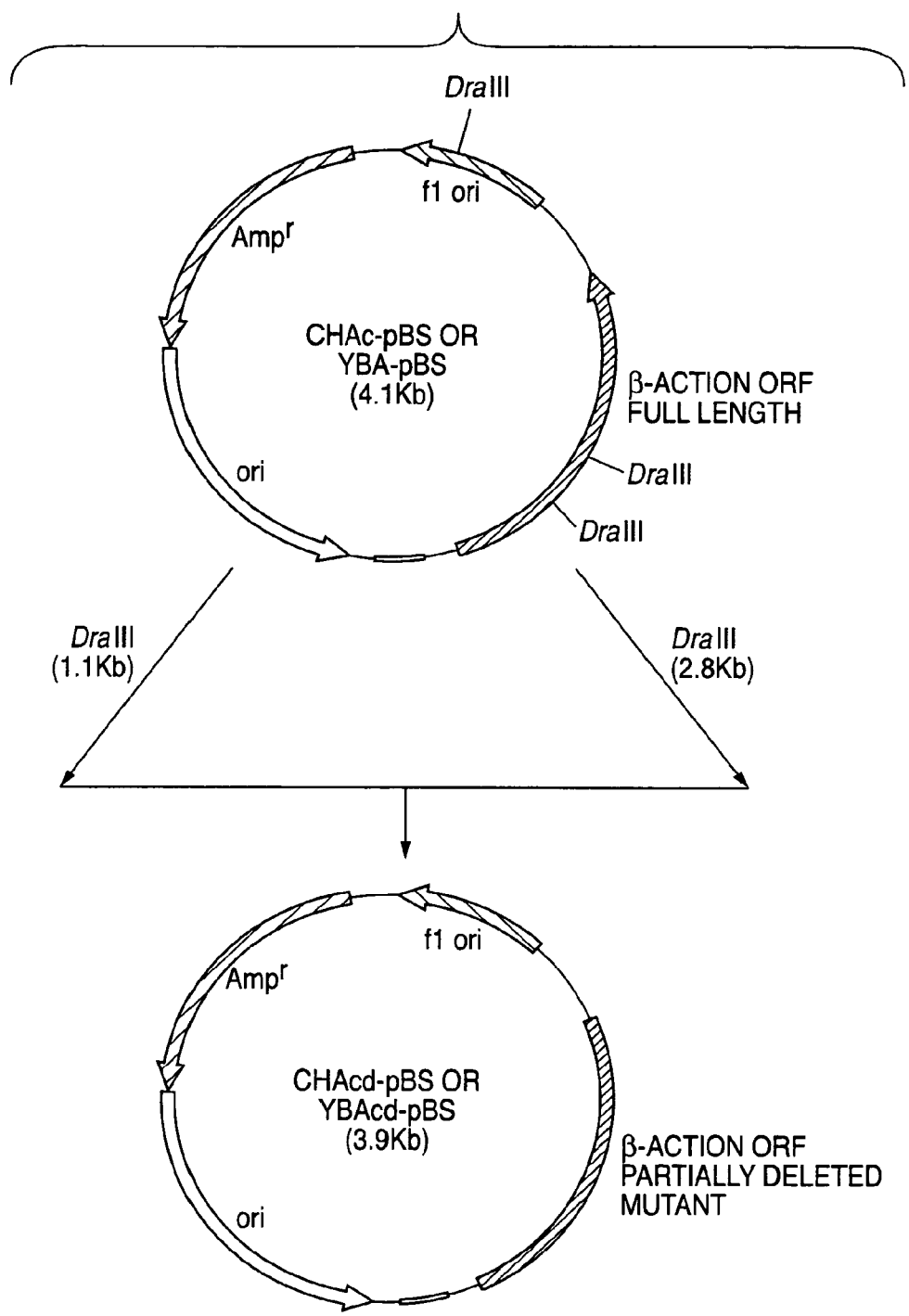
FIG. 15 shows construction of plasmids CHAcd-pBS and YBAcd-pBS.

Chinese hamster β-actin and rat β-actin internal controls were prepared as follows (FIG. 15). In 100 µl of NEBuffer 3 (manufactured by New England Biolabs) containing 100 ng/µl of BSA (manufactured by New England Biolabs), 2 µg of CHAc-pBS was dissolved, and 10 units of a restriction enzyme DraIII (manufactured by New England Biolabs) were added thereto, followed by digestion reaction at 37° C. for 3 hours. DNA fragments were recovered from the reaction solution by ethanol precipitation and the DNA termini were changed to blunt-ends using DNA Blunting Kit (manufactured by Takara Shuzo) in accordance with the manufacture's instructions, and then the reaction solution was divided into two equal parts. First, to one part of the reaction solution, 35 µl of 1 mol/l Tris-HCl buffer (pH 8.0) and 3.5 µl of *E. coli* C15-derived alkaline phosphatase (manufactured by Takara Shuzo) were added thereto, followed by reaction at 65° C. for 30 minutes for dephosphorylating the DNA termini. The DNA fragment was recovered by carrying out dephosphorylation treatment, phenol/chloroform extraction treatment and ethanol precipitation treatment and then dissolved in 10 µl of sterile water. The remaining part of the reaction solution was subjected to 0.8% agarose gel electrophoresis to purify a DNA fragment of about 1.1 Kb containing the ORF partial fragment of Chinese hamster β-actin.

The dephosphorylated DraIII-DraIII fragment (0.5 µl), 4.5 µl of the DraIII-DraIII fragment of about 1.1 Kb and 5 µl of Ligation High (manufactured by Toyobo) were mixed, followed by ligation reaction at 16° C. for 30 minutes. Using the reaction solution, *E. coli* DH5α was transformed, and plasmid DNAs were isolated in accordance with a known method from the obtained ampicillin-resistant colonies. The nucleotide sequence of each plasmid DNA was determined using DNA Sequencer 377 (manufactured by Parkin Elmer) and BigDye Terminator Cycle Sequencing FS Ready Reaction kit (manufactured by Parkin Elmer), and it was confirmed that a Chinese hamster β-actin DraIII-DraIII 180 bp inserted into the plasmid was deleted. The plasmid was named CHAcd-pBS.

Also, a plasmid in which rat β-actin DraIII-DraIII 180 bp was deleted was prepared via same steps of CHAcd-pBS. The plasmid was named YBAcd-pBS.

Next, 2 μg of the plasmid CHAcd-pBS was dissolved in 40 μl of NEBuffer 2 (manufactured by New England Biolabs), and 25 units of a restriction enzyme HindIII (manufactured by Takara Shuzo) and 20 units of PstI (manufactured by Takara Shuzo) were added thereto, followed by digestion reaction at 37° C. for 3 hours. Separately, 2 μg of the plasmid YBAcd-pBS was dissolved in 40 μl of NEBuffer 2 (manufactured by New England Biolabs), and 25 units of a restriction enzyme HindIII (manufactured by Takara Shuzo) and 24 units of KpnI (manufactured by Takara Shuzo) were added thereto, followed by digestion reaction at 37° C. for 3 hours. A part of each of the reaction solutions was subjected to 0.8% agarose gel electrophoresis, and it was confirmed that an HindIII-PstI fragment and HindIII-KpnI fragment (about 1.0 Kb) containing a fragment in which 180 bp of the inner nucleotide sequence of the ORF full length of each cDNA of Chinese hamster β-actin and rat β-actin was deleted were separated from the plasmids CHAcd-pBS and YBAcd-pBS by the restriction enzyme digestion reactions. Dilutions of 200 fg/μl were prepared from the reaction solutions using 1 μg/ml baker's yeast t-RNA (manufactured by SIGMA) and used as the Chinese hamster β-actin and rat β-actin internal controls.

6. Determination of Transcription Amount by Competitive PCR

Competitive PCR was carried out by using the FUT8 internal control DNA prepared in the item 4 of Example 5 and the host cell-derived cDNA obtained in the item 1 of Example 5 as the templates, and the determined value of the FUT8 transcription product in the host clone was calculated from the relative value of the amount of the amplified product derived from each template. On the other hand, since it is considered that the β-actin gene is transcribed constantly in each cell and its transcription amount is approximately the same between cells, transcription amount of the β-actin gene was determined as an indication of the efficiency of synthesis reaction of cDNA derived from each host clone. That is, the PCR was carried out by using the β-actin internal control DNA prepared in the item 5 of Example 5 and the host cell-derived cDNA obtained in the item 1 of Example 5 as the templates, the determined value of the β-actin transcription product in the host clone was calculated from the relative value of the amount of the amplified product derived from each template. Details thereof are described below.

The FUT8 transcription product was determined by the following procedure. First, a set of sequence-specific primers (represented by SEQ ID NOs:13 and 14) common to the inner sequences of the ORF partial sequences of Chinese hamster FUT8 and rat FUT8 obtained in the item 2 of Example 5 were designed.

Next, PCR was carried out by using a DNA polymerase ExTaq (manufactured by Takara Shuzo) in 20 μl in total volume of a reaction solution [1× concentration ExTaq buffer (manufactured by Takara Shuzo), 0.2 mmol/l dNTPs, 0.5 μmol/l of the above gene-specific primers (SEQ ID NOs:13 and 14) and 5% DMSO] containing 5 μl of 50 fold-diluted cDNA solution prepared from each of respective host clone in the item 1 of Example 5 and 5 μl (10 fg) of the plasmid for internal control. The PCR was carried out by heating at 94° C. for 3 minutes and subsequent 32 cycles of heating at 94° C. for 1 minute, 60° C. for 1 minute and 72° C. for 1 minute as one cycle.

Also, PCR was carried out in a series of reaction in which 5 μl (0.1 fg, 1 fg, 5 fg, 10 fg, 50 fg, 100 fg, 500 fg or 1 pg) of the FUT8 standard plasmid obtained in the item 4 of Example 5 was added instead of the each host clone-derived cDNA, and used in the preparation of a calibration curve for the FUT8 transcription amount.

The β-actin transcription product was determined by the following procedure. First, two sets of respective gene-specific primers common to the inner sequences of the ORF full lengths of Chinese hamster β-actin and rat β-actin obtained in the item 3 of Example 5 were designed (the former are represented by SEQ ID NOs:15 and 16, and the latter are represented by SEQ ID NOs:17 and 18).

Next, PCR was carried out by using a DNA polymerase ExTaq (manufactured by Takara Shuzo) in 20 μl in total volume of a reaction solution [1× concentration ExTaq buffer (manufactured by Takara Shuzo), 0.2 mmol/l dNTPs, 0.5 μmol/l of the above gene-specific primers (SEQ ID NOs:15 and 16, or SEQ ID NOs:17 and 18) and 5% DMSO] containing 5 μl of 50 fold-diluted cDNA solution prepared from respective host clone in the item 1 of Example 5 and 5 μl (1 pg) of the plasmid for internal control. The PCR was carried out by heating at 94° C. for 3 minutes and subsequent 17 cycles of heating at 94° C. for 30 seconds, 65° C. for 1 minute and 72° C. for 2 minutes as one cycle.

Also, PCR was carried out in a series of reaction in which 5 μl (10 pg, 5 pg, 1 pg, 500 fg or 100 fg) of the β-actin standard plasmid obtained in the item 5 of Example 5 was added instead of the each host clone-derived cDNA, and used in the preparation of a calibration curve for the β-actin transcription amount.

TABLE 1

| Target gene | Primer set * | Size of PCR amplification product (bp) | |
|---|---|---|---|
| | | Target | Competitor |
| FUT8 | F: 5'-GTCCATGGTGATCCTGCAGTGTGG-3'<br>R: 5'-CACCAATGATATCTCCAGGTTCC-3' | 638 | 431 |
| β-Actin<br>(Chinese hamster) | F: 5'-GATATCGCTGCGCTCGTTGTCGAC-3'<br>R: 5'-CAGGAAGGAAGGCTGGAAAAGAGC-3' | 789 | 609 |
| β-Actin<br>(Rat) | F: 5'-GATATCGCTGCGCTCGTCGTCGAC-3'<br>R: 5'-CAGGAAGGAAGGCTGGAAGAGAGC-3' | 789 | 609 |

* F: forward primer, R: reverse primer

By carrying out PCR using the primer set shown in Table 1, a DNA fragment having a size shown in the target column of Table 1 can be amplified from each gene transcription product and each standard, and a DNA fragment having a size shown in the competitor column of Table 1 can be amplified from each internal control.

After 7 μl of each of the solutions after PCR was subjected to 1.75% agarose gel electrophoresis, the gel was stained by soaking it for 30 minutes in 1× concentration SYBR Green I Nucleic Acid Gel Stain (manufactured by Molecular Probes). The amount of the amplified DNA fragment was measured by calculating luminescence intensity of each amplified DNA using a fluoro-imager (Fluor Imager SI; manufactured by Molecular Dynamics).

The amount of an amplified product formed by PCR using a standard plasmid as the template was measured by the above-mentioned method, and a calibration curve was prepared by plotting the measured values against the amounts of the standard plasmid. Using the calibration curve, the amount of cDNA of a gene of interest in each clone was calculated from the amount of the amplified product when each expression clone-derived total cDNA was used as the template, and the amount was defined as the mRNA transcription amount in each clone.

Figure 16:
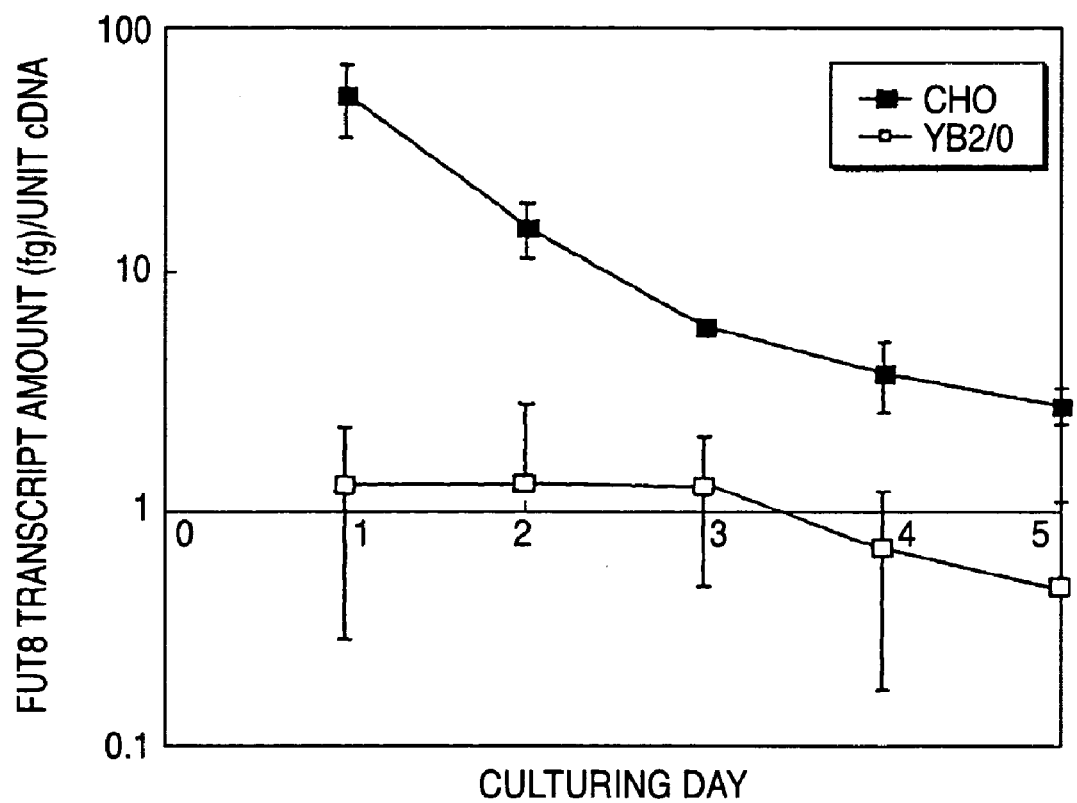
FIG. 16 shows results of determination of an α-1,6-fucosyltransferase (FUT8) transcription product in each host cell line using competitive RT-PCR. Amounts of the FUT8 transcription product in each host cell line when rat FUT8 sequence was used as the standard and internal control are shown. "■" and "□" show results when CHO cell line and YB2/0 cell line, respectively, were used as the host cell.

The amount of the FUT8 transcription product in each host clone when a rat FUT8 sequence was used as the standard and internal control is shown in FIG. 16. Throughout the culturing period, the CHO clone showed a transcription amount 10-fold or higher than that of the YB2/0 clone. The tendency was also found when a Chinese hamster FUT8 sequence was used as the standard and internal control.

Also, the FUT8 transcription amounts are shown in Table 2 as relative values to the amount of the β-actin transcription product. Throughout the culturing period, the FUT8 transcription amount in the YB2/0 clone was around 0.1% of β-actin while it was 0.5% to 2% in the CHO/DG44 clone.

The results shows that the amount of the FUT8 transcription product in YB2/0 clone was significantly smaller than that in the CHO/DG44 clone.

TABLE 2

| Clone | Culture days | | | | |
|---|---|---|---|---|---|
| | 1st | 2nd | 3rd | 4th | 5th |
| CHO | 1.95 | 0.90 | 0.57 | 0.52 | 0.54 |
| YB2/0 | 0.12 | 0.11 | 0.14 | 0.08 | 0.07 |

EXAMPLE 6

Determination of Transcription Product of FUT8 Gene in Anti-GD3 Chimeric Antibody-Producing Clone 1. Preparation of Single-Stranded cDNA Derived from Various Antibody-Producing Clones Single-stranded cDNA was prepared from anti-GD3 chimeric antibody-producing cell clones DCHI01-20 and 61-33 as follows. The clone DCHI01-20 is a transformant clone derived from the CHO/DG44 cell described in item 2(2) of Example 1. Also, the clone 61-33 is a clone obtained by carrying out serum-free adaptation of YB2/0-derived transformant cell clone 7-9-51 (FERM BP-6691, International Patent Organism Depositary, National Institute of Advanced Industrial Science and Technology) and then carrying out single cell isolation by two limiting dilution.

The clone DCHI01-20 were suspended in EXCELL 302 medium (manufactured by JRH BIOSCIENCES) supplemented with 3 mmol/l L-GLN (manufactured by Life Technologies), 0.3% PLURONIC F-68 (manufactured by Life Technologies) and 0.5% fatty acid concentrate (manufactured by Life Technologies), and 15 ml of the suspension was inoculated into T75 flask for suspension cell culture (manufactured by Greiner) at a density of $2\times10^5$ cells/ml. Also, cells of the clone 61-33 were suspended in Hybridoma-SFM medium (manufactured by Life Technologies) supplemented with 0.2% BSA, and 15 ml of the suspension was inoculated into T75 flask for suspension cell culture (manufactured by Greiner) at a density of $2\times10^5$ cells/ml. They were cultured at 37° C. in a 5% $CO_2$ incubator, and 1, 2, 3, 4 and 5 days after culturing, $1\times10^7$ of respective host cells were recovered to extract total RNA using RNAeasy (manufactured by QIAGEN) in accordance with the manufacture's instructions.

The total RNA was dissolved in 45 μl of sterile water, and 1 μl of RQ1 RNase-Free DNase (manufactured by Promega), 5 μl of the attached 10× DNase buffer and 0.5 μl of RNasin Ribonuclease Inhibitor (manufactured by Promega) were added thereto, followed by reaction at 37° C. for 30 minutes to degrade genomic DNA contaminated in the sample. After the reaction, the total RNA was purified again using RNAeasy (manufactured by QIAGEN) and dissolved in 50 μl of sterile water.

In a 20 μl reaction mixture using oligo(dT) as a primer, single-stranded cDNA was synthesized from 3 μg of each of the obtained total RNA samples by reverse transcription reaction using SUPERSCRIPT™ Preamplification System for First Strand cDNA Synthesis (manufactured by Life Technologies) in accordance with the manufacture's instructions. The reaction solution was diluted 50-fold with water and stored at −80° C. until use.

2. Determination of Transcription Amounts of Each Gene by Competitive PCR

The transcription amount of each of the genes of the cDNA derived from the antibody-producing clone obtained in the item 1 of Example 6 was determined by competitive PCR in accordance with the item 6 of Example 5.

The FUT8 gene-derived mRNA transcription amount in each antibody-producing clone was determined by the following procedure.

CHFT8-pCR2.1 and YBFT8-pCR2.1, as plasmids in which cDNA partial fragments prepared in item 2 of Example 5 from Chinese hamster FUT8 and rat FUT8, respectively, were inserted into pCR2.1, were digested with a restriction enzyme EcoRI, and the obtained linear DNAs were used as the standards in the preparation of a calibration curve for determining the FUT8 transcription amount.

CHFT8d-pCR2.1 and YBFT8d-pCR2.1, which were obtained by deleting 203 bp between ScaI and HindIII of an inner nucleotide sequence of Chinese hamster FUT8 and rat FUT8, respectively, in the item 4 of Example 9 were digested with a restriction enzyme EcoRI, and the obtained linear DNAs were used as the internal controls for FUT8 amount determination.

PCR was carried out by using a DNA polymerase ExTaq (manufactured by Takara Shuzo) in 20 μl in total volume of a reaction solution [1× concentration ExTaq buffer (manufactured by Takara Shuzo), 0.2 mmol/l dNTPs, 0.5 μmol/l FUT8 gene-specific primers (SEQ ID NOs:13 and 14) and 5% DMSO] containing 5 μl of 50 fold-diluted cDNA solution derived from each of the antibody-producing clone in the item 1 of Example 6 and 5 μl (10 fg) of the plasmid for internal control. The PCR was carried out by heating at 94° C. for 3 minutes and subsequent 32 cycles of heating at 94° C. for 1 minute, 60° C. for 1 minute and 72° C. for 1 minute as one cycle.

Also, PCR was carried out in a series of reaction in which 5 µl (0.1 fg, 1 fg, 5 fg, 10 fg, 50 fg, 100 fg, 500 fg or 1 pg) of the FUT8 standard plasmid was added instead of the each antibody-producing clone-derived cDNA, and used in the preparation of a calibration curve for the FUT8 transcription amount. In this case, 1 µg/ml of a baker's yeast t-RNA (manufactured by SIGMA) was used for the dilution of the standard plasmid.

On the other hand, since it is considered that the β-actin gene is transcribed constantly in each cell and its transcription amount is approximately the same between cells, the transcription amount of the β-actin gene was determined as an index of the efficiency of synthesis reaction of cDNA in each antibody-producing clone.

CHAc-pBS and YBAc-pBS as plasmids in which the ORF full length of each cDNA of Chinese hamster β-actin and rat β-actin prepared in the item 3 of Example 5 were inserted into pBluescript II KS(+), respectively, were digested with restriction enzymes HindIII and KpnI, and the obtained linear DNAs were used as the standards in the preparation of a calibration curve for determining the β-actin gene transcription amount.

CHAcd-pBS and YBAcd-pBS which were obtained by deleting 180 bp between DraIII and DraIII of an inner nucleotide sequence of Chinese hamster β-actin and rat β-actin, respectively in the item 5 of Example 5, were digested with restriction enzymes HindIII and KpnI, and the obtained linear DNAs were used as the internal controls for β-actin determination.

PCR was carried out by using a DNA polymerase ExTaq (manufactured by Takara Shuzo) in 20 µl in total volume of a reaction solution [1× concentration ExTaq buffer (manufactured by Takara Shuzo), 0.2 mmol/l dNTPs, 0.5 µmol/l β-actin-specific primers (SEQ ID NOs:17 and 18) and 5% DMSO] containing 5 µl of 50 fold-diluted cDNA solution derived from each of the antibody-producing clones and 5 µl (1 pg) of the plasmid for internal control. The PCR was carried out by heating at 94° C. for 3 minutes and subsequent 17 cycles of heating at 94° C. for 30 seconds, 65° C. for 1 minute and 72° C. for 2 minutes as one cycle. Also, PCR was carried out in a series of reaction in which 10 pg, 5 pg, 1 pg, 500 fg or 100 fg of the β-actin standard plasmid was added instead of the each antibody-producing clone-derived cDNA, and used in the preparation of a calibration curve for the β-actin transcription amount. In this case, 1 µg/ml of a baker's yeast t-RNA (manufactured by SIGMA) was used for the dilution of standard plasmid.

By PCR using the primer set described in Table 1, a DNA fragment having a size shown in the target column of Table 1 can be amplified from each gene transcription product and each standard, and a DNA fragment having a size shown in the competitor column of Table 1 can be amplified from each internal control.

After 7 µl of the solutions after PCR was subjected to 1.75% agarose gel electrophoresis, the gel was stained by soaking it for 30 minutes in 1× concentration SYBR Green I Nucleic Acid Gel Stain (manufactured by Molecular Probes). The amount of the amplified DNA fragment was measured by calculating luminescence intensity of each amplified DNA using a fluoro-imager (Fluor Imager SI; manufactured by Molecular Dynamics).

The amount of the amplified product formed by PCR which used a standard plasmid as the template was measured by the above method, and a calibration curve was prepared by plotting the measured values against the amounts of the standard plasmid. Using the calibration curve, the amount of cDNA of a gene of interest in each clone was calculated from the amount of the amplified product when each antibody-producing clone-derived total cDNA was used as the template, and the value was defined as the mRNA transcription amount in each clone.

The FUT8 transcription amounts are shown in Table 3 as relative values to the amount of the β-actin transcription product. Throughout the culturing period, the FUT8 transcription amount in the YB2/0 cell-derived antibody-producing clone 61-33 was 0.3% or less of β-actin while the FUT8 transcription amount in the CHO-derived antibody producing clone DCHI01-20 was 0.7% to 1.5% in the CHO cell-derived antibody-producing cell. The results shows that the amount of the FUT8 transcription product in the YB2/0 cell-derived antibody-producing clone was significantly less than that in the CHO cell-derived antibody-producing clone.

TABLE 3

| Clone | Culture days | | | | |
|---|---|---|---|---|---|
| | 1st | 2nd | 3rd | 4th | 5th |
| DCHI01-20 | 0.75 | 0.73 | 0.99 | 1.31 | 1.36 |
| 61-33 | 0.16 | 0.19 | 0.24 | 0.30 | <0.10 |

EXAMPLE 7

Preparation of Lectin-Resistant CHO/DG44 Cell and Production of Antibody Using the Cell 1. Preparation of Lectin-Resistant CHO/DG44

CHO/DG44 cells were cultured in a 75 cm$^2$ flask for adhesion culture (manufactured by Greiner) in IMDM-FBS(10)-HT(1) medium [IMDM medium comprising 10% of FBS and 1× concentration of HT supplement (manufactured by GIBCO BRL)] to grow until they reached a stage of just before confluent. After washing the cells with 5 ml of PBS (manufactured by Invitrogen), 1.5 ml of 0.05% trypsin (manufactured by Invitrogen) diluted with Dulbecco PBS was added thereto and cultured at 37° C. for 5 minutes to remove the cells from the flask bottom. The removed cells were recovered by a centrifugation operation generally used in cell culture and suspended in IMDM-FBS(10) medium to give a density of 1×10$^5$ cells/ml, and then 0.1 µg/ml of an alkylating agent N-methyl-N'-nitro-N-nitrosoguanidine (hereinafter referred to as "MNNG", manufactured by Sigma) was added or not added thereto. After culturing at 37° C. for 3 days in a CO$_2$ incubator (manufactured by TABAI), the culture supernatant was discarded, and the cells were again washed, removed and recovered by the same operations as described above, suspended in IMDM-FBS(10)-HT(1) medium and then inoculated into an adhesion culture 96 well plate (manufactured by IWAKI Glass) to give a density of 1×10$^3$ cells/well. To each well, as the final concentration in medium, 1 mg/ml Lens culinaris agglutinin (hereinafter referred to as "LCA", manufactured by Vector), 1 mg/ml Aleuria aurantia agglutinin (Aleuria aurantia lectin; hereinafter referred to as "AAL", manufactured by Vector) or 1 mg/ml kidney bean agglutinin (Phaseolus vulgaris leucoagglutinin; hereinafter referred to as "L-PHA", manufactured by Vector) was added. After culturing at 37° C. for 2 weeks in a CO$_2$ incubator, the appeared colonies were obtained as lectin-resistant clone CHO/DG44. Regarding the obtained lectin-resistant clone CHO/DG44, an LCA-resistant clone was named clone CHO-LCA, an AAL-resistant clone was named clone CHO-AAL and an L-PHA-resistant clone was named clone CHO-PHA. When the resistance of these clones to various kinds of lectin was examined, it was found that the clone CHO-LCA was also resistant to AAL and the clone CHO-AAL was also resistant LCA. In addition, the clone CHO-LCA and the clone CHO-AAL also showed a resistance to a lectin which recognizes a sugar chain structure identical to the sugar chain structure recognized by LCA and AAL, namely a lectin which recognizes a sugar chain structure in which 6-position of fucose is bound to 1-position of N-acetylglucosamine residue in the reducing end through α-bond in the N-glycoside-linked sugar chain. Specifically, it was found that the clone CHO-LCA and the clone CHO-AAL can show resistance and survive even in a medium supplemented with 1 mg/ml at a final concentration of a pea agglutinin (*Pisum sativum* agglutinin; hereinafter referred to as "PSA", manufactured by Vector). In addition, even when the alkylating agent MNNG was not added, it was able to obtain lectin-resistant clones by increasing the number of cells to be treated. Hereinafter, these clones were used in analyses.

2. Preparation of Anti-CCR4 Chimeric Antibody-Producing Cell

An anti-CCR4 chimeric antibody expression plasmid pKANTEX2160 was introduced into the three kinds of the lectin-resistant clones obtained in the item 1 of Example 7 by the method described in Example 4, and gene amplification by a drug MTX was carried out to prepare an anti-CCR4 human chimeric antibody-producing clone. By measuring an amount of antibody expression by the ELISA described in the item 2 of Example 4, antibody-expressing transformants were obtained from each of the clone CHO-LCA, the clone CHO-AAL and the clone CHO-PHA. Regarding each of the obtained transformants, a transformant derived from the clone CHO-LCA was named clone CHO/CCR4-LCA, a transformant derived from the clone CHO-AAL was named clone CHO/CCR4-AAL and a transformant derived from the clone CHO-PHA was named clone CHO/CCR4-PHA. Further, the clone CHO/CCR4-LCA, as a name of Nega-13, has been deposited on Sep. 26, 2001, as FERM BP-7756 in International Patent Organism Depositary, National Institute of Advanced Industrial Science and Technology (Tsukuba Central 6, 1, Higashi 1-Chome Tsukuba-shi, Ibaraki-ken, Japan).

3. Production of High ADCC Activity Antibody by Lectin-Resistant CHO Cell

Figure 17:
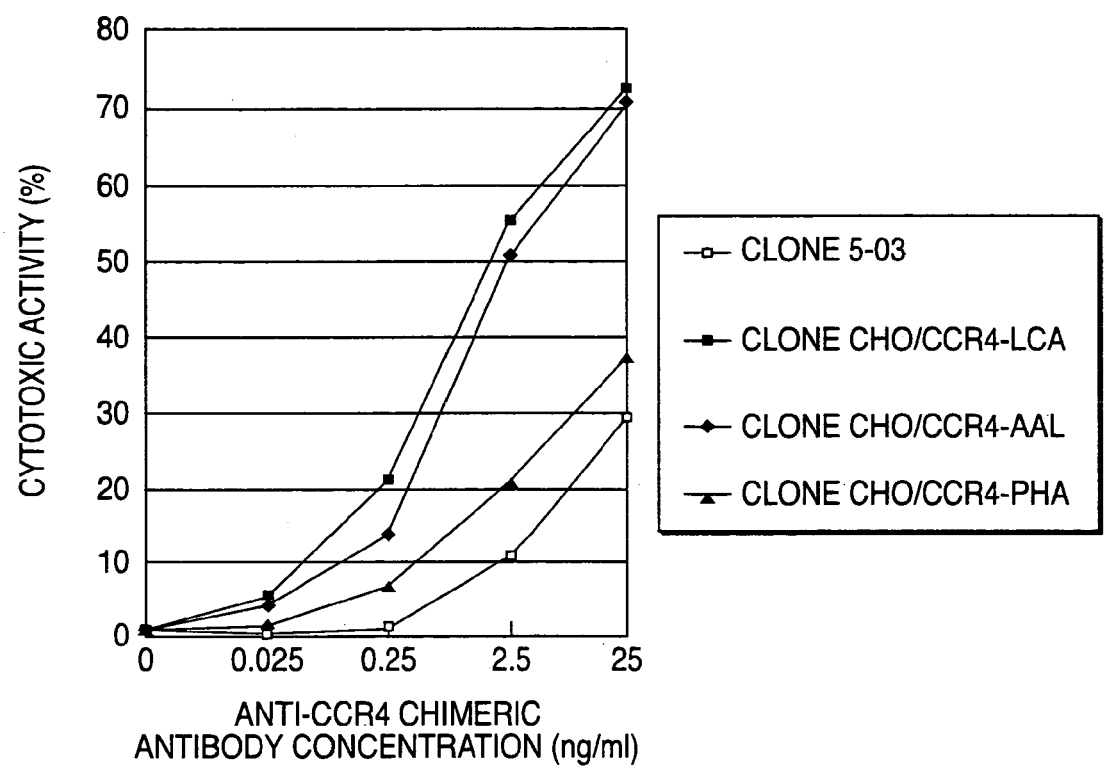
FIG. 17 shows results of evaluation of ADCC activities of anti-CCR4 human chimeric antibodies produced by lectin-resistant cell lines. The ordinate and the abscissa show the cytotoxic activity and the antibody concentration, respectively. "□", "■", "♦" and "▲" show the activities of antibodies produced by the clone 5-03, the clone CHO/CCR4-LCA, the clone CHO/CCR4-AAL and the clone CHO/CCR4-PHA, respectively.
Figure 18:
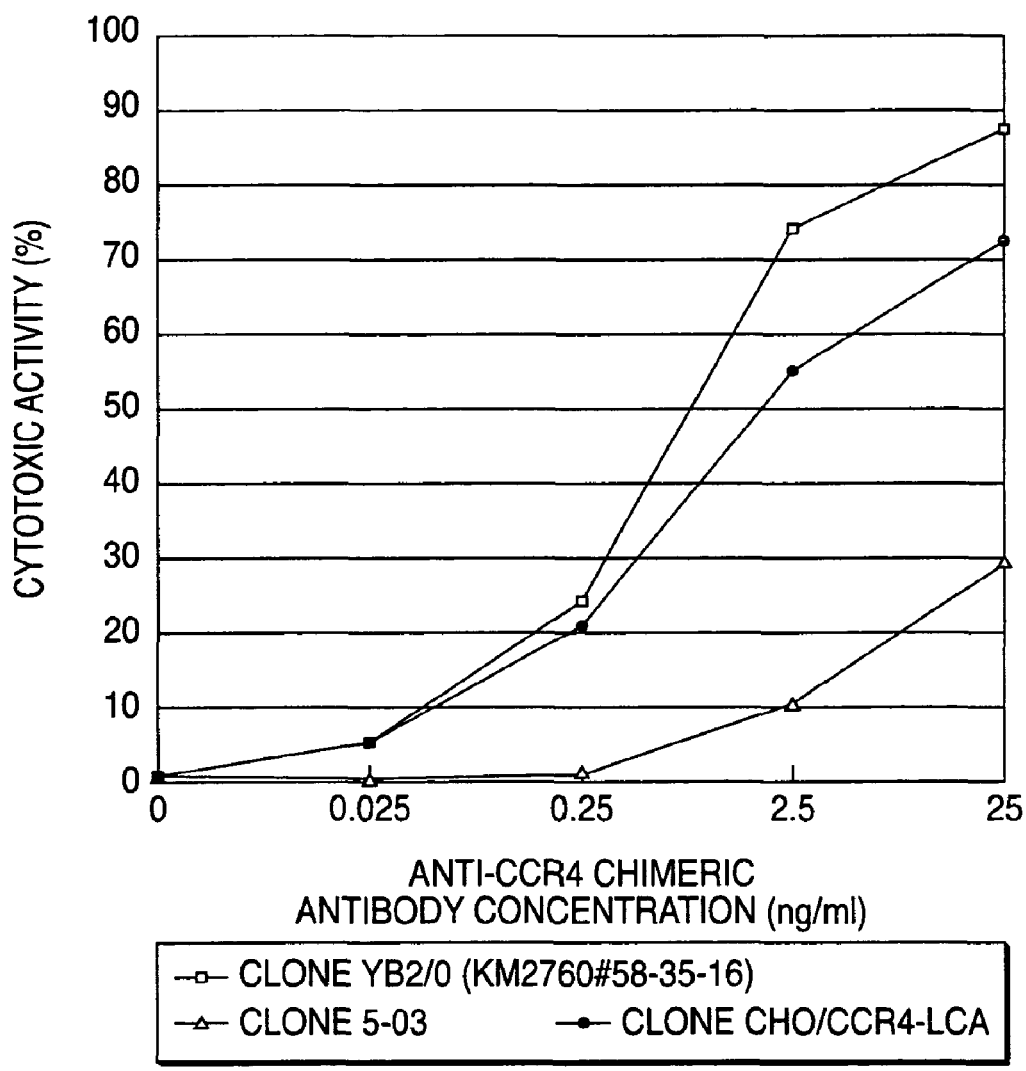
FIG. 18 shows results of evaluation of ADCC activities of anti-CCR4 human chimeric antibodies produced by lectin-resistant clones. The ordinate and the abscissa show the cytotoxic activity and the antibody concentration, respectively. "□", "Δ" and "●" show activities of antibodies produced by the clone YB2/0 (KM2760#58-35-16), the clone 5-03 and the clone CHO/CCR4-LCA, respectively.

Using the three kinds of the transformants obtained in the item 2 of Example 7, purified antibodies were obtained by the method described in the item 3 of Example 4. The antigen binding activity of the purified anti-CCR4 chimeric antibodies was evaluated by the ELISA described in the item 2 of Example 4. The antibodies produced by all transformants showed an antigen binding activity similar to that of the antibody produced by a recombinant clone (clone 5-03) prepared in Example 4 using normal CHO/DG44 cell as the host. Using these purified antibodies, ADCC activity of each of the anti-CCR4 chimeric antibodies was evaluated in accordance with the method described in the item 7 of Example 4. The results are shown in FIG. 17. In comparison with the antibody produced by the clone 5-03, about 100 fold-increased ADCC activity was observed in the antibodies produced by the clone CHO/CCR4-LCA and the clone CHO/CCR4-AAL. On the other hand, no significant increase in the ADCC activity was observed in the antibody produced by the clone CHO/CCR4-PHA. Also, when ADCC activities of the antibodies produced by the clone CHO/CCR4-LCA and the YB2/0 cell-derived clone were compared in accordance with the method described in the item 7 of Example 4, it was found that the antibody produced by the clone CHO/CCR4-LCA shows higher ADCC activity, similar to the case of the antibody KM2760-1 produced by the YB2/0 cell-derived clone prepared in the item 1 of Example 4 (FIG. 18).

4. Sugar Chain Analysis of Antibody Produced by Lectin-Resistant CHO Cell

Figure 19:
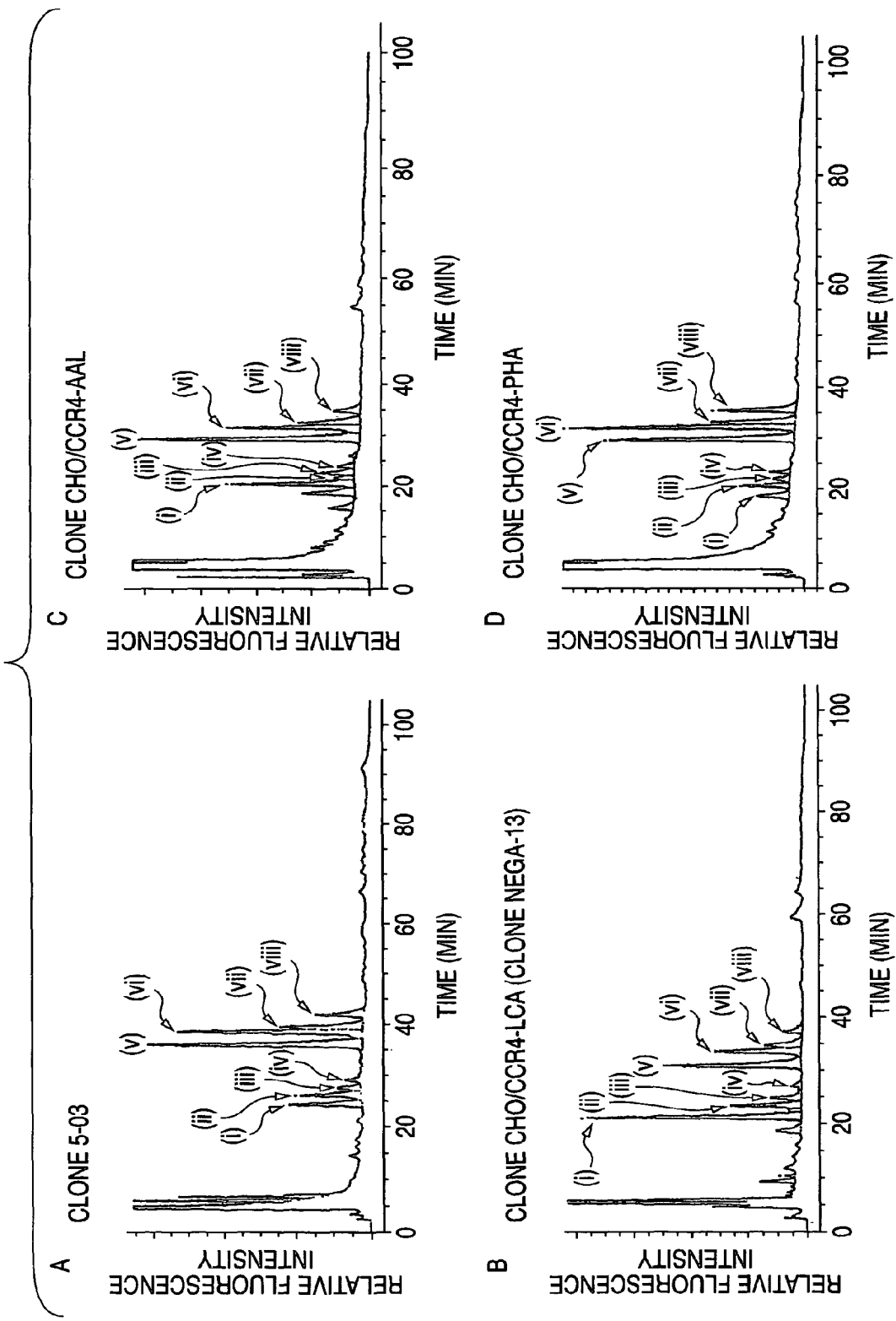
FIG. 19 shows elution patterns of PA-treated sugar chains prepared from purified anti-CCR4 human chimeric antibodies, obtained by analyzing them with reverse phase HPLC. The ordinate and the abscissa show the relative fluorescence intensity and the elution time, respectively.

Sugar chains of the anti-CCR4 chimeric antibodies purified in the item 3 of Example 7 were analyzed according to the method described in the item 1 of Example 3. FIG. 19 shows elution patterns of the purified PA-treated sugar chains of the various anti-CCR4 chimeric antibodies.

Table 4 shows the result of ratios (%) of a sugar chain in which 1-position of fucose was not bound to 6-position of N-acetylglucosamine in the reducing end obtained by the result of the sugar chain analysis of the anti-CCR4 chimeric antibodies produced by various lectin-resistant clones.

TABLE 4

| Antibody producing cell | Ratio of α1,6-Fucose-free sugar chain (%) |
|---|---|
| Clone 5-03 | 9 |
| Clone CHO/CCR4-LCA | 48 |
| Clone CHO/CCR4-AAL | 27 |
| Clone CHO/CCR4-PHA | 8 |

In comparison with the antibody produced by the clone 5-03, the ratio of a sugar chain in which 1-position of fucose was not bound to 6-position of N-acetylglucosamine in the reducing end through α-bond was increased from 9% to 48% in the antibody produced by the clone CHO/CCR4-LCA. The ratio of α1,6-fucose-free sugar chains was increased from 9% to 27% in the antibody produced by the clone CHO/CCR4-AAL. On the other hand, changes in the sugar chain pattern and the ratio of α1,6-fucose-free sugar chains were hardly found in the clone CHO/CCR4-PHA when compared with the clone 5-03.

EXAMPLE 8

Analysis of Lectin-Resistant CHO Clone

1. Analysis of Expression Amount of GMD Enzyme in Anti-CCR4 Chimeric Antibody-Producing Clone CHO/CCR4-LCA The expression amount of each of the genes of GMD, GFPP and FX, known as fucose biosynthesis enzymes and FUT8 as a fucosyltransferase, in the anti-CCR4 human chimeric antibody-producing clone CHO/CCR4-LCA obtained in Example 7, was analyzed using RT-PCR method.

(1) Preparation of RNA from Various Clones

Each of CHO/DG44 cell, the anti-CCR4 human chimeric antibody-producing clone 5-03 obtained in the item 1(2) of Example 4 and the anti-CCR4 chimeric antibody-producing clone CHO/CCR4-LCA obtained in the item 2 of Example 7 was subcultured at 37° C. in a 5% $CO_2$ incubator and then cultured for 4 days. After culturing, RNA was prepared from $1 \times 10^7$ cells of each clone using RNeasy Protect Mini Kit (manufactured by QIAGEN) in accordance with the manufacture's instructions. Subsequently, single-stranded cDNA was synthesized from 5 μg of each RNA in a 20 μl of a reaction solution using SUPER SCRIPT First-Strand Synthesis System for RT-PCR (manufactured by GIBCO BRL) in accordance with the manufacture's instructions.

(2) Analysis of Expression Amount of GMD Gene Using RT-PCR

In order to amplify GMD cDNA by PCR, a 24 mer synthetic DNA primer having the nucleotide sequence shown by SEQ ID NO:32 and a 26 mer synthetic DNA primer having the nucleotide sequence shown by SEQ ID NO:33 were prepared based on the CHO cell-derived GMD cDNA sequence shown in the item 1 of Reference Example 2.

Next, 20 µl of a reaction solution [1× concentration Ex Taq buffer (manufactured by Takara Shuzo), 0.2 mmol/L dNTPs, 0.5 unit of Ex Taq polymerase (manufactured by Takara Shuzo) and 0.5 µL of the synthetic DNA primers of SEQ ID NOs:32 and 33] containing 0.5 µl of the single-stranded cDNA derived from each clone in the item 1(1) of Example 8 as the template was prepared, and PCR was carried out by using DNA Thermal Cycler 480 (manufactured by Perkin Elmer) by heating at 94° C. for 5 minutes and subsequent 30 cycles of heating at 94° C. for 1 minute and 68° C. for 2 minutes as one cycle. After subjecting 10 µl of the PCR reaction solution to agarose electrophoresis, DNA fragments were stained with Cyber Green (manufactured by BMA) and then the amount of the DNA fragment of about 350 bp was measured by using Fluor Imager SI (manufactured by Molecular Dynamics).

(3) Analysis of Expression Amount of GFPP Gene Using RT-PCR

In order to amplify GFPP cDNA by PCR, a 27 mer synthetic DNA primer having the nucleotide sequence shown by SEQ ID NO:34 and a 23 mer synthetic DNA primer having the nucleotide sequence shown by SEQ ID NO:35 were prepared based on the CHO cell-derived GFPP cDNA sequence obtained in the item 2 of Reference Example 1.

Next, 20 µl of a reaction solution [1× Ex Taq buffer (manufactured by Takara Shuzo), 0.2 mmol/L dNTPs, 0.5 unit of Ex Taq polymerase (manufactured by Takara Shuzo) and 0.5 µmol/L of the synthetic DNA primers of SEQ ID NOs:34 and 35] containing 0.5 µl of the single-stranded cDNA prepared from each clone in the item 1(1) of Example 8 as the template was prepared, and PCR was carried out by using DNA Thermal Cycler 480 (manufactured by Perkin Elmer) by heating at 94° C. for 5 minutes and subsequent 24 cycles of heating at 94° C. for 1 minute and 68° C. for 2 minutes as one cycle. After subjecting 10 µl of the PCR reaction solution to agarose electrophoresis, DNA fragments were stained with Cyber Green (manufactured by BMA) and then the amount of the DNA fragment of about 600 bp was measured by using Fluor Imager SI (manufactured by Molecular Dynamics).

(4) Analysis of Expression Amount of FX Gene Using RT-PCR

In order to amplify FX cDNA by PCR, a 28 mer synthetic DNA primer having the nucleotide sequence shown by SEQ ID NO:36 and a 28 mer synthetic DNA primer having the nucleotide sequence shown by SEQ ID NO:37 were prepared based on the CHO cell-derived FX cDNA sequence shown in the item 1 of Reference Example 1.

Next, 20 µl of a reaction solution [1× concentration Ex Taq buffer (manufactured by Takara Shuzo), 0.2 mmol/L dNTPs, 0.5 unit of Ex Taq polymerase (manufactured by Takara Shuzo) and 0.5 µmol/L of the synthetic DNA primers of SEQ ID NO:36 and SEQ ID NO:37] containing 0.5 µl of the single-stranded cDNA derived from each clone in the item 1(1) of Example 8 as the template was prepared, and PCR was carried out by using DNA Thermal Cycler 480 (manufactured by Perkin Elmer) by heating at 94° C. for 5 minutes and subsequent 22 cycles of heating at 94° C. for 1 minute and 68° C. for 2 minutes as one cycle. After subjecting 10 µl of the PCR reaction solution to agarose electrophoresis, DNA fragments were stained with Cyber Green (manufactured by BMA) and then the amount of the DNA fragment of about 300 bp was measured by using Fluor Imager SI (manufactured by Molecular Dynamics).

(5) Analysis of Expression Amount of FUT8 Gene Using RT-PCR

In order to amplify FUT8 cDNA by PCR, 20 µl of a reaction solution [1× Ex Taq buffer (manufactured by Takara Shuzo), 0.2 mmol/L dNTPs, 0.5 unit of Ex Taq polymerase (manufactured by Takara Shuzo) and 0.5 µmol/L of the synthetic DNA primers of SEQ ID NOs:13 and 14] containing 0.5 µl of the single-stranded cDNA derived from each clone in the item 1(1) of Example 8 as the template was prepared, and PCR was carried out by using DNA Thermal Cycler 480 (manufactured by Perkin Elmer) by heating at 94° C. for 5 minutes and subsequent 20 cycles of heating at 94° C. for 1 minute and 68° C. for 2 minutes as one cycle. After subjecting 10 µl of the PCR reaction solution to agarose electrophoresis, DNA fragments were stained with Cyber Green (manufactured by BMA) and then amount of the DNA fragment of about 600 bp was measured using Fluor Imager SI (manufactured by Molecular Dynamics).

(6) Analysis of Expression Amount of β-Actin Gene Using RT-PCR

In order to amplify β-actin cDNA by PCR, 20 µl of a reaction solution [1× Ex Taq buffer (manufactured by Takara Shuzo), 0.2 mmol/L dNTPs, 0.5 unit of Ex Taq polymerase (manufactured by Takara Shuzo) and 0.5 µmol/L of the synthetic DNA primers of SEQ ID NOs:15 and 16] containing 0.5 µl of the single-stranded cDNA derived from each clone in the item 1(1) of Example 8 as the template was prepared, and PCR was carried out by using DNA Thermal Cycler 480 (manufactured by Perkin Elmer) by heating at 94° C. for 5 minutes and subsequent 14 cycles of heating at 94° C. for 1 minute and 68° C. for 2 minutes as one cycle. After subjecting 10 µl of the PCR reaction solution to agarose electrophoresis, DNA fragments were stained with Cyber Green (manufactured by BMA) and then the amount of the DNA fragment of about 800 by was measured using Fluor Imager SI (manufactured by Molecular Dynamics).

(7) Expression Amount of GMD, GFPP, FX and FUT8 Genes in Each Clone

The amount of the PCR-amplified fragment of each gene in the clone 5-03 and the clone CHO/CCR4-LCA was calculated by dividing values of the amounts of PCR-amplified fragments derived from GMD, GFPP, FX and FUT cDNA in each clone measured in the items 1(2) to 1(6) of Example 8 by the value of the amount of PCR-amplified fragment derived from β-actin cDNA in each clone, and defining the amount of the PCR-amplified fragments in CHO/DG44 cell as 1. The results are shown in Table 5.

TABLE 5

|  | GMD | GEPP | FX | FUT8 |
| --- | --- | --- | --- | --- |
| Clone CHO/DG44 | 1 | 1 | 1 | 1 |
| Clone CHO/DG44 Anti-CCR4 antibody-producing cell Clone 5-03 | 1.107 | 0.793 | 1.093 | 0.901 |
| Derived from clone 5-03 LCA-resistant cell CHO/CCR4-LCA | 0.160 | 0.886 | 0.920 | 0.875 |

As shown in Table 5, the expression amount of GMD gene in the clone CHO/CCR4-LCA was decreased to about 1/10 in comparison with other clones. In this case, the test was independently carried out twice, and the average value was used.

2. Analysis Using Anti-CCR4 Chimeric Antibody-Producing Clone CHO/CCR4-LCA in which GMD Gene was Forced to Express (1) Construction of CHO Cell-Derived GMD Gene Expression Vector pAGE249GMD Based on the CHO cell-derived GMD cDNA sequence obtained in the item 1 of Reference Example 2, a 28 mer primer having the nucleotide sequence shown by SEQ ID NO:38 and a 29 mer primer having the nucleotide sequence shown by SEQ ID NO:39 were prepared. Next, 20 µl of a reaction solution [1× concentration Ex Taq buffer (manufactured by Takara Shuzo), 0.2 mmol/L dNTPs, 0.5 unit of Ex Taq polymerase (manufactured by Takara Shuzo) and 0.5 µmol/L of the synthetic DNA primers of SEQ ID NOs:38 and 39] containing 0.5 µl of the CHO cell-derived single-stranded cDNA prepared in the item 1(1) of Example 8 as the template was prepared, and PCR was carried out by using DNA Thermal Cycler 480 (manufactured by Perkin Elmer) by heating at 94° C. for 5 minutes and subsequently 8 cycles of heating at 94° C. for 1 minute, 58° C. for 1 minute and 72° C. for 1 minute as one cycle, and then 22 cycles of heating at 94° C. for 1 minute and 68° C. as one cycle. After completion of the reaction, the PCR reaction solution was fractionated by agarose electrophoresis, and then a DNA fragment of about 600 bp was recovered. The recovered DNA fragment was connected to pT7Blue(R) vector (manufactured by Novagen) by using DNA Ligation Kit (manufactured by Takara Shuzo), and E. coli DH5α (manufactured by Toyobo) was transformed using the obtained recombinant plasmid DNA to obtain a plasmid mt-C (FIG. 20).

Next, based on the CHO cell-derived GMD cDNA sequence obtained in the item 1 of Reference Example 2, a 45 mer primer having the nucleotide sequence shown by SEQ ID NO:40 and a 31 mer primer having the nucleotide sequence shown by SEQ ID NO:41 were prepared. Next, 20 µl of a reaction solution [1× Ex Taq buffer (manufactured by Takara Shuzo), 0.2 mmol/L dNTPs, 0.5 unit of Ex Taq polymerase (manufactured by Takara Shuzo) and 0.5 µmol/L of the synthetic DNA primers of SEQ ID NOs:40 and 41] containing 0.5 µl of the CHO cell-derived single-stranded cDNA prepared in the item 1(1) of Example 8 as the template was prepared, and PCR was carried out by using DNA Thermal Cycler 480 (manufactured by Perkin Elmer) by heating at 94° C. for 5 minutes and subsequently 8 cycles of heating at 94° C. for 1 minute, 57° C. for 1 minute and 72° C. for 1 minute as one cycle, and then 22 cycles of heating at 94° C. for 1 minute and 68° C. for 2 minutes as one cycle. After completion of the reaction, the PCR reaction solution was fractionated by agarose electrophoresis, and then a DNA fragment of about 150 bp was recovered. The recovered DNA fragment was connected to pT7Blue(R) vector (manufactured by Novagen) by using DNA Ligation Kit (manufactured by Takara Shuzo), and E. coli DH5α (manufactured by Toyobo) was transformed using the obtained recombinant plasmid DNA to obtain a plasmid ATG (FIG. 21).

Next, 3 µg of the plasmid CHO-GMD prepared in the item 1 of Reference Example 2 was allowed to react with a restriction enzyme SacI (manufactured by Takara Shuzo) at 37° C. for 16 hours, a DNA was recovered by carrying out phenol/chloroform extraction and ethanol precipitation and allowed to react with a restriction enzyme EcoRI (manufactured by Takara Shuzo) at 37° C. for 16 hours. A digest DNA was fractionated by agarose electrophoresis and then a DNA fragment of about 900 bp was recovered. The plasmid mt-C (1.4 µg) was allowed to react with a restriction enzyme SacI (manufactured by Takara Shuzo) at 37° C. for 16 hours, DNA was recovered by carrying out phenol/chloroform extraction and ethanol precipitation and allowed to react with a restriction enzyme EcoRI (manufactured by Takara Shuzo) at 37° C. for 16 hours. A digested DNA was fractionated by agarose electrophoresis and then a DNA fragment of about 3.1 kbp was recovered. The recovered DNA fragments were ligated by using DNA Ligation Kit (manufactured by Takara Shuzo), and E. coli DH5α was transformed using the obtained recombinant plasmid DNA to obtain a plasmid WT-N(−) (FIG. 22).

Next, 2 µg of the plasmid WT-N(−) was allowed to react with a restriction enzyme BamHI (manufactured by Takara Shuzo) at 37° C. for 16 hours, DNA was recovered by carrying out phenol/chloroform extraction and ethanol precipitation and allowed to react with a restriction enzyme EcoRI (manufactured by Takara Shuzo) at 37° C. for 16 hours. A digested DNA was fractionated by agarose electrophoresis and then a DNA fragment of about 1 kbp was recovered by using Gene Clean II Kit (manufactured by BIO 101) in accordance with the manufacture's instructions. The plasmid pBluescript SK(−) (3 µg; manufactured by Stratagene) was allowed to react with a restriction enzyme BamHI (manufactured by Takara Shuzo) at 37° C. for 16 hours, DNA was recovered by carrying out phenol/chloroform extraction and ethanol precipitation and allowed to react with a restriction enzyme EcoRI (manufactured by Takara Shuzo) at 37° C. for 16 hours. A digested DNA was fractionated by agarose electrophoresis and then a DNA fragment of about 3 kbp was recovered. The respective recovered DNA fragments were ligated by using DNA Ligation Kit (manufactured by Takara Shuzo), and E. coli DH5α was transformed using the obtained recombinant plasmid DNA to obtain a plasmid WT-N(−) in pBS (cf. FIG. 23).

Next, 2 µg of the plasmid WT-N(−) in pBS was allowed to react with a restriction enzyme HindIII (manufactured by Takara Shuzo) at 37° C. for 16 hours, DNA was recovered by carrying out phenol/chloroform extraction and ethanol precipitation and allowed to react with a restriction enzyme EcoRI (manufactured by Takara Shuzo) at 37° C. for 16 hours. A digested DNA was fractionated by agarose electrophoresis and then a DNA fragment of about 4 kbp was recovered. After 2 µg of the plasmid ATG was allowed to react with a restriction enzyme HindIII (manufactured by Takara Shuzo) at 37° C. for 16 hours, DNA was recovered by carrying out phenol/chloroform extraction and ethanol precipitation and allowed to react with a restriction enzyme EcoRI (manufactured by Takara Shuzo) at 37° C. for 16 hours. A digested DNA was fractionated by agarose electrophoresis and then a DNA fragment of about 150 bp was recovered. The respective recovered DNA fragments were ligated by using DNA Ligation Kit (manufactured by Takara Shuzo), and E. coli DH5α was transformed using the obtained recombinant plasmid DNA to obtain a plasmid WT in pBS (FIG. 24).

Next, 2 µg of the plasmid pAGE249 was allowed to react with restriction enzymes HindIII and BamHI (both manufactured by Takara Shuzo) at 37° C. for 16 hours. A digested DNA was fractionated by agarose electrophoresis and then a DNA fragment of about 6.5 kbp was recovered. The plasmid WT (2 µg) in pBS was allowed to react with restriction enzymes HindIII and BamHI (both manufactured by Takara Shuzo) at 37° C. for 16 hours. A digested DNA was fractionated by agarose electrophoresis and then a DNA fragment of about 1.2 kbp was recovered. The respective recovered DNA fragments were ligated by using DNA Ligation Kit (manufactured by Takara Shuzo), and E. coli DH5α was transformed using the obtained recombinant plasmid DNA to obtain a plasmid pAGE249GMD (FIG. 25).

(2) Stable Expression of GMD Gene in Clone CHO/CCR4-LCA

The CHO cell-derived GMD gene expression vector pAGE249GMD (5 µg) which was made into linear form by digesting it with a restriction enzyme FspI (manufactured by NEW ENGLAND BIOLABS), was introduced into $1.6×10^6$ cells of the clone CHO/CCR4-LCA by electroporation [*Cytotechnology*, 3, 133 (1990)]. Then, the cells were suspended in 30 ml of IMDM-dFBS(10) medium [IMDM medium (manufactured by GIBCO BRL) supplemented with 10% of dFBS] comprising 200 nmol/L MTX (manufactured by SIGMA), and cultured in a 182 $cm^2$ flask (manufactured by Greiner) at 37° C. for 24 hours in a 5% $CO_2$ incubator. After culturing, the medium was changed to IMDM-dFBS(10) medium containing 0.5 mg/ml hygromycin and 200 nmol/L MTX (manufactured by SIGMA), followed by culturing for 19 days to obtain colonies of hygromycin-resistant transformants.

In the same manner, the pAGE249 vector was introduced into the clone CHO/CCR4-LCA by the same method as above to obtain colonies of hygromycin-resistant transformants.

(3) Culturing of GMD Gene-Expressed Clone CHO/CCR4-LCA and Purification of Antibody Using IMDM-dFBS(10) medium comprising 200 nmol/L MTX (manufactured by SIGMA) and 0.5 mg/ml hygromycin, the GMD-expressing transformant cells obtained in the item 2(2) of Example 8 were cultured in a 182 $cm^2$ flask (manufactured by Greiner) at 37° C. in a 5% $CO_2$ incubator. Several days thereafter, when the cell density reached confluent, the culture supernatant was discarded and the cells were washed with 25 ml of PBS buffer (manufactured by GIBCO BRL) and mixed with 35 ml of EXCELL301 medium (manufactured by JRH). After culturing at 37° C. in a 5% $CO_2$ incubator for 7 days, the culture supernatant was recovered. An anti-CCR4 chimeric antibody was purified from the culture supernatant by using Prosep-A column (manufactured by Millipore) in accordance with the manufacture's instructions.

In the same manner, the pAGE249 vector-introduced transformant cells were cultured by the same method as above and then anti-CCR4 chimeric antibody was recovered and purified from the culture supernatant.

(4) Measurement of Lectin Resistance in Transformed Cells

The GMD gene-expressing transformant cells obtained in the item 2(2) of Example 8 were suspended in IMDM-dFBS (10) medium comprising 200 nmol/L MTX (manufactured by SIGMA) and 0.5 mg/ml hygromycin to give a density of $6×10^4$ cells/ml, and the suspension was dispensed at 50 µl/well into a 96 well culture plate (manufactured by Iwaki Glass). Next, a medium prepared by suspending LCA (*Lens culinaris* agglutinin manufactured by Vector Laboratories) at concentrations of 0 mg/ml, 0.4 mg/ml, 1.6 mg/ml or 4 mg/ml in IMDM-dFBS(10) medium containing 200 nmol/L MTX (manufactured by SIGMA) and 0.5 mg/ml hygromycin was added to the plate at 50 µl/well, followed by culturing at 37° C. for 96 hours in a 5% $CO_2$ incubator. After culturing, WST-1 (manufactured by Boehringer) was added at 10 µl/well and incubated at 37° C. for 30 minutes in a 5% $CO_2$ incubator for color development, and then the absorbance at 450 nm and 595 nm (hereinafter referred to as "OD450" and "OD595", respectively) was measured by using Microplate Reader (manufactured by BIO-RAD). In the same manner, the pAGE249 vector-introduced transformant cells were measured by the same method as above. The above-mentioned test was carried out twice independently.

FIG. 26 shows the number of survived cells in each well by percentage when a value calculated by subtracting OD595 from OD450 measured in the above is used as the survived number of each cell group and the number of survived cells in each of the LCA-free wells is defined as 100%. As shown in FIG. 26, decrease in the LCA-resistance was observed in the GMD-expressed clone CHO/CCR4-LCA, and the survival ratio was about 40% in the presence of 0.2 mg/ml LCA and the survival ratio was about 20% in the presence of 0.8 mg/ml LCA. On the other hand, in the pAGE249 vector-introduced stain CHO/CCR4-LCA, the survival ratio was 100% in the presence of 0.2 mg/ml LCA and the survival ratio was about 80% even in the presence of 0.8 mg/ml LCA. Based on the above results, it was suggested that expression amount of GMD gene in the clone CHO/CCR4-LCA was decreased and, as a result, the resistance against LCA was obtained.

(5) ADCC Activity of Anti-CCR4 Chimeric Antibody Obtained from GMD-Expressed Clone CHO/CCR4-LCA ADCC activity of the purified anti-CCR4 chimeric antibody obtained in the item 2(3) of Example 8 was measured in accordance with the following method.

i) Preparation of Target Cell Suspension

CCR4/EL4 cell described in WO01/64754 was prepared at $1×10^6$ cells and 3.7 MBq equivalent of a radioactive substance $Na_2{}^{51}CrO_4$ was added to thereto, followed by reaction at 37° C. for 90 minutes to thereby label the cells with a radioisotope. After the reaction, the cells were washed three times by suspension in the RPMI1640-FBS(10) medium and subsequent centrifugation, resuspended in the medium and then incubated at 4° C. for 30 minutes on ice for spontaneous dissociation of the radioactive substance. After centrifugation, the cells were adjusted to $2.0×10^5$ cells/ml by adding 5 ml of the RPMI1640-FBS(10) medium and used as a target cell suspension.

ii) Preparation of Effector Cell Suspension

From a healthy donor, 50 ml of venous blood was collected and gently mixed with 0.5 ml of heparin sodium (manufactured by Takeda Pharmaceutical). Using Lymphoprep (manufactured by Nycomed Pharma AS), the mixture was centrifuged in accordance with the manufacture's instructions to separate a mononuclear cell layer. The cells were washed three times by centrifuging with the RPMI1640-FBS(10) medium and then resuspended in the medium to give a density of $2.5×10^6$ cells/ml and used as a effector cell suspension.

iii) Measurement of ADCC Activity

The target cell suspension prepared in the above i) was dispensed at 50 µl ($1×10^4$ cells/well) into each well of a 96 well U-bottom plate (manufactured by Falcon). Next, 100 µl of the effector cell suspension prepared in the above ii) was added thereto ($2×10^5$ cells/well, ratio of the effector cells to the target cells was 25:1). Each of various anti-CCR4 chimeric antibodies was further added thereto to give a final concentration of 0.0025 to 2.5 µg/ml, followed by reaction at 37° C. for 4 hours. After the reaction, the plate was centrifuged and the amount of $^{51}Cr$ in the supernatant was measured with a γ-counter. The amount of the spontaneously dissociated $^{51}Cr$ was calculated by carrying out the same procedure using the medium alone instead of the effector cell suspension and antibody solution, and measuring the amount of $^{51}Cr$ in the supernatant. The amount of the total dissociated $^{51}Cr$ was calculated by carrying out the same procedure using the medium alone instead of the antibody solution and adding 1 mol/L hydrochloric acid instead of the effector cell suspension and measuring the amount of $^{51}Cr$ in the supernatant. The ADCC activity was calculated based on the above equation (1).

Results of the measurement of ADCC activity are shown in FIG. 27. As shown in FIG. 27, ADCC activity of the purified anti-CCR4 chimeric antibody obtained from the GMD-expressed clone CHO/CCR4-LCA was decreased to a similar degree to that of the KM3060 produced by the normal CHO cell-derived antibody-producing clone obtained in Example 4. On the other hand, ADCC activity of the purified anti-CCR4 chimeric antibody obtained from the pAGE249 vector-introduced clone CHO/CCR4-LCA showed a similar degree of ADCC activity to that of the purified anti-CCR4 chimeric antibody obtained from the clone CHO/CCR4-LCA. Based on the above results, it was suggested that expression amount of GMD gene in the clone CHO/CCR4-LCA is decreased and, as a result, an antibody having high ADCC activity can be produced.

(6) Sugar Chain Analysis of Anti-CCR4 Chimeric Antibody Derived from GMD-Expressed Clone CHO/CCR4-LCA Sugar chains binding to the purified anti-CCR4 chimeric antibody obtained in the item 2(3) of Example 8 were analyzed in accordance with the method shown in the item 1 or Example 3, and the analyzed results are shown in FIG. 28. In comparison with the purified anti-CCR4 chimeric antibody prepared from the clone CHO/CCR4-LCA in Example 7, the ratio of a sugar chain in which 1-position of fucose was not bound to 6-position of N-acetylglucosamine in the reducing end through α-bond in the purified anti-CCR4 chimeric antibody derived from the GMD gene-expressed clone CHO/CCR4-LCA was decreased to 9% when calculated from the peak area. Thus, it was shown that the ratio of a sugar chain in which 1-position of fucose was not bound to 6-position of N-acetylglucosamine in the reducing end through α-bond in the antibody produced by the cell is decreased to similar level of the antibody produced by the clone 5-03.

EXAMPLE 9

Preparation of Anti-Fibroblast Growth Factor-8 Human Chimeric Antibody

1. Preparation of Cells Stably Producing Anti-Fibroblast Growth Factor-8 Human Chimeric Antibody Using a tandem type expression vector pKANTEX134 of an anti-fibroblast growth factor-8 (hereinafter referred to as "FGF-8") human chimeric antibody described in Reference Example 3, cells stably producing the anti-FGF-8 human chimeric antibody (hereinafter referred to as "anti-FGF-8 chimeric antibody") was prepared as follows.

(1) Preparation of Producing Cell Using Rat Myeloma YB2/0 Cell

After introducing 10 μg of the anti-FGF-8 chimeric antibody expression vector pKANTEX1334 into $4 \times 10^6$ cells of rat myeloma YB2/0 cell (ATCC CRL 1662) by electroporation [*Cytotechnology*, 3, 133 (1990)], the cells were suspended in 40 ml of Hybridoma-SFM-FBS(5) [Hybridoma-SFM medium (manufactured by Invitrogen) containing 5% FBS (manufactured by PAA Laboratories)] and dispensed at 200 μl/well into a 96 well culture plate (manufactured by Sumitomo Bakelite). After culturing at 37° C. for 24 hours in a 5% $CO_2$ incubator, G418 was added to give a concentration of 0.5 mg/ml, followed by culturing for 1 to 2 weeks. Culture supernatants were recovered from wells in which colonies of transformants showing G418 resistance were formed and their growth was confirmed, and antigen-binding activity of the anti-FGF-8 chimeric antibody in the supernatants was measured by the ELISA described in the item 2 of Example 9.

Regarding the transformants in wells in which production of the anti-FGF-8 chimeric antibody was found in the culture supernatants, in order to increase the antibody production amount by using a dhfr gene amplification system, each of them was suspended to give a density of 1 to $2 \times 10^5$ cells/ml in the Hybridoma-SFM-FBS(5) medium containing 0.5 mg/ml G418 and 50 nmol/l DHFR inhibitor MTX (manufactured by SIGMA) and dispensed at 1 ml into each well of a 24 well plate (manufactured by Greiner). After culturing at 37° C. for 1 to 2 weeks in a 5% $CO_2$ incubator, transformants showing 50 nmol/l MTX resistance were induced. Antigen-binding activity of the anti-FGF-8 chimeric antibody in culture supernatants in wells where growth of transformants was observed was measured by the ELISA described in the item 2 of Example 9.

Regarding the transformants in wells in which production of the anti-FGF-8 chimeric antibody was found in culture supernatants, the MTX concentration was increased by a method similar to the above to thereby finally obtain a transformant 5-D capable of growing in the Hybridoma-SFM-FBS (5) medium containing 0.5 mg/ml G418 and 200 nmol/l MTX and also highly producing the anti-FGF-8 chimeric antibody. The resulting transformant was subjected to cloning by limiting dilution, and the resulting transformant cell clone was named 5-D-10.

(2) Preparation of Producing Cell Using CHO/DG44 Cell

In accordance with the method described in Example 4, the anti-FGF-8 chimeric antibody expression plasmid pKANTEX1334 was introduced into CHO/DG44 cell and gene amplification was carried out by using the drug MTX to obtain a transformant highly producing the anti-FGF-8 chimeric antibody. The antibody expression amount was measured using the ELISA described in the item 2 of Example 9. The resulting transformant was cloned twice by limiting dilution, and the resulting transformant cell clone was named 7-D-1-5.

2. Binding Activity of Antibody to FGF-8 Partial Peptide (ELISA)

Compound 2 (SEQ ID NO:21) was selected as a human FGF-8 peptide with which the anti-FGF-8 chimeric antibody can react. For the activity measurement by the ELISA, a conjugate with BSA (manufactured by Nacalai Tesque) was prepared by the following method and used as the antigen. That is, 100 ml of a 25 mg/ml SMCC [4-(N-maleimidomethyl)cyclohexane-1-carboxylic acid N-hydroxysuccinimide ester] (manufactured by SIGMA)-DMSO solution was added dropwise to 900 ml of a PBS solution containing 10 mg of BSA under stirring, followed by slowly stirred for 30 minutes. To a gel filtration column such was NAP-10 column or the like which had been equilibrated with 25 ml of PBS, 1 ml of the reaction solution was applied, and the eluate eluted with 1.5 ml of PBS was used as a BSA-SMCC solution (BSA concentration was calculated from $A_{280}$ measurement). Next, 250 ml of PBS was added to 0.5 mg of Compound 2, 250 ml of DMF was added thereto and completely dissolved, and then the above BSA-SMCC solution (1.25 mg as BSA) was added thereto under stirring, followed by slow stirring for 3 hours. The reaction solution was dialyzed against PBS at 4° C. overnight, sodium azide was added thereto to give a final concentration of 0.05% and then filtered through a 0.22 μm filter and used as a BSA-compound 2 solution.

The conjugate prepared in the above was dispensed at 1 μg/ml and 50 μl/well into a 96 well plate for ELISA (manufactured by Greiner) and adhered thereto by allowing it to stand at 4° C. overnight. After washing with PBS, 1% BSA-PBS was added at 100 μl/well and allowed to react at room temperature for 1 hour to block the remaining active groups. After washing each well with Tween-PBS, culture supernatant of a transformant or a purified antibody was added at 50 μl/well and allowed to react at room temperature for 1 hour. After the reaction and subsequent washing of each well with Tween-PBS, a peroxidase-labeled goat anti-human IgG (γ) antibody solution (manufactured by American Qualex) diluted 3,000-fold with 1% BSA-PBS was added as a secondary antibody solution at 50 μl/well and allowed to react at room temperature for 1 hour. After the reaction and subsequent washing with Tween-PBS, the ABTS substrate solution was added at 50 μl/well to develop color, and the reaction was stopped 10 minutes thereafter by adding 5% SDS solution at 50 μl/well. Thereafter, OD415 was measured.

3. Purification of Anti-FGF-8 Chimeric Antibody (1) Culturing of YB2/0 Cell-Derived Producing Cell and Purification of Antibody The anti-FGF-8 chimeric antibody-expressing transformant 5-D obtained in the item 1(1) of Example 9 was cultured in Hybridoma-SFM (manufactured by Invitrogen) medium containing 200 nmol/l of MTX and 5% Daigo's GF21 (manufactured by Wako Pure Chemical Industries) in a 182 cm$^2$ flask (manufactured by Greiner) at 37° C. in a 5% $CO_2$ incubator. After culturing for 8 to 10 days, the anti-FGF-8 chimeric antibody was purified from the culture supernatant recovered by using Prosep-A (manufactured by Millipore) column and in accordance with the attached manufacture's instructions. The purified anti-FGF-8 chimeric antibody was named YB2/0-FGF8 chimeric antibody.

(2) Culturing of CHO-DG44 Cell-Derived Antibody-Producing Cells and Purification of Antibody The anti-FGF-8 chimeric antibody-producing transformant cell clone 7-D-1-5 obtained in the item 1(2) of Example 9 was cultured in the IMDM-dFBS(10) medium in a 182 cm$^2$ flask (manufactured by Greiner) at 37° C. in a 5% $CO_2$ incubator. At the stage where the cell density reached confluent several days thereafter, the culture supernatant was discarded, the cells were washed with 25 ml of PBS buffer and then 35 ml of EXCELL301 medium (manufactured by JRH) was added thereto. After the culturing for 7 days at 37° C. in a 5% $CO_2$ incubator, the culture supernatant was recovered. The anti-FGF-8 chimeric antibody was purified from the culture supernatant by using Prosep-A (manufactured by Millipore) column and in accordance with the manufacture's instructions. The purified anti-FGF-8 chimeric antibody was named CHO-FGF8 chimeric antibody.

When the binding activity of the YB2/0-FGF8 chimeric antibody and CHO-FGF8 chimeric antibody to FGF-8 was measured by the ELISA described in the item 2 of Example 9, they showed similar binding activity.

4. Analysis of Purified Anti-FGF-8 Chimeric Antibody

Each 4 μg of the two anti-FGF-8 chimeric antibodies produced by respective animal cells and purified in the item 3 of Example 9 was subjected to SDS-PAGE according to a known method [*Nature*, 227, 680 (1970)] and the molecular weight and purity were analyzed. In each of the purified anti-FGF-8 chimeric antibodies, a single band of about 150 Kd in molecular weight was found under non-reducing conditions and two bands of about 150 Kd and about 25 Kd were found under reducing conditions. These molecular weights almost coincided with the molecular weights deduced from the cDNA nucleotide sequences of the antibody H chain and L chain (H chain: about 49 Kd, L chain: about 23 Kd, whole molecule: about 144 Kd), and also coincided with the reports showing that the IgG type antibody shows a molecular weight of about 150 Kd under non-reducing conditions and is degraded into H chain having a molecular weight of about 50 Kd and L chain having a molecular weight of about 25 Kd under reducing conditions due to cleavage of the intramolecular S—S bond (*Antibodies*, Chapter 14 (1988); *Monoclonal Antibodies*). Thus it was confirmed that the anti-FGF-8 chimeric antibodies were expressed and purified as antibody molecules having correct structures.

5. Sugar Chain Analysis of Purified Anti-FGF-8 Chimeric Antibodies

Sugar chain analysis of the YB2/0-FGF8 chimeric antibody which is YB2/0 cell-derived anti-FGF-8 chimeric antibody and anti-FGF-8 chimeric antibody CHO-FGF8 chimeric antibody which is CHO/DG44 cell-derived prepared in the item 4 of Example 9 was carried out in accordance with the method described in the item 1 of Example 3. As a result, the ratio of a sugar chain in which 1-position of fucose was not bound to 6-position of N-acetylglucosamine in the reducing end through α-bond were 58% in the YB2/0-FGF8 chimeric antibody and 13% in the CHO-FGF8 chimeric antibody. Hereinafter, these samples are called anti-FGF-8 chimeric antibody (58%) and anti-FGF-8 chimeric antibody (13%).

EXAMPLE 10

Preparation of Soluble Human FcγRIIIa Protein

1. Construction of a Soluble Human FcγRIIIa Protein Expression Vector (1) Preparation of Human Peripheral Blood Monocyte cDNA From a healthy donor, 30 ml of vein blood was collected, gently mixed with 0.5 ml of heparin sodium (manufactured by Shimizu Pharmaceutical) and then mixed with 30 ml of physiological saline (manufactured by Otsuka Pharmaceutical). After the mixing, 10 ml of each mixture was gently overlaid on 4 ml of Lymphoprep (manufactured by NYCOMED PHARMA AS) and centrifuged at 2,000 rpm for 30 minutes at room temperature. The separated monocyte fractions in respective centrifugation tubes were combined and suspended in 30 ml of RPMI1640-FBS(10). After centrifugation at room temperature and at 1,200 rpm for 15 minutes, the supernatant was discarded and the cell were suspended in 20 ml of RPMI1640-FBS(10). This washing operation was repeated twice and then $2 \times 10^6$ cells/ml of peripheral blood monocyte suspension was prepared using RPMI1640-FBS(10).

After 5 ml of the resulting peripheral blood monocyte suspension was centrifuged at room temperature and at 800 rpm for 5 minutes in 5 ml of PBS, the supernatant was discarded and the residue was suspended in 5 mL of PBS. After centrifugation at room temperature and at 800 rpm for 5 minutes, the supernatant was discarded and total RNA was extracted by QIAamp RNA Blood Mini Kit (manufactured by QIAGEN) and in accordance with the manufacture's instructions.

A single-stranded cDNA was synthesized by reverse transcription reaction to 2 μg of the resulting total RNA, in a series of 40 μl containing oligo(dT) as primers using SUPER-SCRITP™ Preamplification System for First Strand cDNA Synthesis (manufactured by Life Technologies) according to the manufacture's instructions.

(2) Preparation Method of cDNA Encoding Human FcγRIIIa Protein

A cDNA encoding a human FcγRIIIa protein (hereinafter referred to as "hFcγRIIIa") was prepared as follows.

First, a specific forward primer containing a translation initiation codon (represented by SEQ ID NO:22) and a specific reverse primer containing a translation termination codon (represented by SEQ ID NO:26) were designed from the nucleotide sequence of hFcγRIIIa cDNA [*J. Exp. Med.*, 170, 481 (1989)].

Next, using a DNA polymerase ExTaq (manufactured by Takara Shuzo), 50 μl of a reaction solution [1× concentration ExTaq buffer (manufactured by Takara Shuzo), 0.2 mmol/l dNTPs, 1 mmol/l of the above gene-specific primers (SEQ ID NOs:22 and 26)] containing 5 μl of 20-fold diluted solution of the human peripheral blood monocyte-derived cDNA solution prepared in the item 1(1) of Example 10 was prepared, and PCR was carried out. The PCR was carried out by 35 cycles of a reaction at 94° C. for 30 seconds, at 56° C. for 30 seconds and at 72° C. for 60 seconds as one cycle.

After the PCR, the reaction solution was purified by using QIAquick PCR Purification Kit (manufactured by QIAGEN) and dissolved in 20 μl of sterile water. The products were digested with restriction enzymes EcoRI (manufactured by Takara Shuzo) and BamHI (manufactured by Takara Shuzo) and subjected to 0.8% agarose gel electrophoresis to recover about 800 bp of a specific amplification fragment.

On the other hand, 2.5 μg of a plasmid pBluescript II SK(–) (manufactured by Stratagene) was digested with restriction enzymes EcoRI (manufactured by Takara Shuzo) and BamHI (manufactured by Takara Shuzo), and digested products were subjected to 0.8% agarose gel electrophoresis to recover a fragment of about 2.9 kbp.

The human peripheral blood monocyte cDNA-derived amplification fragment and plasmid pBluescript II SK(–)-derived fragment obtained in the above were ligated by using DNA Ligation Kit Ver. 2.0 (manufactured by Takara Shuzo). The strain *Escherichia coli* DH5α (manufactured by TOYOBO) was transformed by using the reaction solution, and a plasmid DNA was isolated from each of the resulting ampicillin-resistant colonies according to a known method.

A nucleotide sequence of the cDNA inserted into each plasmid was determined by using DNA Sequencer 377 (manufactured by Parkin Elmer) and BigDye Terminator Cycle Sequencing FS Ready Reaction Kit (manufactured by Parkin Elmer) according to the manufacture's instructions. It was confirmed that all of the inserted cDNAs whose sequences were determined by this method encodes a complete ORF sequence of the cDNA encoding hFcγRIIIa. A plasmid DNA containing absolutely no reading error of bases in the sequence accompanied by PCR was selected from them. Hereinafter, the plasmid is called pBSFcγRIIIa5-3.

The thus determined full length cDNA sequence for hFcγRIIIa is represented by SEQ ID NO:27, and its corresponding amino acid sequence is shown in by SEQ ID NO:28.

(3) Preparation of a cDNA Encoding Soluble hFcγRIIIa

A cDNA encoding soluble hFcγRIIIa (hereinafter referred to as "shFcγRIIIa") having the extracellular region of hFcγRIIIa (positions 1 to 193 in SEQ ID NO:28) and a His-tag sequence at the C-terminal was constructed as follows.

First, a primer FcgR3-1 (represented by SEQ ID NO:29) specific for the extracellular region was designed from the nucleotide sequence of hFcγRIIIa cDNA (represented by SEQ ID NO:27).

Next, using a DNA polymerase ExTaq (manufactured by Takara Shuzo), 50 μl of a reaction solution [1× concentration ExTaq buffer (manufactured by Takara Shuzo), 0.2 mmol/l dNTPs, 1 μmol/l of the primer FcgR3-1, 1 μmol/l of the primer M13M4 (manufactured by Takara Shuzo)] containing 5 ng of the plasmid pBSFcγRIIIa5-3 prepared in the item 1(2) of Example 10 was prepared, and PCR was carried out. The PCR was carried out by 35 cycles of a reaction at 94° C. for 30 seconds, at 56° C. for 30 seconds and at 72° C. for 60 seconds as one cycle.

After the PCR, the reaction solution was purified by using QIAquick PCR Purification Kit (manufactured by QIAGEN) and dissolved in 20 μl of sterile water. The products were digested with restriction enzymes PstI (manufactured by Takara Shuzo) and BamHI (manufactured by Takara Shuzo) and subjected to 0.8% agarose gel electrophoresis to recover about 110 bp of a specific amplification fragment.

On the other hand, 2.5 μg of the plasmid pBSFcγRIIIa5-3 was digested with restriction enzymes PstI (manufactured by Takara Shuzo) and BamHI (manufactured by Takara Shuzo), and the digested products were subjected to 0.8% agarose gel electrophoresis to recover a fragment of about 3.5 kbp.

The hFcγRIIIa cDNA-derived amplification fragment and plasmid pBSFcγRIIIa5-3-derived fragment obtained in the above were ligated by using DNA Ligation Kit Ver. 2.0 (manufactured by Takara Shuzo). The strain *Escherichia coli* DH5α (manufactured by TOYOBO) was transformed by using the reaction solution, and a plasmid DNA was isolated from each of the resulting ampicillin-resistant colonies according to a known method.

A nucleotide sequence of the cDNA inserted into each plasmid was determined by using DNA Sequencer 377 (manufactured by Parkin Elmer) and BigDye Terminator Cycle Sequencing FS Ready Reaction Kit (manufactured by Parkin Elmer) according to the manufacture's instructions. It was confirmed that all of the inserted cDNAs whose sequences were determined by this method encodes a complete ORF sequence of the cDNA encoding shFcγRIIIa of interest. A plasmid DNA containing absolutely no reading error of bases in the sequence accompanied by PCR was selected from them. Hereinafter, this plasmid is named pBSFcγRIIIa+His3.

The thus determined full length cDNA sequence for shFcγRIIIa is represented by SEQ ID NO:30, and its corresponding amino acid sequence is represented by SEQ ID NO:31.

(4) Construction of shFcγRIIIa Expression Vector

The shFcγRIIIa expression vector was constructed as follows.

After 3.0 μg of the plasmid pBSFcγRIIIa+His3 obtained in the item 1(3) of Example 10 was digested with restriction enzymes EcoRI (manufactured by Takara Shuzo) and BamHI (manufactured by Takara Shuzo), the digested products were subjected to 0.8% agarose gel electrophoresis to recover a fragment of about 620 bp.

Separately, 2.0 μg of the plasmid pKANTEX93 described in WO97/10354 was digested with restriction enzymes EcoRI (manufactured by Takara Shuzo) and BamHI (manufactured by Takara Shuzo), and the digested products were subjected to 0.8% agarose gel electrophoresis to recover a fragment of about 10.7 kbp.

The DNA fragment containing shFcγRIIIa cDNA and the plasmid pKANTEX93-derived fragment obtained in the above were ligated by using DNA Ligation Kit Ver. 2.0 (manufactured by Takara Shuzo). The strain *Escherichia coli* DH5α (manufactured by TOYOBO) was transformed by using the reaction solution, and a plasmid DNA was isolated from each of the resulting ampicillin-resistant colonies according to a known method.

A nucleotide sequence of the cDNA inserted into each plasmid was determined by using DNA Sequencer 377 (manufactured by Parkin Elmer) and BigDye Terminator Cycle Sequencing FS Ready Reaction Kit (manufactured by Parkin Elmer) in accordance with the manual attached thereto. It was confirmed that all of the plasmids whose sequences were determined by this method encodes the cDNA of interest encoding shFcγRIIIa. Hereinafter, the obtained expression vector was named pKANTEXFcγRIIIa-His.

2. Preparation of Cell Stably Producing shFcγRIIIa

Cells stably producing shFcγRIIIa were prepared by introducing the shFcγRIIIa expression vector pKANTEXFcγRIIIa-His constructed in the item 1 of Example 10 into rat myeloma YB2/0 cell [ATCC CRL-1662, *J. Cell. Biol.*, 93, 576 (1982)], pKANTEXFcγRIIIa-His was digested with a restriction enzyme AatII to obtain a linear fragment, 10 μg thereof was introduced into 4×10⁶ cells by electroporation [*Cytotechnology*, 3, 133 (1990)], and the resulting cells were suspended in 40 ml of Hybridoma-SFM-FBS(10) [Hybridoma-SFM medium (manufactured by Life Technologies) containing 10% FBS] and dispensed at 200 μl/well into a 96 well culture plate (manufactured by Sumitomo Bakelite). After culturing at 37° C. for 24 hours in a 5% $CO_2$ incubator, G418 was added to give a concentration of 1.0 mg/ml, followed by culturing for 1 to 2 weeks. Culture supernatants were recovered from wells in which colonies of transformants showing G418 resistance were formed and their growth was confirmed, and expression amount of shFcγRIIIa in the supernatants was measured by the ELISA described in the item 3 of Example 10.

Regarding the transformants in wells in which expression of the shFcγRIIIa was confirmed in the culture supernatants, in order to increase the antibody production by using a dhfr gene amplification system, each of them was suspended to give a density of 1 to 2×10⁵ cells/ml in the Hybridoma-SFM-FBS(10) medium containing 1.0 mg/ml G418 and 50 nmol/l DHFR inhibitor MTX (manufactured by SIGMA) and dispensed at 2 ml into each well of a 24 well plate (manufactured by Greiner). After culturing at 37° C. for 1 to 2 weeks in a 5% $CO_2$ incubator, transformants showing 50 nmol/l MTX resistance were induced. Expression level of shFcγRIIIa in culture supernatants in wells where growth of transformants was observed was measured by the ELISA described in The item 3 of Example 10. Regarding the transformants in wells in which expression of the shFcγRIIIa was found in culture supernatants, the MTX concentration was increased to 100 nmol/l and then to 200 nmol/l sequentially by a method similar to the above to thereby finally obtain a transformant capable of growing in the Hybridoma-SFM-FBS(10) medium containing 1.0 mg/ml G418 and 200 nmol/l MTX and also of highly producing shFcγRIIIa. The resulting transformant was cloned twice by limiting dilution. The obtained transformant was named clone KC1107.

3. Detection of shFcγRIIIa (ELISA)

shFcγRIIIa in culture supernatant or purified shFcγRIIIa was detected or determined by the ELISA shown below.

A solution of a mouse antibody against His-tag, Tetra.His Antibody (manufactured by QIAGEN), adjusted to 5 μg/ml with PBS was dispensed at 50 μl/well into each well of a 96 well plate for ELISA (manufactured by Greiner) and allowed to react at 4° C. for 12 hours or more. After the reaction, 1% BSA-PBS was added at 100 μl/well and allowed to react at room temperature for 1 hour to block the remaining active groups. After 1% BSA-PBS was discarded, culture supernatant of the transformant or each of various dilution solutions of purified shFcγRIIIa was added at 50 μl/well and allowed to react at room temperature for 1 hour. After the reaction and subsequent washing of each well with Tween-PBS, a biotin-labeled mouse anti-human CD16 antibody solution (manufactured by PharMingen) diluted 50-fold with 1% BSA-PBS was added at 50 μl/well and allowed to react at room temperature for 1 hour. After the reaction and subsequent washing with Tween-PBS, a peroxidase-labeled Avidin D solution (manufactured by Vector) diluted 4,000-fold with 1% BSA-PBS was added at 50 μl/well and allowed to react at room temperature for 1 hour. After the reaction and subsequent washing with Tween-PBS, the ABTS substrate solution was added at 50 μl/well to develop color, and OD415 was measured.

4. Purification of shFcγRIIIa

The shFcγRIIIa-producing transformant cell clone KC1107 obtained in the item 2 of Example 10 was suspended in Hybridoma-SFM-GF(5) [Hybridoma-SFM medium (manufactured by Life Technologies) containing 5% Daigo's GF21 (manufactured by Wako Pure Chemical Industries)] to give a density of 3×10⁵ cells/ml and dispensed at 50 ml into 182 cm² flasks (manufactured by Greiner). After culturing at 37° C. for 4 days in a 5% $CO_2$ incubator, the culture supernatants were recovered. shFcγRIIIa was purified from the culture supernatants by using Ni-NTA agarose (manufactured by QIAGEN) column according to the manufacture's instructions.

5. Analysis of Purified shFcγRIIIa

A concentration of purified shFcγRIIIa obtained in the item 4 of Example 10 was calculated by amino acid composition analysis as follows. A part of purified shFcγRIIIa was suspended in 6 mol/l hydrochloric acid-1% phenol solution, and hydrolysed in a gas phase at 110° C. for 20 hours. Work Station manufactured by Waters was used for the hydrolysis. Amino acids after the hydrolysis were converted into PTC-amino acid derivatives in accordance with the method of Bidlingmeyer et al. [*J. Chromatogr.*, 336, 93 (1984)] and analyzed by using PicoTag Amino Acid Analyzer (manufactured by Waters).

Next, about 0.5 μg of purified shFcγRIIIa was subjected to SDS-PAGE under reducing conditions according to a known method [*Nature*, 227, 680 (1970)] to analyze its molecular weight and purity. The results are shown in FIG. 6. As shown in FIG. 29, a broad band of 36 to 38 Kd in molecular weight was detected in purified shFcγRIIIa. Since it is known that five sites to which N-glycoside-linked sugar chains can be bound are present in the extracellular region of hFcγRIIIa [*J. Exp. Med.*, 170, 481 (1989)], it was considered that the broad molecular weight distribution of purified shFcγRIIIa is based on the irregularity of sugar chain addition. On the other hand, when the N-terminal amino acid sequence of purified shFcγRIIIa was analyzed by automatic Edman degradation using a protein sequencer PPSQ-10 (manufactured by Shimadzu), a sequence expected from the cDNA of shFcγRIIIa was obtained, so that it was confirmed that shFcγRIIIa of interest was purified.

EXAMPLE 11

Evaluation of Binding Activity of Various Chimeric Antibodies to shFcγRIIIa

1. Evaluation of shFcγRIIIa-Binding Activity of Anti-GD3 Chimeric Antibodies Having a Different Ratio of a Sugar Chain in which 1-Position of Fucose was not Bound to 6-Position of N-acetylglucosamine in the Reducing End Through α-bond The shFcγRIIIa-binding activity of the anti-GD3 chimeric antibody (45%) and anti-GD3 chimeric antibody (7%) described in the item 1 of Example 3 which are two anti-GD3 chimeric antibodies having a different ratio of a sugar chain in which 1-position of fucose was not bound to 6-position of N-acetylglucosamine in the reducing end through α-bond was measured by ELISA as follows.

According to the method described in the item 3 of Example 1, GD3 was immobilized at 100 pmol/well on a 96 well plate for ELISA (manufactured by Greiner). The 1% BSA-PBS was added at 100 μl/well and allowed to react at room temperature for 1 hour to block the remaining active groups. After washing each well with Tween-PBS, a solution of each anti-GD3 chimeric antibody diluted with 1% BSA- PBS was added at 50 µl/well and allowed to react at room temperature for 1 hour. After the reaction and subsequent washing of each well with Tween-PBS, an shFcγRIIIa solution prepared by diluting it to 2.3 µg/ml with 1% BSA-PBS was added at 50 µl/well and allowed to react at room temperature for 1 hour. After the reaction and subsequent washing with Tween-PBS, a solution of a mouse antibody against His-tag, Tetra.His Antibody (manufactured by QIAGEN), adjusted to 1 µg/ml with 1% BSA-PBS was added at 50 µl/well and allowed to react at room temperature for 1 hour. After the reaction and subsequent washing with Tween-PBS, a peroxidase-labeled goat anti-mouse IgG1 antibody solution (manufactured by ZYMED) diluted 200-fold with 1% BSA-PBS was added at 50 µl/well and allowed to react at room temperature for 1 hour. After the reaction and subsequent washing with Tween-PBS, the ABTS substrate solution was added at 50 µl/well to develop color, and OD415 was measured. In addition, it was confirmed that there is no difference in the amount of the anti-GD3 chimeric antibodies bound to the plate by adding each of the anti-GD3 chimeric antibodies to another plate and carrying out the ELISA described in item 3 of Example 1. The results of the measurement of the binding activity of the various anti-GD3 chimeric antibodies for shFcγRIIIa are shown in FIG. 30. As shown in FIG. 30, regarding the binding activity of the anti-GD3 chimeric antibodies to shFcγRIIIa, the anti-GD3 chimeric antibody (45%) having a high ratio of a sugar chain in which 1-position of fucose was not bound to 6-position of N-acetylglucosamine in the reducing end through α-bond had 10 times or more higher activity.

2. Evaluation of shFcγRIIIa-Binding Activity of Anti-FGF-8 Chimeric Antibodies Having a Different Ratio of a Sugar Chain in which 1-Position of Fucose was not Bound to 6-Position of N-acetylglucosamine in the Reducing End Through α-Bond The shFcγRIIIa-binding activity of the anti-FGF-8 chimeric antibody (58%) and anti-FGF-8 chimeric antibody (13%) described in the item 5 of Example 9 which were as two anti-FGF-8 chimeric antibodies having different ratio of a sugar chain in which 1-position of fucose was not bound to 6-position of N-acetylglucosamine in the reducing end through α-bond was measured by ELISA as follows.

The human FGF-8 peptide conjugate prepared in the item 2 of Example 9 at a concentration of 1.0 µg/ml was dispensed at 50 µl/well into a 96-well plate for ELISA (manufactured by Greiner) and adhered thereto by allowing it to stand at 4° C. overnight. After washing with PBS, 1% BSA-PBS was added at 100 µl/well and allowed to react at room temperature for 1 hour to block the remaining active groups. After washing each well with Tween-PBS, a solution of each anti-FGF-8 chimeric antibody diluted with 1% BSA-PBS was added at 50 µl/well and allowed to react at room temperature for 1 hour. After the reaction and subsequent washing of each well with Tween-PBS, an shFcγRIIIa solution prepared by diluting it to 3.0 µg/ml with 1% BSA-PBS was added at 50 µl/well and allowed to react at room temperature for 1 hour. After the reaction and subsequent washing with Tween-PBS, a solution of a mouse antibody against His-tag, Tetra.His Antibody (manufactured by QIAGEN), adjusted to 1 µg/ml with 1% BSA-PBS, was added at 50 µl/well and allowed to react at room temperature for 1 hour. After the reaction and subsequent washing with Tween-PBS, a peroxidase-labeled goat anti-mouse IgG1 antibody solution (manufactured by ZYMED) diluted 200-fold with 1% BSA-PBS was added at 50 µl/well and allowed to react at room temperature for 1 hour. After the reaction and subsequent washing with Tween-PBS, the ABTS substrate solution was added at 50 µl/well to develop color, and OD415 was measured. In addition, by adding each of the anti-FGF-8 chimeric antibodies to another plate and carrying out the ELISA described in the item 2 of Example 9, it was confirmed that there is no difference in the amount of the various anti-FGF-8 chimeric antibodies bound to the plate. The results of the measurement of the binding activity of the various anti-FGF-8 chimeric antibodies for shFcγRIIIa are shown in FIG. 31. As shown in FIG. 31, regarding the binding activity of the anti-FGF8 chimeric antibodies to shFcγRIIIa, the anti-FGF-8 chimeric antibody (58%) having a high ratio of a sugar chain in which 1-position of fucose was not bound to 6-position of N-acetylglucosamine in the reducing end through α-bond had 100 times or more higher activity.

3. Evaluation of shFcγRIIIa-Binding Activity of Anti-CCR4 Chimeric Antibodies Having a Different Ratio of a Sugar Chain in which 1-Position of Fucose is not Bound to 6-Position of N-acetylglucosamine in the Reducing End Through α-Bond The shFcγRIIIa-binding activity of the seven anti-CCR4 chimeric antibodies described in the item 5 of Example 4, having a different ratio of a sugar chain in which 1-position of fucose was not bound to 6-position of N-acetylglucosamine in the reducing end through α-bond, was measured by ELISA as follows.

The human CCR4 extracellular peptide conjugate prepared in the item 2 of Example 4 at a concentration of 1.0 µg/ml was dispensed at 50 µl/well into a 96 well plate for ELISA (manufactured by Greiner) and adhered thereto by allowing it to stand at 4° C. overnight. After washing with PBS, 1% BSA-PBS was added at 100 µl/well and allowed to react at room temperature for 1 hour to block the remaining active groups. After washing each well with Tween-PBS, a solution of each anti-CCR4 chimeric antibody diluted with 1% BSA-PBS was added at 50 µl/well and allowed to react at room temperature for 1 hour. After the reaction and subsequent washing of each well with Tween-PBS, an shFcγRIIIa solution prepared by diluting it to 3.0 µg/ml with 1% BSA-PBS was added at 50 µl/well and allowed to react at room temperature for 1 hour. After the reaction and subsequent washing with Tween-PBS, a solution of a mouse antibody against His-tag, Tetra.His Antibody (manufactured by QIAGEN), adjusted to 1 µg/ml with 1% BSA-PBS, was added at 50 µl/well and allowed to react at room temperature for 1 hour. After the reaction and subsequent washing with Tween-PBS, a peroxidase-labeled goat anti-mouse IgG1 antibody solution (manufactured by ZYMED) diluted 200-fold with 1% BSA-PBS was added at 50 µl/well and allowed to react at room temperature for 1 hour. After the reaction and subsequent washing with Tween-PBS, the ABTS substrate solution was added at 50 µl/well to develop color, and OD415 was measured. In addition, it was confirmed that there is no difference in the amount of the anti-CCR4 chimeric antibodies bound to the plate by adding each of the anti-CCR4 chimeric antibodies to another plate and carrying out the ELISA described in the item 2 of Example 4. The results of the measurement of the binding activity of the various anti-CCR4 chimeric antibodies to shFcγRIIIa are shown in FIG. 32A. As shown in FIG. 32A, the binding activity of the anti-CCR4 chimeric antibodies to shFcγRIIIa increased in proportion to the ratio of a sugar chain in which 1-position of fucose was not bound to 6-position of N-acetylglucosamine in the reducing end through α-bond. FIG. 32B shows a plotted graph on a relationship between the ratio of a sugar chain in which 1-position of fucose was not bound to 6-position of N-acetylglucosamine in the reducing end through α-bond, at antibody concentrations of 4 µg/ml and 40 µg/ml (the abscissa) and the shFcγRIIIa-binding activity (the ordinate). As shown in FIG. 32B, the shFcγRIIIa-binding activity was hardly detected in the anti-CCR4 chimeric antibody (8%), anti-CCR4 chimeric antibody (9%) and anti-CCR4 chimeric antibody (18%), as antibodies having 20% or less of the ratio of a sugar chain in which 1-position of fucose was not bound to 6-position of N-acetylglucosamine in the reducing end through α-bond.

The above results clearly show that antibodies having a sugar chain in which 1-position of fucose is not bound to 6-position of N-acetylglucosamine in the reducing end through α-bond have higher shFcγRIIIa-binding activity than antibodies having a α1,6-fucose sugar chain. In addition, since antibodies having a sugar chain in which 1-position of fucose is not bound to 6-position of N-acetylglucosamine in the reducing end through α-bond has higher ADCC activity than antibodies having a α1,6-fucose sugar chain as shown in Examples 3 and 4, it was strongly suggested that the high ADCC activity of antibodies a sugar chain in which 1-position of fucose is not bound to 6-position of N-acetylglucosamine in the reducing end through α-bond is based on the high shFcγRIIIa-binding activity. As shown in FIG. 32B, the proportion between FcγRIIIa binding activity and the ratio of a sugar chain in which 1-position of fucose is not bound to 6-position of N-acetylglucosamine in the reducing end through α-bond is found. Therefore, FcγRIIIa-binding activity can be measured and the ratio of a sugar chain in which 1-position of fucose is not bound to 6-position of N-acetylglucosamine in the reducing end through α-bond can be determined by constructing such a calibration curve in advance. By using the above method, the cytotoxic activity can be prospected easily without determining the cytotoxic activity of the antibody composition.

EXAMPLE 12

Evaluation of Antibody Produced by Lectin-Resistant CHO/DG44 Cells to shFcγRIIIa Binding activities of the anti-CCR4 chimeric antibody produced by the lectin-resistant clone CHO/CCR4-LCA purified in the item 3 of Example 7 [hereinafter referred to as "anti-CCR4 chimeric antibody (48%)"], the anti-CCR4 chimeric antibody KM2760-1 produced by a YB2/0 cell-derived antibody-producing clone purified in the item 3 of Example 4 [anti-CCR4 chimeric antibody (87%)] and the anti-CCR4 chimeric antibody KM3060 produced by a CHO/DG44 cell-derived antibody-producing clone 5-03 [anti-CCR4 chimeric antibody (8%)] to shFcγRIIIa were measured according to the method described in the item 3 of Example 11. As a result, as shown in FIG. 33, the anti-CCR4 chimeric antibody (48%) produced by the lectin-resistant clone CHO/CCR4-LCA showed 100 times or more higher binding activity to shFcγRIIIa than the anti-CCR4 chimeric antibody (8%) produced by the clone 5-03. Also, this activity was about ⅓ of the anti-CCR4 chimeric antibody (87%) produced by the YB2/0 cell-derived antibody-producing clone.

The above results clearly show that an antibody having 100 times or more higher binding activity to shFcγRIIIa can be prepared by using lectin-resistant CHO/DG44 cell than by using CHO/DG44 cell which is its parent cell.

EXAMPLE 13

Method for Screening Antibody Composition Having High ADCC Activity Based on Binding Activity to shFcγRIIIa An anti-GD3 chimeric antibody expression plasmid pCHi641LHGM4 was introduced into the LCA-resistant clone CHO-LCA obtained in the item 1 of Example 7 according to the method described in the item 2(2) of Example 1, and gene amplification was carried out by using MTX to produce a transformant producing an anti-GD3 chimeric antibody. Cloning was carried out by limiting dilution method using the obtained transformant to obtain several clones. After each clone was cultured, the culture medium was recovered when it became confluent. A concentration of the anti-GD3 chimeric antibody in the culture supernatant way diluted to 1 μg/ml, and the shFcγRIIIa-binding activity was measured using the diluted antibody solution by the ELISA described in the item 1 of Example 11. At the same time, solutions of the anti-GD3 chimeric antibody produced by a YB2/0 cell-derived antibody-producing clone and the anti-GD3 chimeric antibody produced by a CHO/DG44 cell-derived antibody-producing clone, purified in the item 4 of Example 1, were prepared by diluting them to 1 μ/ml, and their shFcγRIIIa-binding activities were also measured.

Based on the measured results, a transformant cell clone capable of producing an antibody showing the activity equal to or higher than the binding activity of the anti-GD3 chimeric antibody produced by the CHO/DG44 cell-derived antibody-producing clone and also equal to or lower than the binding activity of the anti-GD3 chimeric antibody produced by the YB2/0 cell-derived antibody-producing clone was selected.

A purified antibody was obtained from the culture supernatant by culturing the selected transformant cell clone according to the method described in the item 4(2) of Example 1. When monosaccharide composition analysis of the purified antibody was carried out according to the method described in the item 1 of Example 3, the ratio of a sugar chain in which 1-position of fucose was not bound to 6-position of N-acetylglucosamine in the reducing end through α-bond was 42%. Hereinafter, this sample is called anti-GD3 chimeric antibody (42%). When antigen-binding activity of the purified anti-GD3 chimeric antibody (42%) was evaluated by the ELISA described in the item 3 of Example 1, it was equivalent to those of the anti-GD3 chimeric antibody produced by a YB2/0 cell-derived antibody-producing clone and the anti-GD3 chimeric antibody produced by a CHO/DG44 cell-derived antibody-producing clone purified in the item 4 of Example 1. In addition, the ADCC activity of each anti-GD3 chimeric antibody was evaluated according to the method described in the item 2 of Example 2. For comparison, the ADCC activity of a sample of the anti-GD3 chimeric antibody produced by a CHO/DG44 cell-derived antibody-producing clone, wherein the ratio of a sugar chain in which 1-position of fucose was not bound to 6-position of N-acetylglucosamine in the reducing end through α-bond was 12% as a result of its monosaccharide composition analysis [hereinafter named "anti-GD3 chimeric antibody (12%)"] was measured. The results are shown in FIG. 34. In comparison with the anti-GD3 chimeric antibody (12%) produced by a CHO/DG44 cell-derived antibody-producing clone, about 30 times increase in the ADCC activity was observed in the anti-GD3 chimeric antibody (42%) produced by an antibody-producing clone selected based on the high binding activity to shFcγRIIIa.

Based on the above results, it was found that an antibody composition having high ADCC activity can be screened by screening an antibody composition having high binding activity to shFcγRIIIa.

EXAMPLE 14

Preparation of FGF-8b/Fc Fusion Protein

1. Construction of the Expression Vector of FGF-8b/Fc Fusion Protein

A humanized antibody expression vector pKANTEX93 [*Mol. Immunol.*, 37, 1035 (2000)] was digested with restriction enzymes ApaI and BamHI and a fragment containing about 1.0 kbp of human IgG1 subclass CH (hCγ1) was obtained by using QIAquick Gel Extraction Kit (manufactured by QIAGEN). A plasmid pBluescript II SK(−) (manufactured by STRATAGENE) was also digested with similar restriction enzymes to obtain a fragment of about 2.9 kbp. The fragments were ligated using Solution I of TAKARA DNA Ligation Kit Ver. 2 (manufactured by Takara Shuzo) and E. coli DH5α (manufactured by TOYOBO) was transformed to construct a plasmid phCγ1/SK (−).

In order to ligate hCγ 1 with cDNA of FGF8, a synthetic DNA having the nucleotide sequence represented by SEQ ID NO:86 was designed. The synthetic DNA contains plural restriction enzyme recognition sequences at its 5'-terminal for cloning to pBluescript II SK(−), and the synthesis of the DNA was consigned to Proligo. To 50 µl of a solution containing EX Taq Buffer ($Mg^{2+}$ plus) in TaKaRa Ex Taq (manufactured by Takara Shuzo) at 1× concentration, 1 ng of plasmid phCγ 1/SK (−), 0.25 mmol/L dNTPs, 0.5 µmol/l of the synthetic DNA having the nucleotide sequence represented by SEQ ID NO:86, 0.5 µmol/L M13 primer RV and 1.25 unit of TaKaRa Ex Taq were added, and the resulting solution was subjected to 30 cycles of heating at 94° C. for 30 minutes, 56° C. for 30 minutes and 72° C. for 1 minute as one cycle by using DNA thermal cycler GeneAmp PCR System 9700 (manufactured by PERKIN ELMER). A PCR amplified fragment was purified from the total reaction solution by using QIAquick PCR purification Kit (manufactured by QIAGEN). Then, the purified fragment was digested with restriction enzymes KpnI and BamHI to obtain a fragment of about 0.75 kbp. In addition, the pBluescript II SK (−) (manufactured by STRATAGENE) was digested with similar restriction enzymes to obtain a fragment of about 2.9 kbp. These fragments were ligated by using Ligation high (manufactured by TOYOBO) and E. coli DH5α (manufactured by TOYOBO) was transformed to construct a plasmid pΔhCγ1/SK(−).

Using the FGF-8b gene cloned plasmid pSC17 [*Proc. Natl, Acad. Sci.*, 89, 8928 (1992)] as the template, PCR was carried out as follows to obtain a structure gene region fragment of FGF-8b. To 50 µl of a solution containing EX Taq Buffer ($Mg^{2+}$ plus) in TaKaRa Ex Taq (manufactured by Takara Shuzo) at 1× concentration, 1 ng of plasmid pSC17, 0.25 mmol/L dNTPs, 10 µmol/l of synthetic DNAs having the nucleotide sequence represented by SEQ ID NOs:87 and 88 and 2.5 unit of TaKaRa Ex Taq were added, and the resulting solution was subjected to 35 cycles of heating at 94° C. for 1 minute, 55° C. for 1 minute and 72° C. for 2 minutes as one cycle, followed by heating at 72° C. for 10 minutes, by using DNA thermal cycler GeneAmp PCR System 9700 (manufactured by PERKIN ELMER). A PCR amplified fragment was purified from the total reaction solution, and the purified fragment was digested with restriction enzymes EcoRI and BamHI to obtain a fragment of about 0.66 kbp. Also, plasmid pBluescript II SK(−) (manufactured by STRATAGENE) was digested with similar restriction enzymes to obtain a fragment of about 2.9 kbp. Then, the fragments were ligated by using T4 DNA Ligase (manufactured by Takara Shuzo) and E. coli DH5α(manufactured by TOYOBO) was transformed to construct a plasmid pFGF-8b/SK(−).

Next, the plasmid pΔhCγ 1/SK(−) was digested with restriction enzymes ApaI and EcoRI to obtain a fragment of about 3.7 kbp. In addition, the plasmid pFGF-8b/SK(−) was digested with similar restriction enzymes to obtain a fragment of about 0.6 kbp. Then, the fragments were ligated by using Ligation high (manufactured by TOYOBO) and E. coli DH5α (manufactured by TOYOBO) was transformed to construct a plasmid pFGF8b+hIgG/SK(−).

Next, the thus constructed plasmid pFGF8b+hIgG/SK (−) was digested with restriction enzymes EcoRI and BamHI, a fragment of about 1.34 kbp was obtained. Also, pKANTEX93 was digested with similar restriction enzymes to obtain a fragment of about 8.8 kbp. Then, the fragments were ligated by using Ligation high (manufactured by TOYOBO) and E. coli DH5α (manufactured by TOYOBO) was transformed to construct an expression vector pKANTEX/FGF8Fc for animal cell containing cDNA of FGF8b-Fc fusion protein represented by SEQ ID NO:89.

2. Stable Expression Using Animal Cell of FGF-8b/Fc Fusion Protein

A stable expression clone of FGF-8Fc fusion protein was prepared by introducing the FGF-8 fusion protein expression vector pKANTEX/FGF8Fc for animal cell which was constructed in the item 1 of Example 14 into various cells, and selecting a suitable clone.

(1) Preparation of Producing Cell Using Rat Myeloma YB2/0 Cells

After 10 µg of the FGF8b-Fc fusion protein expression vector pKANTEX/FGF8Fc was introduced into $4 \times 10^6$ cells of rat myeloma YB2/0 cell by electroporation, the resulting cells were suspended in 20 to 40 ml of RPMI1640-FBS(10) and the solution was dispensed at 200 µl/well into a 96-well culture plate (manufactured by Sumitomo Bakelite). After culturing at 37° C. for 24 hours in a 5% $CO_2$ incubator, G418 was added thereto to give a concentration of 0.5 ml/ml, followed by culturing for 1 to 2 weeks. The culture supernatant was recovered from wells in which colonies of G418 resistance transformants showing were formed and growth of colonies was observed, and the binding activity of the FGF8-Fc fusion protein in the supernatant to an anti-FGF-8 antibody was measured by the ELISA described in the item 4 of Example 14. As the anti-FGF-8 antibody, KM1334 (U.S. Pat. No. 5,952,472) was used.

Regarding the transformants in wells in which production of the FGF-8/Fc protein was observed in culture supernatants, in order to increase the production amount of the fusion protein by using a dhfr gene amplification system, each of them was suspended in the Hybridoma-SFM-FBS(5) medium comprising 0.5 mg/ml G418 and 50 nmol/L DHFR inhibitor, MTX (manufactured by SIGMA), and dispensed into each well of a 24 well plate for expansion culturing. After culturing at 37° C. for 1 to 2 weeks in a 5% $CO_2$ incubator to induce a transformant showing 50 nmol/l MTX resistance. Binding activity of FGF8b-Fc fusion protein in the supernatant in wells where growth of the transformant was observed, to KM1334 was measured by the ELISA described in the item 4 of Example 14.

Regarding the transformant in wells where production of FGF-8/Fc fusion protein was observed in the culture supernatant, according to the method similar to the above, a transformant KC1178 was obtained, which could grow in Hybridoma-SFM-FBS(5) medium comprising 0.5 mg/ml G418 and 200 nmol/l MTX as final concentrations by increase of the MTX concentration and highly produce FGF8-Fc fusion protein. It was found that KC1178 was a lectin-resistant clone having a relatively low transcript amount obtained by the measuring method of FUT8 gene transcript described in Example 8 of WO00/61739. Also, KC1178 has been deposited on Apr. 1, 2003, as FERM BP-8350 in International Patent Organism Depositary, National Institute of Advanced Industrial Science and Technology (AIST Tsukuba Central 6, 1-1, Higashi 1-Chome Tsukuba-shi, Ibaraki-ken, Japan).

(2) Preparation of Producing Cell Using CHO/DG44 Cells

After 10 µg of the FGF8b-Fc fusion protein expression vector pKANTEX/FGF8Fc was introduced into $1.6 \times 10^6$ cells of CHO/DG44 cell by electroporation, the resulting cells were suspended in 30 ml of IMDM-dFBS(10)-HT(1) and the solution was dispensed at 100 μl/well into a 96-well culture plate (manufactured by Sumitomo Bakelite). After culturing at 37° C. for 24 hours in a 5% $CO_2$ incubator, the medium was changed to IMDM-dFBE(10), followed by culturing for 1 to 2 weeks. The culture supernatant was recovered from wells in which colonies of transformants showing HT-independent growth were formed and growth of colonies was observed, and the binding activity of the FGF8-Fc fusion protein in the supernatant to KM1334 was measured by the ELISA shown in the item 4 of Example 14.

Regarding the transformants in wells in which production of the FGF-8/Fc protein was observed in culture supernatants, in order to increase the production amount of the fusion protein by using a dhfr gene amplification system, each of them was suspended in the IMDM-dFBS(10) medium comprising 50 nmol/L of MTX (manufactured by SIGMA), and dispensed into each well of a 24 well plate for expansion culturing. After culturing at 37° C. for 1 to 2 weeks in a 5% $CO_2$ incubator to induce a transformant showing 50 nmol/l MTX resistance. Binding activity of FGF8b-Fc fusion protein in the supernatant in wells where growth was observed, to KM1334 was measured by the ELISA described in the item 4 of Example 14.

Regarding the transformant in wells where production of FGF-8/Fc fusion protein was observed in the culture supernatant, according to the method similar to the above, a transformant KC1179 was obtained, which could grow in IMDM-dFBS(10) medium comprising 500 nmol/l MTX by increase of the MTX concentration and highly produce FGF8-Fc fusion protein. Also, KC1179 has been deposited on Apr. 1, 2003, as FERM BP-8351 in International Patent Organism Depositary, National Institute of Advanced Industrial Science and Technology (Tsukuba Central 6, 1, Higashi 1-Chome Tsukuba-shi, Ibaraki-ken, Japan).

3. Purification of FGFR8-Fc Fusion Protein

The producing cell of FGF8-Fc fusion protein prepared in the item 2 of Example 14 was cultured in an appropriate culture medium (e.g., H-SFM comprising 5% GF21 (manufactured by Wako Pure Chemical Industries), 0.5 mg/ml of G418 and 200 nmol/l of MTX for YB2/0 cell-derived cells; EXCELL301 (manufactured by JRH) comprising 500 nmol/l MTX for CHO/DG44 cell-derived cells) at a scale of 100 to 200 ml. FGF8-Fc fusion protein was purified from the culture supernatant by using Prosep G (manufactured by Millipore) column according to the manufacture's instruction. The deduced amino acid sequence of the purified protein is shown by SEQ ID NO:90.

4. Binding Activity to Anti-FGF-8 Antibody

Binding activities of the FGF-8/Fc fusion protein produced by YB2/0 and the FGF-8/Fc fusion protein produced by CHO described in the item 2 of Example 14, to KM1334 were measured by the ELISA as follows. KM1334 of 1 μg/ml was dispensed at 50 μl/well into a 96-well plate for ELISA (manufactured by Greiner) and allowed to stand at 4° C. overnight for adsorption. After washing with PBS, 1% BSA-PBS was added at 100 μl/well and allowed to react at room temperature for 1 hour to block the remaining active group. After washing each well with Tween-PBS, the culture supernatant of the transformant or a purified protein was added at 50 μl/well, followed reaction at room temperature. After the reaction, each well was washed with Tween-PBS, and peroxidase labeled goat-anti-human IgG(γ) antibody solution (manufactured by American Qualex), which was diluted 3000-fold with 1% BSA-PBS, was added at 50 μl/well as the secondary antibody solution, followed by reaction at room temperature for 1 hour. After the reaction, each well was washed with Tween-PBS, and ABTS substrate solution was added at 50 μl/well, followed by reaction. After the color developed sufficiently, 5% SDS solution was added at 50 μl/well to stop the reaction. Then, the absorbance was measured at a wavelength of 415 nm and a reference wavelength of 490. As shown in FIG. 35, the FGF-8/Fc fusion protein obtained in the item 2 of Example 14 showed binding activity to KM1334.

5. Binding Activity to FcγRIIIa

Binding activities of FGF-8/Fc fusion protein produced by YB2/0 and FGF-8/Fc fusion protein derived from CHO described in the item 2 of Example 14, to FcγRIIIa was measured by ELISA as follows. Tetra.His Antibody, mouse antibody against His-tag (manufactured by QIAGEN), of 5 μg/ml was dispensed at 50 μl/well into a 96-well plate for ELISA (manufactured by GREINER) and allowed to stand at 4° C. overnight for adsorption. After washing with PBS, 1% BSA-PBS was added at 100 μl/well, followed by reaction at room temperature for 1 hour to block the remaining active group. After washing each well with Tween-PBS, shFcγRIIIa (V) solution diluted to 5 μg/ml with 1% BSA-PBS was added at 50 μl/well, followed by reaction at room temperature for 2 hours. After the reaction, each well was washed with Tween-PBS, and a solution prepared by diluting purified FGF-8/Fc fusion protein to different concentrations with 1% BSA-PBS was added at 50 μl/well, followed by reaction at room temperature for 2 hours. After the reaction, each well was washed with Tween-PBS, and biotinized KM1334 diluted to 1 μg/ml with 1% BSA-PBS was added at 50 μl/well, followed by reaction at room temperature for 1 hour. After the reaction, each well was washed with Tween-PBS, and a solution of peroxidase labeled Avidin-D (manufactured by VECTOR) diluted 4000-fold with 1% BSA-PBS was added at 50 μl/well, followed by reaction at room temperature for 1 hour. After the reaction, each well was washed with Tween-PBS, and ABTS substrate solution was added at 50 μl/well for color development, and after 15 minutes, 5% SDS solution was added at 50 μl/well to stop the reaction. The absorbance of the resulting solution was measured at a wavelength of 415 nm and a reference wavelength of 490 nm.

FIG. 36 shows the measurement results of the binding activity of various FGF-8/Fc fusion proteins to shFcγRIIIa (V). As apparent in FIG. 36, the FGF-8/Fc fusion protein produced by YB2/0 showed higher binding activity to shFcγRIIIa (V) than the FGF-8/Fc fusion protein produced by CHO/DG44 cell.

REFERENCE EXAMPLE 1

Preparation of Genes Encoding Various Enzymes Relating to Sugar Chain Synthesis Derived from CHO Cell 1. Determination of FX cDNA Sequence in CHO Cell
(1) Extraction of Total RNA Derived from CHO/DG44 Cell CHO/DG44 cells were suspended in IMDM medium containing 10% fetal bovine serum (manufactured by Life Technologies) and 1× concentration HT supplement (manufactured by Life Technologies), and 15 ml of the suspension was inoculated into a T75 flask for adhesion cell culture use (manufactured by Greiner) to give a density of $2 \times 10^5$ cells/ml. On the second day after culturing at 37° C. in a 5% $CO_2$ incubator, $1 \times 10^7$ of the cells were recovered and a total RNA was extracted therefrom by using RNAeasy (manufactured by QIAGEN) in accordance with the manufacture's instructions.

(2) Preparation of Total Single-Stranded cDNA from CHO/DG44 Cell

The total RNA prepared in the item 1(1) of Reference Example 1 was dissolved in 45 µl of sterile water, and 1 µl of RQ1 RNase-Free DNase (manufactured by Promega), 5 µl of the attached 10× DNase buffer and 0.5 µl of RNasin Ribonuclease Inhibitor (manufactured by Promega) were added thereto, followed by reaction at 37° C. for 30 minutes to degrade genomic DNA contaminated in the sample. After the reaction, the total RNA was purified again using RNAeasy (manufactured by QIAGEN) and dissolved in 50 µl of sterile water.

In a 20 µl of reaction mixture using oligo(dT) as a primer, single-stranded cDNA was synthesized from 3 µg of the obtained total RNA samples by carrying out reverse transcription reaction using SUPERSCRIPT™ Preamplification System for First Strand cDNA Synthesis (manufactured by Life Technologies) in accordance with the manufacture's instructions. A 50 fold-diluted aqueous solution of the reaction solution was used in the cloning of GFPP and FX. This was stored at −80° C. until use.

(3) Preparation Method of cDNA Partial Fragment of Chinese Hamster-Derived FX

An FX cDNA partial fragment derived from Chinese hamster was prepared by the following procedure.

First, primers (represented by SEQ ID NOs:42 and 43) specific for common nucleotide sequences registered at a public data base, namely a human FX cDNA (Genebank Accession No. U58766) and a mouse cDNA (Genebank Accession No. M30127), were designed.

Next, 25 µl of a reaction solution [1× concentration ExTaq buffer (manufactured by Takara Shuzo), 0.2 mmol/l dNTPs and 0.5 µmol/l of the above gene-specific primers (SEQ ID NOs:42 and 43)] containing 1 µl of the CHO/DG44-derived single-stranded cDNA prepared in the item 1(2) of Reference Example 1 was prepared by using a DNA polymerase ExTaq (manufactured by Takara Shuzo), and PCR was carried out. The PCR was carried out by heating at 94° C. for 5 minutes, subsequent 30 cycles of heating at 94° C. for 1 minute, 58° C. for 2 minutes and 72° C. for 3 minutes as one cycle, and further heating at 72° C. for 10 minutes.

After the PCR, the reaction solution was subjected to 2% agarose gel electrophoresis, and a specific amplified fragment of 301 bp was purified using QuiaexII Gel Extraction Kit (manufactured by QIAGEN) and eluted with 20 µl of sterile water (hereinafter, the method was used for the purification of DNA fragments from agarose gel). Into a plasmid pCR2.1, 4 µl of the above amplified fragment was employed to insert in accordance with the instructions attached to TOPO TA Cloning Kit (manufactured by Invitrogen), and *E. coli* DH5α was transformed with the reaction solution. Each plasmid DNA was isolated in accordance with a known method from the obtained several kanamycin-resistant colonies to obtain 2 clones into which FX cDNA partial fragments were respectively inserted. They were named pCRFX clone 8 and pCRFX clone 12.

The nucleotide sequence of the cDNA inserted into each of the FX clone 8 and FX clone 12 was determined using DNA Sequencer 377 (manufactured by Parkin Elmer) and BigDye Terminator Cycle Sequencing FS Ready Reaction kit (manufactured by Parkin Elmer) in accordance with the method of the manufacture's instructions. It was confirmed that each of the inserted cDNA whose sequence was determined encodes an ORF partial sequence of the Chinese hamster FX.

(4) Synthesis of Single-Stranded cDNA for Race

Single-stranded cDNA samples for 5' and 3' RACE were prepared from the CHO/DG44 total RNA extracted in the item 1(1) of Reference Example 1 using SMART™ RACE cDNA Amplification Kit (manufactured by CLONTECH) in accordance with the manufacture's instructions. In the case, PowerScript™ Reverse Transcriptase (manufactured by CLONTECH) was used as the reverse transcriptase. Each single-stranded cDNA after the preparation was diluted 10-fold with the Tricin-EDTA buffer attached to the kit and used as the template of PCR.

(5) Determination of Chinese Hamster-Derived FX Full Length cDNA by Race Method

Based on the FX partial sequence derived from Chinese hamster determined in the item 1(3) of Reference Example 1, primers FXGSP1-1 (SEQ ID NO:44) and FXGSP1-2 (SEQ ID NO:45) for the Chinese hamster FX-specific 5' RACE and primers FXGSP2-1 (SEQ ID NO:46) and FXGSP2-2 (SEQ ID NO:47) for the Chinese hamster FX-specific 3' RACE were designed.

Next, 50 µl of a reaction solution [1× concentration Advantage2 PCR buffer (manufactured by CLONTECH), 0.2 mmol/L dNTPs, 0.2 µmol/l Chinese hamster FX-specific primers for RACE and 1× concentration of common primers (manufactured by CLONTECH)] containing 1 µl of the CHO/DG44-derived single-stranded cDNA for RACE prepared in the item 1(4) of Reference Example 1 was prepared by using Advantage2 PCR Kit (manufactured by CLONTECH) and PCR was carried out. The PCR was carried out by 20 cycles of heating at 94° C. for 5 seconds, 68° C. for 10 seconds and 72° C. for 2 minutes as one cycle.

After completion of the reaction, 1 µl of the reaction solution was diluted 50-fold with the Tricin-EDTA buffer, and 1 µl of the diluted solution was used as a template. The reaction solution was again prepared and the PCR was carried out under the same conditions. The templates, the combination of primers used in the first and second PCRs and the length of amplified DNA fragments by the PCRs are shown in Table 6.

TABLE 6

Combination of primers used in Chinese hamster FX cDNA RACE PCR and the size of PCR products

| | FX-specific primers | Common primers | PCR-amplified product size |
|---|---|---|---|
| 5' RACE | | | |
| First | FXGSP1-1 | UPM (Universal primer mix) | 300 bp |
| Second | FXGSP1-2 | NUP (Nested Universal primer) | |
| 3' RACE | | | |
| First | FXGSP2-1 | UPM (Universal primer mix) | 1,100 bp |
| Second | FXGSP2-2 | NUP (Nested Universal primer) | |

After the PCR, the reaction solution was subjected to 1% agarose gel electrophoresis, and the specific amplified fragment of interest was recovered and eluted with 20 µl of sterile water. Into a plasmid pCR2.1, 4 µl of the amplified fragment was inserted, and *E. coli* DH5α was transformed by using the reaction solution in accordance with the instructions attached to TOPO TA Cloning Kit (manufactured by Invitrogen). Plasmid DNAs were isolated from the obtained kanamycin-resistant colonies to obtain 5 cDNA clones containing Chinese hamster FX 5' region. They were named FX5' clone 25, FX5' clone 26, FX5' clone 27, FX5' clone 28, FX5' clone 31 and FX5' clone 32.

In the same manner, 5 cDNA clones containing Chinese hamster FX 3' region were obtained. These FX3' clones were named FX3' clone 1, FX3' clone 3, FX3' clone 6, FX3' clone 8 and FX3' clone 9.

The nucleotide sequence of the cDNA moiety of each of the clones obtained by the 5' and 3' RACE was determined by using DNA Sequencer 377 (manufactured by Parkin Elmer) in accordance with the method described in the manufacture's instructions. By comparing the cDNA nucleotide sequences determined by the method, reading errors of nucleotide bases due to PCR were excluded and the full length nucleotide sequence of Chinese hamster FX cDNA was determined. The determined sequence is represented by SEQ ID NO:48.

2. Determination of CHO Cell-Derived GFPP cDNA Sequence (1) Preparation of GFPP cDNA Partial Fragment Derived from Chinese Hamster GFPP cDNA partial fragment derived from Chinese hamster was prepared by the following procedure.

First, nucleotide sequences of a human GFPP cDNA (Genebank Accession No. AF017445), mouse EST sequences having high homology with the sequence (Genebank Accession Nos. AI467195, AA422658, BE304325 and AI466-474) and rat EST sequences (Genebank Accession Nos. BF546372, AI058400 and AW144783), registered at public data bases, were compared, and primers GFPP FW9 and GFPP RV9 (SEQ ID NOs:49 and 50) specific for rat GFPP were designed on a highly preserved region among these three species.

Next, 25 μl of a reaction solution [1× concentration ExTaq buffer (manufactured by Takara Shuzo), 0.2 mmol/L dNTPs and 0.5 mmol/l of the above GFPP-specific primers GFPP FW9 and GFPP RV9 (SEQ ID NOs:49 and 50)] containing 1 μl of the CHO/DG44-derived single-stranded cDNA prepared in the item 1(2) of Reference Example 1 was prepared by using a DNA polymerase ExTaq (manufactured by Takara Shuzo), and PCR was carried out. The PCR was carried out by heating at 94° C. for 5 minutes, subsequent 30 cycles of heating at 94° C. for 1 minute, 58° C. for 2 minutes and 72° C. for 3 minutes as one cycle, and further heating at 72° C. for 10 minutes.

After the PCR, the reaction solution was subjected to 2% agarose gel electrophoresis, and a specific amplified fragment of 1.4 Kbp was recovered and eluted with 20 μl of sterile water. Into a plasmid pCR2.1, 4 μl of the above amplified fragment was inserted in accordance with the instructions attached to TOPO TA Cloning Kit (manufactured by Invitrogen), and *E. coli* DH5α was transformed by using the reaction solution. Plasmid DNAs were isolated from the obtained kanamycin-resistant clones to obtain 3 clones into which GFPP cDNA partial fragments were respectively integrated. They were named GFPP clone 8, GFPP clone 11 and GFPP clone 12.

The nucleotide sequence of the cDNA inserted into each of the GFPP clone 8, GFPP clone 11 and GFPP clone 12 was determined by using DNA Sequencer 377 (manufactured by Parkin Elmer) and BigDye Terminator Cycle Sequencing FS Ready Reaction kit (manufactured by Parkin Elmer) in accordance with the method described in the manufacture's instructions. It was confirmed that the inserted cDNA whose sequence was determined according to the present invention encodes an ORF partial sequence of the Chinese hamster GFPP.

(2) Determination of Chinese Hamster GFPP Full Length cDNA by Race Method

Based on the Chinese hamster FX partial sequence determined in the item 2(1) of Reference Example 1, primers GFPP GSP1-1 (SEQ ID NO:52) and GFPP GSP1-2 (SEQ ID NO:53) for the Chinese hamster FX-specific 5' RACE and primers GFPP GSP2-1 (SEQ ID NO:54) and GFPP GSP2-2 (SEQ ID NO:55) for the Chinese hamster GFPP-specific 3' RACE were designed.

Next, 50 μl of a reaction solution [1× concentration Advantage2 PCR buffer (manufactured by CLONTECH), 0.2 mmol/L dNTPs, 0.2 μmol/l Chinese hamster GFPP-specific primers for RACE and 1× concentration of common primers (manufactured by CLONTECH)] containing 1 μl of the CHO/DG44 cell-derived single-stranded cDNA for RACE prepared in the item 1(4) of Reference Example 1 was prepared by using Advantage2 PCR Kit (manufactured by CLONTECH), and PCR was carried out. The PCR was carried out by 20 cycles of heating at 94° C. for 5 seconds, 68° C. for 10 seconds and 72° C. for 2 minutes as one cycle.

After completion of the reaction, 1 μl of the reaction solution was diluted 50-fold with the Tricin-EDTA buffer, and 1 μl of the diluted solution was used as a template. The reaction solution was again prepared and the PCR was carried out under the same conditions. The templates, the combination of primers used in the first and second PCRs and the size of amplified DNA fragments by the PCRs are shown in Table 7.

TABLE 7

Combination of primers used in Chinese hamster GFPP cDNA RACE PCR and the size of PCR products

| | GFPP-specific primers | Common primers | PCR-amplified product size |
|---|---|---|---|
| 5' RACE | | | |
| First | GFPPGSP1-1 | UPM (Universal primer mix) | 1,100 bp |
| Second | GFPPGSP1-2 | NUP (Nested Universal primer) | |
| 3' RACE | | | |
| First | GFPPGSP2-1 | UPM (Universal primer mix) | 1,400 bp |
| Second | GFPPGSP2-2 | NUP (Nested Universal primer) | |

After the PCR, the reaction solution was subjected to 1% agarose gel electrophoresis, and the specific amplified fragment of interest was recovered and eluted with 20 μl of sterile water. Into a plasmid pCR2.1, 4 μl of the above amplified fragment was inserted and *E. coli* DH5α was transformed with the reaction solution in accordance with the instructions attached to TOPO TA Cloning Kit (manufactured by Invitrogen). Plasmid DNAs were isolated from the obtained several kanamycin-resistant clones to obtain 4 cDNA clones containing Chinese hamster GFPP 5' region. They were named GFPP5' clone 1, GFPP5' clone 2, GFPP5' clone 3 and GFPP5' clone 4.

In the same manner, 5 cDNA clones containing Chinese hamster GFPP 3' region were obtained. They were named GFPP3' clone 10, GFPP3' clone 16 and GFPP3' clone 20.

The nucleotide sequence of the cDNA protein of each of the clones obtained in the above 5' and 3' RACE was determined by using DNA Sequencer 377 (manufactured by Parkin Elmer) in accordance with the method described in the manufacture's instructions. By comparing the cDNA nucleotide sequences after the nucleotide sequence determination, reading errors of bases due to PCR were excluded and the full length nucleotide sequence of Chinese hamster GFPP cDNA was determined. The determined sequence is represented by SEQ ID NO:51.

REFERENCE EXAMPLE 2

Preparation of CHO Cell-Derived GMD Gene

1. Determination of CHO Cell-Derived GMD cDNA Sequence (1) Preparation of CHO Cell-Derived GMD Gene cDNA (Preparation of Partial cDNA Excluding 5'- and 3'-Terminal Sequences)

Rodents-derived GMD cDNA was searched in a public data base (BLAST) using a human-derived GMD cDNA sequence (GenBank Accession No. AF042377) registered at GenBank as a query, and three kinds of mouse EST sequences were obtained (GenBank Accession Nos. BE986856, BF158988 and BE284785). By ligating these EST sequences, a deduced mouse GMD cDNA sequence was determined.

On the basis of the mouse-derived GMD cDNA sequence, a 28 mer primer having the nucleotide sequence represented by SEQ ID NO:56, a 27 mer primer having the nucleotide sequence represented by SEQ ID NO:57, a 25 mer primer having the nucleotide sequence represented by SEQ ID NO:58, a 24 mer primer having the nucleotide sequence represented by SEQ ID NO:59 and a 25 mer primer having the sequence represented by SEQ ID NO:60 were prepared.

Next, in order to amplify the CHO cell-derived GMD cDNA, PCR was carried out by the following method. A reaction solution at 20 µl [1× concentration Ex Taq buffer (manufactured by Takara Shuzo), 0.2 mmol/L dNTPs, 0.5 unit of Ex Taq polymerase (manufactured by Takara Shuzo) and 0.5 µmol/L of two synthetic DNA primers] containing 0.5 µl of the CHO cell-derived single-stranded cDNA prepared in the item 1(1) of Example 8 as the template was prepared. In this case, combinations of SEQ ID NO:56 with SEQ ID NO:57, SEQ ID NO:58 with SEQ ID NO:57, SEQ ID NO:56 with SEQ ID NO:59 and SEQ ID NO:56 with SEQ ID NO:60 were used as the synthetic DNA primers. The reaction was carried out by using DNA Thermal Cycler 480 (manufactured by Perkin Elmer) by heating at 94° C. for 5 minutes and subsequent 30 cycles of heating at 94° C. for 1 minute and 68° C. for 2 minutes as one cycle.

The PCR reaction solution was fractionated by agarose electrophoresis to find that a DNA fragment of about 1.2 kbp was amplified in the PCR product when synthetic DNA primers of SEQ ID NOs:56 and 57 were used, a fragment of about 1.1 kbp was amplified in the PCR product when synthetic DNA primers of SEQ ID NOs:57 and 59 were used, a fragment of about 350 bp was amplified in the PCR product when synthetic DNA primers of SEQ ID NOs:56 and 59 were used and a fragment of about 1 kbp was amplified in the PCR product when synthetic DNA primers of SEQ ID NOs:56 and 60 were used. The DNA fragments were recovered. The recovered DNA fragments were ligated to a pT7Blue(R) vector (manufactured by Novagen) by using DNA Ligation Kit (manufactured by Takara Shuzo), and E. coli DH5 strain (manufactured by Toyobo) was transformed by using the obtained recombinant plasmid DNA samples to thereby obtain plasmids 22-8 (having a DNA fragment of about 1.2 kbp amplified from synthetic DNA primers of SEQ ID NO:56 and SEQ ID NO:57), 23-3 (having a DNA fragment of about 1.1 kbp amplified from synthetic DNA primers of SEQ ID NO:58 and SEQ ID NO:57), 31-5 (a DNA fragment of about 350 bp amplified from synthetic DNA primers of SEQ ID NO:56 and SEQ ID NO:59) and 34-2 (having a DNA fragment of about 1 kbp amplified from synthetic DNA primers of SEQ ID NO:56 and SEQ ID NO:60). The CHO cell-derived GMD cDNA sequence contained in these plasmids was determined in the usual way by using a DNA sequencer ABI PRISM 377 (manufactured by Parkin Elmer) (since a sequence of 28 bases in downstream of the initiation codon methionine in the 5'-terminal side and a sequence of 27 bases in upstream of the termination codon in the 3'-terminal side are originated from synthetic oligo DNA sequences, they are mouse GMD cDNA sequences).

In addition, the following steps were carried out in order to prepare a plasmid in which the CHO cell-derived GMD cDNAs contained in the plasmids 22-8 and 34-2 are combined. The plasmid 22-8 (1 µg) was allowed to react with a restriction enzyme EcoRI (manufactured by Takara Shuzo) at 37° C. for 16 hours, the digest was subjected to agarose electrophoresis and then a DNA fragment of about 4 kbp was recovered. The plasmid 34-2 (2 µg) was allowed to react with a restriction enzyme EcoRI at 37° C. for 16 hours, the digest was subjected to agarose electrophoresis and then a DNA fragment of about 150 bp was recovered. The recovered DNA fragments were respectively subjected to terminal dephosphorylation using Calf Intestine Alkaline Phosphatase (manufactured by Takara Shuzo) and then ligated by using DNA Ligation Kit (manufactured by Takara Shuzo), and E. coli DH5α strain (manufactured by Toyobo) was transformed by using the obtained recombinant plasmid DNA to obtain a plasmid CHO-GMD (cf. FIG. 37).

(2) Determination of 5'-Terminal Sequence of CHO Cell-Derived GMD cDNA

A 24 mer primer having the nucleotide sequence represented by SEQ ID NO:61 was prepared from 5'-terminal side non-coding region nucleotide sequences of CHO cell-derived human and mouse GMD cDNA, and a 32 mer primer having the nucleotide sequence represented by SEQ ID NO:62 from CHO cell-derived GMD cDNA sequence were prepared, and PCR was carried out by the following method to amplify cDNA. Then, 20 µl of a reaction solution [1× concentration Ex Taq buffer (manufactured by Takara Shuzo), 0.2 mmol/L dNTPs, 0.5 unit of Ex Taq polymerase (manufactured by Takara Shuzo) and 0.5 mmol/L of the synthetic DNA primers of SEQ ID NO:61 and SEQ ID NO:62] containing 0.5 µl of the CHO cell-derived single-stranded cDNA obtained in the item 1(1) of Example 8 was prepared as the template, and the reaction was carried out therein by using DNA Thermal Cycler 480 (manufactured by Perkin Elmer) by heating at 94° C. for 5 minutes, subsequent 20 cycles of heating at 94° C. for 1 minute, 55° C. for 1 minute and 72° C. for 2 minutes as one cycle and further 18 cycles of heating at 94° C. for 1 minute and 68° C. for 2 minutes as one cycle. After fractionation of the PCR reaction solution by agarose electrophoresis, a DNA fragment of about 300 bp was recovered. The recovered DNA fragment was ligated to a pT7Blue(R) vector (manufactured by Novagen) by using DNA Ligation Kit (manufactured by Takara Shuzo), and E. coli DH5α strain (manufactured by Toyobo) was transformed by using the obtained recombinant plasmid DNA samples to thereby obtain a plasmid 5'GMD. Using DNA Sequencer 377 (manufactured by Parkin Elmer), the nucleotide sequence of 28 bases in downstream of the initiation methionine of CHO-derived GMD cDNA contained in the plasmid was determined.

(3) Determination of 3'-Terminal Sequence of CHO Cell-Derived GMD cDNA

In order to obtain 3'-terminal cDNA sequence of CHO cell-derived GMD, RACE method was carried out by the following method. A single-stranded cDNA for 3' RACE was prepared from the CHO cell-derived RNA obtained in the item 1(1) of Example 8 by using SMART™ RACE cDNA Amplification Kit (manufactured by CLONTECH) in accordance with the manufacture's instructions. In the case, PowerScript™ Reverse Transcriptase (manufactured by CLON- TECH) was used as the reverse transcriptase. The single-stranded cDNA after the preparation was diluted 10-fold with the Tricin-EDTA buffer attached to the kit and used as the template of PCR.

Next, 20 μl of a reaction solution [1× concentration ExTaq buffer (manufactured by Takara Shuzo), 0.2 mmol/L dNTPs, 0.5 unit of EX Taq polymerase (manufactured by Takara Shuzo), 0.5 mmol/L of the 24 mer synthetic DNA primer represented by SEQ ID NO:63 [prepared on the basis of the CHO cell-derived GMD cDNA sequence determined in the item 1(1) of Reference Example 2] and 1× concentration of Universal Primer Mix (attached to SMART™ RACE cDNA Amplification Kit; manufactured by CLONTECH] containing 1 μl of the above single-stranded cDNA for 3' RACE as the template was prepared, and the reaction was carried out by using DNA Thermal Cycler 480 (manufactured by Perkin Elmer) by heating at 94° C. for 5 minutes and subsequent 30 cycles of heating at 94° C. for 1 minute and 68° C. for 2 minutes as one cycle.

After completion of the reaction, 1 μl of the PCR reaction solution was diluted 20-fold with Tricin-EDTA buffer (manufactured by CLONTECH). Then, 20 μl of a reaction solution [1× concentration ExTaq buffer (manufactured by Takara Shuzo), 0.2 mmol/L dNTPs, 0.5 unit of EX Taq polymerase (manufactured by Takara Shuzo), 0.5 μmol/L of the 25 mer synthetic DNA primer represented by SEQ ID NO:64 [prepared on the basis of the CHO cell-derived GMD cDNA sequence determined in the item 1(1) of Reference Example 2] and 0.5 μmol/L of Nested Universal Primer (attached to SMART™ RACE cDNA Amplification Kit; manufactured by CLONTECH)] containing 1 μl of the 20 fold-diluted aqueous solution as the template was prepared, and the reaction was carried out by using DNA Thermal Cycler 480 (manufactured by Perkin Elmer) by heating at 94° C. for 5 minutes and subsequent 30 cycles of heating at 94° C. for 1 minute and 68° C. for 2 minutes as one cycle.

After completion of the reaction, the PCR reaction solution was fractionated by agarose electrophoresis and then a DNA fragment of about 700 bp was recovered. The recovered DNA fragment was ligated to a pT7Blue(R) vector (manufactured by Novagen) by using DNA Ligation Kit (manufactured by Takara Shuzo), and *E. coli* DH5α strain (manufactured by Toyobo) was transformed by using the obtained recombinant plasmid DNA, thereby obtaining a plasmid 3'GMD. Using DNA Sequencer 377 (manufactured by Parkin Elmer), the nucleotide sequence of 27 bases in upstream of the termination codon of CHO-derived GMD cDNA and 415 bp of 3'-terminal side non-coding region contained in the plasmid was determined.

The full length cDNA sequence of the CHO-derived GMD gene determined by the items 1(1), 1(2) and 1(3) of Reference Example 2 is represented by SEQ ID NO:65, and the corresponding amino acid sequence is represented by SEQ ID NO:71.

2. Determination of Genomic Sequence Containing CHO/DG44-Derived Cell GMD Gene

A 25 mer primer having the nucleotide sequence represented by SEQ ID NO:66 was prepared from the mouse GMD cDNA sequence determined in the item 1 of Reference Example 2. Next, a CHO cell-derived genomic DNA was obtained by the following method. A CHO/DG44 cell-derived KC861 cell was suspended in IMDM-dFBS(10)-HT(1) medium [IMDM-dFBS(10) medium comprising 1× concentration of HT supplement (manufactured by Invitrogen)] to give a density of 3×10⁵ cells/ml, and the suspension was dispensed at 2 ml/well into a 6 well flat bottom plate for adhesion cell use (manufactured by Greiner). After culturing at 37° C. in a 5% $CO_2$ incubator until the cells became confluent on the plate, genomic DNA was prepared from the cells on the plate by a known method [*Nucleic Acids Research*, 3, 2303 (1976)] and dissolved overnight in 150 μl of TE-RNase buffer (pH 8.0) (10 mmol/l Tris-HCl, 1 mmol/l EDTA, 200 μg/ml RNase A).

A reaction solution (20 μl) [1× concentration Ex Taq buffer (manufactured by Takara Shuzo), 0.2 mmol/L dNTPs, 0.5 unit of EX Taq polymerase (manufactured by Takara Shuzo) and 0.5 μmol/L of synthetic DNA primers of SEQ ID NO:59 and SEQ ID NO:66] containing 100 ng of the obtained CHO/DG44 cell-derived genomic DNA was prepared, and PCR was carried out by using DNA Thermal Cycler 480 (manufactured by Perkin Elmer) by heating at 94° C. for 5 minutes and subsequent 30 cycles of heating at 94° C. for 1 minute and 68° C. for 2 minutes as one cycle. After completion of the reaction, the PCR reaction solution was fractionated by agarose electrophoresis and then a DNA fragment of about 100 bp was recovered. The recovered DNA fragment was ligated to a pT7Blue(R) vector (manufactured by Novagen) by using DNA Ligation Kit (manufactured by Takara Shuzo), and *E. coli* DH5α strain (manufactured by Toyobo) was transformed by using the obtained recombinant plasmid DNA, thereby obtaining a plasmid ex3. Using DNA Sequencer 377 (manufactured by Parkin Elmer), the nucleotide sequence of CHO cell-derived genomic DNA contained in the plasmid was determined. The nucleotide sequence was represented by SEQ ID NO:67.

Next, a 25 mer primer having the nucleotide sequence represented by SEQ ID NO:68 and a 25 mer primer having the nucleotide sequence represented by SEQ ID NO:69 were prepared on the basis of the CHO cell-derived GMD cDNA sequence determined in the item 1 of Reference Example 2. Next, 20 μl of a reaction solution [1× concentration Ex Taq buffer (manufactured by Takara Shuzo), 0.2 mmol/L dNTPs, 0.5 unit of EX Taq polymerase (manufactured by Takara Shuzo) and 0.5 μmol/L of the synthetic DNA primers of SEQ ID NO:68 and SEQ ID NO:69] containing 100 ng of the CHO/DG44-derived genomic DNA was prepared, and PCR was carried out by using DNA Thermal Cycler 480 (manufactured by Perkin Elmer) by heating at 94° C. for 5 minutes and subsequent 30 cycles of heating at 94° C. for 1 minute and 68° C. for 2 minutes as one cycle.

After completion of the reaction, the PCR reaction solution was fractionated by agarose electrophoresis and then a DNA fragment of about 200 bp was recovered. The recovered DNA fragment was ligated to a pT7Blue(R) vector (manufactured by Novagen) by using DNA Ligation Kit (manufactured by Takara Shuzo), and *E. coli* DH5α strain (manufactured by Toyobo) was transformed by using the obtained recombinant plasmid DNA, thereby obtaining a plasmid ex4. Using DNA Sequencer 377 (manufactured by Parkin Elmer), the nucleotide sequence of CHO cell-derived genomic DNA contained in the plasmid was determined. The result nucleotide sequence was represented by SEQ ID NO:70.

REFERENCE EXAMPLE 3

Preparation of Anti-FGF-8 Chimeric Antibody

1. Isolation and Analysis of a cDNA Encoding the V Region of a Mouse Antibody Against FGF-8
(1) Preparation of mRNA from Hybridoma Cells which Produces a Mouse Antibody Against FGF-8

About 8 μg of mRNA was prepared from 1×10⁷ cells of a hybridoma KM1334 (FERM BP-5451) which produces a mouse antibody against FGF-8 (anti-FGF-8 mouse antibody), using a mRNA preparation kit Fast Track mRNA Isolation Kit (manufactured by Invitrogen) according to the attached manufacture's instructions.

(2) Production of cDNA Libraries of Anti-FGF-8 Mouse Antibody H Chain and L Chain A cDNA having EcoRI-NotI adapters on both termini was synthesized from 5 µg of the KM1334 mRNA obtained in the item 1(1) of Reference Example 3 by using Time Saver cDNA Synthesis Kit (manufactured by Amersham Pharmacia Biotech) according to the attached manufacture's instructions. A full amount of the prepared cDNA was dissolved in 20 µl of sterile water and then fractionated by agarose gel electrophoresis, and about 1.5 kb of a cDNA fragment corresponding to the H chain of an IgG class antibody and about 1.0 kb of a cDNA fragment corresponding to the L chain of a K class were recovered each at about 0.1 µg. Next, 0.1 µg of the cDNA fragment of about 1.5 kb and 0.1 µg of the cDNA fragment of about 1.0 kb were respectively digested with restriction enzyme EcoRI and then ligated with 1 µg of λZAPII vector whose termini had been dephosphorylated with calf intestine alkaline phosphatase, using λZAPII Cloning Kit (manufactured by Stratagene) according to the attached manufacture's instructions.

Using Gigapack II Packaging Extracts Gold (manufactured by Stratagene), 4 µl of each reaction solution after ligation was packaged in λ phage according to the manufacture's instructions, and *Escherichia coli* XL1-Blue [*Biotechniques*, 5, 376 (1987)] was infected with an adequate amount of the package to obtain about $8.1 \times 10^4$ and $5.5 \times 10^4$ phage clones as H chain cDNA library and L chain cDNA library, respectively, of KM1334. Next, respective phages were immobilized on a nylon membrane according to a known method (*Molecular Cloning*, Second Edition).

(3) Cloning of cDNAs of Anti-FGF-8 Mouse Antibody H Chain and L Chain

Nylon membranes of the H chain cDNA library and L chain cDNA library of KM1334 prepared in the item 1(2) in Reference Example 3 were detected using a cDNA of the C region of a mouse antibody [H chain is a DNA fragment containing mouse Cγ1 cDNA (*J. Immunol.*, 146, 2010 (1991)], L chain is a DNA fragment containing mouse Cκ cDNA [*Cell*, 22, 197 (1980)] as a probe, using ECL Direct Nucleic Acid Labeling and Detection Systems (manufactured by Amersham Pharmacia Biotech) according to the attached manufacture's instructions, and phage clones strongly linked to the probe, 10 clones for each of H chain and L chain, were obtained. Next, each phage clone was converted into a plasmid by the in vivo excision method according to the manufacture's instructions attached to λZAPII Cloning Kit (manufactured by Stratagene). A nucleotide sequence of a cDNA contained in each of the obtained plasmids was determined by the dideoxy method (*Molecular Cloning*, Second Edition) by using Big Dye Terminator Kit ver. 2 (manufactured by Applied Biosystems). As a result, a plasmid pKM1334H7-1 containing a full length and functional H chain cDNA and a plasmid pKM1334L7-1 containing L chain cDNA, having an ATG sequence considered to be the initiation codon in the 5'-terminal of the cDNA were obtained.

(4) Analysis of Amino Acid Sequence of V Region of Anti-FGF-8 Mouse Antibody

A full length nucleotide sequence of VH contained in the plasmid pKM1334H7-1 and a deduced complete length amino acid sequence are represented by SEQ ID NO:72 and SEQ ID NO:73, respectively, and a full length nucleotide sequence of VL contained in the plasmid pKM1334L7-1 and a deduced complete length amino acid sequence are represented by SEQ ID NO:74 and SEQ ID NO:75, respectively.

As a result of comparing these sequences to both known sequence data of mouse antibodies (*Sequences of Proteins of Immunological Interest*, U.S. Dept. Health and Human Services, 1991) and the comparison with the results of analysis of N-terminal amino acid sequences of H chain and L chain of the purified anti-FGF-8 mouse antibody KM1334, carried out by their automatic Edman degradation using a protein sequencer PPSQ-10 (manufactured by Shimadzu), it was found that each of the isolated cDNA is a full length cDNA encoding the anti-FGF-8 mouse antibody KM1334 containing a secretory signal sequence, and positions 1 to 19 in the amino acid sequence represented by SEQ ID NO:73 and positions 1 to 19 in the amino acid sequence described in SEQ ID NO:75 are secretory signal sequences of H chain and L chain, respectively.

Next, novelty of the amino acid sequences (sequences excluding secretory signal sequence) of VH and VL of the anti-FGF-8 mouse antibody KM1334 was examined. Using GCG Package (version 9.1, manufactured by Genetics Computer Group) as a sequence analyzing system, an amino acid sequence data base of known proteins (PIR-Protein (Release 56.0)) was searched by the BLAST method [*J. Mol. Biol.*, 215, 403 (1990)]. As a result, completely coincided sequences were not found for both of the H chain and L chain, so that it was confirmed that the VH and VL of the anti-FGF-8 mouse antibody KM1334 are novel amino acid sequences.

Also, the CDR of VH and VL of the anti-FGF-8 mouse antibody KM1334 was identified by comparing with amino acid sequences of known antibodies. Amino acid sequences of CDR 1, 2 and 3 of VH of the anti-FGF-8 mouse antibody KM1334 are represented by SEQ ID NOs:76, 77 and 78, respectively, and amino acid sequences of CDR 1, 2 and 3 of VL in SEQ ID NOs:79, 80 and 81, respectively.

2. Stable Expression of Anti-FGF-8 Chimeric Antibody Using Animal Cell (1) Construction of Anti-FGF-8 Chimeric Antibody Expression Vector pKANTEX1334

An anti-FGF-8 chimeric antibody expression vector pKANTEX1334 was constructed as follows using the vector pKANTEX93 for humanized antibody expression described in WO97/10354 and the plasmids pKM1334H7-1 and pKM1334L7-1 obtained in the item 1(3) of Reference Example 3.

Using 50 ng of the plasmid pKM1334H7-1 obtained in the item 1(3) of Reference Example 3 as the template and by adding synthetic DNAs having the nucleotide sequences described in SEQ ID NOs:24 and 25 (manufactured by GENSET) as primers to give a final concentration of 0.3 µM, PCR were carried out in a system of 50 µl by first heating at 94° C. for 2 minutes and subsequent 30 cycles of heating at 94° C. for 15 seconds, at 55° C. for 30 seconds and at 68° C. for 1 minute according to the manufacture's instructions attached to KOD plus polymerase (manufactured by TOYOBO). The reaction solution was precipitated with ethanol, dissolved in sterile water and then allowed to react at 37° C. for 1 hour by using 10 units of a restriction enzyme ApaI (manufactured by Takara Shuzo) and 10 units of a restriction enzyme NotI (manufactured by New England Biolabs). About 0.3 µg of an ApaI-NotI fragment of about 0.47 kb was recovered By fractionating the reaction solution by agarose gel electrophoresis.

Next, 3 µg of the vector pKANTEX93 for humanized antibody expression was allowed to react at 37° C. for 1 hour by using 10 units of restriction enzyme ApaI (manufactured by Takara Shuzo) and 10 units of restriction enzyme NotI (manufactured by New England Biolabs). About 2 µg of an ApaI- NotI fragment of about 12.75 kb was recovered, by fractionating the reaction solution by an agarose gel electrophoresis.

Next, 0.1 µg of the NotI-ApaI fragment derived from the PCR product and 0.1 µg of the NotI-ApaI fragment derived from the plasmid pKANTEX93, obtained in the above, were added to 10 µl of sterile water in total amount and ligated by using Ligation High (manufactured by TOYOBO). The plasmid pKANTEX1334H shown in FIG. 38 was obtained by transforming *Escherichia coli* JM109 by using the recombinant plasmid DNA solution obtained in this manner.

Next, using 50 ng of the plasmid pKM1334L7-1 obtained in the item 1(3) of Reference Example 1 as the template and by adding synthetic DNAs having the nucleotide sequences described in SEQ ID NOs:82 and 83 (manufactured by GENSET) as primers to give a final concentration of 0.3 µM, PCR was carried out in a system of 50 µl by first heating at 94° C. for 2 minutes and subsequent 30 cycles of heating at 94° C. for 15 seconds, at 55° C. for 30 seconds and 68° C. for 1 minute according to the manufacture's instructions attached to KOD plus polymerase (manufactured by TOYOBO). The reaction solution was precipitated with ethanol, dissolved in sterile water and then allowed to react at 37° C. for 1 hour by using 10 units of a restriction enzyme EcoRI (manufactured by Takara Shuzo) and 10 units of a restriction enzyme BsiWI (manufactured by New England Biolabs). About 0.3 µg of an EcoRI-BsiWI fragment of about 0.44 kb was recovered by fractionating the reaction solution by agarose gel electrophoresis.

Next, 3 µg of the plasmid pKANTEX1134H obtained in the above was allowed to react at 37° C. for 1 hour by using 10 units of a restriction enzyme EcoRI (manufactured by Takara Shuzo) and a restriction enzyme BsiWI (manufactured by New England Biolabs). About 2 µg of an EcoRI-BsiWI fragment of about 13.20 kb was recovered by fractionating said reaction solution by an agarose gel electrophoresis.

Next, 0.1 µg of the EcoRI-BsiWI fragment derived from the PCR product and 0.1 µg of the EcoRI-BsiWI fragment derived from the plasmid pKANTEX1334H, obtained in the above, were added to 10 µl of sterile water in total amount and ligated by using Ligation High (manufactured by TOYOBO). The plasmid pKANTEX1334 shown in FIG. 38 was obtained by transforming *Escherichia coli* JM109 using the recombinant plasmid DNA solution obtained in this manner.

As a result of carrying out analysis of a nucleotide sequence using 400 ng of the obtained plasmid by the dideoxy method (*Molecular Cloning*, Second Edition) using Big Dye Terminator Kit ver. 2 (manufactured by Applied Biosystems), it was confirmed that a plasmid comprising a cloned DNA of interest was obtained.

While the invention has been described in detail and with reference to specific embodiments thereof, it will be apparent to one skill in the art that various changes and modifications can be made therein without departing from the spirit and scope thereof. All references cited herein are incorporated in their entirety.

This application is based on Japanese application No. 2002-106950 filed on Apr. 9, 2002, the entire contents of which being incorporated hereinto by reference.

What is claimed is:

1. A method for detecting the antibody-dependent cell-mediated cytotoxic (ADCC) activity of an antibody composition, said antibody molecules having a sugar chain, wherein at least part of the antibody molecule has a no-fucose sugar chain in which fucose is not bound to N-acetylglucosamine in the reducing end of the sugar chain of the antibody molecule, the method comprising:

(a) preparing a standard curve from the binding activities of three or more reference antibody compositions to a Fcγ receptor IIIa, wherein the no-fucose sugar chain ratio and the ADCC activity of each reference antibody composition is known, comprising (i) contacting each reference antibody composition, separately, with an antigen which binds to the variable regions of the antibodies in each reference antibody composition, to form a reference antibody-antigen complex for each reference antibody composition; (ii) contacting each reference antibody-antigen complex with Fcγ receptor IIIa; and (iii) measuring the binding activity of each reference antibody-antigen complex to the Fcγ receptor IIIa;

(b) determining the binding activity of a test antibody composition, comprising (i) contacting a test antibody composition with said antigen, wherein said antigen bindgs to the variable regions of the antibodies in said test antibody composition, to form a test antibody-antigen complex; (ii) contacting the test antibody-antigen complex to the Fcγ receptor IIIa; and (iii) measuring the binding activity of the test antibody-antigen complex to the Fcγ receptor IIIa; and (c) determining an ADCC activity for the test antibody composition by comparing the binding activity of the test antibody-antigen complex to the Fcγ receptor IIIa with a standard curve of the binding activities of the reference antibody-antigen complexes to the Fcγ receptor IIIa.

* * * * *